US007872103B2

(12) United States Patent
Garcia-Martinez et al.

(10) Patent No.: US 7,872,103 B2
(45) Date of Patent: Jan. 18, 2011

(54) MODULATING IMMUNE RESPONSES

(75) Inventors: Leon Fernando Garcia-Martinez, Woodinville, WA (US); Yuching Chen, Bellevue, WA (US); Dawn Andrews, Lake Forest Park, WA (US)

(73) Assignee: Celltech R & D, Limited (GB)

( * ) Notice: Subject to any disclaimer, the term of this patent is extended or adjusted under 35 U.S.C. 154(b) by 0 days.

(21) Appl. No.: 12/699,636

(22) Filed: Feb. 3, 2010

(65) Prior Publication Data

US 2010/0249380 A1 Sep. 30, 2010

Related U.S. Application Data

(63) Continuation of application No. 11/805,841, filed on May 23, 2007, now Pat. No. 7,700,740, which is a continuation of application No. 10/719,642, filed on Nov. 21, 2003, now abandoned, and a continuation of application No. PCT/US02/37738, filed on Nov. 21, 2002.

(60) Provisional application No. 60/473,279, filed on May 22, 2003, provisional application No. 60/428,130, filed on Nov. 21, 2002, provisional application No. 60/331,958, filed on Nov. 21, 2001.

(51) Int. Cl.
*C07K 16/00* (2006.01)

(52) U.S. Cl. .................................................. 530/387.9

(58) Field of Classification Search ....................... None
See application file for complete search history.

(56) References Cited

U.S. PATENT DOCUMENTS

| | | | | |
|---|---|---|---|---|
| 5,316,320 | A | 5/1994 | Breaker | 277/611 |
| 5,316,920 | A | 5/1994 | Tedder et al. | |
| 5,766,570 | A | 6/1998 | Tedder et al. | |
| 6,068,984 | A | 5/2000 | Tedder et al. | |
| 6,900,016 | B1 | 5/2005 | Venter et al. | 435/6 |
| 2006/0083740 | A1 | 4/2006 | Ramsdell et al. | |

FOREIGN PATENT DOCUMENTS

| | | | |
|---|---|---|---|
| WO | 95/29236 | | 11/1995 |
| WO | 97/29781 | | 8/1997 |
| WO | 02/074921 | A2 | 9/2002 |
| WO | 03/038072 | A1 | 5/2003 |
| WO | 03/040170 | A2 | 5/2003 |
| WO | 03/045318 | A2 | 6/2003 |

OTHER PUBLICATIONS

Armitage, R.J et al., Evidence for a Function Role of CD83 in T- and B- Cell Responses, *Tissue Antigens*, 48(4-2): 453FF, 1996.

Bancroft et al., Cyokine Production in BALB/c Mice Immunized with Radiation Attenuated Third Stage Lavae of the Filarial Nematode, *The Journal of Immunology*, 150(4):1395-1402, 1993.

Chen et al., In vitro induction of T cell anergy by block B7 and early T cell costimulatory molecule ETC-1/B7-2, *Immunity*, 1:147-154m 1994.

Clerici et al., A TH1→ TH2 switch is a critical step in the etiology of HIV infection., *Immunology Today*, 14(3): 107-111, 1993.

Cramer, S.O. et al., Activation-Induced Expression of a Murine CD83 on T Cells and Identification of a Specific CD83 Ligand on Murin B Cells, *International Immunology*, 12(9): 1347-1351, 2000.

Dallman, Cytokines and transplantation: Th1/Th2 regulation of the immune response to solid organ transplants in the adult, *Current Opinion in Immunology*, 7:632-638, 1995.

Dreher, K.L. et al., cDNA Clone Encoding a Complete Rabbit Immunoglobulin K Light Chain of b4 Allotype, *Pro Natl. Acad. Sci. USA*, 80: 4489-4493, Jul. 1983.

Else et al., Cytokine-mediated regulation of chornic intestinal helminth infection, *J. Exp. Med.*, 179L 347-351, 1994.

Fauci, The human immunodeficiency virus: infectivity and mechanisms of pathogenesis, *Science*, 239:617-622, 1988.

Fowler et al., Donor Lymphoid Cells of Th2 Cytokine Phenotype Reduce Lethal Graft Versus Host Disease and Facsiltate Fully Allogeneic Cell Transfers in Sublethally Irradiated Mice, *Advances in Bone Marrow Purging and Processing: Fourth International Symposium*, 533-540, 1994.

Fowler et al., Donor CD4-Enriched Cells of Th2 Cytokine Phenotype Regulate Graft-Versus-Host Disease Without Impairing Allogeneic Engraftment in Sublethally Irradiated Mice, *Blood*, 84(10): 3540-3549, 1994.

Frasca L et al. 2006. CD38 orchestrates migration, survival and Th1 immune response of human mature dendritic cells, *Blood*, 107(6): 2392-2399.

Fujimoto, Y. et al., CD83 Expression Influences CD4+ T Cell Development in the Thymus, *Cell*, 108: 755-767, 2002.

Fujimoto, Y. et al., Dendritic Cell CD 83 Provides a Progression Signal Required for CD4+ T Cells Positive Selection in the Thymus, *FASEB Journal*,15(4): A672, 2001.

Gorczynski et al., Interleukim 12 in combination with anti-interleukin 10 reverses graft prolongation after portal venous immunization, *Transplantation*, 60(11): 1337-1341, 1995.

Grzych et al., Egg deposition is the major stimulus for the production of Th2 cytokines in murine schistosomiasis mansoni, *The Journal of Immunology*, 146(4): 1322-1329, 1991.

Heinzel et al., Reciprocal expression of interferon gamma or interleukin 4 during the resolution or progression of murine leishmaniasis. Evidence for expansion of distinct helper T cell subsets, *J. Exp. Med.*, 169:59-72, 1989.

Hsieh-Ma, S.T. et al., *Clinical Immunology and Immunopathology*, 80(2) 185-193, 1996.

Hock, B.D. et al., A Soluble Form of CD83 is Release from Activated Dendritic Cells and B Lymphocytes, and Is Detectable in Normal Human Sera, *International Immunology*, v. 13 pp. 959-967 2001.

Jaton, J.C., Completion of the Analysis of the Primary Structure of the Variable Domain of the Hmogeneous Rabbit Antibody to Type III Pneumococcal Polysaccharide, *Biochem J.* 143: 723-732, 1973.

(Continued)

*Primary Examiner*—Michail A Belyavskyi
(74) *Attorney, Agent, or Firm*—C. Rachal Winger, Ph.D.; K&L Gates LLP

(57) ABSTRACT

The invention provides methods for modulating the immune system using anti-CD83 antibodies that can influence CD83 function.

4 Claims, 46 Drawing Sheets

OTHER PUBLICATIONS

Khoury et al., Oral tolerance to myelin basic protein and natural recovery fro experimental autoimmune encephalomyelitis are associated with downregulation of inflammatory cytokines and differential upregulation of transforming grown factor beta, interleukin 4, and prostaglandin E expression in the brain, *J. Exp. Med.*, 176:1355-1364, 1992.

Knappik et al., *Journal of Molecular Biology*, 2000.

Kuchroo et al., Cytokines and adhestion molecules contribute to the ability of myelin proteolipid protein-specific T cell clones to mediate experimental allergic encephalomyelitis, *The Journal of Immunology*, 151(8): 4371-4382, 1993.

Kullberg et al., Infection with Schistosoma mansoni alters Th1/Th2 cytokine responses to a non-parasite antigen, *The Journal of Immunology*, 148(10):3264-3270, 1992.

Leonard et al., Prevention of experimental autoimmune encephalomyelitis by antibodies against interleukin 12, *J. Exp. Med.*, 181:381-386, 1995.

Levy et al., Adminsitration of intragraft interleukin-4 prolongs cardiac allograft survival in rates treated with donor-specific transfusion/cyclosporine, *Transplantation*, 60(5): 405-406, 1995.

Locksley et al., Helper T-cell subsets in mouse leishmaniasis: induction, expansion and effector function, *T-Cell Subsets*, A58-A61, 1991.

Ma, J. K-C and Hein, M.B. *Tibtech* 13:522-527, 1995.

Maeda et al., Adoptive transfer of a Th2-like cell line prolongs MHc class II antigen disparate skin allograft survival in the mouse, *International Immunology*, 6(6): 855-862, 1994.

Marmor, M.D. and Julius , M., *Blood* 98(5): 1489-1497, 2001.

Morrissey et al., Granulocyte-macrophage colony-stimulating factor augments the primary antibody response by enhanving the function of antigen-presenting cells, *The Journal of Immunology*, 139(4): 1113-1119, 1987.

Mosmann et al., Two types of murin helper T cell clone. I. Definition according to profiles of lymphokine activities and secreted proteins, *The Journal of Immunology*, 136(7): 2348-2357, 1986.

Munster, D.J. et al., CD83 Antigen: A Potential New Target for Immunosuppression, *Blood*, 100(11): Abstract No. 3694, 2002.

Paul et al., Lymphocute Responses and Cytokines, *Cell*, 76: 241-251, 1994.

Paul, Fundamental Immunology, (textbook), 1999, under the heading "Immunoglobulins: Structure and Function," pp. 37,43,58 and 59.

Pearce et al., Downregulation of Th1 cytokine production accompanies induction of Th2 responses by a parasitic helminth, Schistosoma mansoni, *J. Exp. Med.*, 173:159-166, 1991.

Pearlman et al., Inducation of Murin T-Helper-Cell Reponses to the Filarial Namatode *Brugia malayi., Infection and Immunity*, 61(3): 1105-1112, 1993.

Pisa et al., Selective expression of interleukin 10, interferon gamma, and granulocyte-macrophage colony-stimulating factor in ovarian cancer biopsies, *Proc. Natl. Acad. Sci. USA*, 89:7708-7712, 1992.

Racke et al., Cytokine-induced immune deviation as a therapy of inflammatory autoimmune disease, *J. Exp. Med.*, 180:1961-1966, 1994.

Rapoport et al., Interleukin 4 reverses T cell proliferate unresponsiveness and prevents the onset of diabetes in nonobese diabetic mice, *J. Exp. Med.*, 178:87-99, 1993.

Rudikoff et al., Singel amino acid substitution altering antigen-binding specificity, *Proc Natl Acad Sci USA*, 1982 vol. 79 p. 1979.

Sadick et al., Cure of murine leishmaniasis with anti-interleukin 4 monoclonal antibody. Evidence for a T cell-dependent interferon gamma-independent mechanism, *J. Exp. Med.*, 171:115-127, 1990.

Scholler, N. et al., CD83 is a Sialic Acid-Binding IG-Like Lection (Siglec) Adhesion Receptor that Binds Monocytes and a Subset of Activated CD8+ T Cells, *Immunology*, 166: 3865-3872, 2001.

Schwartz et al., Autoimmunity and Autoimmune Diseases, *Fundamental Immunology*, Second Edition: New York, 819-856, 1989.

Seder et al., Acquisition of lymphokine-producing phenoltype by CD4+ T cells, *Annu. Rev. Immunol.*, 12:635-673, 1994.

Shearer et al., T helper cell immune dysfunction in asymptomatic, HIV-1-seropositive individuals: the role of TH1-TH2 cross regulation, *Chem. Immunol.*, 54:21-43, 1992.

Simon et al., Divergent T-Cell Cytokine Patterns in Inflammatory Arthritis, *Proc. Natl. Acad. Sci. USA*, 91(18):8562-8566, 1994.

Takeuchi et al., Heart Allografts in Murine Systems, *Transplantation*, 53(6): 1281-1294, 1992.

Thai et al., Cytokine mRNA Profiles in Mouse Orthotopic Liver Transplantation, *Transplantation*, 59(2): 274-281, 1995.

Tkakis et al., Early Tolerance in Pediatric Liver Allograft Recipients, *Journal of Pediatric Surgery*, 29(6): 754-756, 1994.

Willuda et al., Tumor targeting of mono-, di-, and tetravalent anti-p 185 (HER-2) miniantibodies multimerized by self-associating peptides, *J. of Biological Chemistry*, 2001, vol. 276, pp. 14385-14392.

Wolenski, M. et al., Expression of CD83 in the Murine Immune System, *Med Microbiol Immunol*, 192: 189-192, 2003.

Yamamura et al., Local expression of anti-inflammatory cytokines in cancer, *Journal of Clinical Investigation*, 91: 1005-1010, 1993.

Zhou, L. et al., A Novel Cell-Surface Molecule Expressed by Human Interdigitating Reticulum Cells, Langerhans Cells and Activated Lymphocytes is a New Member of the Ig Superfamily, *J. Immunol.*, 149: 735-742, 1992.

Zhou et al., Human blood dendritic cells selectively express CD83, a member of the immunoglobulin superfamily, *Journal of Immunology*, 3821-3835, 1995.

| | Mom | G3 ID | % CD4+ |
|---|---|---|---|
| Pedigree 57 | G2 # 1 | 57.1.1 | 22 |
| | | 57.1.2 | 26 |
| | | 57.1.3 | 24 |
| | G2 # 4 | 57.4.1 | 15 |
| | | 57.4.2 | 18 |
| | G2 # 5 | 57.5.1 | 21 |
| | | 57.5.2 | 19 |
| | | 57.5.3 | 24 |
| | | 57.5.4 | 22 |
| | | 57.5.5 | 19 |
| | | 57.5.6 | 17 |
| Pedigree 9 | G2 # 4 | 9.4.1 | 6 |
| | | 9.4.2 | 20 |
| | | 9.4.3 | 16 |
| | | 9.4.4 | 12 |
| | | 9.4.5 | 20 |
| | | 9.4.6 | 15 |
| | | 9.4.7 | 24 |
| | | 9.4.8 | 27 |
| | | 9.4.9 | 5 |
| | G2 # 5 | 9.5.1 | 18 |
| | | 9.5.2 | 20 |
| | | 9.5.3 | 22 |
| | | 9.5.4 | 20 |
| | | 9.5.5 | 22 |
| | | 9.5.6 | 20 |
| | | 9.5.7 | 23 |

| | |
|---|---|
| average | 19.1 |
| stdev | 5.2 |
| = + 2SD | 29.6 |
| = -2SD | 8.7 |

FIG. 1

```
1    GCGCTCCAGC CGCATGTCGC AAGGCCTCCA GCTCCTGTTT CTAGGCTGCG
51   CCTGCAGCCT GGCACCCGCG ATGGCGATGC GGGAGGTGAC GGTGGCTTGC
101  TCCGAGACCG CCGACTTGCC TTGCACAGCG CCCTGGGACC CGCAGCTCTC
151  CTATGCAGTG TCCTGGGCCA AGGTCTCCGA GAGTGGCACT GAGAGTGTGG
201  AGCTCCCGGA GAGCAAGCAA AACAGCTCCT TCGAGGCCCC CAGGAGAAGG
251  GCCTATTCCC TGACGATCCA AAACACTACC ATCTGCAGCT CGGGCACCTA
301  CAGGTGTGCC CTGCAGGAGC TCGGAGGGCA GCGCAACTTG AGCGGCACCG
351  TGGTTCTGAA GGTGACAGGA TGCCCCAAGG AAGCTACAGA GTCAACTTTC
401  AGGAAGTACA GGGCAGAAGC TGTGTTGCTC TTCTCTCTGG TTGTTTTCTA
451  CCTGACACTC ATCATTTTCA CCTGCAAATT TGCACGACTA CAAAGCATTT
501  TCCCAGATAT TTCTAAACCT GGTACGGAAC AAGCTTTTCT TCCAGTCACC
551  TCCCCAAGCA AACATTTGGG GCCAGTGACC CTTCCTAAGA CAGAAACGGT
601  ATGAGTAGGA TCTCCACTGG TTTTTACAAA GCCAAGGGCA CATCAGATCA
651  GTGTGCCTGA ATGCCACCCG GACAAGAGAA GAATGAGCTC CATCCTCAGA
701  TGGCAACCTT TCTTTGAAGT CCTTCACCTG ACAGTGGGCT CCACACTACT
751  CCCTGACACA GGGTCTTGAG CACCATCATA TGATCACGAA GCATGGAGTA
801  TCACCGCTTC TCTGTGGCTG TCAGCTTAAT GTTTCATGTG GCTATCTGGT
851  CAACCTCGTG AGTGCTTTTC AGTCATCTAC AAGCTATGGT GAGATGCAGG
901  TGAAGCAGGG TCATGGGAAA TTTGAACACT CTGAGCTGGC CCTGTGACAG
951  ACTCCTGAGG ACAGCTGTCC TCTCCTACAT CTGGGATACA TCTCTTTGAA
1001 TTTGTCCTGT TTCGTTGCAC CAGCCCAGAT GTCTCACATC TGGCGGAAAT
1051 TGACAGGCCA AGCTGTGAGC CAGTGGGAAA TATTTAGCAA ATAATTTCCC
1101 AGTGCGAAGG TCCTGCTATT AGTAAGGAGT ATTATGTGTA CATAGAAATG
1151 AGAGGTCAGT GAACTATTCC CCAGCAGGGC CTTTTCATCT GGAAAAGACA
1201 TCCACAAAAG CAGCAATACA GAGGGATGCC ACATTTATTT TTTTAATCTT
1251 CATGTACTTG TCAAAGAAGA ATTTTTCATG TTTTTTCAAA GAAGTGTGTT
1301 TCTTTCCTTT TTTAAAATAT GAAGGTCTAG TTACATAGCA TTGCTAGCTG
1351 ACAAGCAGCC TGAGAGAAGA TGGAGAATGT TCCTCAAAAT AGGGACAGCA
1401 AGCTAGAAGC ACTGTACAGT GCCCTGCTGG GAAGGGCAGA CAATGGACTG
1451 AGAAACCAGA AGTCTGGCCA CAAGATTGTC TGTATGATTC TGGACGAGTC
1501 ACTTGTGGTT TTCACTCTCT GGTTAGTAAA CCAGATAGTT TAGTCTGGGT
1551 TGAATACAAT GGATGTGAAG TTGCTTGGGG AAAGCTGAAT GTAGTGAATA
1601 CATTGGCAAC TCTACTGGGC TGTTACCTTG TTGATATCCT AGAGTTCTGG
1651 AGCTGAGCGA ATGCCTGTCA TATCTCAGCT TGCCCATCAA TCCAAACACA
1701 GGAGGCTACA AAAAGGACAT GAGCATGGTC TTCTGTGTGA ACTCCTCCTG
1751 AGAAACGTGG AGACTGGCTC AGCGCTTTGC GCTTGAAGGA CTAATCACAA
1801 GTTCTTGAAG ATATGGACCT AGGGGAGCTA TTGCGCCACG ACAGGAGGAA
1851 GTTCTCAGAT GTTGCATTGA TGTAACATTG TTGCATTTCT TTAATGAGCT
1901 GGGCTCCTTC CTCATTTGCT TCCCAAAGAG ATTTTGTCCC ACTAATGGTG
1951 TGCCCATCAC CCACACTATG AAAGTAAAAG GGATGCTGAG CAGATACAGC
2001 GTGCTTACCT CTCAGCCATG ACTTTCATGC TATTAAAAGA ATGCATGTGA
2051 A
```

FIG. 3

```
1    GCGCTCCAGC CGCATGTCGC AAGGCCTCCA GCTCCTGTTT CTAGGCTGCG
51   CCTGCAGCCT GGCACCCGCG ATGGCGATGC GGGAGGTGAC GGTGGCTTGC
101  TCCGAGACCG CCGACTTGCC TTGCACAGCG CCCTGGGACC CGCAGCTCTC
151  CTATGCAGTG TCCTGGGCCA AGGTCTCCGA GAGTGGCACT GAGAGTGTGG
201  AGCTCCCGGA GAGCAAGCAA AACAGCTCCT TCGAGGCCCC CAGGAGAAGG
251  GCCTATTCCC TGACGATCCA AAACACTACC ATCTGCAGCT CGGGCACCTA
301  CAGGTGTGCC CTGCAGGAGC TCGGAGGGCA GCGCAACTTG AGCGGCACCG
351  TGGTTCTGAA GGTGACAGGA TGCCCCAAGG AAGCTACAGA GTCAACTTTC
401  AGGAAGTACA GGGCAGAAGC TGTGTTGCTC TTCTCTCTGG TTGTTTTCTA
451  CCTGACACTC ATCATTTTCA CCTGCAAATT TGCACGACTA CAAAGCATTT
501  TCCCAGATAT TTCTAAACCT GGTACGGAAC AAGCTTTTCT TCCAGTCACC
551  TCCCCAAGCA AACATTTGGG GCCAGTGACC CTTCCTAAGA CAGAAACGGT
601  AAGAGTAGGA TCTCCACTGG TTTTTACAAA GCCAAGGGCA CATCAGATCA
651  GTGTGCCTGA ATGCCACCCG GACAAGAGAA GAATGAGCTC CATCCTCAGA
701  TGGCAACCTT TCTTTGAAGT CCTTCACCTG ACAGTGGGCT CCACACTACT
751  CCCTGACACA GGGTCTTGAG CACCATCATA TGATCACGAA GCATGGAGTA
801  TCACCGCTTC TCTGTGGCTG TCAGCTTAAT GTTTCATGTG GCTATCTGGT
851  CAACCTCGTG AGTGCTTTTC AGTCATCTAC AAGCTATGGT GAGATGCAGG
901  TGAAGCAGGG TCATGGGAAA TTTGAACACT CTGAGCTGGC CCTGTGACAG
951  ACTCCTGAGG ACAGCTGTCC TCTCCTACAT CTGGGATACA TCTCTTTGAA
1001 TTTGTCCTGT TTCGTTGCAC CAGCCCAGAT GTCTCACATC TGGCGGAAAT
1051 TGACAGGCCA AGCTGTGAGC CAGTGGGAAA TATTTAGCAA ATAATTTCCC
1101 AGTGCGAAGG TCCTGCTATT AGTAAGGAGT ATTATGTGTA CATAGAAATG
1151 AGAGGTCAGT GAACTATTCC CCAGCAGGGC CTTTTCATCT GGAAAAGACA
1201 TCCACAAAAG CAGCAATACA GAGGGATGCC ACATTTATTT TTTTAATCTT
1251 CATGTACTTG TCAAAGAAGA ATTTTTCATG TTTTTTCAAA GAAGTGTGTT
```

FIG. 4A

```
1301 TCTTTCCTTT TTTAAAATAT GAAGGTCTAG TTACATAGCA TTGCTAGCTG
1351 ACAAGCAGCC TGAGAGAAGA TGGAGAATGT TCCTCAAAAT AGGGACAGCA
1401 AGCTAGAAGC ACTGTACAGT GCCCTGCTGG GAAGGGCAGA CAATGGACTG
1451 AGAAACCAGA AGTCTGGCCA CAAGATTGTC TGTATGATTC TGGACGAGTC
1501 ACTTGTGGTT TTCACTCTCT GGTTAGTAAA CCAGATAGTT TAGTCTGGGT
1551 TGAATACAAT GGATGTGAAG TTGCTTGGGG AAAGCTGAAT GTAGTGAATA
1601 CATTGGCAAC TCTACTGGGC TGTTACCTTG TTGATATCCT AGAGTTCTGG
1651 AGCTGAGCGA ATGCCTGTCA TATCTCAGCT TGCCCATCAA TCCAAACACA
1701 GGAGGCTACA AAAAGGACAT GAGCATGGTC TTCTGTGTGA ACTCCTCCTG
1751 AGAAACGTGG AGACTGGCTC AGCGCTTTGC GCTTGAAGGA CTAATCACAA
1801 GTTCTTGAAG ATATGGACCT AGGGGAGCTA TTGCGCCACG ACAGGAGGAA
1851 GTTCTCAGAT GTTGCATTGA TGTAACATTG TTGCATTTCT TTAATGAGCT
1901 GGGCTCCTTC CTCATTTGCT TCCCAAAGAG ATTTTGTCCC ACTAATGGTG
1951 TGCCCATCAC CCACACTATG AAAGTAAAAG GGATGCTGAG CAGATACAGC
2001 GTGCTTACCT CTCAGCCATG ACTTTCATGC TATTAAAAGA ATGCATGTGA
2051 A
```

FIG. 4B

Wild Type Amino Acid Sequence for CD83 protein [Mus musculus]

MSQGLQLLFL GCACSLAPAM AMREVTVACS ETADLPCTAP WDPQLSYAVS
WAKVSESGTE SVELPESKQN SSFEAPRRRA YSLTIQNTTI CSSGTYRCAL
QELGGQRNLS GTVVLKVTGC PKEATESTFR KYRAEAVLLF SLVVFYLTLI
IFTCKFARLQ SIFPDISKPG TEQAFLPVTS PSKHLGPVTL PKTETV

Mutant CD83 Amino Acid Sequence: novel tail underlined, in bold.

MSQGLQLLFL GCACSLAPAM AMREVTVACS ETADLPCTAP WDPQLSYAVS
WAKVSESGTE SVELPESKQN SSFEAPRRRA YSLTIQNTTI CSSGTYRCAL
QELGGQRNLS GTVVLKVTGC PKEATESTFR KYRAEAVLLF SLVVFYLTLI
IFTCKFARLQ SIFPDISKPG TEQAFLPVTS PSKHLGPVTL PKTETVRVGS
PLVFTKPRAH QISVPECHPD KRRMSSILRW QPFFEVLHLT VGSTLLPDTG
S

FIG. 5

```
                                                         CDR1                  CDR2
20B08H  METGLRWLLLVAVLKGVQCQSVEESGGRLVTPGTPLTLTCTVSGFSLSSYDMTWVRQAPGKGLEWIGIIYAS-
 6G05H  METGLRWLLLVAVLKGVQCQSVEESGGRLVSPGTPLTLTCTASGFSLSSYDMSWVRQAPGKGLEYIGIISSS-
20D04H  METGLRWLLLVAVLKGVQCQSVEESGGRLVTPGTPLTLTCTVSGFSLSSYDMSWVRQAPGKGLEWIGIIYAS-
11G05   METGLRWLLLVAVLKGVQCQSVEESGGRLVTPGTPLTLTCTVSGFTISDYDLSWVRQAPGEGLKYIGFIAID-
14C12   METGLRWLLLVAVLKGVHCQSVEESGGRLVTPGTPLTLTCTASGFSRSSYDMSWVRQAPGKGLEWVGVISTA-

                                       CDR3
20B08H  GSTYYASWAKGRFTISKTSTTVDLEVTSLTTEDTATYFCSREHAGYSGDTGHLWGPGTLVTVSSGQPKAPSVF
6G05H   GTTYYANWAKGRFTISKTSTTVDLKVTSPTIGDTATYFCAREGAGVSMT---LWGPGTLVTVSSGQPKAPSVF
20D04H  GSTYYASWAKGRVAISKTSTTVDLKITSPTTEDTATYFCAREDAGFSNA---LWGPGTLVTVSSGQPKAPSVF
11G05   GNPYYATWAKGRFTISKTSTTVDLKITAPTTEDTATYFCARGAGD-------LWGPGTLVTVSSGQPKAPSVF
14C12   YNSHYASWAKGRFTISRTSTTVDLKMTSLTTEDTATYFCARGGSWLD-----LWGQGTLVTVSSGQPKAPSVF

20B08H  PLAPCCGDTPSS
6G05H   PLAPCCGDTPSS
20D04H  PLAPCCGDTPSS
11G05   PLAPCCGDTPSS
14C12   PLAPCCGDTPSS
```

FIG. 17A

```
                                     CDR1                          CDR2
20B08L   MDMRAPTQLLGLLLLWLPGARC-AYDMTQTPASVEVAVGGTVTIKCQASQSISTY--
6G05L    MDMRAPTQLLGLLLLWLPGARC-AYDMTQTPASVEVAVGGTVAIKCQASQSVSSY--
20D04L   MDMRAPTQLLGLLLLWLPGARCADVVMTQTPASVSAAVGGTVTINCQASESISNY--
11G05L   MDTRAPTQLLGLLLLWLPGARCADVVMTQTPASVSAAVGGTVTINCQSSKNVYNNNW
14C12L   MDXRAPTQLLGLLLLWLPGARCA-LVMTQTPASVSAAVGGTVTINCQSSQSVYDNDE

                                                                CDR3
20B08L   LDWYQQKPGQPPKLLIYDASDLASGVPSRFKGSGSGTQFTLTISDLECADAATYYCQQGYT---
6G05L    LAWYQQKPGQPPKPLIYEASMLAAGVSSRFKGSGSGTDFTLTISDLECDDAATYYCQQGYS---
20D04L   LSWYQQKPGQPPKLLIYRTSTLASGVSSRFKGSGSGTEYTLTISGVQCDDVATYYCQCTSGG-
11G05L   LSWFQQKPGQPPKLLIYYASTLASGVPSRFRGSGSGTQFTLTISDVQCDDAATYYCAG-DYSS--S
14C12L   LSWYQQKPGQPPKLLIYLASKLASGVPSRFKGSGSGTQFALTISGVQCDDAATYYCQATHYSS--D-

20B08L   -HSNVDNVFGGGTEVVVKGDPVAPTVLLFPPSS
6G05L    -ISDIDNAFGGGTEVVVKGDPVAPTVLLFPPSS
20D04L   KFISDGAAFGGGTEVVVKGDPVAPTVLLFPPSS
11G05L       SDNGFGGGTEVVVKGDPVAPTVLLFPPSS
14C12L   -   WYLTFGGGTEVVVKGDPVAPTVLLFPPSS
```

FIG. 17B

| Region | Count | Mean |
|---|---|---|
| Total | 4666 | 12.57 |
| Total | 4705 | 48.85 |
| Total | 4554 | 79.36 |

| Region | Count | Mean |
|---|---|---|
| Total | 4666 | 12.57 |
| Total | 4689 | 16.49 |
| Total | 4697 | 12.37 |

DNA:

ATGGACACGAGGGCCCCCACTCAGCTGCTGGGGCTCCTGCTGCTCTGGCTCCCAGGTGCCACATTTGCG
CAAGTGCTGACCCAGACTGCATCGCCCGTGTCTGCACCTGTGGGAGGCACAGTCACCATCAATTGCCA
GTCCAGTCAGAGTGTTTATAATAACGACTTCTTATCCTGGTATCAGCAGAAACCAGGGCAGCCTCCCAA
ACTCCTGATCTATTATGCATCCACTCTGGCATCTGGGGTCCCATCCCGGTTCAAAGGCAGTGGATCTGG
GACACAGTTCACTCTCACCATCAGCGACCTGGAGTGTGACGATGCTGCCACTTACTACTGTACAGGCA
CTTATGGTAATAGTGCTTGGTACGAGGATGCTTTCGGCGGAGGGACCGAGGTGGTGGTCAAACGTACG
CCAGTTGCACCTACTGTCCTCCTCTTCCCACCATCTAGCGCTGAGCTGGCAACTGGAACAGCCACCATC
GTGTGCGTGGCGAATAAATACTTTCCCGATGGCACCGTCACCTGGAAGGTGGATGGCATCACCCAAAG
CAGCGGCATCAATAACAGTAGAACACCGCAGAATTCTGCAGATTGTACCTACAACCTCAGCAGTACTC
TGACACTGAGCAGCGACGAGTACAACAGCCACGACGAGTACACCTGCCAGGTGGCCCAGGACTCAGG
CTCACCGGTCGTCCAGAGCTTCAGTAGGAAGAGCTGTTAG

Protein:

MDTRAPTQLLGLLLLWLPGATFAQVLTQTASPVSAPVGGTVTINCQSSQSVYNNDFLSWYQQKPGQPPK
LLIYYASTLASGVPSRFKGSGSGTQFTLTISDLECDDAATYYCTGYGNSAWYEDAFGGGTEVVVKRTPV
APTVLLFPPSSAELATGTATIVCVANKYFPDGTVTWKVDGITQSSGINNSRTPQNSADCTYNLSSTLTLSSD
EYNSHDEYTCQVAQDSGSPVVQSFSRKSC

FIG. 21

DNA:

ATGGAGACTGGGCTGCGCTGGCTTCTCCTGGTCGCTGTGCTCAAAGGTGTCCAGTGTCAGTCGGTGGAGGAGTCCGGGGGTCGCCTGGTCACACCTGG
GACACCCCTGACACTCACCTGCACAGTGTCTGGAATCGACCTCAGTAGCGATGGAATAAGCTGGGTCCGCCAGGCTCCAGGGAAGGGGCTGGAATGG
ATCGGAATCATTAGTAGTGGTGGTAACACATACTACGCGAGCTGGGCAAAAGGCCGATTCACCATCTCCAGAACCTCGACCACGGTGGATCTGAAGAT
GACCAGTCTGACAACCGAGGACACGGCCACCTATTTCTGTGCCAGAGTTGTTGGTGGTACTTATAGCATCTGGGGCCAGGGCACCCTCGTCACCGTCTC
GAGCGCTTCTACAAAGGGCCCATCTGTCTATCCACTGGCCCCTGGATCTGCTGCCCAAACTAACTCCATGGTGACCCTGGGATGCCTGGTCAAGGGCTA
TTTCCCTGAGCCAGTGACAGTGACCTGGAACTCTGGATCCCTGTCCAGCGGTGTGCACACCTTCCCAGCTGTCCTGCAGTCTGACCTCTACACTCTGAGC
AGCTCAGTGACTGTCCCCTCCAGCACCTGGCCCAGCGAGACCGTCACCTGCAACGTTGCCCACCCGGCCAGCAGCACCAAGGTGGACAAGAAAATTGT
GCCCAGGGATTGTGGTTGTAAGCCTTGCATATGTACAGTCCCAGAAGTATCATCTGTCTTCATCTTCCCCCCAAAGCCCAAGGATGTGCTCACCATTACT
CTGACTCCTAAGGTCACGTGTGTTGTGGTAGACATCAGCAAGGATGATCCCGAGGTCCAGTTCAGCTGGTTTGTAGATGATGTGGAGGTGCACACAGC
TCAGACGCAACCCCGGGAGGAGCAGTTCAACAGCACTTTCCGCTCAGTCAGTGAACTTCCCATCATGCACCAGGACTGGCTCAATGGCAAGGAGTTCA
AATGCAGGGTCAACAGTGCAGCTTTCCCTGCCCCCATCGAGAAAACCATCTCCAAAACCAAAGGCAGACCGAAGGCTCCACAGGTGTACACCATTCCA
CCTCCCAAGGAGCAGATGGCCAAGGATAAAGTCAGTCTGACCTGCATGATAACAGACTTCTTCCCTGAAGACATTACTGTGGAGTGGCAGTGGAATGG
GCAGCCAGCGGAGAACTACAAGAACACTCAGCCCATCATGGACACAGATGGCTCTTACTTCGTCTACAGCAAGCTCAATGTGCAGAAGAGCAACTGG
GAGGCAGGAAATACTTTCACCTGCTCTGTGTTACATGAGGGCCTGCACAACCACCATACTGAGAAGAGCCTCTCCCACTCTCCTGGTAAATGA

Protein:

METGLRWLLLVAVLKGVQCQSVEESGGRLVTPGTPLTLTCTVSGIDLSSDGISWVRQAPGKGLEWIGIIS
SGGNTYYASWAKGRFTISRTSTTVDLKMTSLTTEDTATYFCARVVGGTYSIWGQGTLVTVSSASTKGPS
VYPLAPGSAAQTNSMVTLGCLVKGYFPEPVTVTWNSGSLSSGVHTFPAVLQSDLYTLSSSVTVPSSTWPS
ETVTCNVAHPASSTKVDKKIVPRDCGCKPCICTVPEVSSVFIFPPKPKDVLTITLTPKVTCVVVDISKDDPE
VQFSWFVDDVEVHTAQTQPREEQFNSTFRSVSELPIMHQDWLNGKEFKCRVNSAAFPAPIEKTISKTKGR
PKAPQVYTIPPPKEQMAKDKVSLTCMITDFFPEDITVEWQWNGQPAENYKNTQPIMDTDGSYFVYSKLN
VQKSNWEAGNTFTCSVLHEGLHNHHTEKSLSHSPGK

FIG. 22

DNA:

ATGGACACGAGGGCCCCCACTCAGCTGCTGGGGCTCCTGCTGCTCTGGCTCCCAGGTGCCACATTTGCCC
AAGCCGTGGTGACCCAGACTACATCGCCCGTGTCTGCACCTGTGGGAGGCACAGTCACCATCAATTGCCA
GTCCAGTCAGAGTGTTTATGGTAACAACGAATTATCCTGGTATCAGCAGAAACCAGGGCAGCCTCCCAAG
CTCCTGATCTACCAGGCATCCAGCCTGGCATCTGGGGTCCCATCGCGGTTCAAAGGCAGTGGATCTGGGA
CACAGTTCACTCTCACCATCAGCGACCTGGAGTGTGACGATGCTGCCACTTACTACTGTCTAGGCGAATAT
AGCATTAGTGCTGATAATCATTTCGGCGGAGGGACCGAGGTGGTGGTCAAACGTACGCCAGTTGCACCTA
CTGTCCTCCTCTTCCCACCATCTAGCGCTGAGCTGGCAACTGGAACAGCCACCATCGTGTGCGTGGCGAAT
AAATACTTTCCCGATGGCACCGTCACCTGGAAGGTGGATGGCATCACCCAAAGCAGCGGCATCAATAACA
GTAGAACACCGCAGAATTCTGCAGATTGTACCTACAACCTCAGCAGTACTCTGACACTGAGCAGCGACGA
GTACAACAGCCACGACGAGTACACCTGCCAGGTGGCCCAGGACTCAGGCTCACCGGTCGTCCAGAGCTTC
AGTAGGAAGAGCTGTTAG

Protein:

MDTRAPTQLLGLLLLWLPGATFAQAVVTQTTSPVSAPVGGTVTINCQSSQSVYGNNELSWYQQKPGQPP
KLLIYQASSLASGVPSRFKGSGSGTQFTLTISDLECDDAATYYCLGEYSISADNHFGGGTEVVVKRTPVAP
TVLLFPPSSAELATGTATIVCVANKYFPDGTVTWKVDGITQSSGINNSRTPQNSADCTYNLSSTLTLSSDEY
NSHDEYTCQVAQDSGSPVVQSFSRKSC

FIG. 23

DNA:

ATGGAGACTGGGCTGCGCTGGCTTCTCCTGGTCGCTGTGCTCAAAGGTGTCCAGTGTCAGTCGGTGGAGGAGTCCGGGGGTCGC
CTGGTCACGCCTGGGACACCCCTGACACTCACCTGCACAGTCTCTGGAATCGACCTCAGTAGCAATGCAATGATCTGGGTCCGC
CAGGCTCCAAGGGAGGGGCTGGAATGGATCGGAGCCATGGATAGTAATAGTAGGACGTACTACGCGACCTGGGCGAAAGGCC
GATTCACCATCTCCAGAACCTCGTCGATTACGGTGGATCTGAAAATCACCAGTCCGACAACCGAGGACACGGCCACCTATTTCT
GTGCCAGAGGGGATGGTGGCAGTAGTGATTATACAGAGATGTGGGGCCCAGGGACCCTCGTCACCGTCTCGAGCGCTTCTACA
AAGGGCCCATCTGTCTATCCACTGGCCCCTGGATCTGCTGCCCAAACTAACTCCATGGTGACCCTGGGATGCCTGGTCAAGGGC
TATTTCCCTGAGCCAGTGACAGTGACCTGGAACTCTGGATCCCTGTCCAGCGGTGTGCACACCTTCCCAGCTGTCCTGCAGTCT
GACCTCTACACTCTGAGCAGCTCAGTGACTGTCCCCTCCAGCACCTGGCCCAGCGAGACCGTCACCTGCAACGTTGCCCACCCG
GCCAGCAGCACCAAGGTGGACAAGAAAATTGTGCCCAGGGATTGTGGTTGTAAGCCTTGCATATGTACAGTCCCAGAAGTATC
ATCTGTCTTCATCTTCCCCCCAAAGCCCAAGGATGTGCTCACCATTACTCTGACTCCTAAGGTCACGTGTGTTGTGGTAGACATC
AGCAAGGATGATCCCGAGGTCCAGTTCAGCTGGTTTGTAGATGATGTGGAGGTGCACACAGCTCAGACGCAACCCCGGGAGGA
GCAGTTCAACAGCACTTTCCGCTCAGTCAGTGAACTTCCCATCATGCACCAGGACTGGCTCAATGGCAAGGAGTTCAAATGCAG
GGTCAACAGTGCAGCTTTCCCTGCCCCCATCGAGAAAACCATCTCCAAAACCAAAGGCAGACCGAAGGCTCCACAGGTGTACA
CCATTCCACCTCCCAAGGAGCAGATGGCCAAGGATAAAGTCAGTCTGACCTGCATGATAACAGACTTCTTCCCTGAAGACATTA
CTGTGGAGTGGCAGTGGAATGGGCAGCCAGCGGAGAACTACAAGAACACTCAGCCCATCATGGACACAGATGGCTCTTACTTC
GTCTACAGCAAGCTCAATGTGCAGAAGAGCAACTGGGAGGCAGGAAATACTTTCACCTGCTCTGTGTTACATGAGGGCCTGCA
CAACCACCATACTGAGAAGAGCCTCTCCCACTCTCCTGGTAAATGA

Protein:

METGLRWLLLVAVLKGVQCQSVEESGGRLVTPGTPLTLTCTVSGIDLSSNAMIWVRQAPREGLEWIGAMDSNSRTYYATWA
KGRFTISRTSSITVDLKITSPTTEDTATYFCARGDGGSSDYTEMWGPGTLVTVSSASTKGPSVYPLAPGSAAQTNSMVTLGCLV
KGYFPEPVTVTWNSGSLSSGVHTFPAVLQSDLYTLSSSVTVPSSTWPSETVTCNVAHPASSTKVDKKIVPRDCGCKPCICTVPE
VSSVFIFPPKPKDVLTITLTPKVTCVVVDISKDDPEVQFSWFVDDVEVHTAQTQPREEQFNSTFRSVSELPIMHQDWLNGKEFK
CRVNSAAFPAPIEKTISKTKGRPKAPQVYTIPPPKEQMAKDKVSLTCMITDFFPEDITVEWQWNGQPAENYKNTQPIMDTDGS
YFVYSKLNVQKSNWEAGNTFTCSVLHEGLHNHHTEKSLSHSPGK

FIG. 24

MODULATING IMMUNE RESPONSES

CROSS-REFERENCE TO RELATED APPLICATIONS

This application is a continuation of application Ser. No. 11/805,841 filed on May 23, 2007, now allowed, which is a continuation of application Ser. No. 10/719,642 filed on Nov. 21, 2003, now abandoned, which is a continuation under 35 U.S.C. 111(a) of International Application No. PCT/US02/37738 filed Nov. 21, 2002 and published in English as WO 03/045318 on Jun. 5, 2003, which claimed priority under 35 U.S.C. 119(e) from U.S. Provisional Application Ser. No. 60/331,958 filed Nov. 21, 2001, application Ser. No. 10/719,642, 11/805,841 and the current application also claim, priority to U.S. Provisional Application Ser. No. 60/428,130 filed Nov. 21, 2002 and U.S. Provisional Application Ser. No. 60/473,279 filed May 22, 2003 All applications referenced in this priority claim are incorporated by reference herein in their entirety.

FIELD OF THE INVENTION

The invention relates to multimerized antibodies directed against the CD83 gene product, and methods of modulating the immune response of an animal by using such multimerized antibodies.

BACKGROUND OF THE INVENTION

CD83 is a 45 kilodalton glycoprotein that is predominantly expressed on the surface of dendritic cells and other cells of the immune system. Structural analysis of the predicted amino acid sequence of CD83 indicates that it is a member of the immunoglobulin superfamily. See, Zhou et al., J. Immunol. 149:735 (1992)). U.S. Pat. No. 5,316,920 and WO 95/29236 disclose further information about CD83. While such information suggests that CD83 plays a role in the immune system, that role is undefined, and the interrelationship of CD83 with cellular factors remains unclear.

Moreover, treatment of many diseases could benefit from more effective methods for increasing or decreasing the immune response. Hence, new reagents and methods are needed for modulating the immune system through the CD83 gene and its gene product.

SUMMARY OF THE INVENTION

The invention provides methods for modulating an immune response. In one aspect, the invention relates to the surprising discovery that multimerized antibodies raised against the CD83 gene product can arrest cellular proliferation of immune cells. Hence, the invention provides a method of modulating the immune response by modulating the activity or expression of the CD83 gene products, for example, by using such multimerized antibodies.

Also according to the invention, the production of a cytokine such as interleukin-2, interleukin-4, or interlekin-10 can be modulated by modulating the activity or expression of a CD83 polypeptide. In some embodiments, a multimerized antibody is used that can modulate the activity or expression of a CD83 polypeptide. For example, the antibody can be administered to the mammal or the immune cell can be contacted with the antibody. In some embodiments, the immune cells are T cells or antigen presenting cells. In other embodiments, the immune cells are CD4+T cells.

The invention also provides a method of modulating granulocyte macrophage colony stimulating factor production in a mammal or in an immune cell by modulating the activity or expression of CD83 polypeptides. In some embodiments, an antibody or a multimerized antibody is used that can modulate the activity or expression of a CD83 polypeptide. For example, the antibody can be administered to the mammal or the immune cell can be contacted with the antibody. In some embodiments, the immune cells are T cells or antigen presenting cells. In other embodiments, the immune cells are CD4+T cells.

The invention also provides a method of modulating tumor necrosis factor production in a mammal or in a mammalian cell by modulating the activity or expression of CD83 polypeptides. In some embodiments, an antibody or a multimerized antibody is used that can modulate the activity or expression of a CD83 polypeptide. For example, the antibody can be administered to the mammal or the mammalian cell can be contacted with the antibody. In some embodiments, the immune cells are T cells or antigen presenting cells. In other embodiments, the immune cells are CD4+T cells.

The invention further provides a method of inhibiting proliferation of a human peripheral blood mononuclear cell by modulating the activity or expression of CD83 polypeptides. In some embodiments, an antibody or a multimerized antibody is used that can modulate the activity or expression of a CD83 polypeptide. For example, the antibody can be administered to the mammal or the human peripheral blood mononuclear cell can be contacted with the antibody.

The invention also provides an antibody that can bind to a CD83 polypeptide comprising SEQ ID NO:4, SEQ ID NO:8 or SEQ ID NO:9, wherein activated $CD4^{+}$T-cells produce lower levels of interleukin-4 when the T-cells are contacted with the antibody. The invention further provides an antibody that can bind to a CD83 polypeptide comprising SEQ ID NO:4, SEQ ID NO:8 or SEQ ID NO:9, wherein $CD4^{+}$T-cells proliferation is decreased when the T-cells are contacted with the antibody. The antibody can be a multimerized antibody. Such multimerized antibodies can be bound to a solid support, covalently crosslinked or bound together by a second entity such as a secondary antibody. Examples of antibodies of the invention include those that have an amino acid sequence that includes SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62, SEQ ID NO:64, SEQ ID NO:67, SEQ ID NO:69, SEQ ID NO:70, SEQ ID NO:71 SEQ ID NO:72, SEQ ID NO:73, SEQ ID NO:78, SEQ ID NO:79, SEQ ID NO:80, SEQ ID NO:81, SEQ ID NO:86, SEQ ID NO:87, SEQ ID NO:88, SEQ ID NO:89, SEQ ID NO:90; SEQ ID NO:91, SEQ ID NO:92, SEQ ID NO:93, SEQ ID NO: 94, SEQ ID NO:95, SEQ ID NO:96, SEQ ID NO:98 or SEQ ID NO:99. Nucleic acids encoding such an antibody can have, for example, a sequence that includes SEQ ID NO:12, SEQ ID NO:14, SEQ ID NO:16, SEQ ID NO:18, SEQ ID NO:20, SEQ ID NO:22, SEQ ID NO:59, SEQ ID NO:61, SEQ ID NO:63, SEQ ID NO:65, SEQ ID NO:74, SEQ ID NO:75, SEQ ID NO:76, SEQ ID NO:77, SEQ ID NO:82, SEQ ID NO:83, SEQ ID NO:84, SEQ ID NO:85 or SEQ ID NO:90.

The invention also provides a method for decreasing the activity of a CD83 gene product, comprising contacting the CD83 gene product with an antibody that comprises amino acid sequence includes SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62, SEQ ID NO:64, SEQ ID NO:67, SEQ ID NO:69, SEQ ID NO:70, SEQ ID NO:71 SEQ ID NO:72, SEQ ID NO:73, SEQ ID NO:78, SEQ ID NO:79, SEQ ID NO:80, SEQ ID NO:81, SEQ ID NO:86, SEQ ID NO:87, SEQ ID NO:88, SEQ ID NO:89, SEQ ID NO:90; SEQ ID NO:91, SEQ ID NO:92, SEQ ID NO:93, SEQ ID NO: 94, SEQ ID NO:95, SEQ ID NO:96, SEQ ID NO:98 or SEQ ID NO:99. The antibody can be a multimerized antibody. The activity of a CD83 gene product can be decreased in a mammal or in a cell that is involved in an immune response, for example, a T cell.

The invention further provides a method for decreasing the translation of a CD83 gene product in a mammalian cell, comprising contacting the mammalian cell with a nucleic acid complementary to a CD83 nucleic acid comprising SEQ ID NO:1, SEQ ID NO:3, SEQ ID NO:5, or SEQ ID NO:10.

In another embodiment, the invention provides a method for decreasing the translation of a CD83 gene product in a mammal, comprising administering to the mammal a nucleic acid complementary to a CD83 nucleic acid comprising SEQ ID NO:1, SEQ ID NO:3, SEQ ID NO:5, or SEQ ID NO:10.

The invention further provides a method for decreasing proliferation of CD4+T-cells in a mammal comprising administering to the mammal an antibody that can bind to a CD83 gene product, wherein the CD83 gene product comprises SEQ ID NO:2 or SEQ ID NO:9. The antibody can have a sequence comprising includes SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62, SEQ ID NO:64, SEQ ID NO:67, SEQ ID NO:69, SEQ ID NO:70, SEQ ID NO:71 SEQ ID NO:72, SEQ ID NO:73, SEQ ID NO:78, SEQ ID NO:79, SEQ ID NO:80, SEQ ID NO:81, SEQ ID NO:86, SEQ ID NO:87, SEQ ID NO:88, SEQ ID NO:89, SEQ ID NO:90; SEQ ID NO:91, SEQ ID NO:92, SEQ ID NO:93, SEQ ID NO: 94, SEQ ID NO:95, SEQ ID NO:96, SEQ ID NO:98 or SEQ ID NO:99. The antibody can be a multimerized antibody.

The invention also provides a method for decreasing interleukin-2 levels and increasing interleukin-4 levels in a mammal comprising administering to the mammal an antibody that can bind to a CD83 gene product, wherein the CD83 gene product comprises SEQ ID NO:2 or SEQ ID NO:9. The antibody can have a sequence comprising includes SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62, SEQ ID NO:64, SEQ ID NO:67, SEQ ID NO:69, SEQ ID NO:70, SEQ ID NO:71 SEQ ID NO:72, SEQ ID NO:73, SEQ ID NO:78, SEQ ID NO:79, SEQ ID NO:80, SEQ ID NO:81, SEQ ID NO:86, SEQ ID NO:87, SEQ ID NO:88, SEQ ID NO:89, SEQ ID NO:90; SEQ ID NO:91, SEQ ID NO:92, SEQ ID NO:93, SEQ ID NO: 94, SEQ ID NO:95, SEQ ID NO:96, SEQ ID NO:98 or SEQ ID NO:99. The antibody can be a multimerized antibody.

The invention further provides a method for decreasing interleukin-2 levels and increasing interleukin-4 levels in a mammal comprising administering to the mammal a nucleic acid complementary to a CD83 nucleic acid comprising SEQ ID NO:1, SEQ ID NO:3, SEQ ID NO:5, or SEQ ID NO:10. In some embodiments the interleukin-2 levels are decreased and the interleukin-4 levels are increased to treat an autoimmune disease. In other embodiments, the interleukin-2 levels are decreased and the interleukin-4 levels are increased to stimulate production of Th2-associated cytokines in transplant recipients, for example, to prolong survival of transplanted tissues.

The invention also provides a method for increasing interleukin-10 levels in a mammal comprising administering to the mammal an antibody that can bind to a CD83 gene product, wherein the CD83 gene product comprises SEQ ID NO:2 or SEQ ID NO:9. The antibody can have a sequence comprising includes SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62, SEQ ID NO:64, SEQ ID NO:67, SEQ ID NO:69, SEQ ID NO:70, SEQ ID NO:71 SEQ ID NO:72, SEQ ID NO:73, SEQ ID NO:78, SEQ ID NO:79, SEQ ID NO:80, SEQ ID NO:81, SEQ ID NO:86, SEQ ID NO:87, SEQ ID NO:88, SEQ ID NO:89, SEQ ID NO:90; SEQ ID NO:91, SEQ ID NO:92, SEQ ID NO:93, SEQ ID NO: 94, SEQ ID NO:95, SEQ ID NO:96, SEQ ID NO:98 or SEQ ID NO:99. The antibody can be a multimerized antibody.

The invention further provides a method for increasing interleukin-10 levels in a mammal comprising administering to the mammal a nucleic acid complementary to a CD83 nucleic acid comprising SEQ ID NO:1, SEQ ID NO:3, SEQ ID NO:5, or SEQ ID NO:10. In some embodiments, the interleukin-10 levels are increased to treat neoplastic disease. In other embodiments, the interleukin-10 levels are increased to treat a tumor.

The invention also provides a method for increasing interleukin-2 levels in a mammal comprising administering to the mammal a functional CD83 polypeptide that comprises SEQ ID NO:9.

The invention further provides a method for increasing interleukin-2 levels in a mammal comprising: (a) transforming a T cell from the mammal with a nucleic acid encoding a functional CD83 polypeptide operably linked to a promoter functional in a mammalian cell, to generate a transformed T cell; (b) administering the transformed T cell to the mammal to provide increased levels of interleukin-2. In some embodiments, the CD83 polypeptide has a sequence that comprises SEQ ID NO:9 or the nucleic acid has a sequence that comprises SEQ ID NO:1, SEQ ID NO:3, SEQ ID NO:5, or SEQ ID NO:10. Such methods for increasing interleukin-2 levels can be used to treat an allergy or an infectious disease.

The invention also provides a method for increasing granulocyte macrophage colony stimulating factor levels in a mammal comprising administering to the mammal an antibody that can bind to a CD83 gene product, wherein the CD83 gene product comprises SEQ ID NO:2 or SEQ ID NO:9.

Such an antibody can have a sequence comprising includes SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62, SEQ ID NO:64, SEQ ID NO:67, SEQ ID NO:69, SEQ ID NO:70, SEQ ID NO:71 SEQ ID NO:72, SEQ ID NO:73, SEQ ID NO:78, SEQ ID NO:79, SEQ ID NO:80, SEQ ID NO:81, SEQ ID NO:86, SEQ ID NO:87, SEQ ID NO:88, SEQ ID NO:89, SEQ ID NO:90; SEQ ID NO:91, SEQ ID NO:92, SEQ ID NO:93, SEQ ID NO: 94, SEQ ID NO:95, SEQ ID NO:96, SEQ ID NO:98 or SEQ ID NO:99. The antibody can be a multimerized antibody.

The invention further provides a method for increasing granulocyte macrophage colony stimulating factor levels in a mammal comprising administering to the mammal a nucleic acid complementary to a CD83 nucleic acid comprising SEQ ID NO:1, SEQ ID NO:3, SEQ ID NO:5, or SEQ ID NO:10.

The invention also provides a method for increasing tumor necrosis factor levels at a selected site in a mammal comprising administering to the site a functional CD83 polypeptide. In another embodiment, the invention provides a method for increasing tumor necrosis factor levels in a selected mammalian cell comprising transforming the cell with a nucleic acid encoding a functional CD83 polypeptide. The CD83 polypeptide employed can, for example, have a sequence comprising SEQ ID NO:9.

Animals such as mammals and birds may be treated by the methods and compositions described herein. Such mammals and birds include humans, dogs, cats, and livestock, for example, horses, cattle, sheep, goats, chickens, turkeys and the like.

The invention further provides a mutant mouse that can serve as an animal model of diminished T cell activation or altered cytokine levels. The mutant mouse has an altered CD83 gene that produces a larger gene product, having SEQ ID NO:4 or containing SEQ ID NO:8. Also provided are methods of using the mutant mouse model to study the effects of cytokines on the immune system, inflammation, the function and regulation of CD83, T cell and dendritic cell activity, the immune response and conditions and treatments related thereto. Hence, the invention further provides a mutant mouse whose somatic and germ cells comprise a mutant CD83 gene encoding a polypeptide comprising SEQ ID NO:4 or SEQ ID NO:8, wherein expression of the mutant CD83 gene reduces CD4+T cell activation. The mutant CD83 gene can, for example, comprise SEQ ID NO:3.

The invention further provides a method of identifying a compound that can modulate CD4+T cell activation comprising administering a test compound to a mouse having a mutant or wild type transgenic CD83 gene and observing whether CD4+T cell activation is decreased or increased. The somatic and/or germ cells of the mutant mouse can comprise a mutant CD83 gene encoding a polypeptide comprising SEQ ID NO:4 or SEQ ID NO:8. Alternatively, the somatic and/or germ cells of the mouse can contain a wild type CD83 gene, for example, SEQ ID NO:1 or SEQ ID NO:9.

The invention also provides a mutant CD83 gene encoding a polypeptide comprising SEQ ID NO:4 or SEQ ID NO:8. The invention further provides a mutant CD83 gene comprising nucleotide sequence SEQ ID NO:3.

DESCRIPTION OF THE FIGURES

FIG. 1 summarizes flow cytometry data for G3 animals. As shown, reduced numbers of CD4+T cells are seen in two animals from Pedigree 9, mouse 9.4.1 and mouse 9.4.9. All other animals analyzed on that day exhibit normal numbers of CD4+T cells.

FIG. 3 provides the nucleotide sequence of wild type mouse CD83 (SEQ ID NO:1). The ATG start codon and the TGA stop codon are underlined.

FIG. 4A-B provides the nucleotide sequence of the mutant CD83 gene (SEQ ID NO:3) of the invention derived from the mutant LCD4.1 animal. The ATG start codon, the mutation and the TGA stop codon are underlined.

FIG. 5 provides the amino acid sequence for wild type (top, SEQ ID NO:2) and mutant (bottom, SEQ ID NO:4) CD83 coding regions. The additional C-terminal sequences arising because of the CD83 mutation are underlined.

FIG. 17A provides a sequence alignment of anti-CD83 heavy chain variable regions isolated by the invention. Sequences for isolates 20B08H (SEQ ID NO:52), 6G05H (SEQ ID NO:53), 20D04H (SEQ ID NO:54), 11G05 (SEQ ID NO:66) and 14C12 (SEQ ID NO:67) are provided. The CDR regions are highlighted in bold.

FIG. 17B provides a sequence alignment of anti-CD83 light chain variable regions isolated by the invention. Sequences for isolates 20B08L (SEQ ID NO:55), 6G05L (SEQ ID NO:56), 20D04L (SEQ ID NO:57), 11G05L (SEQ ID NO:68) and 14C12L (SEQ ID NO:69) are provided. The CDR regions are highlighted in bold.

FIG. 21 provides nucleotide and amino acid sequences for the monoclonal antibody 96G08 light chain.

FIG. 22 provides nucleotide and amino acid sequences for the monoclonal antibody 96G08 heavy chain.

FIG. 23 provides nucleotide and amino acid sequences for the monoclonal antibody 95F04 light chain.

FIG. 24 provides nucleotide and amino acid sequences for the monoclonal antibody 95F04 heavy chain.

As illustrated in FIG. 25A many plate-bound anti-CD83 antibody preparations inhibit proliferation of activated lymphocytes, including the 94c09, 98a02, 94d08, 98d11, 101b08, 6g05, 20d04, 14c12, 11g05, 12g04, 32f12 and 98b11 preparations. FIG. 25B further illustrates that some antibody preparations are highly effective inhibitors (e.g. 117G12) but others are not (e.g. 824pb and 98g08).

DETAILED DESCRIPTION OF THE INVENTION

Figure 2:
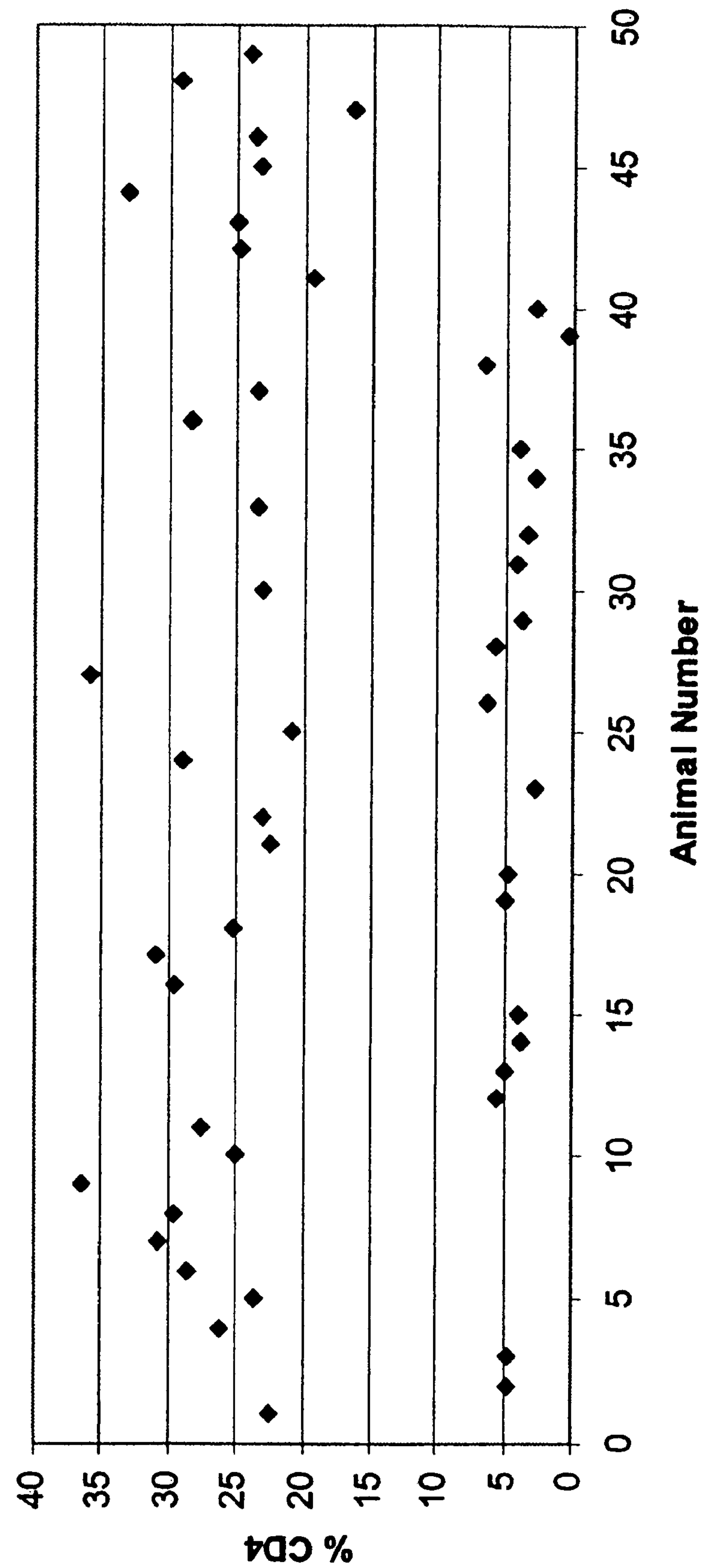
FIG. 2 provides a graph of flow cytometry data for G3 animals that may have a mutant CD83 gene. Each diamond symbol represents an individual animal. As shown, multiple animals from the N2 generation exhibit a reduced percentage of CD4+T cells.

The invention provides methods for modulating the immune system. For example, according to the invention, loss or reduction of CD83 activity in vivo results in decreased numbers of immune cells, for example, decreased numbers of T cells. In some embodiments, binding entities such as monoclonal antibodies that are capable of inhibiting the function of CD83 are provided for use in the invention. In other embodiments the binding entities or antibodies are multimerized. The compositions and methods of the invention can be used for treating conditions involving an inappropriate immune response, for example, autoimmune diseases, inflammation, tissue rejection, arthritis, atherosclerosis and the like.

CD83

CD83 is a lymphocyte and dendritic cell activation antigen that is expressed by activated lymphocytes and dendritic cells. CD83 is also a single-chain cell-surface glycoprotein with a molecular weight of about 45,000 that is believed to be a member of the Ig superfamily. The structure predicted from the CD83 amino acid sequence indicates that CD83 is a membrane glycoprotein with a single extracellular Ig-like domain, a transmembrane domain and cytoplasmic domain of approximately forty amino acids. The mature CD83 protein has about 186 amino acids and is composed of a single extracellular V type immunoglobulin (Ig)-like domain, a transmembrane domain and a thirty nine amino acid cytoplasmic domain. Northern blot analysis has revealed that CD83 is translated from three mRNA transcripts of about 1.7, 2.0 and 2.5 kb that are expressed by lymphoblastoid cell lines. It is likely that CD83 undergoes extensive post-translational processing because CD83 is expressed as a single chain molecule, but the determined molecular weight is twice the predicted size of the core protein. See U.S. Pat. No. 5,766,570.

An example of a human CD83 gene product that can be used in the invention is provided below (SEQ ID NO:9):

```
  1 MSRGLQLLLL SCAYSLAPAT PEVKVACSED VDLPCTAPWD
 41 PQVPYTVSWV KLLEGGEERM ETPQEDHLRG QHYHQKGQNG
 81 SFDAPNERPY SLKIRNTTSC NSGTYRCTLQ DPDGQRNLSG
121 KVILRVTGCP AQRKEETFKK YRAEIVLLLA LVIFYLTLII
161 FTCKFARLQS IFPDFSKAGM ERAFLPVTSP NKHLGLVTPH
201 KTELV
```

Such a CD83 gene product can be encoded by a number of different nucleic acids. One example of a human CD83 nucleic acid is provided below (SEQ ID NO:10).

```
   1 CCTGGCGCAG CCGCAGCAGC GACGCGAGCG AACTCGGCCG
  41 GGCCCGGGCG CGCGGGGGCG GGACGCGCAC GCGGCGAGGG
  81 CGGCGGGTGA GCCGGGGGCG GGGACGGGGG CGGGACGGGG
 121 GCGAAGGGGG CGGGGACGGG GGCGCCCGCC GGCCTAACGG
 161 GATTAGGAGG GCGCGCCACC CGCTTCCGCT GCCCGCCGGG
 201 GAATCCCCCG GGTGGCGCCC AGGGAAGTTC CCGAACGGGC
 241 GGGCATAAAA GGGCAGCCGC GCCGGCGCCC CACAGCTCTG
 281 CAGCTCGTGG CAGCGGCGCA GCGCTCCAGC CATGTCGCGC
 321 GGCCTCCAGC TTCTGCTCCT GAGCTGCGCC TACAGCCTGG
 361 CTCCCGCGAC GCCGGAGGTG AAGGTGGCTT GCTCCGAAGA
 401 TGTGGACTTG CCCTGCACCG CCCCCTGGGA TCCGCAGGTT
 441 CCCTACACGG TCTCCTGGGT CAAGTTATTG GAGGGTGGTG
 481 AAGAGAGGAT GGAGACACCC CAGGAAGACC ACCTCAGGGG
 521 ACAGCACTAT CATCAGAAGG GGCAAAATGG TTCTTTCGAC
 561 GCCCCCAATG AAAGGCCCTA TTCCCTGAAG ATCCGAAACA
 601 CTACCAGCTG CAACTCGGGG ACATACAGGT GCACTCTGCA
 641 GGACCCGGAT GGGCAGAGAA ACCTAAGTGG CAAGGTGATC
 681 TTGAGAGTGA CAGGATGCCC TGCACAGCGT AAAGAAGAGA
 721 CTTTTAAGAA ATACAGAGCG GAGATTGTCC TGCTGCTGGC
 761 TCTGGTTATT TTCTACTTAA CACTCATCAT TTTCACTTGT
 801 AAGTTTGCAC GGCTACAGAG TATCTTCCCA GATTTTTCTA
 841 AAGCTGGCAT GGAACGAGCT TTTCTCCCAG TTACCTCCCC
 881 AAATAAGCAT TTAGGGCTAG TGACTCCTCA CAAGACAGAA
 921 CTGGTATGAG CAGGATTTCT GCAGGTTCTT CTTCCTGAAG
 961 CTGAGGCTCA GGGGTGTGCC TGTCTGTTAC ACTGGAGGAG
1001 AGAAGAATGA GCCTACGCTG AAGATGGCAT CCTGTGAAGT
1041 CCTTCACCTC ACTGAAAACA TCTGGAAGGG GATCCCACCC
1081 CATTTTCTGT GGGCAGGCCT CGAAAACCAT CACATGACCA
1121 CATAGCATGA GGCCACTGCT GCTTCTCCAT GGCCACCTTT
```

-continued

```
1161 TCAGCGATGT ATGCAGCTAT CTGGTCAACC TCCTGGACAT
1201 TTTTTCAGTC ATATAAAAGC TATGGTGAGA TGCAGCTGGA
1241 AAAGGGTCTT GGGAAATATG AATGCCCCCA GCTGGCCCGT
1281 GACAGACTCC TGAGGACAGC TGTCCTCTTC TGCATCTTGG
1321 GGACATCTCT TTGAATTTTC TGTGTTTTGC TGTACCAGCC
1361 CAGATGTTTT ACGTCTGGGA GAAATTGACA GATCAAGCTG
1401 TGAGACAGTG GGAAATATTT AGCAAATAAT TTCCTGGTGT
1441 GAAGGTCCTG CTATTACTAA GGAGTAATCT GTGTACAAAG
1481 AAATAACAAG TCGATGAACT ATTCCCCAGC AGGGTCTTTT
1521 CATCTGGGAA AGACATCCAT AAAGAAGCAA TAAAGAAGAG
1561 TGCCACATTT ATTTTTATAT CTATATGTAC TTGTCAAAGA
1601 AGGTTTGTGT TTTTCTGCTT TTGAAATCTG TATCTGTAGT
1641 GAGATAGCAT TGTGAACTGA CAGGCAGCCT GGACATAGAG
1681 AGGGAGAAGA AGTCAGAGAG GGTGACAAGA TAGAGAGCTA
1721 TTTAATGGCC GGCTGGAAAT GCTGGGCTGA CGGTGCAGTC
1761 TGGGTGCTCG CCCACTTGTC CCACTATCTG GGTGCATGAT
1801 CTTGAGCAAG TTCCTTCTGG TGTCTGCTTT CTCCATTGTA
1841 AACCACAAGG CTGTTGCATG GGCTAATGAA GATCATATAC
1881 GTGAAAATTA TTTGAAAACA TATAAAGCAC TATACAGATT
1921 CGAAACTCCA TTGAGTCATT ATCCTTGCTA TGATGATGGT
1961 GTTTTGGGGA TGAGAGGGTG CTATCCATTT CTCATGTTTT
2001 CCATTGTTTG AAACAAAGAA GGTTACCAAG AAGCCTTTCC
2041 TGTAGCCTTC TGTAGGAATT CTTTTGGGGA AGTGAGGAAG
2081 CCAGGTCCAC GGTCTGTTCT TGAAGCAGTA GCCTAACACA
2121 CTCCAAGATA TGGACACACG GGAGCCGCTG GCAGAAGGGA
2161 CTTCACGAAG TGTTGCATGG ATGTTTTAGC CATTGTTGGC
2201 TTTCCCTTAT CAAACTTGGG CCCTTCCCTT CTTGGTTTCC
2241 AAAGGCATTT ATTGCTGAGT TATATGTTCA CTGTCCCCCT
2281 AATATTAGGG AGTAAAACGG ATACCAAGTT GATTTAGTGT
2321 TTTTACCTCT GTCTTGGCTT TCATGTTATT AAACGTATGC
2361 ATGTGAAGAA GGGTGTTTTT CTGTTTTATA TTCAACTCAT
2401 AAGACTTTGG GATAGGAAAA ATGAGTAATG GTTACTAGGC
2441 TTAATACCTG GGTGATTACA TAATCTGTAC AACGAACCCC
2481 CATGATGTAA GTTTACCTAT GTAACAAACC TGCACTTATA
2521 CCCATGAACT TAAAATGAAA GTTAAAAATA AAAAACATAT
2561 ACAAATAAAA AAAA
```

A sequence of a wild type mouse CD83 gene that can be used in the invention is provided herein as SEQ ID NO:1. SEQ ID NO:1 is provided below with the ATG start codon and the TGA stop codon identified by underlining.

```
   1 GCGCTCCAGC CGCATGTCGC AAGGCCTCCA GCTCCTGTTT
  41 CTAGGCTGCG CCTGCAGCCT GGCACCCGCG ATGGCGATGC
  81 GGGAGGTGAC GGTGGCTTGC TCCGAGACCG CCGACTTGCC
 121 TTGCACAGCG CCCTGGGACC CGCAGCTCTC CTATGCAGTG
 161 TCCTGGGCCA AGGTCTCCGA GAGTGGCACT GAGAGTGTGG
 201 AGCTCCCGGA GAGCAAGCAA AACAGCTCCT TCGAGGCCCC
 241 CAGGAGAAGG GCCTATTCCC TGACGATCCA AAACACTACC
 281 ATCTGCAGCT CGGGCACCTA CAGGTGTGCC CTGCAGGAGC
 321 TCGGAGGGCA GCGCAACTTG AGCGGCACCG TGGTTCTGAA
 361 GGTGACAGGA TGCCCCAAGG AAGCTACAGA GTCAACTTTC
 401 AGGAAGTACA GGGCAGAAGC TGTGTTGCTC TTCTCTCTGG
 441 TTGTTTTCTA CCTGACACTC ATCATTTTCA CCTGCAAATT
 481 TGCACGACTA CAAAGCATTT TCCCAGATAT TTCTAAACCT
 521 GGTACGGAAC AAGCTTTTCT TCCAGTCACC TCCCCAAGCA
 561 AACATTTGGG GCCAGTGACC CTTCCTAAGA CAGAAACGGT
 601 ATGAGTAGGA TCTCCACTGG TTTTTACAAA GCCAAGGGCA
 641 CATCAGATCA GTGTGCCTGA ATGCCACCCG GACAAGAGAA
 681 GAATGAGCTC CATCCTCAGA TGGCAACCTT TCTTTGAAGT
 721 CCTTCACCTG ACAGTGGGCT CCACACTACT CCCTGACACA
 761 GGGTCTTGAG CACCATCATA TGATCACGAA GCATGGAGTA
 801 TCACCGCTTC TCTGTGGCTG TCAGCTTAAT GTTTCATGTG
 841 GCTATCTGGT CAACCTCGTG AGTGCTTTTC AGTCATCTAC
 881 AAGCTATGGT GAGATGCAGG TGAAGCAGGG TCATGGGAAA
 921 TTTGAACACT CTGAGCTGGC CCTGTGACAG ACTCCTGAGG
 961 ACAGCTGTCC TCTCCTACAT CTGGGATACA TCTCTTTGAA
1001 TTTGTCCTGT TTCGTTGCAC CAGCCCAGAT GTCTCACATC
1041 TGGCGGAAAT TGACAGGCCA AGCTGTGAGC CAGTGGGAAA
1081 TATTTAGCAA ATAATTTCCC AGTGCGAAGG TCCTGCTATT
1121 AGTAAGGAGT ATTATGTGTA CATAGAAATG AGAGGTCAGT
1161 GAACTATTCC CCAGCAGGGC CTTTTCATCT GGAAAAGACA
1201 TCCACAAAAG CAGCAATACA GAGGGATGCC ACATTTATTT
1241 TTTTAATCTT CATGTACTTG TCAAAGAAGA ATTTTTCATG
1281 TTTTTTCAAA GAAGTGTGTT TCTTTCCTTT TTTAAAATAT
1321 GAAGGTCTAG TTACATAGCA TTGCTAGCTG ACAAGCAGCC
1361 TGAGAGAAGA TGGAGAATGT TCCTCAAAAT AGGGACAGCA
1401 AGCTAGAAGC ACTGTACAGT GCCCTGCTGG GAAGGGCAGA
1441 CAATGGACTG AGAAACCAGA AGTCTGGCCA CAAGATTGTC
1481 TGTATGATTC TGGACGAGTC ACTTGTGGTT TTCACTCTCT
1521 GGTTAGTAAA CCAGATAGTT TAGTCTGGGT TGAATACAAT
1561 GGATGTGAAG TTGCTTGGGG AAAGCTGAAT GTAGTGAATA
```

-continued

```
1601 CATTGGCAAC TCTACTGGGC TGTTACCTTG TTGATATCCT
1641 AGAGTTCTGG AGCTGAGCGA ATGCCTGTCA TATCTCAGCT
1681 TGCCCATCAA TCCAAACACA GGAGGCTACA AAAAGGACAT
1721 GAGCATGGTC TTCTGTGTGA ACTCCTCCTG AGAAACGTGG
1761 AGACTGGCTC AGCGCTTTGC GCTTGAAGGA CTAATCACAA
1801 GTTCTTGAAG ATATGGACCT AGGGGAGCTA TTGCGCCACG
1841 ACAGGAGGAA GTTCTCAGAT GTTGCATTGA TGTAACATTG
1881 TTGCATTTCT TTAATGAGCT GGGCTCCTTC CTCATTTGCT
1921 TCCCAAAGAG ATTTTGTCCC ACTAATGGTG TGCCCATCAC
1961 CCACACTATG AAAGTAAAAG GGATGCTGAG CAGATACAGC
2001 GTGCTTACCT CTCAGCCATG ACTTTCATGC TATTAAAAGA
2041 ATGCATGTGA A
```

Nucleic acids having SEQ ID NO:1 encode a mouse polypeptide having SEQ ID NO:2, provided below.

```
  1 MSQGLQLLFL GCACSLAPAM AMREVTVACS ETADLPCTAP
 41 WDPQLSYAVS WAKVSESGTE SVELPESKQN SSFEAPRRRA
 81 YSLTIQNTTI CSSGTYRCAL QELGGQRNLS GTVVLKVTGC
121 PKEATESTFR KYRAEAVLLF SLVVFYLTLI IFTCKFARLQ
161 SIFPDISKPG TEQAFLPVTS PSKHLGPVTL PKTETV
```

According to the invention, loss or reduction of CD83 activity in vivo results in a decreased immune response, for example, decreased numbers of T cells. The effect of CD83 on the immune response was initially ascertained through use of a mutant mouse that encodes a mutant CD83. Such a mutant mouse has a CD83 gene encoding SEQ ID NO:4, with added C-terminal sequences provided by SEQ ID NO:8. In contrast to these wild type CD83 nucleic acids and polypeptides, the mutant CD83 gene of the invention has SEQ ID NO:3. SEQ ID NO:3 is provided below with the ATG start codon, the mutation, and the TGA stop codon are identified by underlining.

```
  1 GCGCTCCAGC CGCATGTCGC AAGGCCTCCA GCTCCTGTTT
 41 CTAGGCTGCG CCTGCAGCCT GGCACCCGCG ATGGCGATGC
 81 GGGAGGTGAC GGTGGCTTGC TCCGAGACCG CCGACTTGCC
121 TTGCACAGCG CCCTGGGACC CGCAGCTCTC CTATGCAGTG
161 TCCTGGGCCA AGGTCTCCGA GAGTGGCACT GAGAGTGTGG
201 AGCTCCCGGA GAGCAAGCAA AACAGCTCCT TCGAGGCCCC
241 CAGGAGAAGG GCCTATTCCC TGACGATCCA AAACACTACC
281 ATCTGCAGCT CGGGCACCTA CAGGTGTGCC CTGCAGGAGC
321 TCGGAGGGCA GCGCAACTTG AGCGGCACCG TGGTTCTGAA
361 GGTGACAGGA TGCCCCAAGG AAGCTACAGA GTCAACTTTC
401 AGGAAGTACA GGGCAGAAGC TGTGTTGCTC TTCTCTCTGG
441 TTGTTTTCTA CCTGACACTC ATCATTTTCA CCTGCAAATT
```

-continued

```
 481 TGCACGACTA CAAAGCATTT TCCCAGATAT TTCTAAACCT
 521 GGTACGGAAC AAGCTTTTCT TCCAGTCACC TCCCCAAGCA
 561 AACATTTGGG GCCAGTGACC CTTCCTAAGA CAGAAACGGT
 601 AAGAGTAGGA TCTCCACTGG TTTTTACAAA GCCAAGGGCA
 641 CATCAGATCA GTGTGCCTGA ATGCCACCCG GACAAGAGAA
 681 GAATGAGCTC CATCCTCAGA TGGCAACCTT TCTTTGAAGT
 721 CCTTCACCTG ACAGTGGGCT CCACACTACT CCCTGACACA
 761 GGGTCTTGAG CACCATCATA TGATCACGAA GCATGGAGTA
 801 TCACCGCTTC TCTGTGGCTG TCAGCTTAAT GTTTCATGTG
 841 GCTATCTGGT CAACCTCGTG AGTGCTTTTC AGTCATCTAC
 881 AAGCTATGGT GAGATGCAGG TGAAGCAGGG TCATGGGAAA
 921 TTTGAACACT CTGAGCTGGC CCTGTGACAG ACTCCTGAGG
 961 ACAGCTGTCC TCTCCTACAT CTGGGATACA TCTCTTTGAA
1001 TTTGTCCTGT TTCGTTGCAC CAGCCCAGAT GTCTCACATC
1041 TGGCGGAAAT TGACAGGCCA AGCTGTGAGC CAGTGGGAAA
1081 TATTTAGCAA ATAATTTCCC AGTGCGAAGG TCCTGCTATT
1121 AGTAAGGAGT ATTATGTGTA CATAGAAATG AGAGGTCAGT
1161 GAACTATTCC CCAGCAGGGC CTTTTCATCT GGAAAAGACA
1201 TCCACAAAAG CAGCAATACA GAGGGATGCC ACATTTATTT
1241 TTTTAATCTT CATGTACTTG TCAAAGAAGA ATTTTTCATG
1281 TTTTTTCAAA GAAGTGTGTT TCTTTCCTTT TTTAAAATAT
1321 GAAGGTCTAG TTACATAGCA TTGCTAGCTG ACAAGCAGCC
1361 TGAGAGAAGA TGGAGAATGT TCCTCAAAAT AGGGACAGCA
1401 AGCTAGAAGC ACTGTACAGT GCCCTGCTGG GAAGGGCAGA
1441 CAATGGACTG AGAAACCAGA AGTCTGGCCA CAAGATTGTC
1481 TGTATGATTC TGGACGAGTC ACTTGTGGTT TTCACTCTCT
1521 GGTTAGTAAA CCAGATAGTT TAGTCTGGGT TGAATACAAT
1561 GGATGTGAAG TTGCTTGGGG AAAGCTGAAT GTAGTGAATA
1601 CATTGGCAAC TCTACTGGGC TGTTACCTTG TTGATATCCT
1641 AGAGTTCTGG AGCTGAGCGA ATGCCTGTCA TATCTCAGCT
1681 TGCCCATCAA TCCAAACACA GGAGGCTACA AAAAGGACAT
1721 GAGCATGGTC TTCTGTGTGA ACTCCTCCTG AGAAACGTGG
1761 AGACTGGCTC AGCGCTTTGC GCTTGAAGGA CTAATCACAA
1801 GTTCTTGAAG ATATGGACCT AGGGGAGCTA TTGCGCCACG
1841 ACAGGAGGAA GTTCTCAGAT GTTGCATTGA TGTAACATTG
1881 TTGCATTTCT TTAATGAGCT GGGCTCCTTC CTCATTTGCT
1921 TCCCAAAGAG ATTTTGTCCC ACTAATGGTG TGCCCATCAC
1961 CCACACTATG AAAGTAAAAG GGATGCTGAG CAGATACAGC
2001 GTGCTTACCT CTCAGCCATG ACTTTCATGC TATTAAAAGA
2041 ATGCATGTGA A
```

The change from a thymidine in SEQ ID NO:1 to an adenine in SEQ ID NO:3 at the indicated position (602) leads to read-through translation because the stop codon at positions 602-604 in SEQ ID NO:1 is changed to a codon that encodes an arginine. Accordingly, mutant CD83 nucleic acids having SEQ ID NO:3 encode an elongated polypeptide having SEQ ID NO:4, provided below, where the extra amino acids are underlined.

```
  1 MSQGLQLLFL GCACSLAPAM AMREVTVACS ETADLPCTAP
 41 WDPQLSYAVS WAKVSESGTE SVELPESKQN SSFEAPRRRA
 81 YSLTIQNTTI CSSGTYRCAL QELGGQRNLS GTVVLKVTGC
121 PKEATESTFR KYRAEAVLLF SLVVFYLTLI IFTCKFARLQ
161 SIFPDISKPG TEQAFLPVTS PSKHLGPVTL PKTETVRVGS
201 PLVFTKPRAH QISVPECHPD KRRMSSILRW QPFFEVLHLT
241 VGSTLLPDTG S
```

In another embodiment, the invention provides mutant CD83 nucleic acids that include SEQ ID NO:5.

```
  1 ATGTCGCAAG GCCTCCAGCT CCTGTTTCTA GGCTGCGCCT
 41 GCAGCCTGGC ACCCGCGATG GCGATGCGGG AGGTGACGGT
 81 GGCTTGCTCC GAGACCGCCG ACTTGCCTTG CACAGCGCCC
121 TGGGACCCGC AGCTCTCCTA TGCAGTGTCC TGGGCCAAGG
161 TCTCCGAGAG TGGCACTGAG AGTGTGGAGC TCCCGGAGAG
201 CAAGCAAAAC AGCTCCTTCG AGGCCCCCAG GAGAAGGGCC
241 TATTCCCTGA CGATCCAAAA CACTACCATC TGCAGCTCGG
281 GCACCTACAG GTGTGCCCTG CAGGAGCTCG GAGGGCAGCG
321 CAACTTGAGC GGCACCGTGG TTCTGAAGGT GACAGGATGC
361 CCCAAGGAAG CTACAGAGTC AACTTTCAGG AAGTACAGGG
401 CAGAAGCTGT GTTGCTCTTC TCTCTGGTTG TTTTCTACCT
441 GACACTCATC ATTTTCACCT GCAAATTTGC ACGACTACAA
481 AGCATTTTCC CAGATATTTC TAAACCTGGT ACGGAACAAG
521 CTTTTCTTCC AGTCACCTCC CCAAGCAAAC ATTTGGGGCC
561 AGTGACCCTT CCTAAGACAG AAACGGTAAG AGTAGGATCT
601 CCACTGGTTT TTACAAAGCC AAGGGCACAT CAGATCAGTG
641 TGCCTGAATG CCACCCGGAC AAGAGAAGAA TGAGCTCCAT
681 CCTCAGATGG CAACCTTTCT TTGAAGTCCT TCACCTGACA
721 GTGGGCTCCA CACTACTCCC TGACACAGGG TCTTGA
```

Nucleic acids having SEQ ID NO:5 also encode a polypeptide having SEQ ID NO:4.

In another embodiment, the invention provides mutant CD83 nucleic acids that include SEQ ID NO:7.

```
  1 AGAGTAGGAT CTCCACTGGT TTTTACAAAG CCAAGGGCAC
 41 ATCAGATCAG TGTGCCTGAA TGCCACCCGG ACAAGAGAAG
 81 AATGAGCTCC ATCCTCAGAT GGCAACCTTT CTTTGAAGTC
```

-continued

```
121 CTTCACCTGA CAGTGGGCTC CACACTACTC CCTGACACAG

161 GGTCTTGA
```

The invention also provides a mutant CD83 containing SEQ ID NO:8, provided below.

```
 1 RVGSPLVFTK PRAHQISVPE CHPDKRRMSS ILRWQPFFEV

41 LHLTVGSTLL PDTGS
```

SEQ ID NO:8 contains read through sequences that are not present in the wild type CD83 polypeptide but are present in the mutant CD83 gene product provided by the invention.

In some embodiments, the CD83 gene product is used for generating antibodies. While any of the CD83 gene products described herein can be employed for immunization of animal, in some embodiments the extracellular Ig-like domain of the CD83 gene product is used for immunization, or antibodies are screened for reactivity with the extracellular Ig-like domain. The extracellular Ig-like domain of the human CD83 gene product spans amino acids 21-127, and is provided below (SEQ ID NO:97):

```
 21                       PEVKVACSED VDLPCTAPWD

 41 PQVPYTVSWV KLLEGGEERM ETPQEDHLRG QHYHQKGQNG

 81 SFDAPNERPY SLKIRNTTSC NSGTYRCTLQ DPDGQRNLSG

121 KVILRVT
```

CD83 Antibodies

The invention provides antibody preparations directed against the mutant and wild type CD83 polypeptides of the invention, for example, against a polypeptide having SEQ ID NO:2, SEQ ID NO:4, SEQ ID NO:7, SEQ ID NO:8 or SEQ ID NO:9. Other antibodies of interest can bind to the cytoplasmic tail of CD83.

In some embodiments, the anti-CD83 antibodies are multimerized antibodies. According to the invention, multimerized anti-CD83 antibodies are surprisingly effective inhibitors of lymphocyte cell proliferation. As used herein, an "multimerized" anti-CD83 antibody is a collection of anti-CD83 antibodies that are in close proximity. While such multimerized antibodies can be covalently linked, no such covalent linkage is necessary. Instead, multimerization of anti-CD83 antibodies can simply involve bringing the antibodies into close proximity, for example, by attachment to a solid support such as a plate or a bead. Alternatively, the antibodies can be non-covalently linked together through another entity, for example, any convenient non-covalent binding entity or secondary antibody. Hence, any available means for bringing the anti-CD83 antibodies into proximity can be used to generate the multimerized antibodies of the invention.

In some embodiments, the anti-CD83 binding proteins or antibodies can be chemically cross-linked or genetically fused with any available crosslinking reagent. Crosslinking can be achieved using one or a combination of a wide variety of multifunctional reagents. Such crosslinking agents include glutaraldehyde, succinaldehyde, octanedialdehyde and glyoxal. Additional multifunctional crosslinking agents include halo-triazines, e.g., cyanuric chloride; halo-pyrimidines, e.g., 2,4,6-trichloro/bromo-pyrimidine; anhydrides or halides of aliphatic or aromatic mono- or di-carboxylic acids, e.g., maleic anhydride, (meth)acryloyl chloride, chloroacetyl chloride; N-methylol compounds, e.g., N-methylol-chloro acetamide; di-isocyanates or di-isothiocyanates, e.g., phenylene-1,4-di-isocyanate and aziridines. Other crosslinking agents include epoxides, such as, for example, di-epoxides, tri-epoxides and tetra-epoxides. Other crosslinking agents include, for example, dimethyl 3,3'-dithiobispropionimidate-HCl (DTBP); dithiobis (succinimidylpropionate) (DSP); bis-maleimidohexane (BMH); bis[Sulfosuccinimidyl]suberate (BS); 1,5-difluoro-2,4-dinitrobenzene (DFDNB); dimethylsuberimidate-2HCl (DMS); disuccinimidyl glutarate (DSG); disulfosuccinimidyl tartarate (Sulfo-DST); 1-ethyl-3-[3-dimethylaminopropyl]carbodiimide hydrochloride (EDC); ethylene glycolbis[sulfo -succinimidylsuccinate] (Sulfo-EGS); N-[?-maleimido-butyryloxy]succinimide ester (GMBS); N-hydroxysulfosuccinimidyl-4-azidobenzoate (Sulfo-HSAB); sulfosuccinimidyl-6-[a-methyl-a-(2-pyridyldithio)toluamido]hexanoate (Sulfo-LC -SMPT); bis-[β-(4-azidosalicylamido) ethyl]disulfide (BASED); and NHS-PEG-Vinylsulfone (NHS-PEG-VS).

In some embodiments, crosslinkers useful with various preparations of anti-CD83 antibodies of this invention include (1) those which create covalent links from one cysteine side chain of a protein to another cysteine side chain, (2) those which create covalent links from one lysine side chain of a protein to another, or (3) those which create covalent links from one cysteine side chain of a protein to a lysine side chain.

In other embodiments, the anti-CD83 antibodies are reversibly crosslinked. Such reversibly crosslinked antibodies are useful for short term use, for example, for short term control of the immune response either in vivo or in vitro, or for controlled dissipation of the anti-CD83 antibodies at a localized site after administration for short term therapeutic purposes. Examples of reversible crosslinkers are described in T. W. Green, Protective Groups in Organic Synthesis, John Wiley & Sons (Eds.) (1981). Other types of reversible crosslinkers are disulfide bond-containing crosslinkers. The crosslinks formed by such crosslinkers can be broken by the addition of reducing agent, such as cysteine, to the environment of the crosslinked anti-CD83 antibodies. Disulfide crosslinkers are described in the Pierce Catalog and Handbook (1994-1995).

Examples of crosslinkers that may be used also include: Homobifunctional (Symmetric); DSP—Dithiobis(succinimidylpropionate), also know as Lomant,'s Reagent; DTSSP-3-3'-Dithiobis(sulfosuccinimidyl-propionate), water soluble version of DSP; DTBP—Dimethyl 3,3'-dithiobispropionimidate-HC1; BASED—Bis-(β-[4-azidosalicylamido]ethyl) disulfide; DPDPB-1,4-Di-(3'-[2'-pyridyldithio]-propionamido)butane; Heterobifunctional (Asymmetric); SPDP—N-Succinimidyl-3-(2-pyridyldithio)propionate; LC-SPDP—Succinimidyl-6-(3-[2-pyridyldithio]propionate)hexanoate; Sulfo-LC-SPDP—Sulfosuccinimidyl-6-(3-[2-pyridyldlthio] propionate)hexanoate, water soluble version of LC-SPDP; APDP—N-(4-[p-azidosalicylamido]butyl)-3'-(2'-pyridyldithio) propionamide; SADP—N-Succinimidyl(4-azidophenyl)1,3'-dithiopropionate; Sulfo-SADP—Sulfosuccinimidyl(4-azidophenyl) 1,3'-dithiopropionate, water soluble version of SADP; SAED Sulfosuccinimidyl-2-(7-azido-4-methycoumarin-3-acetamide)ethyl-1,3' dithiopropionate; SAND—Sulfosuccinimidyl-2-(m-azido-o -nitrobenzamido) ethyl-1,3'-dithiopropionate; SASD Sulfosuccinimidyl-2-(p-azidosalicylamido)ethyl-1,3'-dithiopropionate; SMPB Succinimidyl-4-(p-maleimidophenyl)butyrate; Sulfo-SMPB Sulfosuccinimidyl-4-(p-maleimidophenyl)butyrate; SMPT 4-Succinimidyloxycarbonyl-methyl-a-(2-pyridylthio)toluene; Sulfo-LC-SMPT Sulfosuccinimidyl-6-(a-methyl-a-(2-pyridylthio)toluamido)hexanoate.

In another embodiment, a fusion protein can be made with a selected anti-CD83 antibody to allow a domain to be attached to one or both of the polypeptides comprising the anti-CD83 antibody to be bound to a solid substrate. For example, glutathione-S-transferase/anti-CD83 fusion proteins can be linked to another anti-CD83 preparation having glutathione attached thereto or the glutathione-S-transferase/anti-CD83 fusion proteins can be adsorbed onto a solid support having glutathione attached thereto, such as glutathione sepharose beads (Sigma Chemical, St. Louis, Mo.) or glutathione derivatized microtiter plate. In another embodiment, DSP-crosslinked antibodies can be linked to protein G agarose beads. Other techniques for immobilizing polypeptides on solid support materials can also be used. For example, an anti-CD83 antibody can be immobilized utilizing conjugation of biotin and streptavidin. Biotinylated anti-CD83 polypeptides can be prepared from biotin-NHS(N-hydroxy-succinimide) using techniques known in the art (e.g., biotinylation kit, Pierce Chemicals, Rockford, Ill.), and immobilized with a streptavidin-linked antiCD83 antibody preparation, streptavidin-coated beads or another solid support material.

Therefore, in one embodiment, the invention provides antibodies capable of reducing CD83 activity and decreasing an immune response in a mammal. Such antibodies can be multimerized antibodies. These antibodies may be used as CD83 inhibitory agents in the methods of the invention as described herein. In another embodiment, the antibodies of the invention can activate CD83 activity. Such activating antibodies may be used as CD83 stimulatory agents.

All antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82, 4592-4596 (1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha ($\alpha$), delta (d), epsilon (e), gamma (?) and mu (g), respectively. The light chains of antibodies can be assigned to one of two clearly distinct types, called kappa (?) and lambda (?), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely adopting a $\beta$-sheet configuration, connected by three CDRs, which form loops connecting, and in some cases forming part of, the $\beta$-sheet structure. The CDRs in each chain are held together in close proximity by the FR regions and, with the CDRs from the other chain, contribute to the formation of the antigen binding site of antibodies. The constant domains are not involved directly in binding an antibody to an antigen, but exhibit various effector function, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody that includes the variable domain complementarity determining regions (CDR), and the like forms, all of which fall under the broad term "antibody," as used herein. Moreover, the multimerized antibodies of the invention can be an aggregation or multimerization of whole immunoglobulins. Alternatively, the multimerized antibodies of the invention can be an aggregation or multimerization of antibody fragments such as Fv, Fab, single chain antibodies that include the variable domain complementarity determining regions (CDR), CDRs and the like. Such intact antibodies or antibody fragments can be multimerized by any convenient means, including covalent linkage or non-covalent association.

The present invention contemplates the use of any specificity of an antibody, polyclonal or monoclonal, and is not limited to antibodies that recognize and immunoreact with a specific epitope. In preferred embodiments, in the context of both the therapeutic and screening methods described below, an antibody or fragment thereof is used that is immunospecific for an extracellular portion of the CD83 protein.

The term "antibody fragment" refers to a portion of a full-length antibody, generally the antigen binding or variable region. Examples of antibody fragments include Fab, Fab', $F(ab')_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an $F(ab')_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and $F(ab')_2$ fragments.

Antibody fragments retain some ability to selectively bind with its antigen or receptor and are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) $(Fab')_2$ is the fragment of an antibody that can be obtained by treating whole antibody with the enzyme pepsin without subsequent reduction. $F(ab')_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269-315 (1994).

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad. Sci. USA 90: 6444-6448 (1993).

The preparation of polyclonal antibodies is well-known to those skilled in the art. See, for example, Green, et al., Production of Polyclonal Antisera, in: *Immunochemical Protocols* (Manson, ed.), pages 1-5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference.

The preparation of monoclonal antibodies likewise is conventional. See, for example, Kohler & Milstein, Nature, 256: 495 (1975); Coligan, et al., sections 2.5.1-2.6.7; and Harlow, et al., in: *Antibodies: A Laboratory Manual*, page 726 (Cold Spring Harbor Pub. (1988)), which are hereby incorporated by reference. Methods of in vitro and in vivo manipulation of monoclonal antibodies are also available to those skilled in the art. For example, the monoclonal antibodies to be used in accordance with the present invention may be made by the hybridoma method first described by Kohler and Milstein, Nature 256, 495 (1975), or they may be made by recombinant methods, for example, as described in U.S. Pat. No. 4,816,567. The monoclonal antibodies for use with the present invention may also be isolated from antibody libraries using the techniques described in Clackson et al. Nature 352: 624-628 (1991), as well as in Marks et al., J. Mol Biol. 222: 581-597 (1991).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: *Methods in Molecular Biology*, Vol. 10, pages 79-104 (Humana Press (1992).

Another method for generating antibodies involves a Selected Lymphocyte Antibody Method (SLAM). The SLAM technology permits the generation, isolation and manipulation of monoclonal antibodies without the process of hybridoma generation. The methodology principally involves the growth of antibody forming cells, the physical selection of specifically selected antibody forming cells, the isolation of the genes encoding the antibody and the subsequent cloning and expression of those genes.

More specifically, an animal is immunized with a source of specific antigen. The animal can be a rabbit, mouse, rat, or any other convenient animal. This immunization may consist of purified protein, in either native or recombinant form, peptides, DNA encoding the protein of interest or cells expressing the protein of interest. After a suitable period, during which antibodies can be detected in the serum of the animal (usually weeks to months), blood, spleen or other tissues are harvested from the animal. Lymphocytes are isolated from the blood and cultured under specific conditions to generate antibody-forming cells, with antibody being secreted into the culture medium. These cells are detected by any of several means (complement mediated lysis of antigen-bearing cells, fluorescence detection or other) and then isolated using micromanipulation technology. The individual antibody forming cells are then processed for eventual single cell PCR to obtain the expressed Heavy and Light chain genes that encode the specific antibody. Once obtained and sequenced, these genes are cloned into an appropriate expression vector and recombinant, monoclonal antibody produced in a heterologous cell system. These antibodies are then purified via standard methodologies such as the use of protein A affinity columns. These types of methods are further described in Babcook, et al., Proc. Natl. Acad. Sci. (USA) 93: 7843-7848 (1996); U.S. Pat. No. 5,627,052; and PCT WO 92/02551 by Schrader.

Another method involves humanizing a monoclonal antibody by recombinant means to generate antibodies containing human specific and recognizable sequences. See, for review, Holmes, et al., J. Immunol., 158:2192-2201 (1997) and Vaswani, et al., Annals Allergy, Asthma & Immunol., 81:105-115 (1998). The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the antibody is obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al. Proc. Natl. Acad Sci. 81, 6851-6855 (1984).

Methods of making antibody fragments are also known in the art (see for example, Harlow and Lane, *Antibodies: A Laboratory Manual*, Cold Spring Harbor Laboratory, New York, (1988), incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab=monovalent fragments. Alternatively, an enzymatic cleavage using pepsin produces two monovalent Fab' fragments and an Fc fragment directly. These methods are described, for example, in U.S. Pat. No. 4,036,945 and No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., Science 242:423-426 (1988); Ladner, et al, U.S. Pat. No. 4,946,778; and Pack, et al., *Bio/Technology* 11:1271-77 (1993).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991).

The invention further contemplates human and humanized forms of non-human (e.g. murine) antibodies. Such humanized antibodies can be chimeric immunoglobulins, immunoglobulin chains or fragments thereof (such as Fv, Fab, Fab', $F(ab')_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies can comprise substantially all of at least one, and typically two, variable domains, in which all or substantially all of the CDR regions correspond to those of a non-human immunoglobulin and all or substantially all of the Fv regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522-525 (1986); Reichmann et al., Nature 332, 323-329 (1988); Presta, Curr. Op. Struct. Biol. 2, 593-596 (1992); Holmes, et al., J. Immunol., 158:2192-2201 (1997) and Vaswani, et al., Annals Allergy, Asthma & Immunol., 81:105-115 (1998); U.S. Pat. Nos. 4,816,567 and 6,331,415; PCT/GB84/00094; PCT/US86/02269; PCT/US89/00077; PCT/US88/02514; and WO91/09967, each of which is incorporated herein by reference in its entirety.

The invention also provides methods of mutating antibodies to optimize their affinity, selectivity, binding strength or other desirable property. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody.

The antibodies of the invention are isolated antibodies. An isolated antibody is one that has been identified and separated and/or recovered from a component of the environment in which it was produced. Contaminant components of its production environment are materials that would interfere with diagnostic or therapeutic uses for the antibody, and may include enzymes, hormones, and other proteinaceous or non-proteinaceous solutes. The term “isolated antibody” also includes antibodies within recombinant cells because at least one component of the antibody’s natural environment will not be present. Ordinarily, however, isolated antibody will be prepared by at least one purification step.

If desired, the antibodies of the invention can be purified by any available procedure. For example, the antibodies can be affinity purified by binding an antibody preparation to a solid support to which the antigen used to raise the antibodies is bound. After washing off contaminants, the antibody can be eluted by known procedures. Those of skill in the art will know of various techniques common in the immunology arts for purification and/or concentration of polyclonal antibodies, as well as monoclonal antibodies (see for example, Coligan, et al., Unit 9, *Current Protocols in Immunology*, Wiley Interscience, 1991, incorporated by reference).

In preferred embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or, preferably, silver stain.

The invention also provides antibodies that can bind to CD83 polypeptides. Sequences of complementarity determining regions (CDRs) or hypervariable regions from light and heavy chains of these anti-CD83 antibodies are provided. For example, a heavy chain variable region having a CDR1 sequence of SYDMT (SEQ ID NO:23), SYDMS (SEQ ID NO:24), DYDLS (SEQ ID NO:25) or SYDMS (SEQ ID NO:26) can be used in an antibody, multimerized antibody or other single- or multi-valent binding moiety to bind to CD83 gene products and/or modulate the immune response. In other embodiments, a heavy chain variable region having a CDR2 sequence of YASGSTYY (SEQ ID NO:27), SSSGTTYY (SEQ ID NO:28), YASGSTYY (SEQ ID NO:29), AIDGNPYY (SEQ ID NO:30) or STAYNSHY (SEQ ID NO:31) can be used in an antibody, multimerized antibody or other single- or multi-valent binding moiety to bind to CD83 gene products or modulate the immune system. In further embodiments of the invention, a heavy chain variable region having a CDR3 sequence of EHAGYSGDTGH (SEQ ID NO:32), EGAGVSMT (SEQ ID NO:33), EDAGFSNA (SEQ ID NO:34), GAGD (SEQ ID NO:35) or GGSWLD (SEQ ID NO:36) can be used in an antibody, multimerized antibody or other single- or multi-valent binding moiety to bind to CD83 gene products or modulate the immune system.

Moreover, a light chain variable region having a CDR1 sequence of RCAYD (SEQ ID NO:37), RCADVV (SEQ ID NO:38), or RCALV (SEQ ID NO:39) can be used in an antibody, multimerized antibody or other single- or multi-valent binding moiety to bind to CD83 gene products or modulate the immune system. In other embodiments, a light chain variable region having a CDR2 sequence of QSISTY (SEQ ID NO:40), QSVSSY (SEQ ID NO:41), ESISNY (SEQ ID NO:42), KNVYNNNW (SEQ ID NO:43), or QSVYDNDE (SEQ ID NO:98) can be used in an antibody, multimerized antibody or other single- or multi-valent binding moiety to bind to CD83 gene products or modulate the immune system. In further embodiments, a light chain variable region having a CDR3 sequence of QQGYTHSNVDNV (SEQ ID NO:44), QQGYSISDIDNA (SEQ ID NO:45), QCTSGGKFISDGAA (SEQ ID NO:46), AGDYSSSSDNG (SEQ ID NO:47), or QATHYSSDWLTY (SEQ ID NO:48) can be used in an antibody, multimerized antibody or other single- or multi-valent binding moiety to bind to CD83 gene products.

Light and heavy chains that can bind CD83 polypeptides are also provided by the invention. For example, in one embodiment, the invention provides a 20D04 light chain that can bind to CD83 polypeptides. The amino acid sequence for this 20D04 light chain is provided below (SEQ ID NO:11).

```
  1 MDMRAPTQLL GLLLLWLPGA RCADVVMTQT PASVSAAVGG
 41 TVTINCQASE SISNYLSWYQ QKPGQPPKLL IYRTSTLASG
 81 VSSRFKGSGS GTEYTLTISG VQCDDVATYY CQCTSGGKFI
121 SDGAAFGGGT EVVVKGDPVA PTVLLFPPSS DEVATGTVTI
161 VCVANKYFPD VTVTWEVDGT TQTTGIENSK TPQNSADCTY
201 NLSSTLTLTS TQYNSHKEYT CKVTQGTTSV VQSFSRKNC
```

A nucleic acid sequence for this 20D04 anti-CD83 light chain is provided below (SEQ ID NO:12).

```
  1 ATGGACATGA GGGCCCCCAC TCAGCTGCTG GGGCTCCTGC
 41 TGCTCTGGCT CCCAGGTGCC AGATGTGCCG ATGTCGTGAT
 81 GACCCAGACT CCAGCCTCCG TGTCTGCAGC TGTGGGAGGC
121 ACAGTCACCA TCAATTGCCA GGCCAGTGAA AGCATTAGCA
161 ACTACTTATC CTGGTATCAG CAGAAACCAG GGCAGCCTCC
201 CAAGCTCCTG ATCTACAGGA CATCCACTCT GGCATCTGGG
241 GTCTCATCGC GGTTCAAAGG CAGTGGATCT GGGACAGAGT
281 ACACTCTCAC CATCAGCGGC GTGCAGTGTG ACGATGTTGC
321 CACTTACTAC TGTCAATGCA CTTCTGGTGG GAAGTTCATT
361 AGTGATGGTG CTGCTTTCGG CGGAGGGACC GAGGTGGTGG
401 TCAAAGGTGA TCCAGTTGCA CCTACTGTCC TCCTCTTCCC
441 ACCATCTAGC GATGAGGTGG CAACTGGAAC AGTCACCATC
481 GTGTGTGTGG CGAATAAATA CTTTCCCGAT GTCACCGTCA
521 CCTGGGAGGT GGATGGCACC ACCCAAACAA CTGGCATCGA
561 GAACAGTAAA ACACCGCAGA ATTCTGCAGA TTGTACCTAC
601 AACCTCAGCA GCACTCTGAC ACTGACCAGC ACACAGTACA
641 ACAGCCACAA AGAGTACACC TGCAAGGTGA CCCAGGGCAC
681 GACCTCAGTC GTCCAGAGCT TCAGTAGGAA GAACTGTTAA
```

In another embodiment, the invention provides a 20D04 heavy chain that can bind to CD83 polypeptides. The amino acid sequence for this 20D04 heavy chain is provided below (SEQ ID NO:13).

```
  1 METGLRWLLL VAVLKGVQCQ SVEESGGRLV TPGTPLTLTC
 41 TVSGFSLSNN AINWVRQAPG KGLEWIGYIW SGGLTYYANW
 81 AEGRFTISKT STTVDLKMTS PTIEDTATYF CARGINNSAL
121 WGPGTLVTVS SGQPKAPSVF PLAPCCGDTP SSTVTLGCLV
161 KGYLPEPVTV TWNSGTLTNG VRTFPSVRQS SGLYSLSSVV
```

-continued

```
201 SVTSSSQPVT CNVAHPATNT KVDKTVAPST CSKPTCPPPE

241 LLGGPSVFIF PPKPKDTLMI SRTPEVTCVV VDVSQDDPEV

281 QFTWYINNEQ VRTARPPLRE QQFNSTIRVV STLPIAHQDW

321 LRGKEFKCKV HNKALPAPIE KTISKARGQP LEPKVYTMGP

361 PREELSSRSV SLTCMINGFY PSDISVEWEK NGKAEDNYKT

401 TPAVLDSDGS YFLYNKLSVP TSEWQRGDVF TCSVMHEALH

441 NHYTQKSISR SPGK
```

A nucleic acid sequence for this 20D04 anti-CD83 heavy chain is provided below (SEQ ID NO:14).

```
   1 ATGGAGACAG GCCTGCGCTG GCTTCTCCTG GTCGCTGTGC

  41 TCAAAGGTGT CCAGTGTCAG TCGGTGGAGG AGTCCGGGGG

  81 TCGCCTGGTC ACGCCTGGGA CACCCCTGAC ACTCACCTGC

 121 ACCGTCTCTG GATTCTCCCT CAGTAACAAT GCAATAAACT

 161 GGGTCCGCCA GGCTCCAGGG AAGGGGCTAG AGTGGATCGG

 201 ATACATTTGG AGTGGTGGGC TTACATACTA CGCGAACTGG

 241 GCGGAAGGCC GATTCACCAT CTCCAAAACC TCGACTACGG

 281 TGGATCTGAA GATGACCAGT CCGACAATCG AGGACACGGC

 321 CACCTATTTC TGTGCCAGAG GGATTAATAA CTCCGCTTTG

 361 TGGGGCCCAG GCACCCTGGT CACCGTCTCC TCAGGGCAAC

 401 CTAAGGCTCC ATCAGTCTTC CCACTGGCCC CCTGCTGCGG

 441 GGACACACCC TCTAGCACGG TGACCTTGGG CTGCCTGGTC

 481 AAAGGCTACC TCCCGGAGCC AGTGACCGTG ACCTGGAACT

 521 CGGGCACCCT CACCAATGGG GTACGCACCT TCCCGTCCGT

 561 CCGGCAGTCC TCAGGCCTCT ACTCGCTGAG CAGCGTGGTG

 601 AGCGTGACCT CAAGCAGCCA GCCCGTCACC TGCAACGTGG

 641 CCCACCCAGC CACCAACACC AAAGTGGACA AGACCGTTGC

 681 GCCCTCGACA TGCAGCAAGC CCACGTGCCC ACCCCCTGAA

 721 CTCCTGGGGG GACCGTCTGT CTTCATCTTC CCCCCAAAAC

 761 CCAAGGACAC CCTCATGATC TCACGCACCC CCGAGGTCAC

 801 ATGCGTGGTG GTGGACGTGA GCCAGGATGA CCCCGAGGTG

 841 CAGTTCACAT GGTACATAAA CAACGAGCAG GTGCGCACCG

 881 CCCGGCCGCC GCTACGGGAG CAGCAGTTCA ACAGCACGAT

 921 CCGCGTGGTC AGCACCCTCC CCATCGCGCA CCAGGACTGG

 961 CTGAGGGGCA AGGAGTTCAA GTGCAAAGTC CACAACAAGG

1001 CACTCCCGGC CCCCATCGAG AAAACCATCT CCAAAGCCAG

1041 AGGGCAGCCC CTGGAGCCGA AGGTCTACAC CATGGGCCCT

1081 CCCCGGGAGG AGCTGAGCAG CAGGTCGGTC AGCCTGACCT

1121 GCATGATCAA CGGCTTCTAC CCTTCCGACA TCTCGGTGGA

1161 GTGGGAGAAG AACGGGAAGG CAGAGGACAA CTACAAGACC

1201 ACGCCGGCCG TGCTGGACAG CGACGGCTCC TACTTCCTCT
```

-continued

```
1241 ACAACAAGCT CTCAGTGCCC ACGAGTGAGT GGCAGCGGGG

1281 CGACGTCTTC ACCTGCTCCG TGATGCACGA GGCCTTGCAC

1321 AACCACTACA CGCAGAAGTC CATCTCCCGC TCTCCGGGTA

1361 AA
```

In another embodiment, the invention provides a 11G05 light chain that can bind to CD83 polypeptides. The amino acid sequence for this 11G05 light chain is provided below (SEQ ID NO:15).

```
  1 MDTRAPTQLL GLLLLWLPGA RCADVVMTQT PASVSAAVGG

 41 TVTINCQSSK NVYNNNWLSW FQQKPGQPPK LLIYYASTLA

 81 SGVPSRFRGS GSGTQFTLTI SDVQCDDAAT YYCAGDYSSS

121 SDNGFGGGTE VVVKGDPVAP TVLLFPPSSD EVATGTVTIV

161 CVANKYFPDV TVTWEVDGTT QTTGIENSKT PQNSADCTYN

201 LSSTLTLTST QYNSHKEYTC KVTQGTTSVV QSFSRKNC
```

A nucleic acid sequence for this 11G05 anti-CD83 light chain is provided below (SEQ ID NO:16).

```
  1 ATGGACACCA GGGCCCCCAC TCAGCTGCTG GGGCTCCTGC

 41 TGCTCTGGCT CCCAGGTGCC AGATGTGCCG ACGTCGTGAT

 81 GACCCAGACT CCAGCCTCCG TGTCTGCAGC TGTGGGAGGC

121 ACAGTCACCA TCAATTGCCA GTCCAGTAAG AATGTTTATA

161 ATAACAACTG GTTATCCTGG TTTCAGCAGA AACCAGGGCA

201 GCCTCCCAAG CTCCTGATCT ATTATGCATC CACTCTGGCA

241 TCTGGGGTCC CATCGCGGTT CAGAGGCAGT GGATCTGGGA

281 CACAGTTCAC TCTCACCATT AGCGACGTGC AGTGTGACGA

321 TGCTGCCACT TACTACTGTG CAGGCGATTA TAGTAGTAGT

361 AGTGATAATG GTTTCGGCGG AGGGACCGAG GTGGTGGTCA

401 AAGGTGATCC AGTTGCACCT ACTGTCCTCC TCTTCCCACC

441 ATCTAGCGAT GAGGTGGCAA CTGGAACAGT CACCATCGTG

481 TGTGTGGCGA ATAAATACTT TCCCGATGTC ACCGTCACCT

521 GGGAGGTGGA TGGCACCACC CAAACAACTG GCATCGAGAA

561 CAGTAAAACA CCGCAGAATT CTGCAGATTG TACCTACAAC

601 CTCAGCAGCA CTCTGACACT GACCAGCACA CAGTACAACA

641 GCCACAAAGA GTACACCTGC AAGGTGACCC AGGGCACGAC

681 CTCAGTCGTC CAGAGCTTCA GTAGGAAGAA CTGTTAA
```

In another embodiment, the invention provides a 11005 heavy chain that can bind to CD83 polypeptides. The amino acid sequence for this 11G05 heavy chain is provided below (SEQ ID NO:17).

```
  1 METGLRWLLL VAVLKGVQCQ SVEESGGRLV TPGTPLTLTC

 41 TVSGFTISDY DLSWVRQAPG EGLKYIGFIA IDGNPYYATW
```

-continued

```
 81 AKGRFTISKT STTVDLKITA PTTEDTATYF CARGAGDLWG

121 PGTLVTVSSG QPKAPSVFPL APCCGDTPSS TVTLGCLVKG

161 YLPEPVTVTW NSGTLTNGVR TFPSVRQSSG LYSLSSVVSV

201 TSSSQPVTCN VAHPATNTKV DKTVAPSTCS KPTCPPPELL

241 GGPSVFIFPP KPKDTLMISR TPEVTCVVVD VSQDDPEVQF

281 TWYINNEQVR TARPPLREQQ FNSTIRVVST LPIAHQDWLR

321 GKEFKCKVHN KALPAPIEKT ISKARGQPLE PKVYTMGPPR

361 EELSSRSVSL TCMINGFYPS DISVEWEKNG KAEDNYKTTP

401 AVLDSDGSYF LYNKLSVPTS EWQRGDVFTC SVMHEALHNH

441 YTQKSISRSP GK
```

A nucleic acid sequence for this 11G05 anti-CD83 heavy chain is provided below (SEQ ID NO:18).

```
   1 ATGGAGACAG GCCTGCGCTG GCTTCTCCTG GTCGCTGTGC

  41 TCAAAGGTGT CCAGTGTCAG TCGGTGGAGG AGTCCGGGGG

  81 TCGCCTGGTC ACGCCTGGGA CACCCCTGAC ACTCACCTGC

 121 ACAGTCTCTG GATTCACCAT CAGTGACTAC GACTTGAGCT

 161 GGGTCCGCCA GGCTCCAGGG GAGGGGCTGA AATACATCGG

 201 ATTCATTGCT ATTGATGGTA ACCCATACTA CGCGACCTGG

 241 GCAAAAGGCC GATTCACCAT CTCCAAAACC TCGACCACGG

 281 TGGATCTGAA AATCACCGCT CCGACAACCG AAGACACGGC

 321 CACGTATTTC TGTGCCAGAG GGGCAGGGGA CCTCTGGGGC

 361 CCAGGGACCC TCGTCACCGT CTCTTCAGGG CAACCTAAGG

 401 CTCCATCAGT CTTCCCACTG GCCCCCTGCT GCGGGGACAC

 441 ACCCTCTAGC ACGGTGACCT TGGGCTGCCT GGTCAAAGGC

 481 TACCTCCCGG AGCCAGTGAC CGTGACCTGG AACTCGGGCA

 521 CCCTCACCAA TGGGGTACGC ACCTTCCCGT CCGTCCGGCA

 561 GTCCTCAGGC CTCTACTCGC TGAGCAGCGT GGTGAGCGTG

 601 ACCTCAAGCA GCCAGCCCGT CACCTGCAAC GTGGCCCACC

 641 CAGCCACCAA CACCAAAGTG GACAAGACCG TTGCGCCCTC

 681 GACATGCAGC AAGCCCACGT GCCCACCCCC TGAACTCCTG

 721 GGGGGACCGT CTGTCTTCAT CTTCCCCCCA AAACCCAAGG

 761 ACACCCTCAT GATCTCACGC ACCCCCGAGG TCACATGCGT

 801 GGTGGTGGAC GTGAGCCAGG ATGACCCCGA GGTGCAGTTC

 841 ACATGGTACA TAAACAACGA GCAGGTGCGC ACCGCCCGGC

 881 CGCCGCTACG GGAGCAGCAG TTCAACAGCA CGATCCGCGT

 921 GGTCAGCACC CTCCCCATCG CGCACCAGGA CTGGCTGAGG

 961 GGCAAGGAGT TCAAGTGCAA AGTCCACAAC AAGGCACTCC

1001 CGGCCCCCAT CGAGAAAACC ATCTCCAAAG CCAGAGGGCA

1041 GCCCCTGGAG CCGAAGGTCT ACACCATGGG CCCTCCCCGG
```

-continued

```
1081 GAGGAGCTGA GCAGCAGGTC GGTCAGCCTG ACCTGCATGA

1120 TCAACGGCTT CTACCCTTCC GACATCTCGG TGGAGTGGGA

1161 GAAGAACGGG AAGGCAGAGG ACAACTACAA GACCACGCCG

1201 GCCGTGCTGG ACAGCGACGG CTCCTACTTC CTCTACAACA

1241 AGCTCTCAGT GCCCACGAGT GAGTGGCAGC GGGGCGACGT

1281 CTTCACCTGC TCCGTGATGC ACGAGGCCTT GCACAACCAC

1321 TACACGCAGA AGTCCATCTC CCGCTCTCCG GGTAAA
```

In another embodiment, the invention provides a 14C12 light chain that can bind to CD83 polypeptides. The amino acid sequence for this 14C12 light chain is provided below (SEQ ID NO:19).

```
  1 MDXRAPTQLL GLLLLWLPGA RCALVMTQTP ASVSAAVGGT

 41 VTINCQSSQS VYDNDELSWY QQKPGQPPKL LIYLASKLAS

 81 GVPSRFKGSG SGTQFALTIS GVQCDDAATY YCQATHYSSD

121 WYLTFGGGTE VVVKGDPVAP TVLLFPPSSD EVATGTVTIV

161 CVANKYFPDV TVTWEVDGTT QTTGIENSKT PQNSADCTYN

201 LSSTLTLTST QYNSHKEYTC KVTQGTTSVV QSFSRKNC
```

A nucleic acid sequence for this 14C12 anti-CD83 light chain is provided below (SEQ ID NO:20).

```
  1 ATGGACATRA GGGCCCCCAC TCAGCTGCTG GGGCTCCTGC

 41 TGCTCTGGCT CCCAGGTGCC AGATGTGCCC TTGTGATGAC

 81 CCAGACTCCA GCCTCCGTGT CTGCAGCTGT GGGAGGCACA

121 GTCACCATCA ATTGCCAGTC CAGTCAGAGT GTTTATGATA

161 ACGACGAATT ATCCTGGTAT CAGCAGAAAC CAGGGCAGCC

201 TCCCAAGCTC CTGATCTATC TGGCATCCAA GTTGGCATCT

241 GGGGTCCCAT CCCGATTCAA AGGCAGTGGA TCTGGGACAC

281 AGTTCGCTCT CACCATCAGC GGCGTGCAGT GTGACGATGC

321 TGCCACTTAC TACTGTCAAG CCACTCATTA TAGTAGTGAT

361 TGGTATCTTA CTTTCGGCGG AGGGACCGAG GTGGTGGTCA

401 AAGGTGATCC AGTTGCACCT ACTGTCCTCC TCTTCCCACC

441 ATCTAGCGAT GAGGTGGCAA CTGGAACAGT CACCATCGTG

481 TGTGTGGCGA ATAAATACTT TCCCGATGTC ACCGTCACCT

521 GGGAGGTGGA TGGCACCACC CAAACAACTG GCATCGAGAA

561 CAGTAAAACA CCGCAGAATT CTGCAGATTG TACCTACAAC

601 CTCAGCAGCA CTCTGACACT GACCAGCACA CAGTACAACA

641 GCCACAAAGA GTACACCTGC AAGGTGACCC AGGGCACGAC

681 CTCAGTCGTC CAGAGCTTCA GTAGGAAGAA CTGTTAA
```

In another embodiment, the invention provides a 14C12 heavy chain that can bind to CD83 polypeptides. The amino acid sequence for this 14C12 heavy chain is provided below (SEQ ID NO:21).

```
  1 METGLRWLLL VAVLKGVHCQ SVEESGGRLV TPGTPLTLTC
 41 TASGFSRSSY DMSWVRQAPG KGLEWVGVIS TAYNSHYASW
 81 AKGRFTISRT STTVDLKMTS LTTEDTATYF CARGGSWLDL
121 WGQGTLVTVS SGQPKAPSVF PLAPCCGDTP SSTVTLGCLV
161 KGYLPEPVTV TWNSGTLTNG VRTFPSVRQS SGLYSLSSVV
201 SVTSSSQPVT CNVAHPATNT KVDKTVAPST CSKPTCPPPE
241 LLGGPSVFIF PPKPKDTLMI SRTPEVTCVV VDVSQDDPEV
281 QFTWYINNEQ VRTARPPLRE QQFNSTIRVV STLPIAHQDW
321 LRGKEFKCKV HNKALPAPIE KTISKARGQP LEPKVYTMGP
361 PREELSSRSV SLTCMINGFY PSDISVEWEK NGKAEDNYKT
401 TPAVLDSDGS YFLYNKLSVP TSEWQRGDVF TCSVMHEALH
441 NHYTQKSISR SPGK
```

A nucleic acid sequence for this 14C12 anti-CD83 heavy chain is provided below (SEQ ID NO:22).

```
   1 ATGGAGACAG GCCTGCGCTG GCTTCTCCTG GTCGCTGTGC
  41 TCAAAGGTGT CCACTGTCAG TCGGTGGAGG AGTCCGGGGG
  81 TCGCCTGGTC ACGCCTGGGA CACCCCTGAC ACTCACCTGC
 121 ACAGCCTCTG GATTCTCCCG CAGCAGCTAC GACATGAGCT
 161 GGGTCCGCCA GGCTCCAGGG AAGGGGCTGG AATGGGTCGG
 201 AGTCATTAGT ACTGCTTATA ACTCACACTA CGCGAGCTGG
 241 GCAAAAGGCC GATTCACCAT CTCCAGAACC TCGACCACGG
 281 TGGATCTGAA AATGACCAGT CTGACAACCG AAGACACGGC
 321 CACCTATTTC TGTGCCAGAG GGGGTAGTTG GTTGGATCTC
 361 TGGGGCCAGG GCACCCTGGT CACCGTCTCC TCAGGGCAAC
 401 CTAAGGCTCC ATCAGTCTTC CCACTGGCCC CCTGCTGCGG
 441 GGACACACCC TCTAGCACGG TGACCTTGGG CTGCCTGGTC
 481 AAAGGCTACC TCCCGGAGCC AGTGACCGTG ACCTGGAACT
 521 CGGGCACCCT CACCAATGGG GTACGCACCT TCCCGTCCGT
 561 CCGGCAGTCC TCAGGCCTCT ACTCGCTGAG CAGCGTGGTG
 601 AGCGTGACCT CAAGCAGCCA GCCCGTCACC TGCAACGTGG
 641 CCCACCCAGC CACCAACACC AAAGTGGACA AGACCGTTGC
 681 GCCCTCGACA TGCAGCAAGC CCACGTGCCC ACCCCCTGAA
 721 CTCCTGGGGG GACCGTCTGT CTTCATCTTC CCCCCAAAAC
 761 CCAAGGACAC CCTCATGATC TCACGCACCC CCGAGGTCAC
 801 ATGCGTGGTG GTGGACGTGA GCCAGGATGA CCCCGAGGTG
 841 CAGTTCACAT GGTACATAAA CAACGAGCAG GTGCGCACCG
 881 CCCGGCCGCC GCTACGGGAG CAGCAGTTCA ACAGCACGAT
 921 CCGCGTGGTC AGCACCCTCC CCATCGCGCA CCAGGACTGG
 961 CTGAGGGGCA AGGAGTTCAA GTGCAAAGTC CACAACAAGG
1001 CACTCCCGGC CCCCATCGAG AAAACCATCT CCAAAGCCAG
```

-continued

```
1041 AGGGCAGCCC CTGGAGCCGA AGGTCTACAC CATGGGCCCT
1081 CCCCGGGAGG AGCTGAGCAG CAGGTCGGTC AGCCTGACCT
1121 GCATGATCAA CGGCTTCTAC CCTTCCGACA TCTCGGTGGA
1161 GTGGGAGAAG AACGGGAAGG CAGAGGACAA CTACAAGACC
1200 ACGCCGGCCG TGCTGGACAG CGACGGCTCC TACTTCCTCT
1241 ACAACAAGCT CTCAGTGCCC ACGAGTGAGT GGCAGCGGGG
1281 CGACGTCTTC ACCTGCTCCG TGATGCACGA GGCCTTGCAC
1321 AACCACTACA CGCAGAAGTC CATCTCCCGC TCTCCGGGTA
1361 AA
```

In another embodiment, the invention provides a M83 020B08L light chain that can bind to CD83 polypeptides. The amino acid sequence for this M83 020B08L light chain is provided below (SEQ ID NO:58).

```
  1 MDMRAPTQLL GLLLLWLPGA RCAYDMTQTP ASVEVAVGGT
 41 VTIKCQASQS ISTYLDWYQQ KPGQPPKLLI YDASDLASGV
 81 PSRFKGSGSG TQFTLTISDL ECADAATYYC QQGYTHSNVD
121 NVFGGGTEVV VKGDPVAPTV LLFPPSSDEV ATGTVTIVCV
161 ANKYFPDVTV TWEVDGTTQT TGIENSKTPQ NSADCTYNLS
201 STLTLTSTQY NSHKEYTCKV TQGTTSVVQS FSRKNC
```

A nucleic acid sequence for this M83 020B08L anti-CD83 light chain is provided below (SEQ ID NO:59).

```
  1 ATGGACATGA GGGCCCCCAC TCAGCTGCTG GGGCTCCTGC
 41 TGCTCTGGCT CCCAGGTGCC AGATGTGCCT ATGATATGAC
 81 CCAGACTCCA GCCTCTGTGG AGGTAGCTGT GGGAGGCACA
121 GTCACCATCA AGTGCCAGGC CAGTCAGAGC ATTAGTACCT
161 ACTTAGACTG GTATCAGCAG AAACCAGGGC AGCCTCCCAA
201 GCTCCTGATC TATGATGCAT CCGATCTGGC ATCTGGGGTC
241 CCATCGCGGT TCAAAGGCAG TGGATCTGGG ACACAGTTCA
281 CTCTCACCAT CAGCGACCTG GAGTGTGCCG ATGCTGCCAC
321 TTACTACTGT CAACAGGGTT ATACACATAG TAATGTTGAT
361 AATGTTTTCG GCGGAGGGAC CGAGGTGGTG GTCAAAGGTG
401 ATCCAGTTGC ACCTACTGTC CTCCTCTTCC CACCATCTAG
441 CGATGAGGTG GCAACTGGAA CAGTCACCAT CGTGTGTGTG
481 GCGAATAAAT ACTTTCCCGA TGTCACCGTC ACCTGGGAGG
521 TGGATGGCAC CACCCAAACA ACTGGCATCG AGAACAGTAA
561 AACACCGCAG AATTCTGCAG ATTGTACCTA CAACCTCAGC
601 AGCACTCTGA CACTGACCAG CACACAGTAC AACAGCCACA
641 AAGAGTACAC CTGCAAGGTG ACCCAGGGCA CGACCTCAGT
681 CGTCCAGAGC TTCAGTAGGA AGAACTGTTA A
```

In another embodiment, the invention provides a M83 020B08H heavy chain that can bind to CD83 polypeptides.

The amino acid sequence for this M83 020B08H heavy chain is provided below (SEQ ID NO:60).

```
  1 METGLRWLLL VAVLKGVQCQ SVEESGGRLV TPGTPLTLTC
 41 TVSGFSLSSY DMTWVRQAPG KGLEWIGIIY ASGTTYYANW
 81 AKGRFTISKT STTVDLKVTS PTIGDTATYF CAREGAGVSM
121 TLWGPGTLVT VSSGQPKAPS VFPLAPCCGD TPSSTVTLGC
161 LVKGYLPEPV TVTWNSGTLT NGVRTFPSVR QSSGLYSLSS
201 VVSVTSSSQP VTCNVAHPAT NTKVDKTVAP STCSKPTCPP
241 PELLGGPSVF IFPPKPKDTL MISRTPEVTC VVVDVSQDDP
281 EVQFTWYINN EQVRTARPPL REQQFNSTIR VVSTLPIAHQ
321 DWLRGKEFKC KVHNKALPAP IEKTISKARG QPLEPKVYTM
361 GPPREELSSR SVSLTCMING FYPSDISVEW EKNGKAEDNY
401 KTTPAVLDSD GSYFLYNKLS VPTSEWQRGD VFTCSVMHEA
441 LHNHYTQKSI SRSPGK
```

A nucleic acid sequence for this M83 020B08H anti-CD83 heavy chain is provided below (SEQ ID NO:61).

```
   1 ATGGAGACAG GCCTGCGCTG GCTTCTCCTG GTCGCTGTGC
  41 TCAAAGGTGT CCAGTGTCAG TCGGTGGAGG AGTCCGGGGG
  81 TCGCCTGGTC ACGCCTGGGA CACCCCTGAC ACTCACCTGC
 121 ACAGTCTCTG GATTCTCCCT CAGCAGCTAC GACATGACCT
 161 GGGTCCGCCA GGCTCCAGGG AAGGGGCTGG AATGGATCGG
 201 AATCATTTAT GCTAGTGGTA CCACATACTA CGCGAACTGG
 241 GCGAAAGGCC GATTCACCAT CTCCAAAACC TCGACCACGG
 281 TGGATCTGAA AGTCACCAGT CCGACAATCG GGGACACGGC
 321 CACCTATTTC TGTGCCAGAG AGGGGGCTGG TGTTAGTATG
 361 ACCTTGTGGG GCCCAGGCAC CCTGGTCACC GTCTCCTCAG
 401 GGCAACCTAA GGCTCCATCA GTCTTCCCAC TGGCCCCCTG
 441 CTGCGGGGAC ACACCCTCTA GCACGGTGAC CTTGGGCTGC
 481 CTGGTCAAAG GCTACCTCCC GGAGCCAGTG ACCGTGACCT
 521 GGAACTCGGG CACCCTCACC AATGGGGTAC GCACCTTCCC
 561 GTCCGTCCGG CAGTCCTCAG GCCTCTACTC GCTGAGCAGC
 601 GTGGTGAGCG TGACCTCAAG CAGCCAGCCC GTCACCTGCA
 641 ACGTGGCCCA CCCAGCCACC AACACCAAAG TGGACAAGAC
 681 CGTTGCGCCC TCGACATGCA GCAAGCCCAC GTGCCCACCC
 721 CCTGAACTCC TGGGGGGACC GTCTGTCTTC ATCTTCCCCC
 761 CAAAACCCAA GGACACCCTC ATGATCTCAC GCACCCCCGA
 801 GGTCACATGC GTGGTGGTGG ACGTGAGCCA GGATGACCCC
 841 GAGGTGCAGT TCACATGGTA CATAAACAAC GAGCAGGTGC
 881 GCACCGCCCG GCCGCCGCTA CGGGAGCAGC AGTTCAACAG
 921 CACGATCCGC GTGGTCAGCA CCCTCCCCAT CGCGCACCAG
 961 GACTGGCTGA GGGGCAAGGA GTTCAAGTGC AAAGTCCACA
```

-continued

```
1001 ACAAGGCACT CCCGGCCCCC ATCGAGAAAA CCATCTCCAA
1041 AGCCAGAGGG CAGCCCCTGG AGCCGAAGGT CTACACCATG
1081 GGCCCTCCCC GGGAGGAGCT GAGCAGCAGG TCGGTCAGCC
1121 TGACCTGCAT GATCAACGGC TTCTACCCTT CCGACATCTC
1161 GGTGGAGTGG GAGAAGAACG GGAAGGCAGA GGACAACTAC
1201 AAGACCACGC CGGCCGTGCT GGACAGCGAC GGCTCCTACT
1241 TCCTCTACAA CAAGCTCTCA GTGCCCACGA GTGAGTGGCA
1281 GCGGGGCGAC GTCTTCACCT GCTCCGTGAT GCACGAGGCC
1321 TTGCACAACC ACTACACGCA GAAGTCCATC TCCCGCTCTC
1361 CGGGTAAA
```

In another embodiment, the invention provides a M83 006G05L light chain that can bind to CD83 polypeptides. The amino acid sequence for this M83 006G05L light chain is provided below (SEQ ID NO:62).

```
  1 MDMRAPTQLL GLLLLWLPGA RCAYDMTQTP ASVEVAVGGT
 41 VAIKCQASQS VSSYLAWYQQ KPGQPPKPLI YEASMLAAGV
 81 SSRFKGSGSG TDFTLTISDL ECDDAATYYC QQGYSISDID
121 NAFGGGTEVV VKGDPVAPTV LLFPPSSDEV ATGTVTIVCV
161 ANKYFPDVTV TWEVDGTTQT TGIENSKTPQ NSADCTYNLS
201 STLTLTSTQY NSHKEYTCKV TQGTTSVVQS FSRKNC
```

A nucleic acid sequence for M83 006G05L anti-CD83 light chain is provided below (SEQ ID NO:63).

```
  1 ATGGACATGA GGGCCCCCAC TCAACTGCTG GGGCTCCTGC
 41 TGCTCTGGCT CCCAGGTGCC AGATGTGCCT ATGATATGAC
 81 CCAGACTCCA GCCTCTGTGG AGGTAGCTGT GGGAGGCACA
121 GTCGCCATCA AGTGCCAGGC CAGTCAGAGC GTTAGTAGTT
161 ACTTAGCCTG GTATCAGCAG AAACCAGGGC AGCCTCCCAA
201 GCCCCTGATC TACGAAGCAT CCATGCTGGC GGCTGGGGTC
241 TCATCGCGGT TCAAAGGCAG TGGATCTGGG ACAGACTTCA
281 CTCTCACCAT CAGCGACCTG GAGTGTGACG ATGCTGCCAC
321 TTACTATTGT CAACAGGGTT ATTCTATCAG TGATATTGAT
361 AATGCTTTCG GCGGAGGGAC CGAGGTGGTG GTCAAAGGTG
401 ATCCAGTTGC ACCTACTGTC CTCCTCTTCC CACCATCTAG
441 CGATGAGGTG GCAACTGGAA CAGTCACCAT CGTGTGTGTG
481 GCGAATAAAT ACTTTCCCGA TGTCACCGTC ACCTGGGAGG
521 TGGATGGCAC CACCCAAACA ACTGGCATCG AGAACAGTAA
561 AACACCGCAG AATTCTGCAG ATTGTACCTA CAACCTCAGC
601 AGCACTCTGA CACTGACCAG CACACAGTAC AACAGCCACA
641 AAGAGTACAC CTGCAAGGTG ACCCAGGGCA CGACCTCAGT
681 CGTCCAGAGC TTCAGTAGGA AGAACTGTTA A
```

In another embodiment, the invention provides a M83 006G05L heavy chain that can bind to CD83 polypeptides. The amino acid sequence for this M83 006G05L heavy chain is provided below (SEQ ID NO:64).

```
  1 METGLRWLLL VAVLKGVQCQ SVEESGGRLV SPGTPLTLTC
 41 TASGFSLSSY DMSWVRQAPG KGLEYIGIIS SSGSTYYASW
 81 AKGRFTISKT STTVDLEVTS LTTEDTATYF CSREHAGYSG
121 DTGHLWGPGT LVTVSSGQPK APSVFPLAPC CGDTPSSTVT
161 LGCLVKGYLP EPVTVTWNSG TLTNGVRTFP SVRQSSGLYS
201 LSSVVSVTSS SQPVTCNVAH PATNTKVDKT VAPSTCSKPT
241 CPPPELLGGP SVFIFPPKPK DTLMISRTPE VTCVVVDVSQ
281 DDPEVQFTWY INNEQVRTAR PPLREQQFNS TIRVVSTLPI
321 AHQDWLRGKE FKCKVHNKAL PAPIEKTISK ARGQPLEPKV
361 YTMGPPREEL SSRSVSLTCM INGFYPSDIS VEWEKNGKAE
401 DNYKTTPAVL DSDGSYFLYN KLSVPTSEWQ RGDVFTCSVM
441 HEALHNHYTQ KSISRSPGK
```

A nucleic acid sequence for this M83 006G05L anti-CD83 heavy chain is provided below (SEQ ID NO:65).

```
   1 ATGGAGACAG GCCTGCGCTG GCTTCTCCTG GTCGCTGTGC
  41 TCAAAGGTGT CCAGTGTCAG TCGGTGGAGG AGTCCGGGGG
  81 TCGCCTGGTC TCGCCTGGGA CACCCCTGAC ACTCACCTGC
 121 ACAGCCTCTG GATTCTCCCT CAGTAGCTAC GACATGAGCT
 161 GGGTCCGCCA GGCTCCAGGG AAGGGGCTGG AATACATCGG
 201 AATCATTAGT AGTAGTGGTA GCACATACTA CGCGAGCTGG
 241 GCGAAAGGCC GATTCACCAT CTCCAAAACC TCGACCACGG
 281 TGGATCTGGA AGTGACCAGT CTGACAACCG AGGACACGGC
 321 CACCTATTTC TGTAGTAGAG AACATGCTGG TTATAGTGGT
 361 GATACGGGTC ACTTGTGGGG CCCAGGCACC CTGGTCACCG
 401 TCTCCTCGGG GCAACCTAAG GCTCCATCAG TCTTCCCACT
 441 GGCCCCCTGC TGCGGGGACA CACCCTCTAG CACGGTGACC
 481 TTGGGCTGCC TGGTCAAAGG CTACCTCCCG GAGCCAGTGA
 521 CCGTGACCTG GAACTCGGGC ACCCTCACCA ATGGGGTACG
 561 CACCTTCCCG TCCGTCCGGC AGTCCTCAGG CCTCTACTCG
 601 CTGAGCAGCG TGGTGAGCGT GACCTCAAGC AGCCAGCCCG
 641 TCACCTGCAA CGTGGCCCAC CCAGCCACCA ACACCAAAGT
 681 GGACAAGACC GTTGCGCCCT CGACATGCAG CAAGCCCACG
 721 TGCCCACCCC CTGAACTCCT GGGGGGACCG TCTGTCTTCA
 761 TCTTCCCCCC AAAACCCAAG GACACCCTCA TGATCTCACG
 801 CACCCCCGAG GTCACATGCG TGGTGGTGGA CGTGAGCCAG
 841 GATGACCCCG AGGTGCAGTT CACATGGTAC ATAAACAACG
 881 AGCAGGTGCG CACCGCCCGG CCGCCGCTAC GGGAGCAGCA
```

-continued

```
 921 GTTCAACAGC ACGATCCGCG TGGTCAGCAC CCTCCCCATC
 961 GCGCACCAGG ACTGGCTGAG GGGCAAGGAG TTCAAGTGCA
1001 AAGTCCACAA CAAGGCACTC CCGGCCCCCA TCGAGAAAAC
1041 CATCTCCAAA GCCAGAGGGC AGCCCCTGGA GCCGAAGGTC
1081 TACACCATGG GCCCTCCCCG GGAGGAGCTG AGCAGCAGGT
1121 CGGTCAGCCT GACCTGCATG ATCAACGGCT TCTACCCTTC
1162 CGACATCTCG GTGGAGTGGG AGAAGAACGG GAAGGCAGAG
1201 GACAACTACA AGACCACGCC GGCCGTGCTG GACAGCGACG
1241 GCTCCTACTT CCTCTACAAC AAGCTCTCAG TGCCCACGAG
1281 TGAGTGGCAG CGGGGCGACG TCTTCACCTG CTCCGTGATG
1321 CACGAGGCCT TGCACAACCA CTACACGCAG AAGTCCATCT
1361 CCCGCTCTCC GGGTAAA
```

In another embodiment, the invention provides a 96G08 light chain that can bind to CD83 polypeptides and can inhibit proliferation of human peripheral blood mononuclear cells (PBMCs). The amino acid sequence for this 96G08 light chain is provided below (SEQ ID NO:70).

```
  1 MDTRAPTQLL GLLLLWLPGA TFAQVLTQTA SPVSAPVGGT
 41 VTINCQSSQS VYNNDFLSWY QQKPGQPPKL LIYYASTLAS
 81 GVPSRFKGSG SGTQFTLTIS DLECDDAATY YCTGTYGNSA
121 WYEDAFGGGT EVVVKRTPVA PTVLLFPPSS AELATGTATI
161 VCVANKYFPD GTVTWKVDGI TQSSGINNSR TPQNSADCTY
201 NLSSTLTLSS DEYNSHDEYT CQVAQDSGSP VVQSFSRKSC
```

The amino acid sequence for this 96G08 light chain with the CDR regions identified by underlining is provided below (SEQ ID NO:70).

```
  1 MDTRAPTQLL GLLLLWLPGA TFAQVLTQTA SPVSAPVGGT
 41 VTINCQSSQS VYNNDFLSWY QQKPGQPPKL LIYYASTLAS
 81 GVPSRFKGSG SGTQFTLTIS DLECDDAATY YCTGTYGNSA
121 WYEDAFGGGT EVVVKRTPVA PTVLLFPPSS AELATGTATI
161 VCVANKYFPD GTVTWKVDGI TQSSGINNSR TPQNSADCTY
201 NLSSTLTLSS DEYNSHDEYT CQVAQDSGSP VVQSFSRKSC
```

Hence, the CDR regions in the 96G08 light chain include amino acid sequences QSSQSVYNNDFLS (SEQ ID NO:71), YASTLAS (SEQ ID NO:72), and TGTYGNSAWYEDA (SEQ ID NO:73).

A nucleic acid sequence for this 96G08 anti-CD83 light chain is provided below (SEQ ID NO:74).

```
  1 ATGGACACGA GGGCCCCCAC TCAGCTGCTG GGGCTCCTGC
 41 TGCTCTGGCT CCCAGGTGCC ACATTTGCGC AAGTGCTGAC
 81 CCAGACTGCA TCGCCCGTGT CTGCACCTGT GGGAGGCACA
121 GTCACCATCA ATTGCCAGTC CAGTCAGAGT GTTTATAATA
```

-continued

```
161 ACGACTTCTT ATCCTGGTAT CAGCAGAAAC CAGGGCAGCC
201 TCCCAAACTC CTGATCTATT ATGCATCCAC TCTGGCATCT
241 GGGGTCCCAT CCCGGTTCAA AGGCAGTGGA TCTGGGACAC
281 AGTTCACTCT CACCATCAGC GACCTGGAGT GTGACGATGC
321 TGCCACTTAC TACTGTACAG GCACTTATGG TAATAGTGCT
361 TGGTACGAGG ATGCTTTCGG CGGAGGGACC GAGGTGGTGG
401 TCAAACGTAC GCCAGTTGCA CCTACTGTCC TCCTCTTCCC
441 ACCATCTAGC GCTGAGCTGG CAACTGGAAC AGCCACCATC
481 GTGTGCGTGG CGAATAAATA CTTTCCCGAT GGCACCGTCA
521 CCTGGAAGGT GGATGGCATC ACCCAAAGCA GCGGCATCAA
561 TAACAGTAGA ACACCGCAGA ATTCTGCAGA TTGTACCTAC
601 AACCTCAGCA GTACTCTGAC ACTGAGCAGC GACGAGTACA
641 ACAGCCACGA CGAGTACACC TGCCAGGTGG CCCAGGACTC
681 AGGCTCACCG GTCGTCCAGA GCTTCAGTAG GAAGAGCTGT
721 TAG
```

This nucleic acid sequence for the 96G08 anti-CD83 light chain with CDR regions identified by underlining is provided below (SEQ ID NO:99).

```
  1 ATGGACACGA GGGCCCCCAC TCAGCTGCTG GGGCTCCTGC
 41 TGCTCTGGCT CCCAGGTGCC ACATTTGCGC AAGTGCTGAC
 81 CCAGACTGCA TCGCCCGTGT CTGCACCTGT GGGAGGCACA
121 GTCACCATCA ATTGCCAGTC CAGTCAGAGT GTTTATAATA
161 ACGACTTCTT ATCCTGGTAT CAGCAGAAAC CAGGGCAGCC
201 TCCCAAACTC CTGATCTATT ATGCATCCAC TCTGGCATCT
241 GGGGTCCCAT CCCGGTTCAA AGGCAGTGGA TCTGGGACAC
281 AGTTCACTCT CACCATCAGC GACCTGGAGT GTGACGATGC
321 GCCACTTACT ACTGTACAGG CACTTATGGT AATAGTGCTT
361 GGTACGAGGA TGCTTTCGGC GGAGGGACCG AGGTGGTGGT
401 CAAACGTACG CCAGTTGCAC CTACTGTCCT CCTCTTCCCA
441 CCATCTAGCG CTGAGCTGGC AACTGGAACA GCCACCATCG
481 TGTGCGTGGC GAATAAATAC TTTCCCGATG GCACCGTCAC
521 CTGGAAGGTG GATGGCATCA CCCAAAGCAG CGGCATCAAT
561 AACAGTAGAA CACCGCAGAA TTCTGCAGAT TGTACCTACA
601 ACCTCAGCAG TACTCTGACA CTGAGCAGCG ACGAGTACAA
641 CAGCCACGAC GAGTACACCT GCCAGGTGGC CCAGGACTCA
681 GGCTCACCGG TCGTCCAGAG CTTCAGTAGG AAGAGCTGTT
```

Hence, the CDR regions in the 96G08 light chain include nucleic acid sequences CAGTCCAGTCAGAGTGTT-TATAATA (SEQ ID NO:75), ATGCATCCACTCTG-GCATCT (SEQ ID NO:76), and ACAGGCACTTATGGT AATAGTGCTT (SEQ ID NO:77).

In another embodiment, the invention provides a 96G08 heavy chain that can bind to CD83 polypeptides and can inhibit proliferation of human peripheral blood mononuclear cells (PBMCs). The amino acid sequence for this 96G08 heavy chain is provided below (SEQ ID NO:78).

```
  1 METGLRWLLL VAVLKGVQCQ SVEESGGRLV TPGTPLTLTC
 41 TVSGIDLSSD GISWVRQAPG KGLEWIGIIS SGGNTYYASW
 81 AKGRFTISRT STTVDLKMTS LTTEDTATYF CARVVGGTYS
121 IWGQGTLVTV SSASTKGPSV YPLAPGSAAQ TNSMVTLGCL
161 VKGYFPEPVT VTWNSGSLSS GVHTFPAVLQ SDLYTLSSSV
201 TVPSSTWPSE TVTCNVAHPA SSTKVDKKIV PRDCGCKPCI
241 CTVPEVSSVF IFPPKPKDVL TITLTPKVTC VVVDISKDDP
281 EVQFSWFVDD VEVHTAQTQP REEQFNSTFR SVSELPIMHQ
321 DWLNGKEFKC RVNSAAFPAP IEKTISKTKG RPKAPQVYTI
361 PPPKEQMAKD KVSLTCMITD FFPEDITVEW QWNGQPAENY
401 KNTQPIMDTD GSYFVYSKLN VQKSNWEAGN TFTCSVLHEG
441 LHNHHTEKSL SHSPGK
```

The amino acid sequence for the 96G08 heavy chain with the CDR regions identified by underlining is provided below (SEQ ID NO:78).

```
  1 METGLRWLLL VAVLKGVQCQ SVEESGGRLV TPGTPLTLTC
 41 TVSGIDLSSD GISWVRQAPG KGLEWIGIIS SGGNTYYASW
 81 AKGRFTISRT STTVDLKMTS LTTEDTATYF CARVVGGTYS
121 IWGQGTLVTV SSASTKGPSV YPLAPGSAAQ TNSMVTLGCL
161 VKGYFPEPVT VTWNSGSLSS GVHTFPAVLQ SDLYTLSSSV
201 TVPSSTWPSE TVTCNVAHPA SSTKVDKKIV PRDCGCKPCI
241 CTVPEVSSVF IFPPKPKDVL TITLTPKVTC VVVDISKDDP
281 EVQFSWFVDD VEVHTAQTQP REEQFNSTFR SVSELPIMHQ
321 DWLNGKEFKC RVNSAAFPAP IEKTISKTKG RPKAPQVYTI
361 PPPKEQMAKD KVSLTCMITD FFPEDITVEW QWNGQPAENY
401 KNTQPIMDTD GSYFVYSKLN VQKSNWEAGN TFTCSVLHEG
441 LHNHHTEKSL SHSPGK
```

Hence, the CDR regions in the 96G08 heavy chain include amino acid sequences SDGIS (SEQ ID NO:79), IISSGGN-TYYASWAKG (SEQ ID NO:80) and VVGGTYSI (SEQ ID NO:81).

A nucleic acid sequence for the 96G08 anti-CD83 heavy chain is provided below (SEQ ID NO:82).

```
  1 ATGGAGACTG GGCTGCGCTG GCTTCTCCTG GTCGCTGTGC
 41 TCAAAGGTGT CCAGTGTCAG TCGGTGGAGG AGTCCGGGGG
 81 TCGCCTGGTC ACACCTGGGA CACCCCTGAC ACTCACCTGC
121 ACAGTGTCTG GAATCGACCT CAGTAGCGAT GGAATAAGCT
161 GGGTCCGCCA GGCTCCAGGG AAGGGGCTGG AATGGATCGG
```

-continued

```
 201 AATCATTAGT AGTGGTGGTA ACACATACTA CGCGAGCTGG
 241 GCAAAAGGCC GATTCACCAT CTCCAGAACC TCGACCACGG
 281 TGGATCTGAA GATGACCAGT CTGACAACCG AGGACACGGC
 321 CACCTATTTC TGTGCCAGAG TTGTTGGTGG TACTTATAGC
 361 ATCTGGGGCC AGGGCACCCT CGTCACCGTC TCGAGCGCTT
 401 CTACAAAGGG CCCATCTGTC TATCCACTGG CCCCTGGATC
 441 TGCTGCCCAA ACTAACTCCA TGGTGACCCT GGGATGCCTG
 481 GTCAAGGGCT ATTTCCCTGA GCCAGTGACA GTGACCTGGA
 521 ACTCTGGATC CCTGTCCAGC GGTGTGCACA CCTTCCCAGC
 561 TGTCCTGCAG TCTGACCTCT ACACTCTGAG CAGCTCAGTG
 601 ACTGTCCCCT CCAGCACCTG GCCCAGCGAG ACCGTCACCT
 641 GCAACGTTGC CCACCCGGCC AGCAGCACCA AGGTGGACAA
 681 GAAAATTGTG CCCAGGGATT GTGGTTGTAA GCCTTGCATA
 721 TGTACAGTCC CAGAAGTATC ATCTGTCTTC ATCTTCCCCC
 761 CAAAGCCCAA GGATGTGCTC ACCATTACTC TGACTCCTAA
 801 GGTCACGTGT GTTGTGGTAG ACATCAGCAA GGATGATCCC
 841 GAGGTCCAGT TCAGCTGGTT TGTAGATGAT GTGGAGGTGC
 881 ACACAGCTCA GACGCAACCC CGGGAGGAGC AGTTCAACAG
 921 CACTTTCCGC TCAGTCAGTG AACTTCCCAT CATGCACCAG
 961 GACTGGCTCA ATGGCAAGGA GTTCAAATGC AGGGTCAACA
1001 GTGCAGCTTT CCCTGCCCCC ATCGAGAAAA CCATCTCCAA
1041 AACCAAAGGC AGACCGAAGG CTCCACAGGT GTACACCATT
1081 CCACCTCCCA AGGAGCAGAT GGCCAAGGAT AAAGTCAGTC
1121 TGACCTGCAT GATAACAGAC TTCTTCCCTG AAGACATTAC
1161 TGTGGAGTGG CAGTGGAATG GGCAGCCAGC GGAGAACTAC
1201 AAGAACACTC AGCCCATCAT GGACACAGAT GGCTCTTACT
1241 TCGTCTACAG CAAGCTCAAT GTGCAGAAGA GCAACTGGGA
1281 GGCAGGAAAT ACTTTCACCT GCTCTGTGTT ACATGAGGGC
1321 CTGCACAACC ACCATACTGA GAAGAGCCTC TCCCACTCTC
1361 CTGGTAAATG A
```

The nucleic acid sequence for the 96G08 anti-CD83 heavy chain with CDR regions identified by underlining is provided below is provided below (SEQ ID NO:82).

```
   1 ATGGAGACTG GGCTGCGCTG GCTTCTCCTG GTCGCTGTGC
  41 TCAAAGGTGT CCAGTGTCAG TCGGTGGAGG AGTCCGGGGG
  81 TCGCCTGGTC ACACCTGGGA CACCCCTGAC ACTCACCTGC
 121 ACAGTGTCTG GAATCGACCT CAGTAGCGAT GGAATAAGCT
 161 GGGTCCGCCA GGCTCCAGGG AAGGGGCTGG AATGGATCGG
 201 AATCATTAGT AGTGGTGGTA ACACATACTA CGCGAGCTGG
 241 GCAAAAGGCC GATTCACCAT CTCCAGAACC TCGACCACGG
```

-continued

```
 281 TGGATCTGAA GATGACCAGT CTGACAACCG AGGACACGGC
 321 CACCTATTTC TGTGCCAGAG TTGTTGGTGG TACTTATAGC
 361 ATCTGGGGCC AGGGCACCCT CGTCACCGTC TCGAGCGCTT
 401 CTACAAAGGG CCCATCTGTC TATCCACTGG CCCCTGGATC
 441 TGCTGCCCAA ACTAACTCCA TGGTGACCCT GGGATGCCTG
 481 GTCAAGGGCT ATTTCCCTGA GCCAGTGACA GTGACCTGGA
 521 ACTCTGGATC CCTGTCCAGC GGTGTGCACA CCTTCCCAGC
 561 TGTCCTGCAG TCTGACCTCT ACACTCTGAG CAGCTCAGTG
 601 ACTGTCCCCT CCAGCACCTG GCCCAGCGAG ACCGTCACCT
 641 GCAACGTTGC CCACCCGGCC AGCAGCACCA AGGTGGACAA
 681 GAAAATTGTG CCCAGGGATT GTGGTTGTAA GCCTTGCATA
 721 TGTACAGTCC CAGAAGTATC ATCTGTCTTC ATCTTCCCCC
 761 CAAAGCCCAA GGATGTGCTC ACCATTACTC TGACTCCTAA
 801 GGTCACGTGT GTTGTGGTAG ACATCAGCAA GGATGATCCC
 841 GAGGTCCAGT TCAGCTGGTT TGTAGATGAT GTGGAGGTGC
 881 ACACAGCTCA GACGCAACCC CGGGAGGAGC AGTTCAACAG
 921 CACTTTCCGC TCAGTCAGTG AACTTCCCAT CATGCACCAG
 961 GACTGGCTCA ATGGCAAGGA GTTCAAATGC AGGGTCAACA
1001 GTGCAGCTTT CCCTGCCCCC ATCGAGAAAA CCATCTCCAA
1041 AACCAAAGGC AGACCGAAGG CTCCACAGGT GTACACCATT
1081 CCACCTCCCA AGGAGCAGAT GGCCAAGGAT AAAGTCAGTC
1121 TGACCTGCAT GATAACAGAC TTCTTCCCTG AAGACATTAC
1161 TGTGGAGTGG CAGTGGAATG GGCAGCCAGC GGAGAACTAC
1201 AAGAACACTC AGCCCATCAT GGACACAGAT GGCTCTTACT
1241 TCGTCTACAG CAAGCTCAAT GTGCAGAAGA GCAACTGGGA
1281 GGCAGGAAAT ACTTTCACCT GCTCTGTGTT ACATGAGGGC
1321 CTGCACAACC ACCATACTGA GAAGAGCCTC TCCCACTCTC
1361 CTGGTAAATG A
```

Hence, the CDR regions in the 96G08 anti-CD83 heavy chain include

```
                                            (SEQ ID NO: 83)
AGCGATGGAATAAGC,

                                            (SEQ ID NO: 84)
ATCATTAGTAGTGGTGGTAACACATACTACGCGAGCTGGGCAAAAGGC,
and

                                            (SEQ ID NO: 85)
GTTGTTGGTGG TACTTATAGC ATC.
```

In another embodiment, the invention provides a 95F04 light chain that can bind to CD83 polypeptides and can inhibit proliferation of human peripheral blood mononuclear cells (PBMCs). The amino acid sequence for this 95F04 light chain is provided below (SEQ ID NO:86).

```
1 MDTRAPTQLL GLLLLWLPGA TFAQAVVTQT TSPVSAPVGG
41 TVTINCQSSQ SVYGNNELSW YQQKPGQPPK LLIYQASSLA
81 SGVPSRFKGS GSGTQFTLTI SDLECDDAAT YYCLGEYSIS
121 ADNHFGGGTE VVVKRTPVAP TVLLFPPSSA ELATGTATIV
161 CVANKYFPDG TVTWKVDGIT QSSGINNSRT PQNSADCTYN
201 LSSTLTLSSD EYNSHDEYTC QVAQDSGSPV VQSFSRKSC
```

The amino acid sequence for the 95F04 anti-CD83 light chain with the CDR regions identified by underlining is provided below (SEQ ID NO:86).

```
1 MDTRAPTQLL GLLLLWLPGA TFAQAVVTQT TSPVSAPVGG
41 TVTINCQSSQ SVYGNNELSW YQQKPGQPPK LLIYQASSLA
81 SGVPSRFKGS GSGTQFTLTI SDLECDDAAT YYCLGEYSIS
121 ADNHFGGGTE VVVKRTPVAP TVLLFPPSSA ELATGTATIV
161 CVANKYFPDG TVTWKVDGIT QSSGINNSRT PQNSADCTYN
201 LSSTLTLSSD EYNSHDEYTC QVAQDSGSPV VQSFSRKSC
```

Hence, the CDR regions in the 95F04 anti-CD83 light chain include amino acid sequences QSSQSVYGNNELS (SEQ ID NO:87), QASSLAS (SEQ ID NO:88) and LGEYSISADNH (SEQ ID NO:89).

A nucleic acid sequence for this 95F04 anti-CD83 light chain is provided below (SEQ ID NO:90).

```
1 ATGGACACGA GGGCCCCCAC TCAGCTGCTG GGGCTCCTGC
41 TGCTCTGGCT CCCAGGTGCC ACATTTGCCC AAGCCGTGGT
81 GACCCAGACT ACATCGCCCG TGTCTGCACC TGTGGGAGGC
121 ACAGTCACCA TCAATTGCCA GTCCAGTCAG AGTGTTTATG
161 GTAACAACGA ATTATCCTGG TATCAGCAGA AACCAGGGCA
201 GCCTCCCAAG CTCCTGATCT ACCAGGCATC CAGCCTGGCA
241 TCTGGGGTCC CATCGCGGTT CAAAGGCAGT GGATCTGGGA
281 CACAGTTCAC TCTCACCATC AGCGACCTGG AGTGTGACGA
321 TGCTGCCACT TACTACTGTC TAGGCGAATA TAGCATTAGT
361 GCTGATAATC ATTTCGGCGG AGGGACCGAG GTGGTGGTCA
401 AACGTACGCC AGTTGCACCT ACTGTCCTCC TCTTCCCACC
441 ATCTAGCGCT GAGCTGGCAA CTGGAACAGC CACCATCGTG
481 TGCGTGGCGA ATAAATACTT TCCCGATGGC ACCGTCACCT
521 GGAAGGTGGA TGGCATCACC CAAAGCAGCG GCATCAATAA
561 CAGTAGAACA CCGCAGAATT CTGCAGATTG TACCTACAAC
601 CTCAGCAGTA CTCTGACACT GAGCAGCGAC GAGTACAACA
641 GCCACGACGA GTACACCTGC CAGGTGGCCC AGGACTCAGG
681 CTCACCGGTC GTCCAGAGCT TCAGTAGGAA GAGCTGTTAG
```

The nucleic acid sequence for the 95F04 anti-CD83 light chain with CDR regions identified by underlining is provided below (SEQ ID NO:90).

```
1 ATGGACACGA GGGCCCCCAC TCAGCTGCTG GGGCTCCTGC
41 TGCTCTGGCT CCCAGGTGCC ACATTTGCCC AAGCCGTGGT
81 GACCCAGACT ACATCGCCCG TGTCTGCACC TGTGGGAGGC
121 ACAGTCACCA TCAATTGCCA GTCCAGTCAG AGTGTTTATG
161 GTAACAACGA ATTATCCTGG TATCAGCAGA AACCAGGGCA
201 GCCTCCCAAG CTCCTGATCT ACCAGGCATC CAGCCTGGCA
241 TCTGGGGTCC CATCGCGGTT CAAAGGCAGT GGATCTGGGA
281 CACAGTTCAC TCTCACCATC AGCGACCTGG AGTGTGACGA
321 TGCTGCCACT TACTACTGTC TAGGCGAATA TAGCATTAGT
361 GCTGATAATC ATTTCGGCGG AGGGACCGAG GTGGTGGTCA
401 AACGTACGCC AGTTGCACCT ACTGTCCTCC TCTTCCCACC
441 ATCTAGCGCT GAGCTGGCAA CTGGAACAGC CACCATCGTG
481 TGCGTGGCGA ATAAATACTT TCCCGATGGC ACCGTCACCT
521 GGAAGGTGGA TGGCATCACC CAAAGCAGCG GCATCAATAA
561 CAGTAGAACA CCGCAGAATT CTGCAGATTG TACCTACAAC
601 CTCAGCAGTA CTCTGACACT GAGCAGCGAC GAGTACAACA
641 GCCACGACGA GTACACCTGC CAGGTGGCCC AGGACTCAGG
681 CTCACCGGTC GTCCAGAGCT TCAGTAGGAA GAGCTGTTAG
```

In another embodiment, the invention provides a 95F04 heavy chain that can bind to CD83 polypeptides and can inhibit proliferation of human peripheral blood mononuclear cells (PBMCs). The amino acid sequence for this 95F04 heavy chain is provided below (SEQ ID NO:91).

```
1 METGLRWLLL VAVLKGVQCQ SVEESGGRLV TPGTPLTLTC
41 TVSGIDLSSN AMIWVRQAPR EGLEWIGAMD SNSRTYYATW
81 AKGRFTISRT SSITVDLKIT SPTTEDTATY FCARGDGGSS
121 DYTEMWGPGT LVTVSSASTK GPSVYPLAPG SAAQTNSMVT
161 LGCLVKGYFP EPVTVTWNSG SLSSGVHTFP AVLQSDLYTL
201 SSSVTVPSST WPSETVTCNV AHPASSTKVD KKIVPRDCGC
241 KPCICTVPEV SSVFIFPPKP KDVLTITLTP KVTCVVVDIS
281 KDDPEVQFSW FVDDVEVHTA QTQPREEQFN STFRSVSELP
321 IMHQDWLNGK EFKCRVNSAA FPAPIEKTIS KTKGRPKAPQ
361 VYTIPPPKEQ MAKDKVSLTC MITDFFPEDI TVEWQWNGQP
401 AENYKNTQPI MDTDGSYFVY SKLNVQKSNW EAGNTFTCSV
441 LHEGLHNHHT EKSLSHSPGK
```

The amino acid sequence for the 95F04 anti-CD83 heavy chain with the CDR regions identified by underlining is provided below (SEQ ID NO:91).

```
1 METGLRWLLL VAVLKGVQCQ SVEESGGRLV TPGTPLTLTC
41 TVSGIDLSSN AMIWVRQAPR EGLEWIGAMD SNSRTYYATW
81 AKGRFTISRT SSITVDLKIT SPTTEDTATY FCARGDGGSS
```

-continued

```
121 DYTEMWGPGT LVTVSSASTK GPSVYPLAPG SAAQTNSMVT

161 LGCLVKGYFP EPVTVTWNSG SLSSGVHTFP AVLQSDLYTL

201 SSSVTVPSST WPSETVTCNV AHPASSTKVD KKIVPRDCGC

241 KPCICTVPEV SSVFIFPPKP KDVLTITLTP KVTCVVVDIS

281 KDDPEVQFSW FVDDVEVHTA QTQPREEQFN STFRSVSELP

321 IMHQDWLNGK EFKCRVNSAA FPAPIEKTIS KTKGRPKAPQ

361 VYTIPPPKEQ MAKDKVSLTC MITDFFPEDI TVEWQWNGQP

401 AENYKNTQPI MDTDGSYFVY SKLNVQKSNW EAGNTFTCSV

441 LHEGLHNHHT EKSLSHSPGK
```

Hence, the CDR regions in the 95F04 anti-CD83 heavy chain include amino acid sequences SNAMI (SEQ ID NO:92), AMDSNSRTYYATWAKG (SEQ ID NO:93), and GDGGSSDYTEM (SEQ ID NO:94).

A nucleic acid sequence for this 95F04 anti-CD83 heavy chain is provided below (SEQ ID NO:95).

```
   1 ATGGAGACTG GGCTGCGCTG GCTTCTCCTG GTCGCTGTGC

  41 TCAAAGGTGT CCAGTGTCAG TCGGTGGAGG AGTCCGGGGG

  81 TCGCCTGGTC ACGCCTGGGA CACCCCTGAC ACTCACCTGC

 121 ACAGTCTCTG GAATCGACCT CAGTAGCAAT GCAATGATCT

 161 GGGTCCGCCA GGCTCCAAGG GAGGGGCTGG AATGGATCGG

 201 AGCCATGGAT AGTAATAGTA GGACGTACTA CGCGACCTGG

 241 GCGAAAGGCC GATTCACCAT CTCCAGAACC TCGTCGATTA

 281 CGGTGGATCT GAAAATCACC AGTCCGACAA CCGAGGACAC

 321 GGCCACCTAT TTCTGTGCCA GAGGGGATGG TGGCAGTAGT

 361 GATTATACAG AGATGTGGGG CCCAGGGACC CTCGTCACCG

 401 TCTCGAGCGC TTCTACAAAG GGCCCATCTG TCTATCCACT

 441 GGCCCCTGGA TCTGCTGCCC AAACTAACTC CATGGTGACC

 481 CTGGGATGCC TGGTCAAGGG CTATTTCCCT GAGCCAGTGA

 521 CAGTGACCTG GAACTCTGGA TCCCTGTCCA GCGGTGTGCA

 561 CACCTTCCCA GCTGTCCTGC AGTCTGACCT CTACACTCTG

 601 AGCAGCTCAG TGACTGTCCC CTCCAGCACC TGGCCCAGCG

 641 AGACCGTCAC CTGCAACGTT GCCCACCCGG CCAGCAGCAC

 681 CAAGGTGGAC AAGAAAATTG TGCCCAGGGA TTGTGGTTGT

 721 AAGCCTTGCA TATGTACAGT CCCAGAAGTA TCATCTGTCT

 761 TCATCTTCCC CCCAAAGCCC AAGGATGTGC TCACCATTAC

 801 TCTGACTCCT AAGGTCACGT GTGTTGTGGT AGACATCAGC

 841 AAGGATGATC CCGAGGTCCA GTTCAGCTGG TTTGTAGATG

 881 ATGTGGAGGT GCACACAGCT CAGACGCAAC CCCGGGAGGA

 921 GCAGTTCAAC AGCACTTTCC GCTCAGTCAG TGAACTTCCC

 961 ATCATGCACC AGGACTGGCT CAATGGCAAG GAGTTCAAAT

1001 GCAGGGTCAA CAGTGCAGCT TTCCCTGCCC CCATCGAGAA
```

-continued

```
1041 AACCATCTCC AAAACCAAAG GCAGACCGAA GGCTCCACAG

1081 GTGTACACCA TTCCACCTCC CAAGGAGCAG ATGGCCAAGG

1141 ATAAAGTCAG TCTGACCTGC ATGATAACAG ACTTCTTCCC

1161 TGAAGACATT ACTGTGGAGT GGCAGTGGAA TGGGCAGCCA

1201 GCGGAGAACT ACAAGAACAC TCAGCCCATC ATGGACACAG

1241 ATGGCTCTTA CTTCGTCTAC AGCAAGCTCA ATGTGCAGAA

1281 GAGCAACTGG GAGGCAGGAA ATACTTTCAC CTGCTCTGTG

1321 TTACATGAGG GCCTGCACAA CCACCATACT GAGAAGAGCC

1361 TCTCCCACTC TCCTGGTAAA TGA
```

A related nucleic acid sequence for the 95F04 anti-CD83 light chain is provided below (SEQ ID NO:96).

```
   1 ATGGAGACTG GGCTGCGCTG GCTTCTCCTG GTCGCTGTGC

  41 TCAAAGGTGT CCAGTGTCAG TCGGTGGAGG AGTCCGGGGG

  81 TCGCCTGGTC ACGCCTGGGA CACCCCTGAC ACTCACCTGC

 121 ACAGTCTCTG GAATCGACCT CAGTAGCAAT GCAATGATCT

 161 GGGTCCGCCA GGCTCCAAGG GAGGGGCTGG AATGGATCGG

 201 AGCCATGGAT AGTAATAGTA GGACGTACTA CGCGACCTGG

 241 GCGAAAGGCC GATTCACCAT CTCCAGAACC TCGTCGATTA

 281 CGGTGGATCT GAAAATCACC AGTCCGACAA CCGAGGACAC

 321 GGCCACCTAT TTCTGTGCCA GAGGGGATGG TGGCAGTAGT

 361 GATTATACAG AGATGTGGGG CCCAGGGACC CTCGTCACCG

 401 TCTCGAGCGC TTCTACAAAG GGCCCATCTG TCTATCCACT

 441 GGCCCCTGGA TCTGCTGCCC AAACTAACTC CATGGTGACC

 481 CTGGGATGCC TGGTCAAGGG CTATTTCCCT GAGCCAGTGA

 521 CAGTGACCTG GAACTCTGGA TCCCTGTCCA GCGGTGTGCA

 561 CACCTTCCCA GCTGTCCTGC AGTCTGACCT CTACACTCTG

 601 AGCAGCTCAG TGACTGTCCC CTCCAGCACC TGGCCCAGCG

 641 AGACCGTCAC CTGCAACGTT GCCCACCCGG CCAGCAGCAC

 681 CAAGGTGGAC AAGAAAATTG TGCCCAGGGA TTGTGGTTGT

 721 AAGCCTTGCA TATGTACAGT CCCAGAAGTA TCATCTGTCT

 761 TCATCTTCCC CCCAAAGCCC AAGGATGTGC TCACCATTAC

 801 TCTGACTCCT AAGGTCACGT GTGTTGTGGT AGACATCAGC

 841 AAGGATGATC CCGAGGTCCA GTTCAGCTGG TTTGTAGATG

 881 ATGTGGAGGT GCACACAGCT CAGACGCAAC CCCGGGAGGA

 921 GCAGTTCAAC AGCACTTTCC GCTCAGTCAG TGAACTTCCC

 961 ATCATGCACC AGGACTGGCT CAATGGCAAG GAGTTCAAAT

1001 GCAGGGTCAA CAGTGCAGCT TTCCCTGCCC CCATCGAGAA

1041 AACCATCTCC AAAACCAAAG GCAGACCGAA GGCTCCACAG

1081 GTGTACACCA TTCCACCTCC CAAGGAGCAG ATGGCCAAGG
```

-continued

```
1121 ATAAAGTCAG TCTGACCTGC ATGATAACAG ACTTCTTCCC

1161 TGAAGACATT ACTGTGGAGT GGCAGTGGAA TGGGCAGCCA

1201 GCGGAGAACT ACAAGAACAC TCAGCCCATC ATGGACACAG

1241 ATGGCTCTTA CTTCGTCTAC AGCAAGCTCA ATGTGCAGAA

1281 GAGCAACTGG GAGGCAGGAA ATACTTTCAC CTGCTCTGTG

1321 TTACATGAGG GCCTGCACAA CCACCATACT GAGAAGAGCC

1361 TCTCCCACTC TCCTGGTAAA TGA
```

CD83 Modulation of the Immune System

The invention also provides compositions and methods for decreasing inappropriate immune responses in animals, including humans. According to the invention, the CD83 gene has a profound effect upon T cell activity. In particular, CD4+T cells require CD83-related functions. Without CD83, CD4+T cell activation and/or proliferation is impaired. The therapeutic manipulation of CD83 may thus represent a mechanism for the specific regulation of T cell function in the treatment of T cell mediated diseases, including autoimmune disorders. For example, antibodies capable of blocking CD83 function can be used as therapeutics in the treatment of immune diseases.

In some embodiments, the CD83-related compositions and methods of the invention can be used in the treatment of autoimmune diseases. Many autoimmune disorders are the result of inappropriate activation of T cells that are reactive against “self tissues” and that promote the production of cytokines and auto-antibodies involved in the pathology of the diseases. Modulation of T cell activity by modulating CD83 can have an effect on the course of the autoimmune disease.

Non-limiting examples of autoimmune diseases and disorders having an autoimmune component that may be treated according to the invention include diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren’s Syndrome, including keratoconjunctivitis sicca secondary to Sjogren’s Syndrome, alopecia greata, allergic responses due to arthropod bite reactions, Crohn’s disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener’s granulomatosis, chronic active hepatitis, Stevens-Johnson syndrome, idiopathic sprue, lichen planus, Crohn’s disease, Graves opthalmopathy, sarcoidosis, primary biliary cirrhosis, uveitis posterior, and interstitial lung fibrosis.

As illustrated and provided herein, anti-CD83 antibodies can inhibit T cell proliferation. The efficacy of anti-CD83-related compositions for treating autoimmune diseases can be tested in the animal models provided herein or other models of human diseases (e.g., EAE as a model of multiple sclerosis and the NOD mice as a model for diabetes). Such animal models include the mrl/lpr/lpr mouse as a model for lupus erythematosus, murine collagen-induced arthritis as a model for rheumatoid arthritis, and murine experimental myasthenia gravis (see Paul ed., Fundamental Immunology, Raven Press, New York, 1989, pp. 840-856). A CD83-modulatory (e.g., inhibitory) agent of the invention is administered to test animals and the course of the disease in the test animals is then monitored by the standard methods for the particular model being used. Effectiveness of the modulatory agent is evidenced by amelioration of the disease condition in animals treated with the agent as compared to untreated animals (or animals treated with a control agent).

Similarly, the compositions and methods of the invention that involve decreasing CD83 function can be used to decrease transplant rejection and prolong survival of the tissue graft. These methods can be used both in solid organ transplantation and in bone marrow transplantation (e.g., to inhibit graft-versus-host disease). These methods can involve either direct administration of a CD83 inhibitory agent to the transplant recipient or ex vivo treatment of cells obtained from the subject (e.g., T cells, Th1 cells, B cells, non-lymphoid cells) with an inhibitory agent followed by re-administration of the cells to the subject.

According to the invention, any agent that can modulate CD83 or to further decrease T cell levels can also be used in the compositions and methods of the invention. In some embodiments, anti-CD83 antibodies of the invention are used to either activate or inhibit CD83 activity.

Stimulating or Inhibiting CD83

According to the invention, any agent that can inhibit CD83 from performing its natural functions can be used in the compositions and methods of the invention as a CD83 inhibitory agent. Indicators that CD83 activity is inhibited include decreased T cell counts, increased IL-4 cytokine levels, increased IL-10 levels, decreased IL-2 production, and decreased TNF levels relative to uninhibited levels in wild type CD83 cells.

Examples of CD83 inhibitors include anti-CD83 antibodies, CD83 anti-sense nucleic acids (e.g. nucleic acids that can hybridize to CD83 nucleic acids), organic compounds, peptides and agents that can mutate an endogenous CD83 gene.

In some embodiments, the CD83 stimulatory or inhibitory agents are proteins, for example, CD83 gene products, anti-CD83 antibody preparations, CD83 inhibitors, peptides and protein factors that can promote CD83 transcription or translation. In other embodiments, the CD83 stimulatory or inhibitory agents are peptides or organic molecules. Such proteins, organic molecules and organic molecules can be prepared and/or purified as described herein or by methods available in the art, and administered as provided herein.

In other embodiments, the CD83 inhibitory agents can be nucleic acids including recombinant expression vectors or expression cassettes encoding CD83 anti-sense nucleic acid, intracellular antibodies capable of binding to CD83 or dominant negative CD83 inhibitors. Such nucleic acids can be operably linked to a promoter that is functional in a mammalian cell, and then introduced into cells of the subject mammal using methods known in the art for introducing nucleic acid (e.g., DNA) into cells.

The “promoter functional in a mammalian cell” or “mammalian promoter” is capable of directing transcription of a polypeptide coding sequence operably linked to the promoter. The promoter should generally be active in T cells and antigen presenting cells and may be obtained from a gene that is expressed in T cells or antigen presenting cells. However, it need not be a T cell-specific or an antigen presenting cell specific-promoter. Instead, the promoter may be selected from any mammalian or viral promoter that can function in a T cell. Hence the promoter may be an actin promoter, an immunoglobulin promoter, a heat-shock promoter, or a viral promoter obtained from the genome of viruses such as adenoviruses, retroviruses, lentiviruses, herpes viruses, including but not limited to, polyoma virus, fowlpox virus, adenovirus 2, bovine papilloma virus, avian sarcoma virus, cytomegalovirus (CMV), hepatitis-B virus, Simian Virus 40 (SV40), Epstein Barr virus (EBV), feline immunodeficiency virus (FIV), and Sra, or are respiratory synsitial viral promoters (RSV) or long terminal repeats (LTRs) of a retrovirus, i.e., a Moloney Murine Leukemia Virus (MoMuLv) (Cepko et al. (1984) Cell 37:1053-1062). The promoter functional in a mammalian cell can be inducible or constitutive.

Any cloning procedure used by one of skill in the art can be employed to make the expression vectors or expression that comprise a promoter operably linked to a CD83 nucleic acid, CD83 transcription factor or a nucleic acid encoding an anti-CD83 antibody. See, e.g., Sambrook et al., Molecular Cloning, A Laboratory Manual, Cold Spring Harbor Laboratory, N.Y., 1989; Sambrook et al., Molecular Cloning, A Laboratory Manual, Cold Spring Harbor Laboratory, N.Y., 2001.

After constructing an expression vector or an expression cassette encoding CD83 transcription factors, CD83 antisense nucleic acid, intracellular antibodies capable of binding to CD83 or dominant negative CD83 inhibitors, mammalian cells can be transformed with the vector or cassette. Examples of such methods include:

Direct Injection: Naked DNA can be introduced into cells in vivo by directly injecting the DNA into the cells (see e.g., Acsadi et al. (1991) Nature 332:815-818; Wolff et al. (1990) Science 247:1465-1468). For example, a delivery apparatus (e.g., a "gene gun") for injecting DNA into cells in vivo can be used. Such an apparatus is commercially available (e.g., from BioRad).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) J. Biol. Chem. 263:14621; Wilson et al. (1992) J. Biol. Chem. 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids that naturally disrupt endosomes, thereby releasing material into the cytoplasm can be used to avoid degradation of the complex by intracellular lysosomes (see for example Curiel et al. (1991) Proc. Natl. Acad Sci. USA 88:8850; Cristiano et al. (1993) Proc. Natl. Acad. Sci. USA 90:2122-2126).

Retroviruses: Defective retroviruses are well characterized for use in gene transfer for gene therapy purposes (for a review see Miller, A. D. (1990) Blood 76:271). A recombinant retrovirus can be constructed having nucleotide sequences of interest incorporated into the retroviral genome. Additionally, portions of the retroviral genome can be removed to render the retrovirus replication defective. The replication defective retrovirus is then packaged into virions that can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are available to those skilled in the art. Examples of suitable packaging virus lines include ? Crip, ? Cre, ? 2 and ? Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad Sci USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See, for example, Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 d1324 or other strains of adenovirus (e.g., Ad2, Ad3, Ad7 etc.) are available to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication -defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97-129). It is also one of the few viruses that may integrate its DNA into non -dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J Virol. 51:611-619; and Flotte et al. (1993) J. Biol. Chem. 268:3781-3790).

Transformed mammalian cells can then be identified and administered to the mammal from whence they came to permit expression of a CD83 transcription factor, CD83 antisense nucleic acid, intracellular antibody capable of binding to CD83 proteins, or dominant negative CD83 inhibitors. The efficacy of a particular expression vector system and method of introducing nucleic acid into a cell can be assessed by standard approaches routinely used in the art. For example, DNA introduced into a cell can be detected by a filter hybridization technique (e.g., Southern blotting). RNA produced by transcription of an introduced DNA can be detected, for example, by Northern blotting, RNase protection or reverse transcriptase-polymerase chain reaction (RT-PCR). The CD83 gene product can be detected by an appropriate assay, for example, by immunological detection of a produced CD83 protein, such as with a CD83-specific antibody.

Anti-Sense Nucleic Acids

Anti-sense nucleic acids can be used to inhibit the function of CD83. In general, the function of CD83 RNA is inhibited, for example, by administering to a mammal a nucleic acid that can inhibit the functioning of CD83 RNA. Nucleic acids that can inhibit the function of a CD83 RNA can be generated from coding and non-coding regions of the CD83 gene. However, nucleic acids that can inhibit the function of a CD83 RNA are often selected to be complementary to CD83 nucleic acids that are naturally expressed in the mammalian cell to be treated with the methods of the invention. In some embodiments, the nucleic acids that can inhibit CD83 RNA functions are complementary to CD83 sequences found near the 5' end of the CD83 coding region. For example, nucleic acids that can inhibit the function of a CD83 RNA can be complementary to the 5' region of SEQ ID NO:1, SEQ ID NO:3, SEQ ID NO:5 or SEQ ID NO:10.

A nucleic acid that can inhibit the functioning of a CD83 RNA need not be 100% complementary to SEQ ID NO:1, SEQ ID NO:3, SEQ ID NO:5 or SEQ ID NO:10. Instead, some variability the sequence of the nucleic acid that can inhibit the functioning of a CD83 RNA is permitted. For example, a nucleic acid that can inhibit the functioning of a CD83 RNA from a human can be complementary to a nucleic acid encoding either a human or a mouse CD83 gene product.

Moreover, nucleic acids that can hybridize under moderately or highly stringent hybridization conditions to a nucleic acid comprising SEQ ID NO:1, SEQ ID NO:3, SEQ ID NO:5 or SEQ ID NO:10 are sufficiently complementary to inhibit the functioning of a CD83 RNA and can be utilized in the methods of the invention.

"Stringent hybridization conditions" and "stringent hybridization wash conditions" in the context of nucleic acid hybridization are somewhat sequence dependent, and may differ depending upon the environmental conditions of the nucleic acid. For example, longer sequences tend to hybridize specifically at higher temperatures. An extensive guide to the hybridization of nucleic acids is found in Tijssen, Laboratory Techniques in Biochemistry and Molecular biology-Hybridization with Nucleic Acid Probes, page 1, chapter 2 "Overview of principles of hybridization and the strategy of nucleic acid probe assays" Elsevier, New York (1993). See also, J. Sambrook et al., Molecular Cloning: A Laboratory Manual, Cold Spring Harbor Press, N.Y., pp 9.31-9.58 (1989); J. Sambrook et al., Molecular Cloning: A Laboratory Manual, Cold Spring Harbor Press, N.Y. (3rd ed. 2001).

Generally, highly stringent hybridization and wash conditions are selected to be about 5° C. lower than the thermal melting point ($T_m$) for the specific double-stranded sequence at a defined ionic strength and pH. For example, under "highly stringent conditions" or "highly stringent hybridization conditions" a nucleic acid will hybridize to its complement to a detectably greater degree than to other sequences (e.g., at least 2-fold over background). By controlling the stringency of the hybridization and/or washing conditions nucleic acids that are 100% complementary can be hybridized.

For DNA-DNA hybrids, the $T_m$ can be approximated from the equation of Meinkoth and Wahl Anal. Biochem. 138:267-284 (1984):

$$T_m 81.5^\circ\text{ C.}+16.6(\log M)+0.41\ (\%GC)-0.61(\%\text{ form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe.

Very stringent conditions are selected to be equal to the $T_m$ for a particular probe.

Alternatively, stringency conditions can be adjusted to allow some mismatching in sequences so that lower degrees of similarity can hybridize. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl and 0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

The degree of complementarity or sequence identity of hybrids obtained during hybridization is typically a function of post-hybridization washes, the critical factors being the ionic strength and temperature of the final wash solution. The type and length of hybridizing nucleic acids also affects whether hybridization will occur and whether any hybrids formed will be stable under a given set of hybridization and wash conditions.

An example of stringent hybridization conditions for hybridization of complementary nucleic acids that have more than 100 complementary residues on a filter in a Southern or Northern blot is 50% formamide with 1 mg of heparin at 42° C., with the hybridization being carried out overnight. An example of highly stringent conditions is 0.1 5 M NaCl at 72° C. for about 15 minutes. An example of stringent wash conditions is a 0.2×SSC wash at 65° C. for 15 minutes (see also, Sambrook, infra). Often, a high stringency wash is preceded by a low stringency wash to remove background probe signal. An example of medium stringency for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C.

Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to detect and isolate homologous nucleic acids that are substantially identical to reference nucleic acids of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

In general, $T_m$ is reduced by about 1° C. for each 1% of mismatching. Thus, $T_m$, hybridization, and/or wash conditions can be adjusted to hybridize to sequences of the desired sequence identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$).

If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part 1, Chapter 2 (Elsevier, New York); and Ausubel et al., eds. (1995) Current Protocols in Molecular Biology, Chapter 2 (Greene Publishing and Wiley—Interscience, New York). See Sambrook et al. (1989) Molecular Cloning: A Laboratory Manual (2d ed., Cold Spring Harbor Laboratory Press, Plainview, N.Y.). Using these references and the teachings herein on the relationship between $T_m$, mismatch, and hybridization and wash conditions, those of ordinary skill can generate variants of the present homocysteine S-methyltransferase nucleic acids.

Precise complementarity is therefore not required for successful duplex formation between a nucleic acid that can inhibit a CD83 RNA and the complementary coding sequence of a CD83 RNA Inhibitory nucleic acid molecules that comprise, for example, 2, 3, 4, or 5 or more stretches of contiguous nucleotides that are precisely complementary to a CD83 coding sequence, each separated by a stretch of contiguous nucleotides that are not complementary to adjacent CD83 coding sequences, can inhibit the function of CD83 RNA. In general, each stretch of contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an anti-sense nucleic acid hybridized to a sense nucleic acid to determine the degree of mismatching that will be tolerated between a particular anti-sense nucleic acid and a particular CD83 RNA.

Nucleic acids that complementary a CD83 RNA can be administered to a mammal or to directly to the site of the inappropriate immune system activity. Alternatively, nucleic acids that are complementary to a CD83 RNA can be generated by transcription from an expression cassette that has been administered to a mammal. For example, a complementary RNA can be transcribed from a CD83 nucleic acid that has been inserted into an expression cassette in the 3' to 5' orientation, that is, opposite to the usual orientation employed to generate sense RNA transcripts. Hence, to generate a complementary RNA that can inhibit the function of an endogenous CD83 RNA, the promoter would be positioned to transcribe from a 3' site towards the 5' end of the CD83 coding region.

In some embodiments an RNA that can inhibit the function of an endogenous CD83 RNA is an anti-sense oligonucleotide. The anti-sense oligonucleotide is complementary to at least a portion of the coding sequence of a gene comprising SEQ ID NO:1, SEQ ID NO:3, SEQ ID NO:5 or SEQ ID NO:10. Such anti-sense oligonucleotides are generally at least six nucleotides in length, but can be about 8, 12, 15, 20, 25, 30, 35, 40, 45, or 50 nucleotides long. Longer oligonucleotides can also be used. CD83 anti-sense oligonucleotides can be provided in a DNA construct and introduced into cells whose division is to be decreased, for example, into CD4+T cells, Th-1 cells, Th-2 cells or lymphocyte precursor cells.

Anti-sense oligonucleotides can be composed of deoxyribonucleotides, ribonucleotides, or a combination of both. Oligonucleotides can be synthesized endogenously from transgenic expression cassettes or vectors as described herein. Alternatively, such oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, Meth. Mol. Biol. 20:1-8; Sonveaux, 1994, Meth. Mol. Biol. 26:1-72; Uhlmann et al., 1990, Chem. Rev. 90:543-583.

CD83 anti-sense oligonucleotides can be modified without affecting their ability to hybridize to a CD83 RNA. These modifications can be internal or at one or both ends of the anti-sense molecule. For example, internucleoside phosphate linkages can be modified by adding peptidyl, cholesteryl or diamine moieties with varying numbers of carbon residues between these moieties and the terminal ribose. Modified bases and/or sugars, such as arabinose instead of ribose, or a 3',5'-substituted oligonucleotide in which the 3' hydroxyl group or the 5' phosphate group are substituted, can also be employed in a modified anti-sense oligonucleotide. These modified oligonucleotides can be prepared by methods available in the art. Agrawal et al., 1992, Trends Biotechnol. 10:152-158; Uhlmann et al., 1990, Chem. Rev. 90:543-584; Uhlmann et al., 1987, Tetrahedron. Lett. 215:3539-3542.

In one embodiment of the invention, expression of a CD83 gene is decreased using a ribozyme. A ribozyme is an RNA molecule with catalytic activity. See, e.g., Cech, 1987, Science 236: 1532-1539; Cech, 1990, Ann. Rev. Biochem. 59:543-568; Cech, 1992, Curr. Opin. Struct. Biol. 2: 605-609; Couture and Stinchcomb, 1996, Trends Genet. 12: 510-515. Ribozymes can be used to inhibit gene function by cleaving an RNA sequence, as is known in the art (see, e.g., Haseloff et al., U.S. Pat. No. 5,641,673).

CD83 nucleic acids complementary to SEQ ID NO:1, SEQ ID NO:3, SEQ ID NO:5 or SEQ ID NO:10 can be used to generate ribozymes that will specifically bind to mRNA transcribed from a CD83 gene. Methods of designing and constructing ribozymes that can cleave other RNA molecules in trans in a highly sequence specific manner have been developed and described in the art (see Haseloff et al. (1988), Nature 334:585-591). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201). The target sequence can be a segment of about 10, 12, 15, 20, or 50 contiguous nucleotides selected from a nucleotide sequence shown in SEQ ID NO:1, SEQ ID NO:3, SEQ ID NO:5 or SEQ ID NO:10. Longer complementary sequences can be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target.

Other CD83 Modulating Molecules

A wide variety of molecules may be used to modulate CD83 activity or function. Such molecules can also be used to modulate the immune system independent of CD83. Compositions and methods for modulating CD83 activity or expression can include these molecules as well as other components. Representative examples that are discussed in more detail below include transcription factors, RNA-binding factors, organic molecules, or peptides.

RNA-Binding Factors:

One class of molecules that can be used to modulate the CD83 gene is the RNA binding factors. Such factors include those described in PCT/EP01/14820 and other sources.

For example, the HuR protein (Genbank accession number U38175) has the ability to specifically bind to CD83 RNA at AU-rich elements or sites. Such AU-rich elements comprise sequences such as AUUUA (SEQ ID NO:49), AUUUUA (SEQ ID NO:50) and AUUUUUA (SEQ ID NO:51). Binding by such HuR proteins to CD83 mRNA is thought to increase the stability, transport and translation of CD83 mRNA, and thereby increase the expression of CD83 polypeptides. Hence, CD83 expression may be increase by administering HuR proteins or nucleic acids to a mammal.

Conversely, CD83 expression may be decreased by administering factors that block HuR binding to CD83 mRNA. Factors that block HuR binding include proteins or nucleic acids that can bind to the AU-rich elements normally bound by HuR, for example, nucleic acids or anti-sense nucleic acids that are complementary to AU-rich elements.

Organic Molecules:

Numerous organic molecules may be used to modulate the immune system. These compounds include any compound that can interact with a component of the immune system. Such compounds may interact directly with CD83, indirectly with CD83 or with some other polypeptide, cell or factor that plays a role in the function of the immune system. In some embodiments, the organic molecule can bind to a CD83 polypeptide or a CD83 nucleic acid.

Organic molecules can be tested or assayed for their ability to modulate CD83 activity, CD83 function or for their ability to modulate components of the immune system. For example, within one embodiment of the invention suitable organic molecules may be selected either from a chemical library, wherein chemicals are assayed individually, or from combinatorial chemical libraries where multiple compounds are assayed at once, then deconvoluted to determine and isolate the most active compounds.

Representative examples of such combinatorial chemical libraries include those described by Agrafiotis et al., "System and method of automatically generating chemical compounds with desired properties," U.S. Pat. No. 5,463,564; Armstrong, R. W., "Synthesis of combinatorial arrays of organic compounds through the use of multiple component combinatorial array syntheses," WO 95/02566; Baldwin, J. J. et al., "Sulfonamide derivatives and their use," WO 95/24186; Baldwin, J. J. et al., "Combinatorial dihydrobenzopyran library," WO 95/30642; Brenner, S., "New kit for preparing combinatorial libraries," WO 95/16918; Chenera, B. et al., "Preparation of library of resin-bound aromatic carbocyclic compounds," WO 95/16712; Ellman, J. A., "Solid phase and combinatorial synthesis of benzodiazepine compounds on a solid support," U.S. Pat. No. 5,288,514; Felder, E. et al., "Novel combinatorial compound libraries," WO 95/16209; Lerner, R. et al., "Encoded combinatorial chemical libraries," WO 93/20242; Pavia, M. R. et al., "A method for preparing and selecting pharmaceutically useful non-peptide compounds from a structurally diverse universal library," WO 95/04277; Summerton, J. E. and D. D. Weller, "Morpholino -subunit combinatorial library and method," U.S. Pat. No. 5,506,337; Holmes, C., "Methods for the Solid Phase Synthesis of Thiazolidinones, Metathiazanones, and Derivatives thereof," WO 96/00148; Phillips, G. B. and G. P. Wei, "Solid-phase Synthesis of Benzimidazoles," *Tet. Letters* 37:4887-90, 1996; Ruhland, B. et al., "Solid-supported Combinatorial Synthesis of Structurally Diverse-Lactams," *J. Amer. Chem. Soc.* 111:253-4, 1996; Look, G. C. et al., "The Indentification of Cyclooxygenase-1 Inhibitors from 4-Thiazolidinone Combinatorial Libraries," *Bioorg and Med. Chem. Letters* 6:707-12, 1996.

Peptides:

Peptide molecules that modulate the immune system may be obtained through the screening of combinatorial peptide libraries. Such libraries may either be prepared by one of skill in the art (see e.g., U.S. Pat. Nos. 4,528,266 and 4,359,535, and Patent Cooperation Treaty Publication Nos. WO 92/15679, WO 92/15677, WO 90/07862, WO 90/02809, or purchased from commercially available sources (e.g., New England Biolabs Ph.D.™ Phage Display Peptide Library Kit).

Methods of Using the CD83 Mutant Mouse

In one embodiment, the invention provides a method for identifying ligands, receptors, therapeutic drugs and other molecules that can modulate the phenotype of the mutant CD83 in vivo. This method involves administering a test compound to the mutant CD83 mouse of the invention and observing whether the compound causes a change in the phenotype of the mutant mouse. Changes in phenotype that are of interest include increases or decreases in T cells (especially CD4+T cells), increases or decreases in GMCSF, IL-2, IL-4 or IL-10 cytokine production, increases or decreases in inflammation, increases or decreases in dendritic cell function and other T cell responses known to one of skill in the art.

Test compounds can be screened in vitro to ascertain whether they interact directly with CD83. In vitro screening can, for example, identify whether a test compound or molecule can bind to the cytoplasmic tail or the membrane-associated portions of CD83. Such information, combined with observation of the in vivo phenotype before and after administration of the test compound provides further insight into the function of CD83 and provides targets for manipulation T cell activation and other functions modulated by CD83.

The invention is not limited to identification of molecules that directly associate with CD83. The in vivo screening methods provided herein can, also identify test compounds that have an indirect effect on CD83, or that partially or completely replace a function of CD83.

Increases or decreases in T cell numbers can be observed in blood samples or in samples obtained from thymus, spleen or lymph node tissues. In order to observe the activation of T cells and/or the interaction of T cells and dendritic cells, dendritic cells can be pulsed with antigens ex vivo and then injected into mice to prime CD4+T cells in draining lymphoid organs. See Inaba et al., J. Exp. Med. 172: 631-640, 1990; Liu, et al., J. Exp. Med. 177: 1299-1307, 1993; Somasse et al., J. Exp. Med. 175: 15-21, 1992. Antigens can also be deposited intramuscularly and dendritic cells from the corresponding afferent lymphatics can carry that antigen in a form stimulatory for T cells. Bujdoso et al., J. Exp. Med. 170: 1285-1302, 1989. According to the invention, factors stimulating the interaction of dendritic cells with T cells in vivo can be identified by administering antigens in this manner and then observing how T cell respond, e.g. by observing whether T cell activation occurs.

Increases or decreases in cytokine levels can be observed by methods provided herein or by other methods available in the art.

Compositions

The CD83 nucleic acids, polypeptides and antibodies of the invention, including their salts, are administered so as to achieve a reduction in at least one symptom associated with an infection, indication or disease.

To achieve the desired effect(s), the nucleic acid, polypeptide or antibody, a variant thereof or a combination thereof, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the nucleic acid, polypeptide or antibody chosen, the disease, the weight, the physical condition, the health, the age of the mammal, whether prevention or treatment is to be achieved, and if the nucleic acid, polypeptide or antibody is chemically modified. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the CD83 nucleic acids, polypeptides and antibodies of the invention may be essentially continuous over a preselected period of time or may be in a series of spaced doses. Both local and systemic administration is contemplated.

To prepare the composition, CD83 nucleic acids, polypeptides and antibodies are synthesized or otherwise obtained, purified as necessary or desired and then lyophilized and stabilized. The nucleic acid, polypeptide or antibody can then be adjusted to the appropriate concentration, and optionally combined with other agents. The absolute weight of a given nucleic acid, polypeptide or antibody included in a unit dose can vary widely. For example, about 0.01 to about 2 g, or about 0.1 to about 500 mg, of at least one nucleic acid, polypeptide or antibody of the invention, or a plurality of CD83 nucleic acid, polypeptides and antibodies specific for a particular cell type can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the CD83 nucleic acids, polypeptides or antibodies of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Thus, one or more suitable unit dosage forms comprising the therapeutic CD83 nucleic acids, polypeptides or antibodies of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic CD83 nucleic acids, polypeptides or antibodies may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic CD83 nucleic acids, polypeptides or antibodies of the invention are prepared for oral administration, they are generally combined with a pharmaceutically acceptable carrier, diluent or excipient to form a pharmaceutical formulation, or unit dosage form. For oral administration, the CD83 nucleic acids, polypeptides or antibodies may be present as a powder, a granular formulation, a solution, a suspension, an emulsion or in a natural or synthetic polymer or resin for ingestion of the active ingredients from a chewing gum. The active CD83 nucleic acids, polypeptides or antibodies may also be presented as a bolus, electuary or paste. Orally administered therapeutic CD83 nucleic acids, polypeptides or antibodies of the invention can also be formulated for sustained release, e.g., the CD83 nucleic acids, polypeptides or antibodies can be coated, micro-encapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic CD83 nucleic acids, polypeptides or antibodies of the invention can be prepared by procedures known in the art using well-known and readily available ingredients. For example, the nucleic acid, polypeptide or antibody can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the CD83 nucleic acids, polypeptides or antibodies of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one nucleic acid, polypeptide or antibody of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more CD83 nucleic acids, polypeptides or antibodies of the invention are designed to resist disintegration in the stomach and dissolve in the more neutral to alkaline environment of the duodenum.

The therapeutic CD83 nucleic acids, polypeptides or antibodies of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic CD83 nucleic acids, polypeptides or antibodies of the invention can also take the form of an aqueous or anhydrous solution or dispersion, or alternatively the form of an emulsion or suspension or salve.

Thus, the therapeutic CD83 nucleic acids, polypeptides or antibodies may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The active CD83 nucleic acids; polypeptides or antibodies and other ingredients may form suspensions, solutions, or emulsions in oily or aqueous vehicles, and may contain formulatory agents such as suspending, stabilizing and/or dispersing agents. Alternatively, the active CD83 nucleic acids, polypeptides or antibodies and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and a-tocopherol and its derivatives can be added.

Also contemplated are combination products that include one or more CD83 nucleic acids, polypeptides or antibodies of the present invention and one or more other anti-microbial agents. For example, a variety of antibiotics can be included in the pharmaceutical compositions of the invention, such as aminoglycosides (e.g., streptomycin, gentamicin, sisomicin, tobramycin and amicacin), ansamycins (e.g. rifamycin), antimycotics (e.g. polyenes and benzofuran derivatives), β-lactams (e.g. penicillins and cephalosporins), chloramphenical (including thiamphenol and azidamphenicol), linosamides (lincomycin, clindamycin), macrolides (erythromycin, oleandomycin, spiramycin), polymyxins, bacitracins, tyrothycin, capreomycin, vancomycin, tetracyclines (including oxytetracycline, minocycline, doxycycline), phosphomycin and fusidic acid.

Additionally, the CD83 nucleic acids, polypeptides or antibodies are well suited to formulation as sustained release dosage forms and the like. The formulations can be so constituted that they release the active nucleic acids, polypeptide or antibody, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the therapeutic agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic CD83 nucleic acids, polypeptides or antibodies of the invention can be delivered via patches or bandages for dermal administration. Alternatively, the nucleic acid, polypeptide or antibody can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents; dispersing agents, suspending agents, thickening agents, or coloring agents. The active CD83 nucleic acids, polypeptides or antibodies can also be delivered via iontophoresis, e.g., as disclosed in U.S. Pat. No. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic CD83 nucleic acids, polypeptides or antibodies in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic nucleic acids, polypeptide or antibody may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0. The CD83 nucleic acids, polypeptides or antibodies of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, indication or disease. Any statistically significant attenuation of one or more symptoms of an infection, indication or disease that has been treated pursuant to the method of the present invention is considered to be a treatment of such infection, indication or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197-224, Butterworths, London, England, 1984).

Therapeutic CD83 nucleic acids, polypeptides or antibodies of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the CD83 nucleic acids, polypeptides or antibodies of the present invention specific for the indication or disease to be treated. Dry aerosol in the form of finely divided solid nucleic acid, polypeptide or antibody particles that are not dissolved or suspended in a liquid are also useful in the practice of the present invention. CD83 nucleic acids, polypeptides or antibodies of the present invention may be formulated as dusting powders and comprise finely divided particles having an average particle size of between about 1 and 5 μm, alternatively between 2 and 3 μm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic CD83 nucleic acids, polypeptides or antibodies of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intranasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, antihistamines, bronchodilators and the like, whether for the conditions described or some other condition.

The present invention further pertains to a packaged pharmaceutical composition for controlling microbial infections such as a kit or other container. The kit or container holds a therapeutically effective amount of a pharmaceutical composition for modulating immune responses and instructions for using the pharmaceutical composition for control of the immune response. The pharmaceutical composition includes at least one nucleic acid, polypeptide or antibody of the present invention, in a therapeutically effective amount such that the selected disease or immunological condition is controlled.

The invention will be further described by reference to the following detailed examples, which are given for illustration of the invention, and are not intended to be limiting thereof.

Example 1

Mouse Mutation and Characterization

Mutant Generation

Male C57BL6 mice received 3 weekly injections of N-ethyl-N-nitrosourea (ENU) at a concentration of 100 mg/kg. N-Ethyl-N-nitrosourea was quantified prior to injection by spectrophotometry. Mice that regained fertility after a minimum period of 12 weeks were then used to generate pedigree founder G1 animals. G1 male mice were crossed to C57BL6J females and their female progeny (G2 animals) crossed back to their fathers to generate G3 animals for screening.

G3 mice were weaned at 3 weeks of age. Each animal then underwent a series of screens designed to assess a number of parameters, including immune function, inflammatory response and bone development. In the initial screen, conducted at 6 weeks of age, 150-200 μl of whole blood was collected by retro-orbital bleed into heparinized tubes. Cells were pelleted and red blood cells lysed. Samples were then stained with antibodies to cell surface markers expressed on distinct lymphoid and myeloid sub-populations. These samples were analyzed by flow-cytometry.

Mutant Identification

A group of 27 G3 mice from 2 different pedigrees, pedigree 9 and pedigree 57 (i.e. derived from 2 distinct G1 fathers) were analyzed in this screen. Two animals from pedigree 9 were identified as having a reduced (>2 standard deviation from normal) percentage of CD4+T cells in peripheral blood (FIG. 1). Both animals were descended from the same G1 and shared the same mother. All other animals screened on that day had a normal percentage of CD4+T cells. The number of phenodeviants identified (2 from a litter of 9 animals) was suggestive of a trait controlled by a single gene and inherited in a Mendelian fashion.

A second litter generated from Pedigree 9 bred to G2 daughter #4 exhibited an identical phenotype with reduced numbers of CD4+T cells, further suggesting that the trait had a genetic basis. The phenotype was designated LCD4.1 (Low CD4 Mutant #1) and was used for mapping experiments.

Mutation Mapping

In order to map the LCD4.1 mutant phenotype, affected G3 male mice (presumptive homozygous for the mutation) were bred to female animals from the C3HeB/FeJ strain to generate F1 progeny. These F1 females (presumptively heterozygous for the mutation) were then mated back to their affected father to generate N2 progeny.

Blood was collected from N2 animals and flow cytometric analysis was performed to identify CD4+T cells. For a phenotype controlled by a single gene, breeding homozygous fathers to heterozygous daughters should yield 50% normal N2 animals and 50% affected N2 animals. This ratio of normal to affected animals was observed in the N2 generation: Multiple N2 animals exhibited a reduced percentage of CD4+T cells, indicating that the phenotype was heritable (FIG. 2).

DNA samples were prepared from samples of tail tissue collected from these N2 mice and used for a genome scan, using a collection of assembled markers, and performed on the ABI 3100 DNA analyzer. Initial genetic linkage was seen to the tip of chromosome 13, where the closest microsatellite marker was D13Mit139 with a LOD score of 8.2. By calculating upper and lower confidence limits, the mutant gene was located between 13.4 and 29.6 cM on chromosome 13. Through additional genotyping, this region was reduced to an 11 cM interval on chromosome 13. No significant linkage to other chromosomal regions was seen.

Mutation Identification

A candidate gene; CD83, was identified for gene-testing based upon its reported position within the interval. CD83 has previously been used as a marker of dendritic cell activation, suggesting that it might play a role in dendritic cell function and hence in regulating T cell development and function.

Sequence analysis of the mutant DNA revealed a mutation in the stop codon of CD83. All affected animals were homozygous for this mutation while non-affected animals carried one wild-type allele and one mutant allele (FIG. 3 and FIG. 4). The mutation destroyed the stop codon and resulted in the addition of a unique 55 amino acid tail to the C-terminus of CD83 (FIG. 5).

Additional Functional Data

A reduction in CD4+T cells was seen in peripheral blood, spleen tissues and lymph nodes from homozygous LCD4.1 mice. Although there were a reduced number of CD4+T cells in the thymus there is no overt block in the developmental process and there was substantially no alteration in B cell development in the bone marrow. Histological evaluation of thymus, spleen and lymph nodes from affected mice revealed no gross alteration in tissue architecture.

Dendritic cells can be differentiated from bone marrow of wild type mice by culture in GM-CSF. These cells can be characterized by the surface expression of dendritic cell markers, including CD86 and CD11c. Both LCD4.1 affected and normal animals were capable of giving rise to CD86+ CD11c+ cells under these culture conditions. LCD4.1 mutant mice thus were capable of generating dendritic cells under in vitro culture conditions. These data suggest that the phenotype seen in LCD4.1 mice is not due to a failure of dendritic cells to develop but rather may reflect a defect in function.

To track dendritic cells, the sensitizing agent FITC was applied to the dorsal surface of the ears of LCD4.1 affected and wild-type mice. FITC was picked up by dendritic cells that then migrated to the draining auricular lymph nodes, where the presence of the FITC label on the dendritic cell surface permitted detection by flow-cytometry. FITC labeled cells expressing CD86 were detected in equal proportions in draining lymph node from normal and affected LCD4.1 mice. These data indicate that LCD4.1 mutant animals are capable of generating dendritic cells in vivo and that these cells are able to pick up antigen in the ear and travel to the draining lymph node.

Example 2

CD83 and CD4+T Cell Function

Materials and Methods

Spleens were removed from wild type and mutant mice and digested with collagenase to liberate dendritic cells. Spleens were stained for surface expression of CD4 (helper T cells) and CD11c (dendritic cells). Cells expressing these markers were purified by fluorescence activated cell sorting (FACS sorting). CD11c and CD4+ positive cells were also purified from an allogeneic mouse strain, BALBc.

Mixed lymphocyte cultures were set up using purified cell populations. Dendritic cells from BALBc animals were used to stimulate CD4+T cells from wild type and mutant mice. In a reciprocal experiment dendritic cells prepared from wild type and mutant mice were used to stimulate BALBc CD4+T cells. After 5 days in culture proliferative responses were measured by incorporation of tritiated thymidine.

Figure 6A:
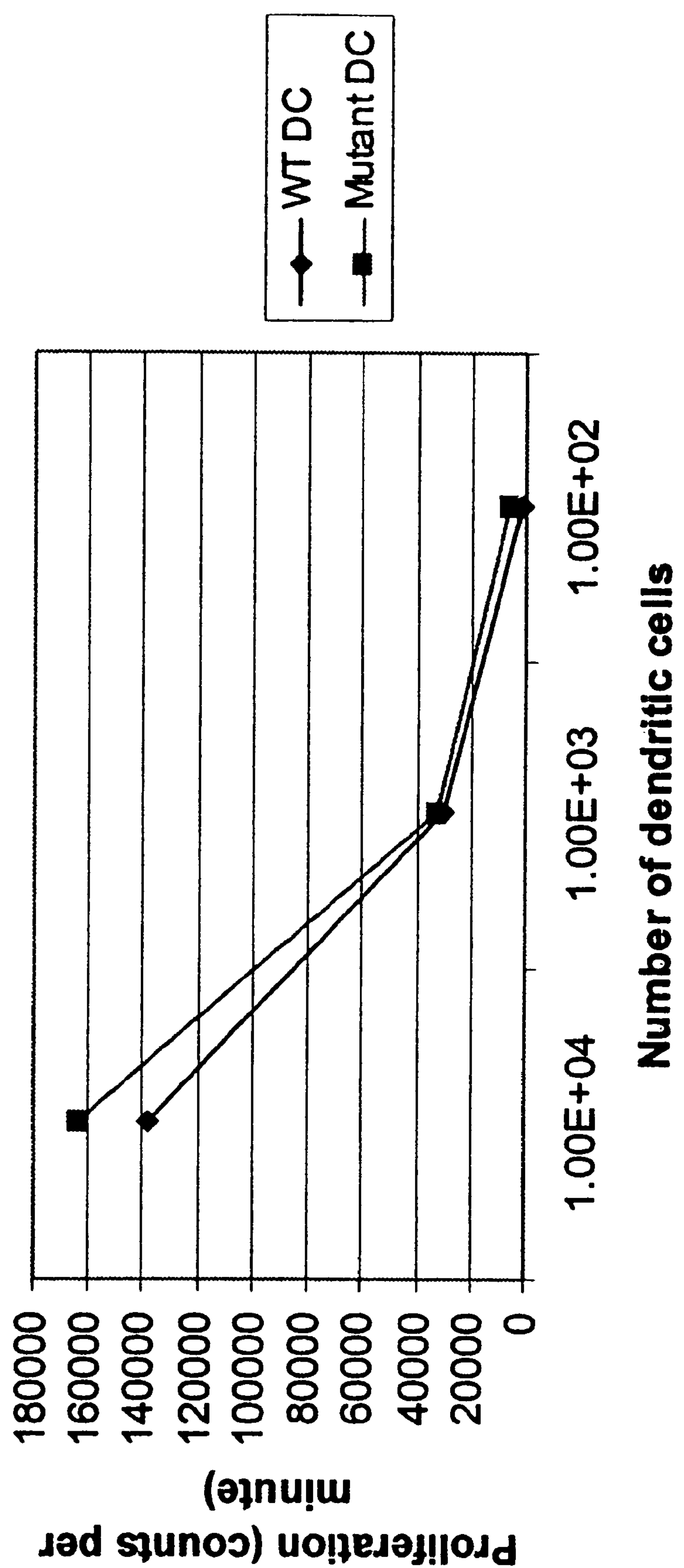
FIG. 6A illustrates that dendritic cells from wild type (?, WT DC) and mutant (¦, mutant DC) mice are capable of the allogeneic activation of CD4+T cells. CD4+T cells were stimulated with 10,000, 1000 or 100 dendritic cells for 5 days and proliferation was measured by incorporation of tritiated thymidine.
Figure 6B:
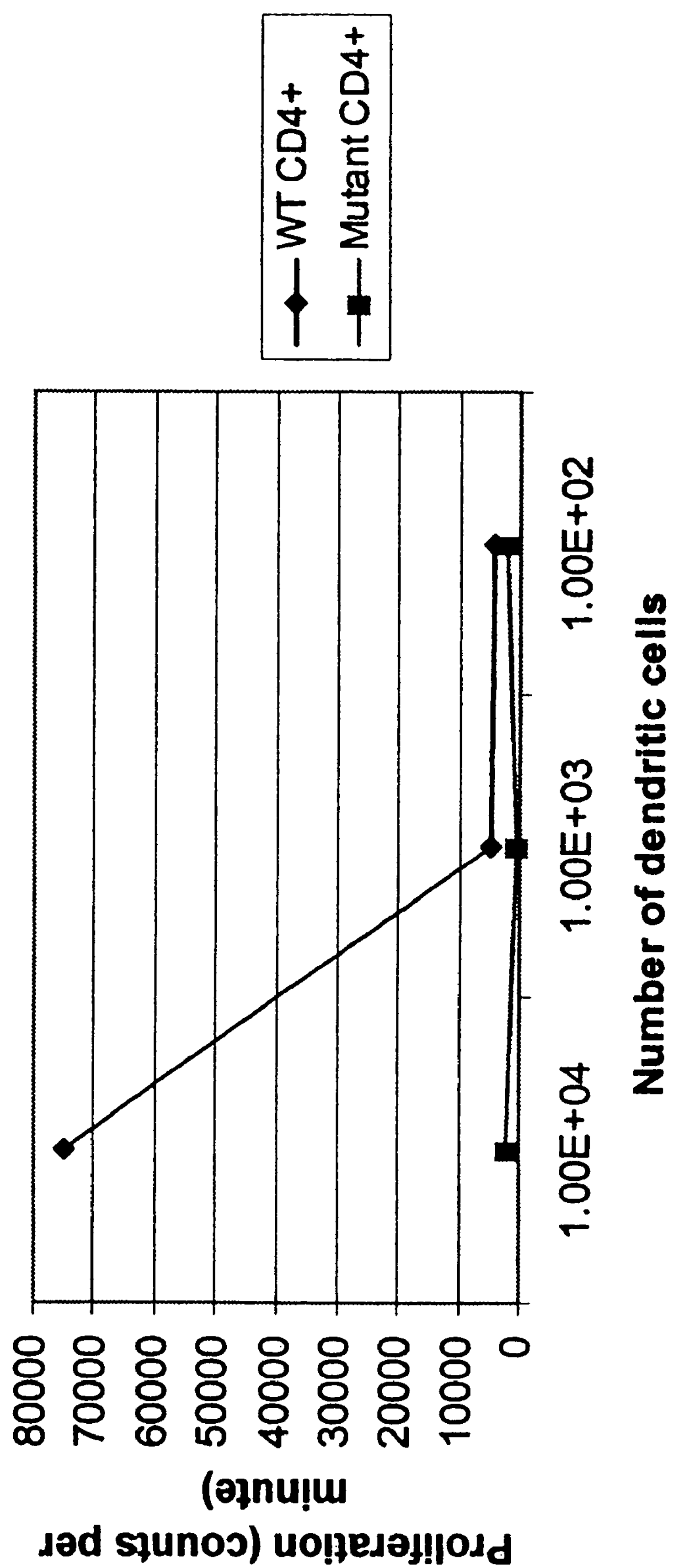
FIG. 6B illustrates that CD4+T cells from mutant mice (¦, mutant CD4) fail to respond to allogeneic stimulation with BALBc dendritic cells, although wild type animals (?, WT CD4+) respond normally. CD4+T cells were stimulated with 10,000, 1000 or 100 dendritic cells for 5 days and proliferation measured by incorporation of tritiated thymidine.

Dendritic cells from wild type and mutant mice were both capable of activating allogeneic T cells, suggesting that dendritic cell function was unimpaired in the mutant animal (FIG. 6*a*). In contrast CD4+T cells from mutant animals exhibited a diminished response after 5 days of stimulation (FIG. 6*b*).

These data suggest that the mutation in the CD83 gene has minimal effect on dendritic cells intrinsic function but rather has a profound effect upon T cell activity. The CD4+T cell therefore may have a novel requirement for CD83 functionality on T cells during allogeneic activation. CD83 may be influencing the extent of CD4+T cell activation or altering the duration of the CD4+T cell proliferative response. The therapeutic manipulation of CD83 may thus represent a mechanism for the specific regulation of T cell function in the treatment of T cell mediated diseases, including autoimmune disorders. Antibodies capable of blocking CD83 function may be used as therapeutics in the treatment of immune diseases whilst the activation of CD83 may have utility in enhancing immune responses in cancer and other circumstances.

Conclusion

Although CD83 has been described as a marker of dendritic cell activation there has previously been little data describing its function in vivo. However, the mutation provided by the invention destabilizes or inactivates the protein and leads to impaired surface expression. As a consequence, CD4+T cell function is impaired. However, the development of dendritic cells is not inhibited and mutant dendritic cells retain functionality. Nonetheless, the result is impaired development of CD4+T cells. This impaired ability to activate T cells is also seen in a slight decrease in contact sensitivity responses in LCD4.1 mutant mice.

Example 3

Mutant CD83 have Different Cytokine Levels than Wild Type Mice

This Example demonstrates that $CD4^+$T-cells from CD83 mutant animals express higher levels of IL-4 and lower levels of IL-2 compared to $CD4^+$T-cells from CD83 wild type animals.

Methods for Cell Activation and Cytokine Measurements:

Spleens cells from 6-8-week-old homozygous CD83 wild type or CD83 mutant (LCD4.1) mice were used to isolate $CD4^+$T-cells by positive selection using magnetic beads (Miltenyi Biotec). A 96 round bottom plate was coated with 504, per well of a solution containing either 1 or 10 μg/mL of anti-CD3 and 0.1 or 0.2 μg/mL of anti-CD28 antibodies (both from Pharmingen) in PBS overnight. This plate was then washed using 150 μL of PBS three times. To this pre-coated plate, 20,000 $CD4^+$T-cells (either wild type or CD83 mutant) were added in a 200 μL final volume of RPMI containing 10% FBS, 55 μM β-mercaptoethanol and antibiotics. The plates were then incubated in a $CO_2$ incubator at 37° C. for 44 to 72 hours. For determination of cytokine levels, supernatants were harvested and cytokines were measured using either a Cytometric Bead Array system (Pharmingen) or ELISA (R&D). For RNA measurements, the cells were harvested and RNA was isolated using Tri reagent (Sigma). IL-10 and IL-4 mRNA levels were measured by reverse transcription and TaqMan (Applied Biosystems) analysis.

Figure 7:
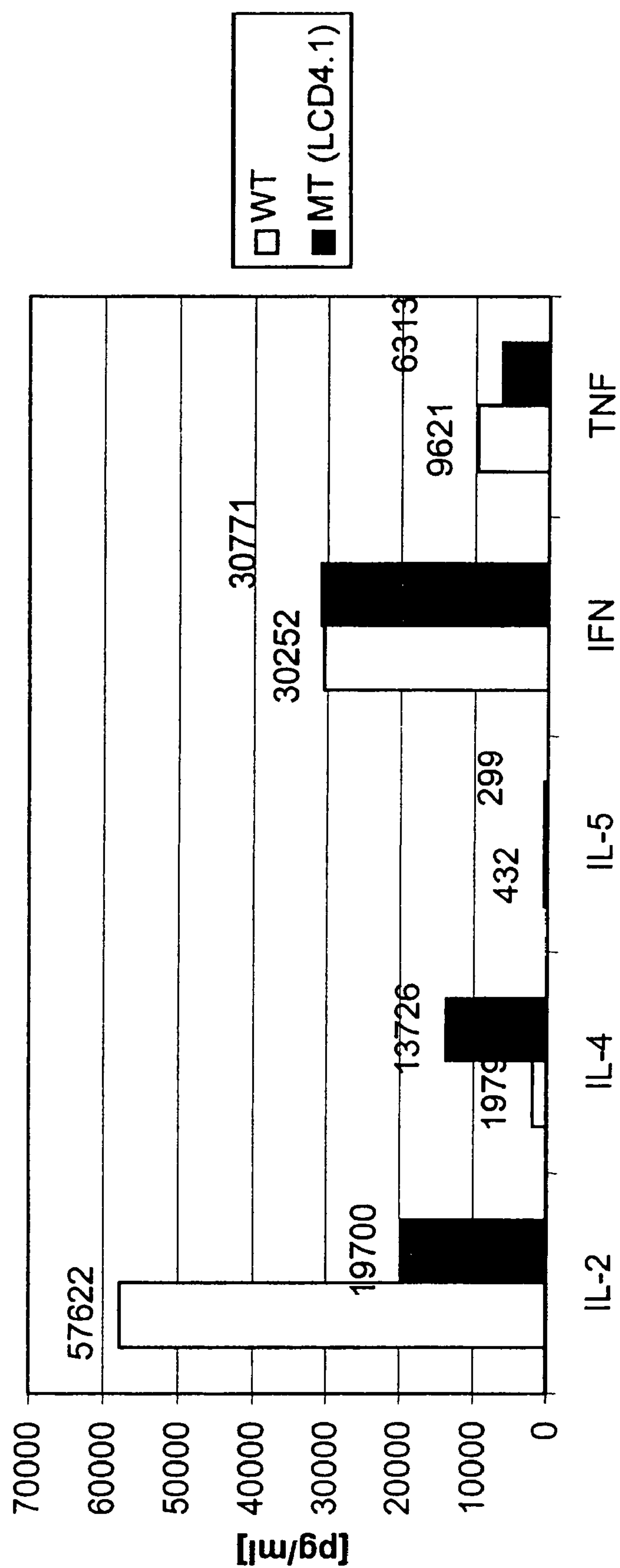
FIG. 7 provides a bar graph illustrating IL-2, IL-4, IL-5, TNFa, and IFN? production from wild type CD4+T cells (white bar) or CD83 mutant CD4+T cells (dark bar) that had been stimulated with 1 μg/ml of anti-CD3 antibodies and 0.2 μg/ml of anti-CD28 antibodies for 72 hours. As illustrated, IL-2 levels are lower, and IL-4 levels are higher in the CD83 mutant T cells.

Results:

FIG. 7 shows the IL-2, IL-4, IL-5, TNFa and IFN? levels produced by either wild type or CD83 mutant $CD4^+$T-cells. Purified cells were incubated as described above in the presence of 1 μg/mL of anti-CD3 and 0.2 μg/mL of anti-CD28 antibodies for 72 hours. The supernatants were then simultaneously analyzed for production of IL-2, IL-4, IL-5, TNFa and IFN? using the cytometric bead array system from Pharmingen.

Figure 8:
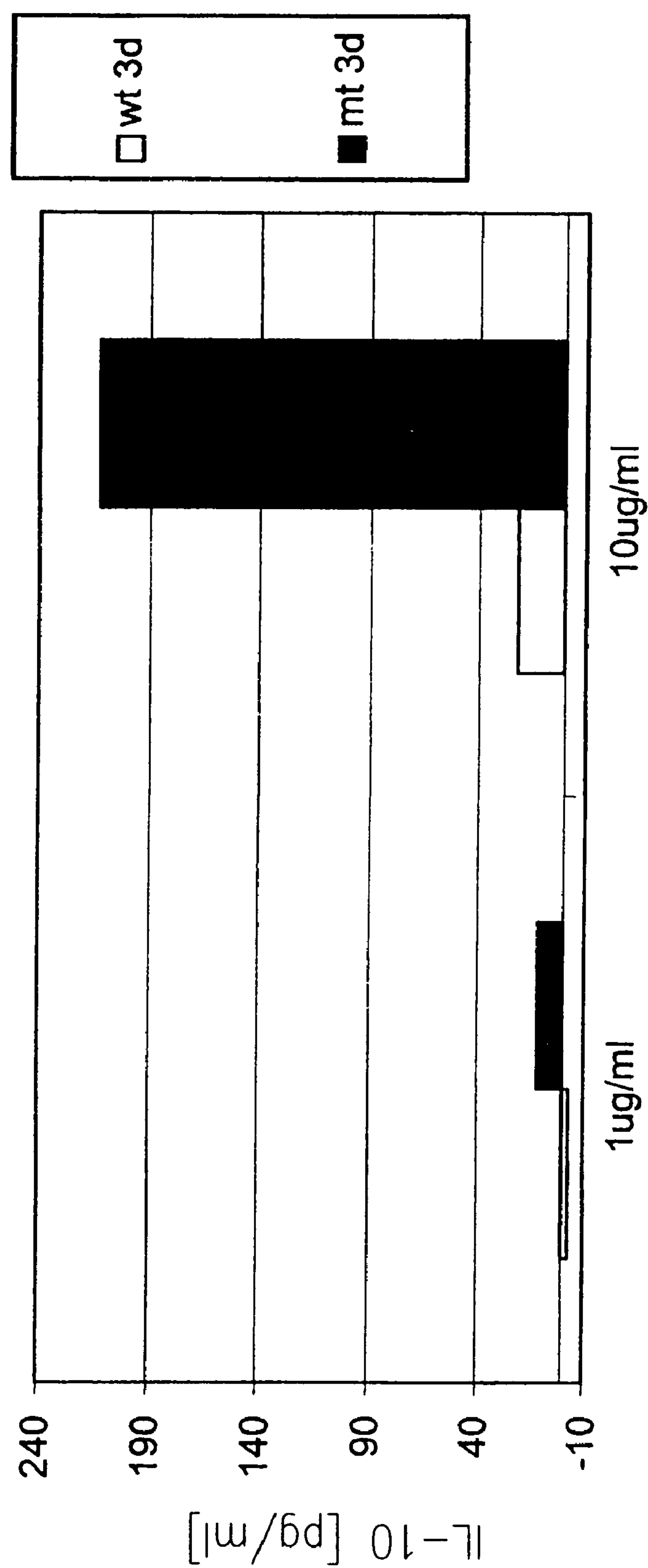
FIG. 8 provides a bar graph illustrating IL-10 production from wild type CD4+T cells (white bar) or CD83 mutant CD4+T cells (dark bar) that had been stimulated with 0.1 μg/ml of anti-CD28 antibodies and 1 to 10 μg/ml of anti-CD3 antibodies for 72 hours. As illustrated, IL-10 levels are higher in the CD83 mutant T cells.
Figure 9:
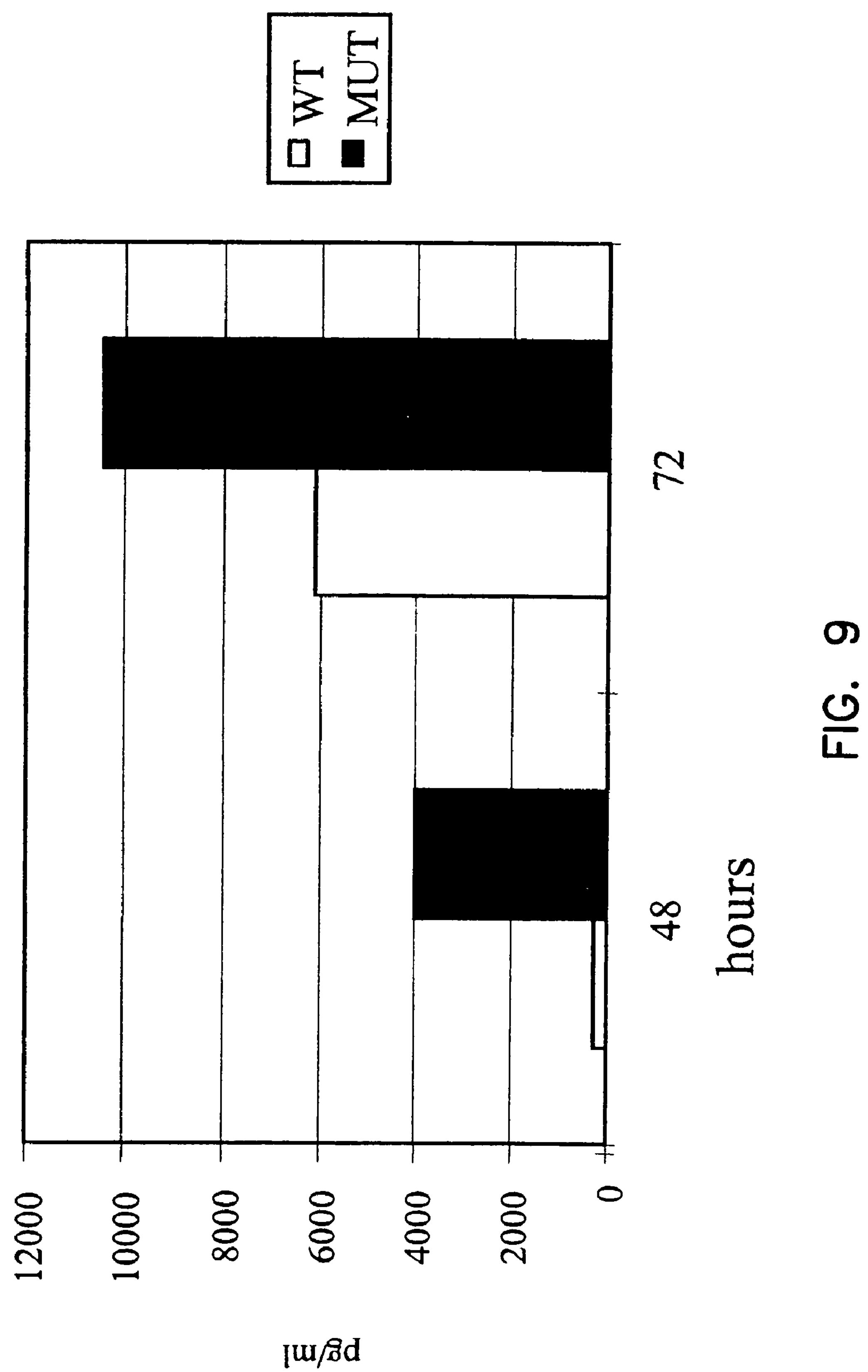
FIG. 9 provides a bar graph illustrating GM-CSF production from wild type CD4+T cells (white bar) or CD83 mutant CD4+T cells (dark bar) that had been stimulated with anti-CD3 and anti-CD28 antibodies. As illustrated, GM-CSF production is higher in the CD83 mutant cells than in wild type cells.
Figures 10A, 10B:
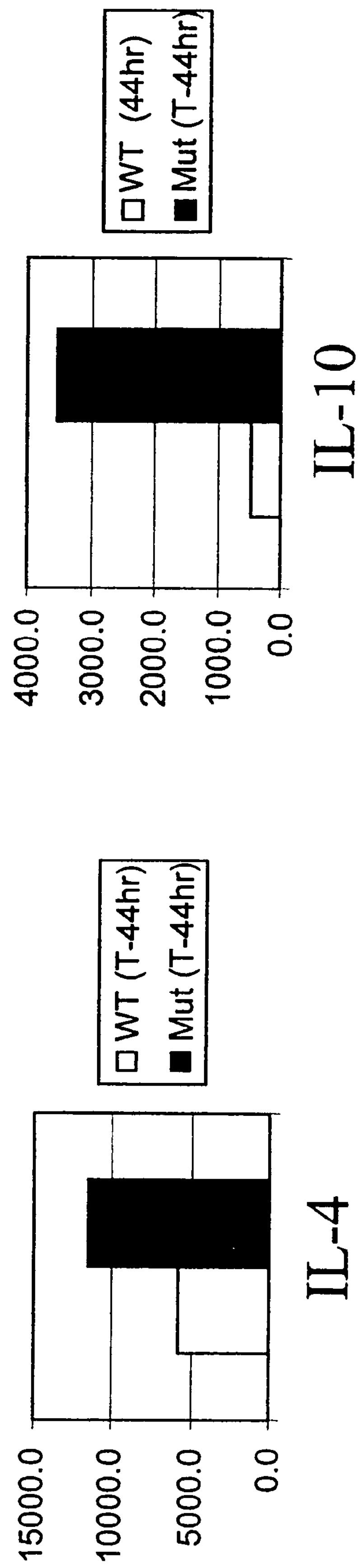
FIG. 10A provides a bar graph illustrating IL-4 mRNA levels from wild type CD4+T cells (white bar) or CD83 mutant CD4+T cells (dark bar) that had been stimulated with anti-CD3 and anti-CD28 antibodies. As illustrated, the IL-4 mRNA levels are higher in the CD83 mutant cells.
FIG. 10B provides a bar graph illustrating IL-10 mRNA levels from wild type CD4+T cells (white bar) or CD83 mutant CD4+T cells (dark bar) that had been stimulated with anti-CD3 and anti-CD28 antibodies. As illustrated, the IL-10 mRNA levels are higher in the CD83 mutant cells.

FIG. 7 demonstrates that $CD4^+$T-cells from CD83 mutant animals expressed higher levels of IL-4 and lower levels of IL-2 compared to $CD4^+$T-cells from CD83 wild type animals. Other cytokines and a new set of stimulation assays were analyzed including the production levels of IL-10 and GMCSF by these cells (FIGS. 8 and 9). In both cases, cells from mutant animals produce larger amounts of IL-10 and GMCSF than did wild type animals. FIG. 10 shows that mRNA levels for both IL-4 and IL-10 were increased in cells from activated mutant CD83, $CD4^+$T-cells compared with cells from wild type animals.

Example 4

Anti-CD83 Antibodies Mimic the Effects of the CD83 Mutation

Methods for Antibody Testing:

For modulation of cytokine production by anti-CD83 antibodies, $CD4^+$T-cells were isolated and activated as described above. Activation was performed in the presence of increasing concentrations of anti-CD83 antibodies. For proliferation assays, $CD4^+$T-cells were isolated from an OT2tg mouse. OT2tg mice are transgenic mice with a T-cell receptor specific for chicken ovalbumin (OVA) 323-339 peptide. Dendritic cells were isolated from a C57BL6 mouse by a negative selection using B220 magnetic beads (Miltenyi Biotec) followed by positive selection using CD11-c magnetic beads (Milteny Biotec). Five thousand $CD4^+$T -cells were then mixed with five thousand dendritic cells in a 96 well plate in the presences of 1 μM OVA peptide using RPMI (55 μM BME, 10% FBS plus antibiotics) in a final 200 uL volume. These cells were then incubated for 48 to 72 hours in a $CO_2$ incubator at 37° C. and pulsed using [$^3$H] thymidine for 8 hours. Cells were then harvested and [$^3$H] thymidine incorporation was quantified using a top counter.

Figure 11:
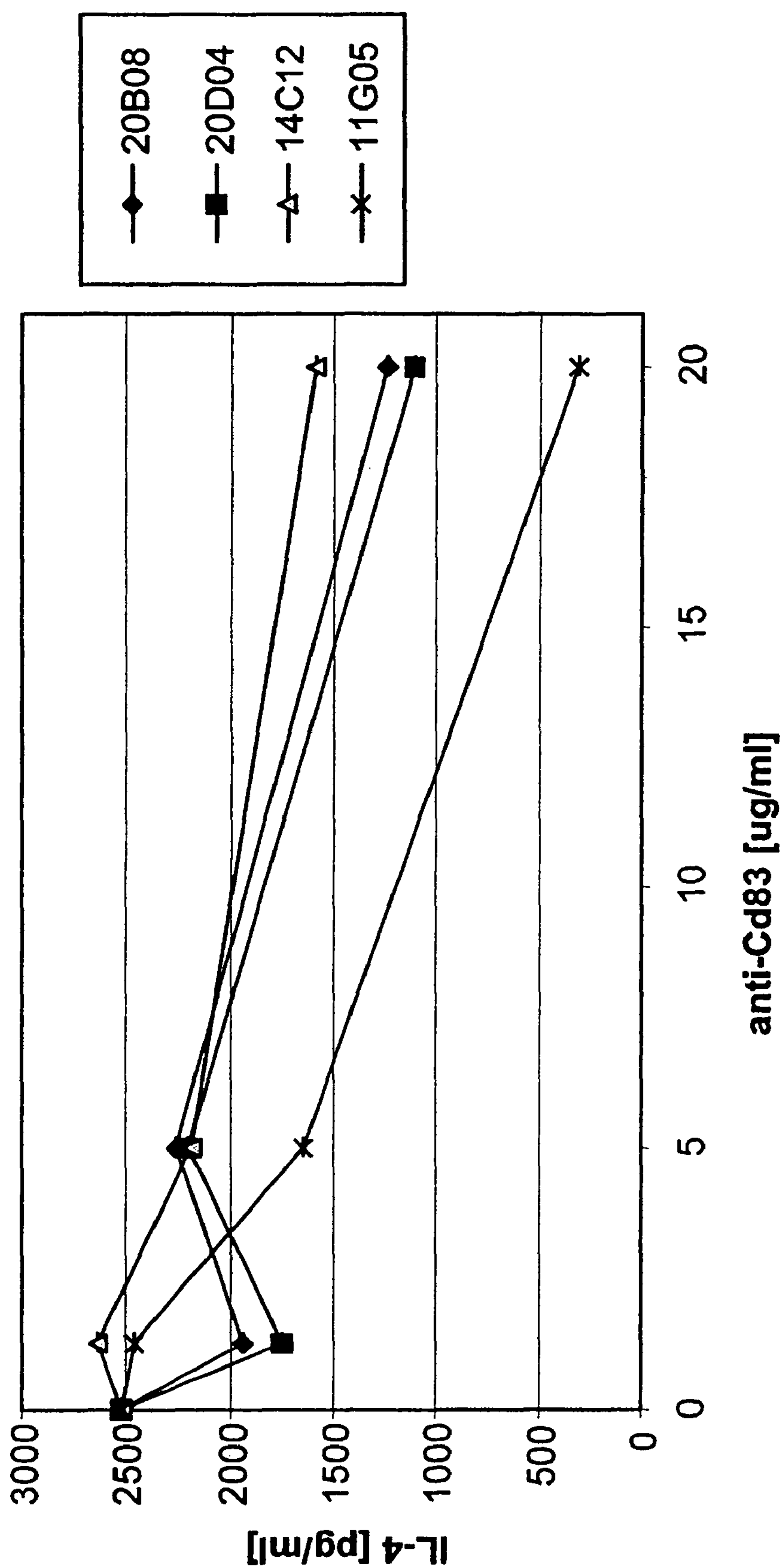
FIG. 11 provides a graph illustrating that various preparations of anti-CD83 antibodies inhibit IL-4 production in anti-CD3 and anti-CD28 antibody stimulated T cells. The amount of IL-4 produced by T cells in pg/ml is plotted versus the concentration of different anti-CD83 antibody preparations, including the 20B08 (?) anti-CD83 preparation, the 20D04 ( ) anti-CD83 preparation, the 14C12 (?) anti-CD83 preparation and the 11G05 (X) anti-CD83 antibody preparation.

Results:

In some assays, anti-CD83 antibodies decreased production of IL-4 by activated $CD4^+$T-cells in a dose dependent manner. Different antibody preparations did provide somewhat different degrees of inhibition of IL-4 production (FIG. 11). Accordingly, the epitope and/or degree of affinity of the antibodies for the CD83 antigen may influence whether or not IL-4 production is significantly inhibited.

Figure 12:
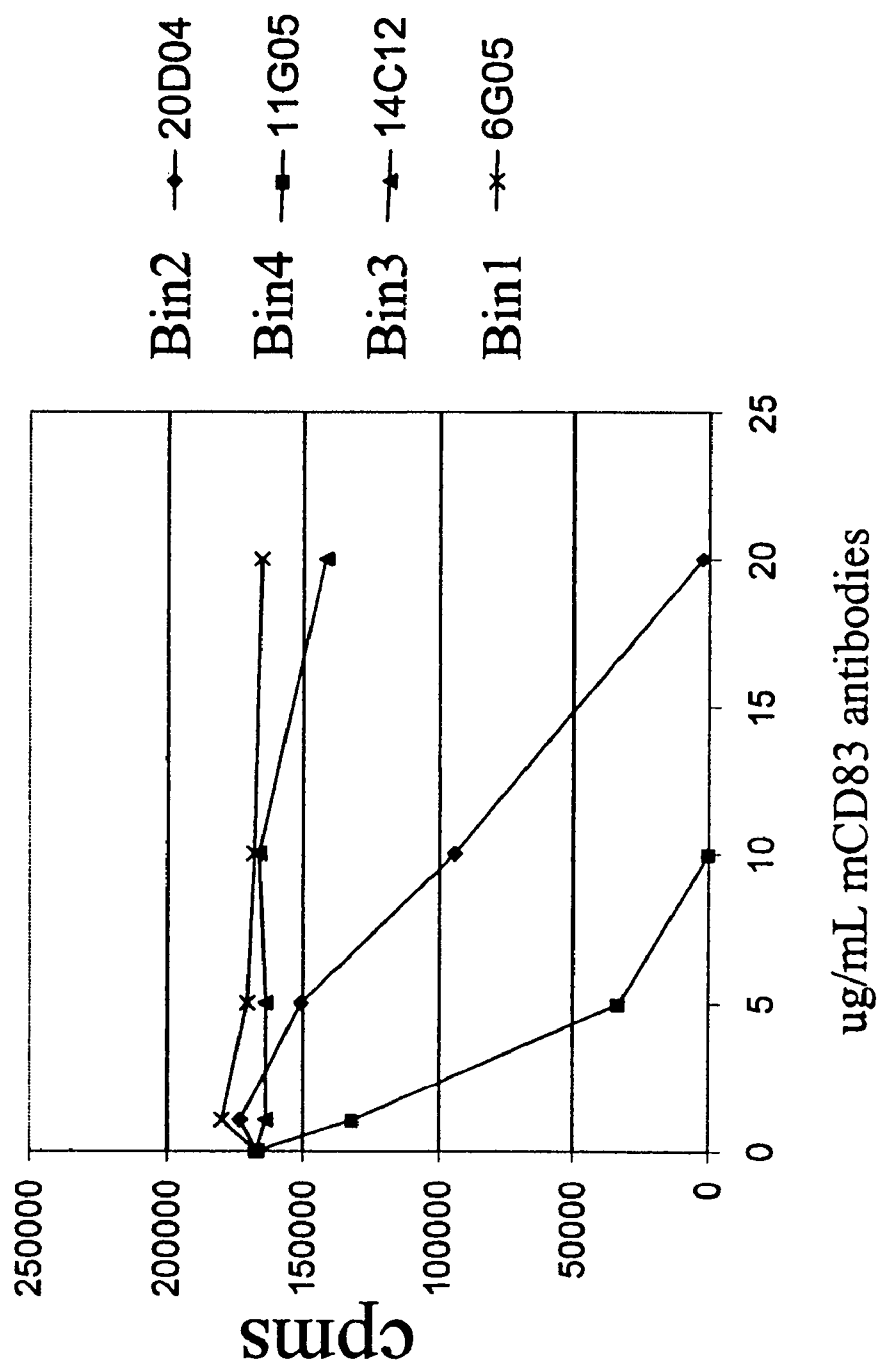
FIG. 12 provides a graph illustrating that various preparations of anti-CD83 antibodies inhibit T cell proliferation. The graph plots the incorporation of radioactive thymidine in cpms, which was used as an indicator of the amount of T cell proliferation, versus the concentration of the different anti-CD83 antibody preparations, including the 20D04 (?) anti-CD83 preparation, the 11G05 (¦) anti-CD83 antibody preparation, the 14C12 (?) anti-CD83 preparation and the 6G05 anti-CD83 preparation (X).

The effects of anti CD83 antibodies on proliferation of a peptide specific T-cell proliferation assay using the OT2 T-cell receptor (TCR) transgenic system were also observed. $CD4^+$T-cells derived from these TCR transgenic animals express high levels of a T-cell receptor specific for chicken ovalbumin (OVA) 323-339 peptide and thus have high levels of proliferation when mixed with antigen presenting cells (dendritic cells were used) in the presence of the OVA peptide. In such assays, anti-CD83 antibodies were able to decrease proliferation of $CD4^+$T-cells in this system (FIG. 12). However, different antibody preparations had somewhat different effects on the proliferation of $CD4^+$T-cells. Accordingly, the CD83 epitope and/or degree of affinity of the antibodies for the CD83 antigen may influence whether or not $CD4^+$T-cell proliferation is significantly inhibited.

Example 5

Increased T-Cell Proliferation by Transgenic Expression of CD83

This Example illustrates that over expression of CD83 in transgenic mice leads to increased T-cell proliferation.

Materials and Methods

A 34.3 kb fragment of normal mouse genomic DNA, including the ~18 kb coding region of the CD83 gene, as well as ~10.6 kb of upstream flanking sequences and ~5.7 kb of downstream sequences was microinjected into normal mouse one-cell embryos. Four individual founder animals were generated. Transgenic mice were then crossed to a male OT2tg mouse. Male offspring carrying both the CD83 and OT2 transgene were used to analyze peptide specific T-cell proliferation.

For proliferation assays, $CD4^+$T-cells and dendritic cells were isolated from either OT2tg [transgenic mice with a T-cell receptor specific for chicken ovalbumin (OVA) 323-339 peptide] CD83 wild type or from OT2tg CD83 transgenic mice as described above (Example 4). Five thousand OT2tg $CD4^+$T-cells from either wild type or CD83 transgenic animals were then mixed with five thousand wild type dendritic cells or five thousand CD83 transgenic dendritic cells in a 96 well plate in the presence of increasing concentrations of OVA peptide using RPMI (55 μM BME, 10% FBS plus antibiotics) in a final 200 uL volume. These cells were then incubated for 48 to 72 hours in a $CO_2$ incubator at 37 C and pulsed using [$^3$H] thymidine for 8 hours. Cells were then harvested and [$^3$H] thymidine incorporation was quantified using a top counter.

Figure 13:
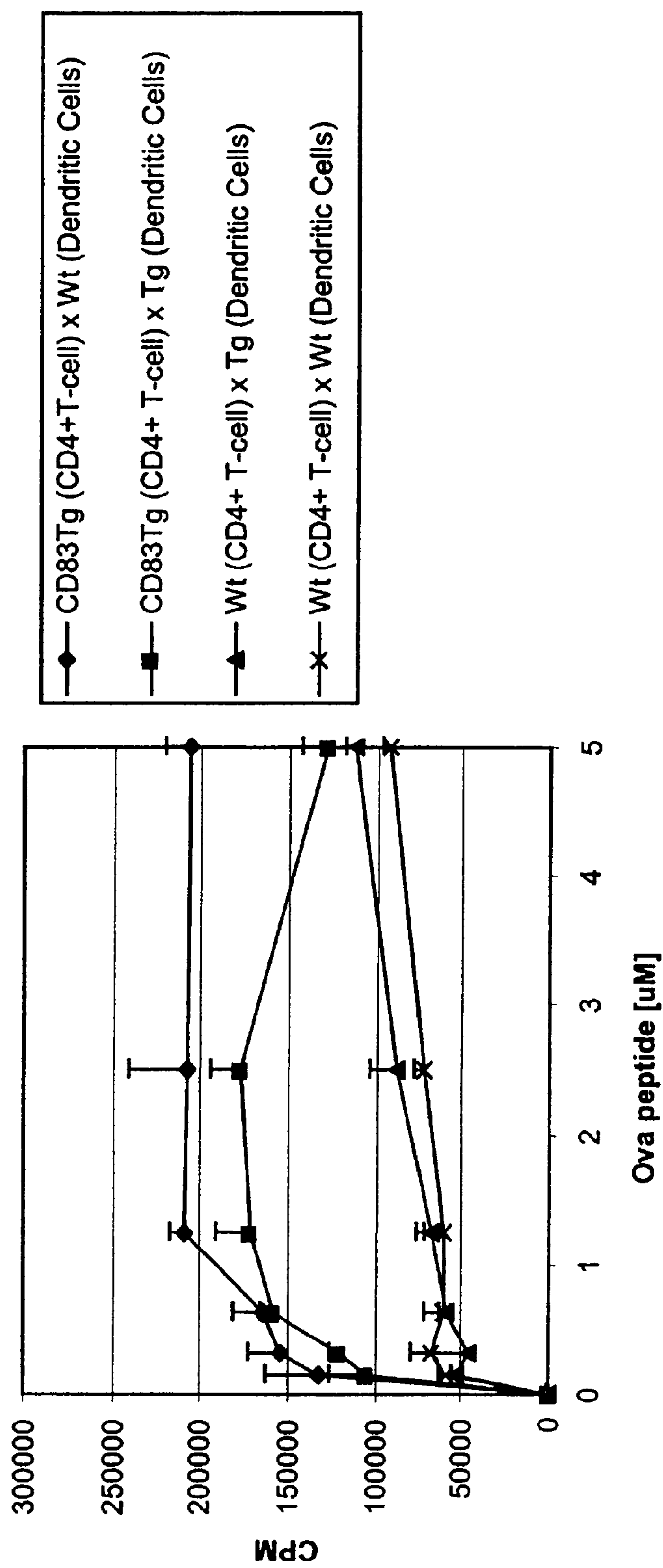
FIG. 13 provides a graph illustrating that transgenic mice that over-express wild type CD83 have increased T cell proliferation. The graph plots the incorporation of radioactive thymidine in cpms, which was used as an indicator of the amount of T cell proliferation, versus the concentration of OVA peptide. The transgenic mice utilized had a T-cell receptor specific for chicken ovalbumin (OVA) 323-339 peptide that can activate T-cells. When mixed with either transgenic or wild type dendritic cells in the presence of OVA peptide, transgenic CD4+T cells had increased T-cell proliferation. However, transgenic dendritic cells could not substantially increase wild type CD4+T cell proliferation. Transgenic CD83 CD4+T cells mixed with wild type dendritic cells (?); transgenic CD83 CD4+T cells mixed with transgenic dendritic cells (¦); wild type CD4+T cells mixed with transgenic dendritic cells (?); and wild type CD4+T cells mixed with wild type dendritic cells (X).

Results:

OT2tg $CD4^+$T-cells derived from CD83 transgenic mice proliferated at higher rates than the same cell population derived from a CD83 wild type animal (FIG. 13). This increased proliferation was seen at all the concentrations of OVA peptide tested. Whereas OT2tg $CD4^+$T-cells derived from CD83 transgenic animals exhibited increased proliferation, dendritic cells from CD83 transgenic animals did not exhibit a substantial increase in proliferation. Therefore, it appears that transgenic expression in the $CD4^+$T-cell, and not in dendritic cells is what led to the increased proliferation of $CD4^+$T-cells.

Example 6

Inhibition of Proliferation of PHA Activated Human PBMCs by Protein A Purified Rabbit Anti-Mouse CD83 Antibodies This Example shows that antibodies raised against the CD83 protein can inhibit proliferation of human peripheral blood mononuclear cells.

Materials and Methods

Figure 14:
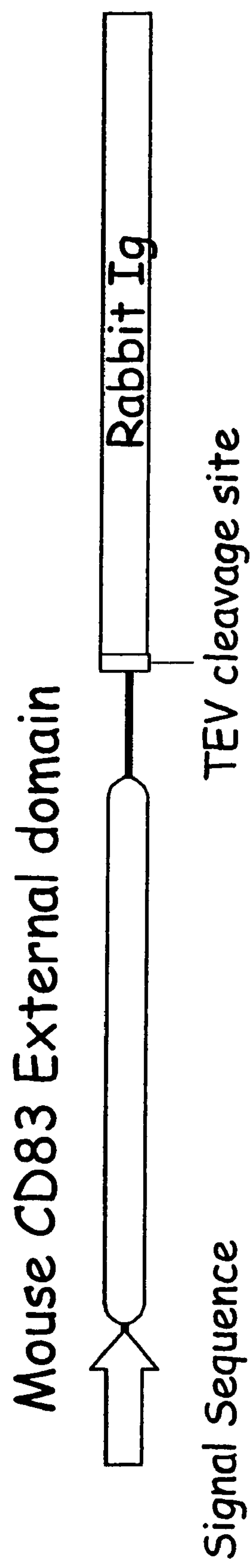
FIG. 14 provides a schematic diagram of the structural elements included in the mouse CD83 protein used for generating antibodies.
Figure 15:
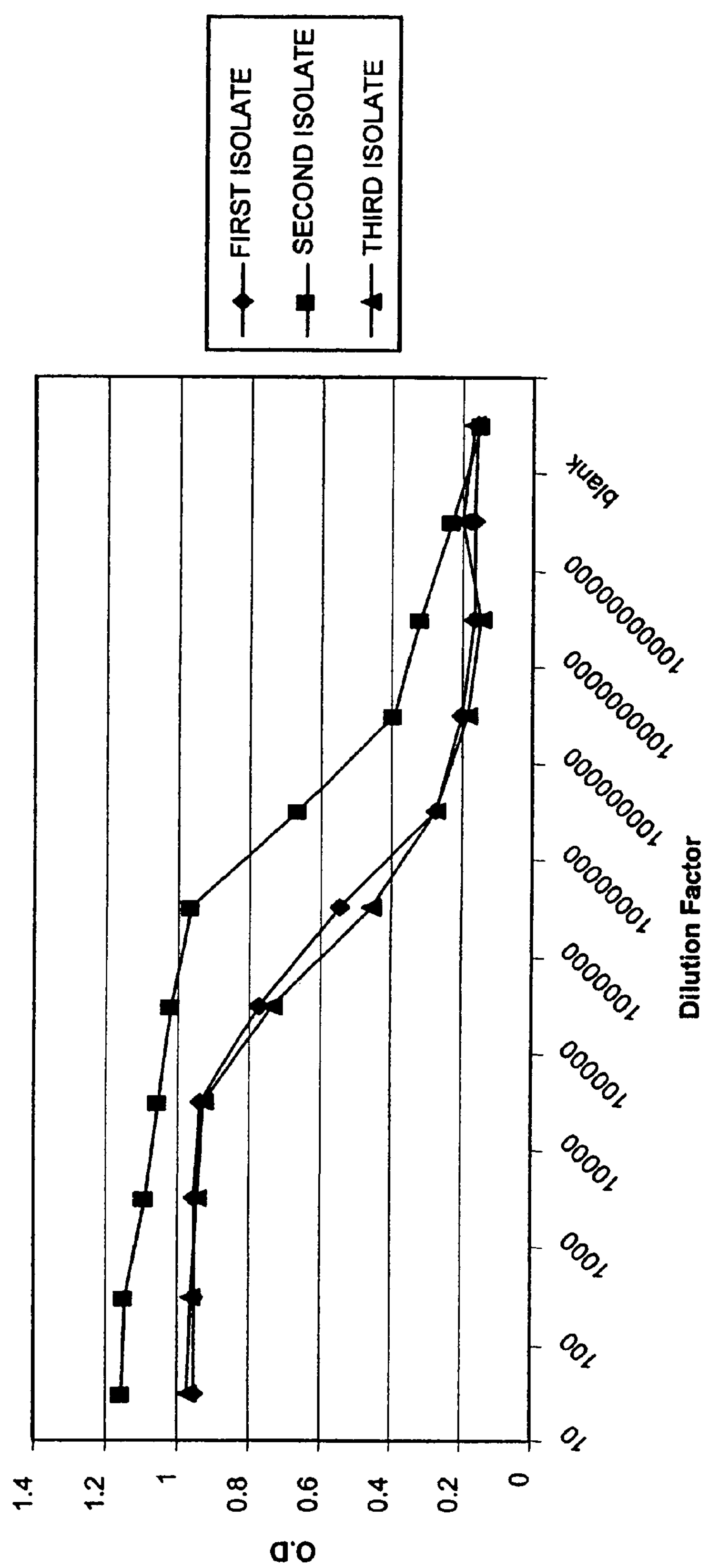
FIG. 15 provides a graph of ELISA data illustrating the titer obtained for different isolates of polyclonal anti-CD83 anti-sera. The first (?), second (¦) and third (?) isolates had similar titers, though the titer of the second isolate (¦) was somewhat higher.

Rabbit polyclonal sera was raised against mouse CD83 protein by immunizing rabbits using a mouse CD83 external domain protein fused to a rabbit Ig domain (FIG. 14). Preimmune sera and anti-mouse polyclonal sera were then purified using a protein A column (Pharmacia Biotech) as described by the manufacturer, then dialyzed against PBS and stored at 4° C. To monitor the recognition of mouse CD83 protein by the polyclonal sera, which was obtained at different dates post immunization, a titer was obtained using an antigen specific ELISA (FIG. 15). As illustrated by FIG. 15, a good polyclonal response was obtained against the mouse CD83 protein.

Human peripheral blood mononuclear cells (PBMCs) were isolated using a Ficoll gradient (Ficoll Paque Plus, Pharmacia) and washed with PBS buffer. For activation and proliferation studies, five thousand cells were incubated in 200 μL of media (RPMI, 10% FBS, antibiotics) and 5 ug/mL of *Phaseolus vulgaris* leucoagglutinin (PHA) in the presence or absence of increasing concentrations of Protein A purified pre-immune sera or with similarly purified anti-CD83 polyclonal antibodies. After 48 hours at 37° C. in a $CO_2$ incubator the cells were pulsed with [$^3$H] thymidine for ~8 hours and harvested. Thymidine incorporation into the PBMCs was measured using a top counter for analysis.

A Selected Lymphocyte Antibody Method (SLAM) procedure was used to establish monoclonal antibody cell lines from the rabbits used to generate the anti-CD83 antibodies. Antibody forming cells were isolated from the immunized rabbits that produced antibodies capable of binding CD83, the genes encoding antibodies that recognized CD83 and inhibited proliferation of lymphocytes were then cloned by PCR amplification and sequenced. Separate lines of monoclonal antibody producing cells were then established and expanded in culture. Antibodies were purified using Protein A chromatography according to manufacturer's instructions and tested for their ability to recognize CD83 proteins and to inhibit proliferation of PHA stimulated human PBMCs.

Results

Figure 16:
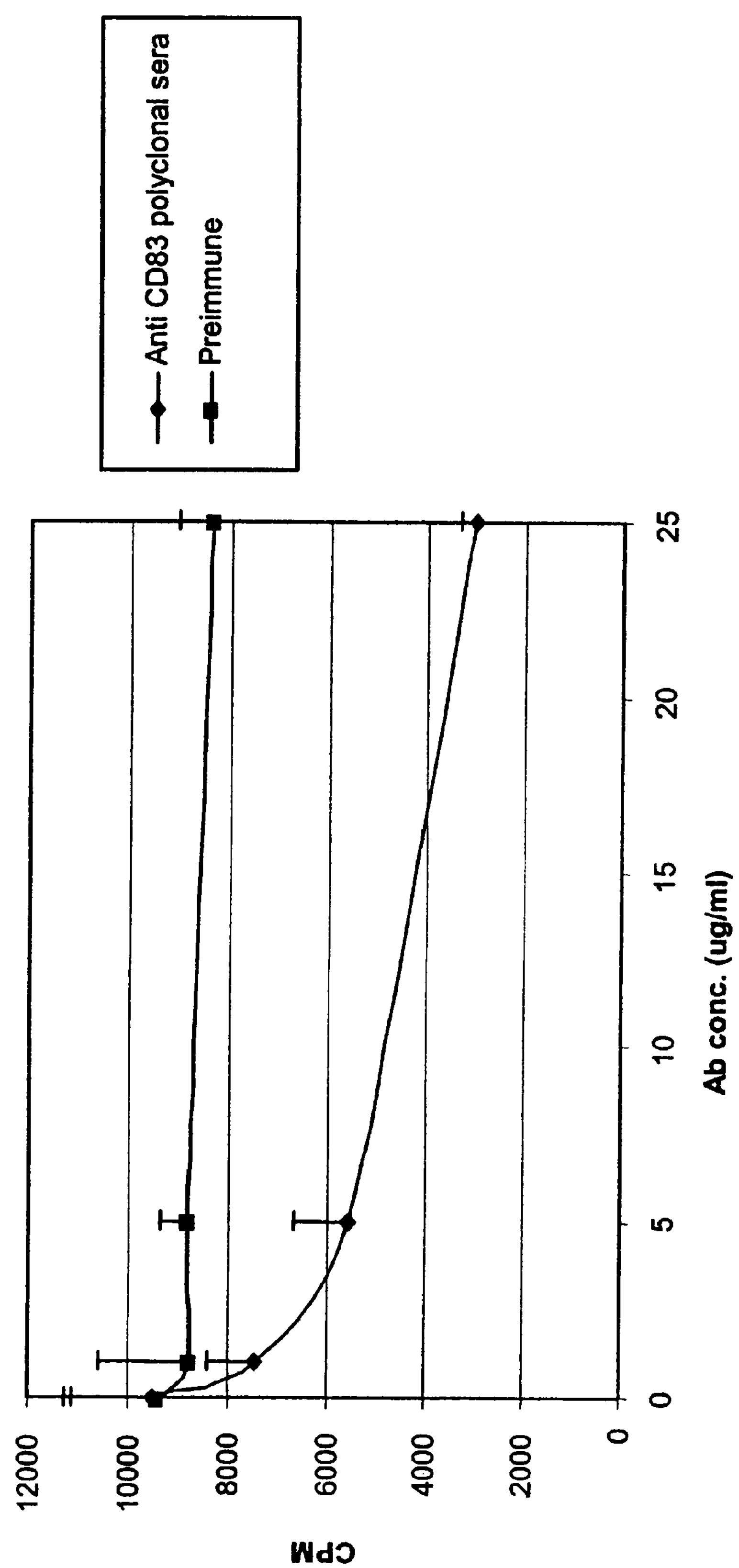
FIG. 16 illustrates that proliferation of PHA-activated human PBMCs was inhibited by antibodies raised against the external region of the mouse CD83 protein (?). Pre-immune serum (¦) had little effect on the proliferation of human PBMCs.

FIG. 16 illustrates that proliferation of PHA-activated human PBMCs was inhibited by polyclonal antibodies raised against the external region of the mouse CD83 protein. Proliferation of PHA-activated human PBMCs was not affected by addition of increasing concentrations of protein A purified rabbit pre-immune sera. When increasing concentrations of protein A purified rabbit polyclonal sera raised against the mouse CD83 protein was added, a concentration dependent decrease in proliferation was observed.

These data indicate that antibodies raised against the mouse protein are able to cross-react with the human protein. Moreover, antibodies raised against the mouse protein are able to inhibit proliferation of PHA-activated human PBMCs.

A summary of the characteristics of two monoclonal antibody preparations having functional activity is shown in Table 1. Isolated recombinant mouse and human CD83 protein preparations were used for the BIACORE and ELISA assays. Endogenous human CD83 protein expressed in a human KMH2 cell line was used for FACS assays.

TABLE 1

Monoclonal Antibody Functionality and Reactivity with Mouse and Human CD83

| Assay | 95F04 Antibodies | 96G08 Antibodies |
|---|---|---|
| Inhibition of human PBMC proliferation | ++ | +++ |
| Biacore - mouse CD83 | +++ | +++ |
| Biacore - human CD83 | ++ | − |
| ELISA - mouse CD83 | +++ | +++ |
| ELISA- human CD83 | ++ | − |
| FACS - human CD83 | ND | ++ |

ND: not determined

Figure 18:
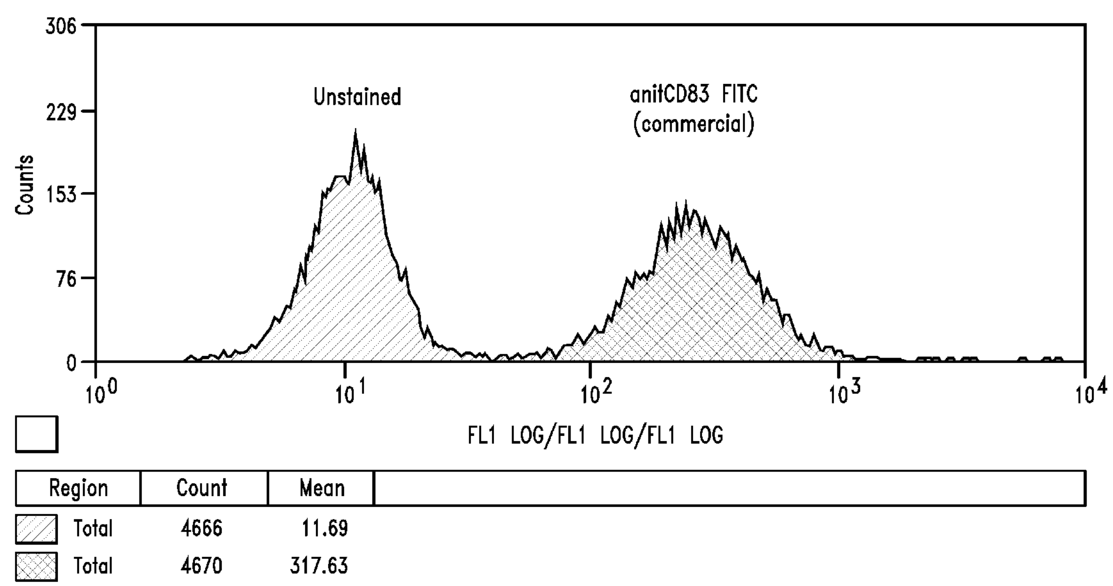
FIG. 18 graphically illustrates that cells expressing CD83 can be detected and sorted using an anti-CD83 antibody preparation. In this study, a Hodgkin's lymphoma cell line, KMH2, and a commercially available anti-CD83 antibody preparation was used for FACS sorting.
Figure 19A:
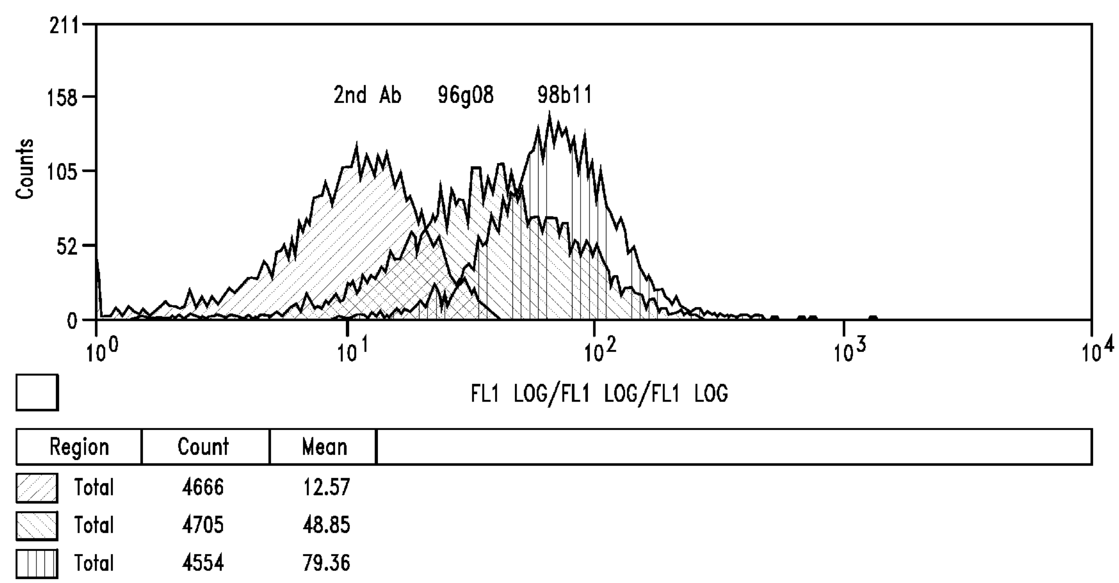
FIG. 19A-B shows that two antibody preparations of the invention can bind to endogenously produced human CD83, as detected by FACS sorting of KMH2 cells (see also FIG. 18). Note that "Beer" is another name used for CD83.
Figure 19B:
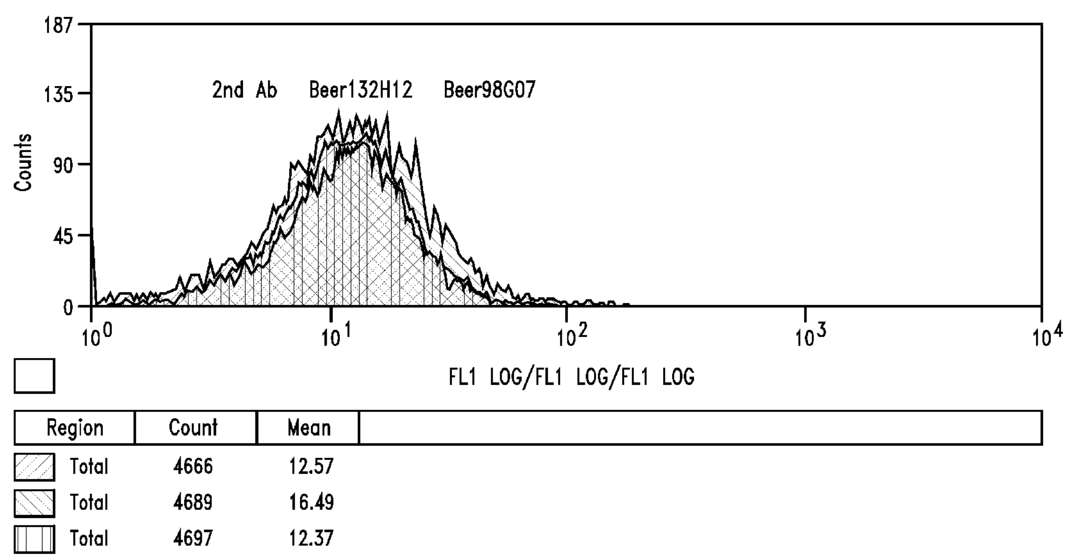
Figure 20:
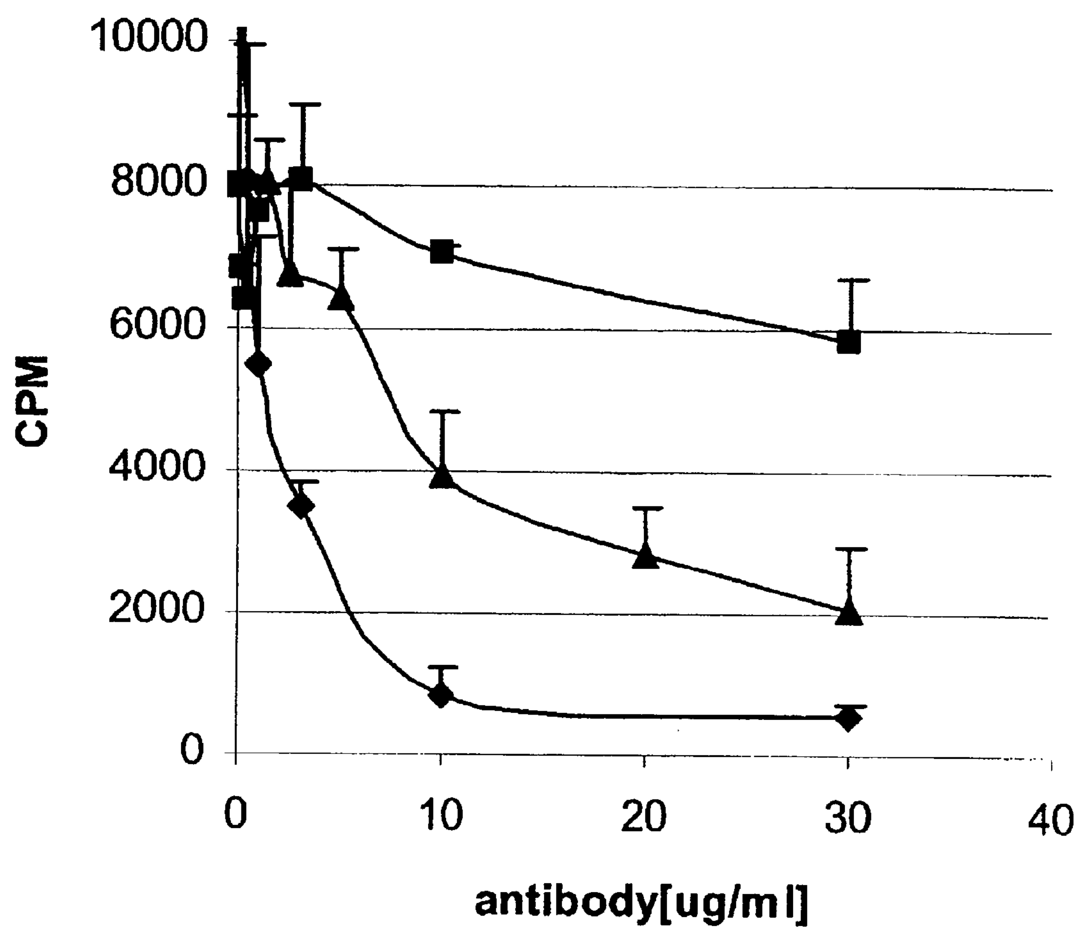
FIG. 20 illustrates that the 95F04 and 96G08 antibody preparations described herein can inhibit proliferation of human peripheral blood mononuclear cells as detected by [$^{3}$H] thymidine incorporation. As shown, when 30 μg/ml of the 95F04 (?) antibody preparation was present, incorporation of [$^{3}$H] thymidine dropped to about 2000 cpm. When 30 μg/ml 96G08 antibody preparation (?) was added to human peripheral blood mononuclear cells, [$^{3}$H] thymidine incorporation was reduced to about 300 cpm. A third antibody preparation (98B11, ¦) provided slight inhibition of PBMC proliferation. These data indicate that the 95F04 and 96G08 antibody preparations can alter the function of human CD83 in vivo.

While the 96G08 antibodies appeared to have reduced affinity for human CD83 protein via the Biacore and ELISA assays, the FACS assay indicated that this antibody preparation could bind to endogenously produced human CD83 (FIGS. 18 and 19). Moreover, the 96G08 antibodies were able to inhibit proliferation of human peripheral blood mononuclear cells (PBMCs), as illustrated in FIG. 20. Hence, some aspect of either the purification or the structure of the isolated recombinant human protein may have influenced the in vitro binding of 96G08 antibodies to the recombinant human CD83. For example, the recombinant human CD83 protein employed for the Biacore and ELISA assays is a chimeric protein that is joined to a portion of an immunoglobulin Fc fragment. Removal of this Fc fragment may improve in vitro binding to the human CD83 protein.

FIG. 20 illustrates that the 95F04 and 96G08 antibody preparations can inhibit proliferation of PHA activated human peripheral blood mononuclear cells as detected by incorporation of [$^3$H] thymidine. As shown, when no antibody was present about 10,000 cpm of [$^3$H] thymidine was incorporated into human peripheral blood mononuclear cells. However, when 30 μg/ml of the 95F04 antibody preparation was present, incorporation of [$^3$H] thymidine dropped to about 2000 cpm. The 96G08 antibody preparation had an even greater effect on [$^3$H] thymidine incorporation. When 30 μg/ml 96G08 antibody preparation was added to human peripheral blood mononuclear cells, [$^3$H] thymidine incorporation was reduced to about 300 cpm. These data indicate that the 95F04 and 96G08 antibody preparations can alter the function of human CD83 in vitro.

Example 7

Multimerized Anti-CD83 Antibodies Inhibit Proliferation of Immune Cells

This Example shows that antibodies raised against the CD83 protein as described in the previous example are particularly effective at inhibiting proliferation of immune cells after the antibodies are multimerized or multimerized by binding the antibodies to a solid support or by cross-linking in solution.

Materials and Methods

Round bottom microtiter plates were coated with different preparations of anti-CD83 antibody preparations by incubating the plates with 50 μl of 50 μg/ml antibody preparation per well either for 2 hours at 37° C. or overnight at 4° C. As a positive control, some wells were coated with anti-LFA antibodies that are known to inhibit proliferation of lymphocytes. After coating, the wells were then washed thoroughly with PBS.

Mouse (C57B16) spleen cells were isolated and plated in the antibody or control treated wells at 30,000 cells per well. For activation, Concavalin A was added to a final concentration of 1.0 μg/ml. Cellular proliferation was assessed by measuring the incorporation of tritiated thymidine during the last 6 to 8 hours of a 48 hour incubation. In another experiment, the specificity of the observed antibody-induced inhibition of lymphocyte proliferation was tested by repeating this experiment with addition of mouse CD83 protein before adding the lymphocytes to the antibody coated microtiter wells.

As described in more detail below, the 6G05 antibody preparation was identified as a good inhibitor of lymphocyte proliferation. In contrast, the 112D08 antibody preparation was identified as having little or no inhibitory activity when bound to microtiter wells. The 112D08 antibody preparation was used as a negative control in some of the subsequent experiments.

The inhibitory activities of plate-bound versus soluble, cross-linked 6G05 antibodies were compared in another experiment. Plate-bound 6G05 antibodies were prepared as described above. Approximately 30,000 activated lymphocytes were added per well to antibody coated plates or to non-coated plates containing 1.0 or 5.0 μg/ml soluble 6G05 antibody preparation. A secondary rabbit anti -mouse antibody (10 μg/ml or 25 μg/ml) was added to the wells containing the soluble 6G05 antibody preparation to act as a cross-linking reagent for the 6G05 antibodies. Cellular proliferation was assessed by incorporation of tritiated thymidine as described above.

Results

Figure 25A:
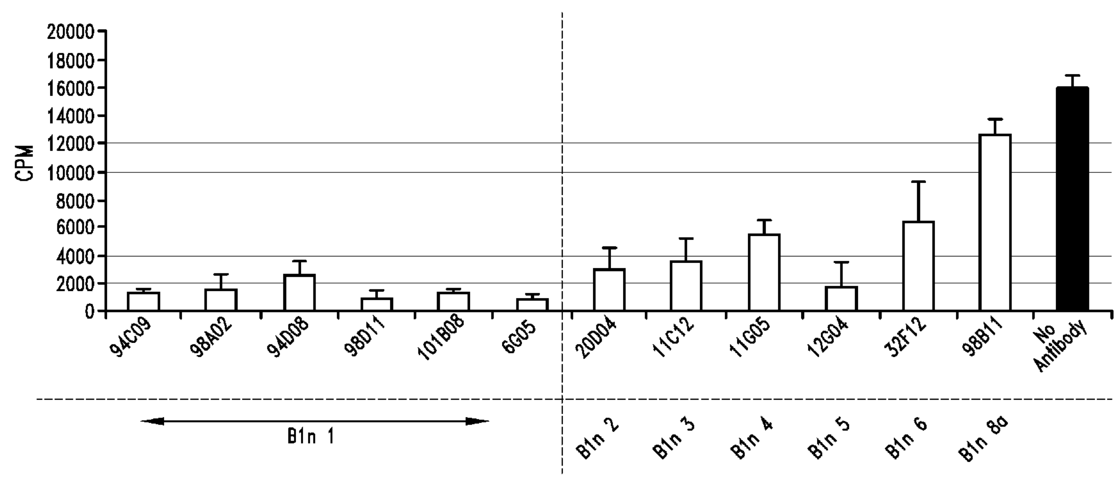
FIG. 25A-B provides the results of one screen of anti-CD83 antibody preparations that were multimerized by binding them to microtiter plates. The plate-bound antibodies were screened for an ability to inhibit lymphocyte proliferation as measured by tritiated thymidine incorporation.
Figure 25B:
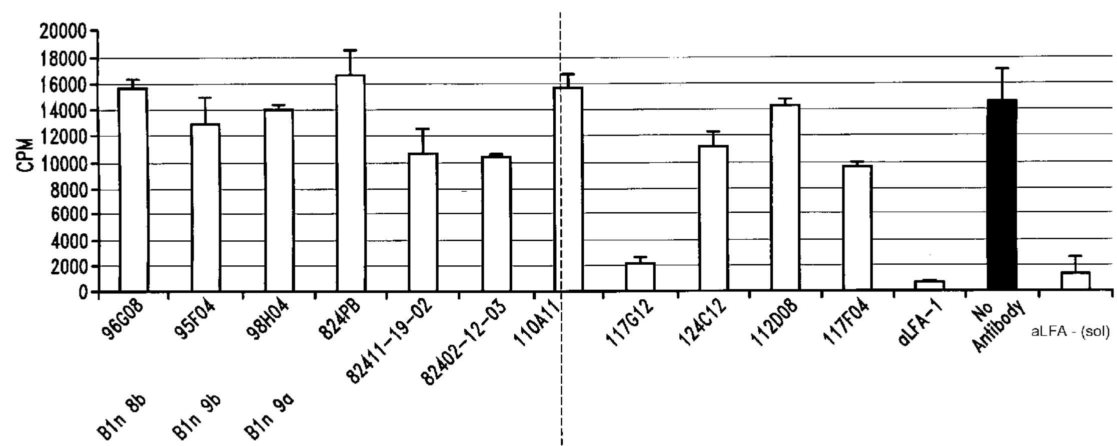

The results of one screen for anti-CD83 antibody preparations that can inhibit lymphocyte proliferation are shown in FIG. 25A-B. As illustrated in FIG. 25A many anti-CD83 antibody preparations inhibit proliferation of activated lymphocytes, including the 94c09, 98a02, 94d08, 98d11, 101b08, 6g05, 20d04, 14c12, 11g05, 12g04, 32f12 and 98b11 preparations. Note that some variation in the degree of inhibition obtained is observed. For example, while the 98b11 preparation is not so effective, the 6g05 antibody preparation is a highly effective inhibitor of lymphocyte proliferation.

Figure 26:
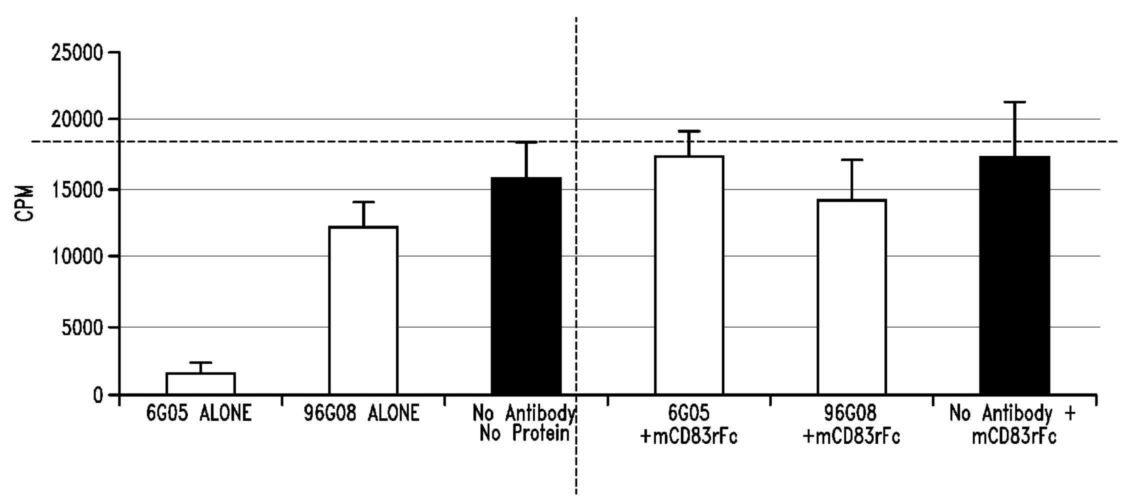
FIG. 26 illustrates that the inhibitory activity of the multimerized (plate-bound) 6g05 antibody preparation is quenched by soluble mouse CD83 protein (mCD83rFc). Lymphocyte proliferation was measured by tritiated thymidine incorporation. As shown, the multimerized 6g05 antibody preparation is strongly inhibitory of proliferation when no CD83 protein is added. However, when the mouse CD83 protein is added to assay, little or no inhibition of lymphocyte proliferation is observed. The 98g08 antibody preparation was used as a negative control because it exhibited little or no lymphocyte inhibition in previous tests (see FIG. 25B).

FIG. 25B further illustrates that some antibody preparations are highly effective inhibitors (e.g. 117G12) but others are not (e.g. 98g08). The 824pb antibody refers to rabbit polyclonal antisera; as shown this polyclonal antisera was not particularly effective at inhibiting lymphocyte proliferation FIG. 26 illustrates that the inhibitory activity of the 6g05 antibody preparation is quenched by soluble mouse CD83 protein. In this assay, mouse CD83 protein was added to anti-CD83 antibody-coated wells before activated lymphocytes were introduced. Both a highly effective proliferation inhibitor (6g05) and an antibody preparation with little or no inhibitory activity (98g08) were tested. A control having no antibody and no mouse CD83 protein as well as a control with added mouse CD83 and no antibody was included. Cellular proliferation of the activated lymphocytes was assessed by observing the incorporation of tritiated thymidine as described above. As shown in FIG. 26, the 6g05 antibody strongly inhibits lymphocyte proliferation when no mouse CD83 is present. However, when mouse CD83 is added before the lymphocytes, the 6g05 antibody exhibits little or no inhibition of lymphocyte proliferation. These data indicate that the inhibitory activity of the 6g05 antibody preparation operates through the CD83 gene product, rather than through some non-specific interaction with lymphocytes.

Figure 27:
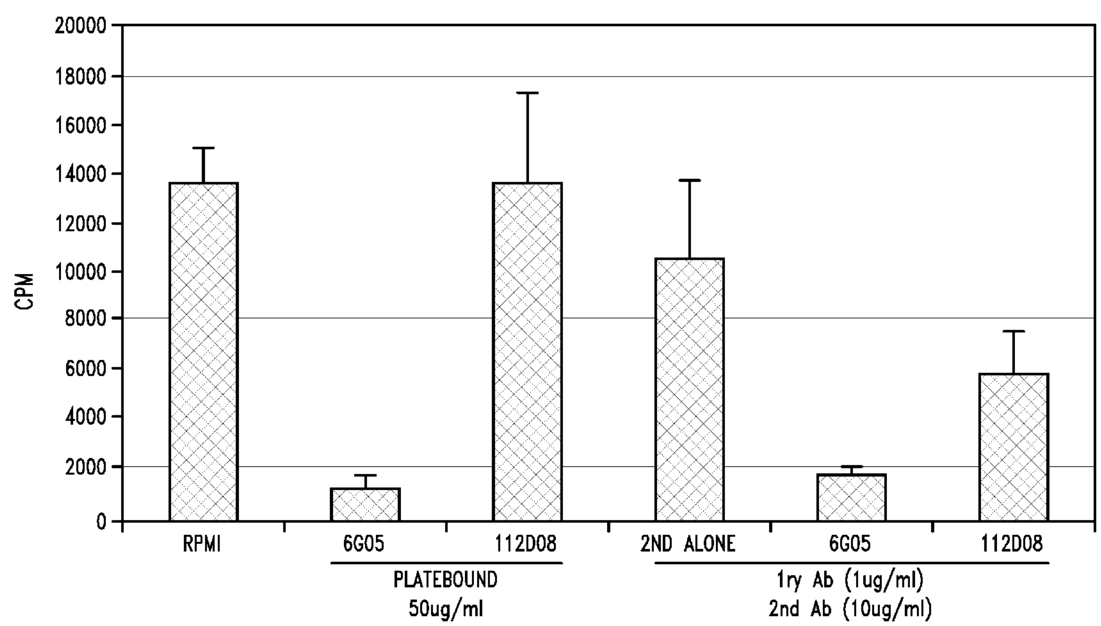
FIG. 27 is a bar graph showing that both plate-bound and cross-linked 6g05 antibodies are highly effective inhibitors of lymphocyte proliferation. Lymphocyte proliferation was measured by tritiated thymidine incorporation. As shown on the left side of the graph above "plate-bound" the presence of plate-bound 6g05 antibodies in the lymphocyte proliferation assay cause little tritiated thymidine incorporation (about 1000 cpm). Similarly, as shown on the right side of the graph above "$1^{st}$ Ab (1 μg/ml)" soluble cross-linked 6g05 antibodies also cause little tritiated thymidine incorporation (about 1800 cpm).
Figure 28:
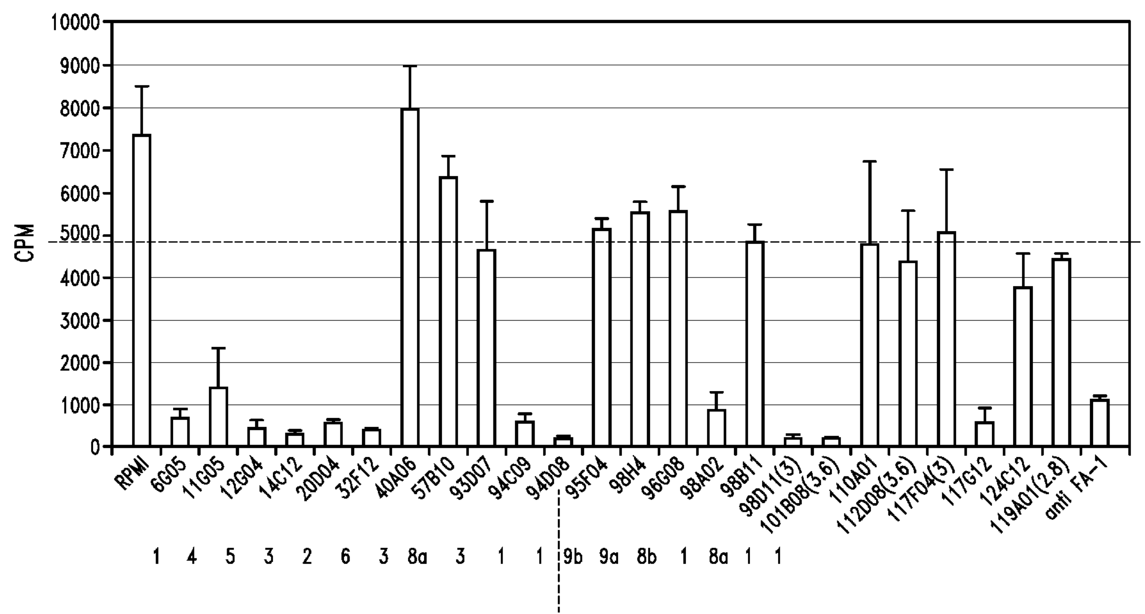
FIG. 28 is a bar graph showing that several preparations of soluble cross-linked anti-CD83 antibodies are highly effective inhibitors of lymphocyte proliferation. Antibody preparations were cross-linked with the rabbit anti-mouse secondary antibody and lymphocyte proliferation was measured by tritiated thymidine incorporation. As shown, soluble cross-linked antibody preparations including the 6g05, 11g04, 12g04, 14c12, 20d04, 32f12, 94c09, 94d08, 98a02, 98d11(3), 101B08(2.7) and 117g12 preparations caused little tritiated thymidine incorporation.

FIGS. 27 and 28 illustrate that anti-CD83 antibodies that are multimerized by use of a rabbit anti-mouse antibody have inhibitory activity that is like that of plate-bound anti-CD83 antibodies. The proliferation of lymphocytes was measured by observing the incorporation of tritiated thymidine with and without anti-CD83 antibodies as described above. In one set of assays plate-bound 6g05 antibodies were used and in another soluble 6g05 antibodies were employed. The soluble 6g05 antibodies were cross-linked by addition of rabbit anti-mouse antibodies that bind to the Fc region of the 6g05 antibodies. For comparison, a soluble and plate-bound antibody preparation with no inhibitory activity (the 112D08 antibody preparation was also tested. A similar series of assays were set up using a panel of soluble anti-CD83 antibodies.

As shown in FIG. 27, both plate-bound and crosslinked 6g05 antibodies were highly effective inhibitors of lymphocyte proliferation. These data indicate that the method of aggregating anti-CD83 antibodies is not particularly important. In other words the multimerization can be achieved by adhering or attaching antibodies to a solid support or by crosslinking the anti-CD83 antibodies through their Fc regions using a rabbit anti-mouse secondary antibody. So long as the anti-CD83 antibodies are in close proximity, they are effective inhibitors of lymphocyte proliferation.

FIG. 28 shows that many soluble anti-CD83 antibodies exhibit good inhibition of lymphocyte proliferation when they are cross-linked with the rabbit anti-mouse secondary antibody. For example, the 6g05, 11g04, 12g04, 14c12, 20d04, 32f12, 94c09, 94d08, 98a02, 98d11(3), 101B08(2.7) and 117g12 antibody preparations strongly inhibit lymphocyte multimerization when cross-linked with the rabbit anti-mouse antibodies.

Example 8

Multimerized Anti-CD83 Antibodies Inhibit Proliferation of Immune Cells in a Mixed Lymphocyte Reaction This Example shows that multimerized anti-CD83 antibodies inhibit proliferation of lymphocytes in a mixed lymphocyte reaction (MLR) assay.

Materials and Methods

The MLR assay employed was a modification of the procedure described in Bradley, pp 162-166 in Mishell et al., eds. Selected Methods in Cellular Immunology (Freeman, San Francisco, 1980); and Battisto, et al., Meth, in Enzymol. 150:83-91 (1987).

Spleens were removed from BALBc and C57B16 mice and digested with collagenase to liberate dendritic and $CD4^{+}$ cells, respectively. Spleens were stained for surface expression of CD4 (helper T cells) or CD11c (dendritic cells). Cells expressing these markers were purified by using magnetic beads (Miltenyi) according to the manufacturer's instructions.

Mixed lymphocyte cultures were set up using purified cell populations. Plates with different anti-CD83 antibody preparations bound thereto were prepared as described in the previous examples. Approximately 1250 CD11c dendritic cells were used to stimulate approximately 20,000 CD4+T cells. After 4 days in culture, proliferative responses were measured by incorporation of tritiated thymidine. A positive control antibody, the anti-LFA antibody, was also used for comparison purposes in this assay because it is known to inhibit lymphocyte proliferation in MLR assays.

A similar experiment was performed to assess the recall response of lymphocytes exposed to 100 μg/ml anti-CD83 antibodies. Prior to spleen removal and CD11c and CD4+ cell isolation, BALBc mice were first immunized with keyhole limpet hemocyanin (KLH) in a 1:1 ratio with complete Freund's adjuvant close to the lymph node area. Lymph nodes were harvested and challenged in vitro with KLH at a final concentration of 2.5 μg/ml and the proliferative response of the cells was assayed as described above by observing incorporation of tritiated thymidine.

Results

Figure 29:
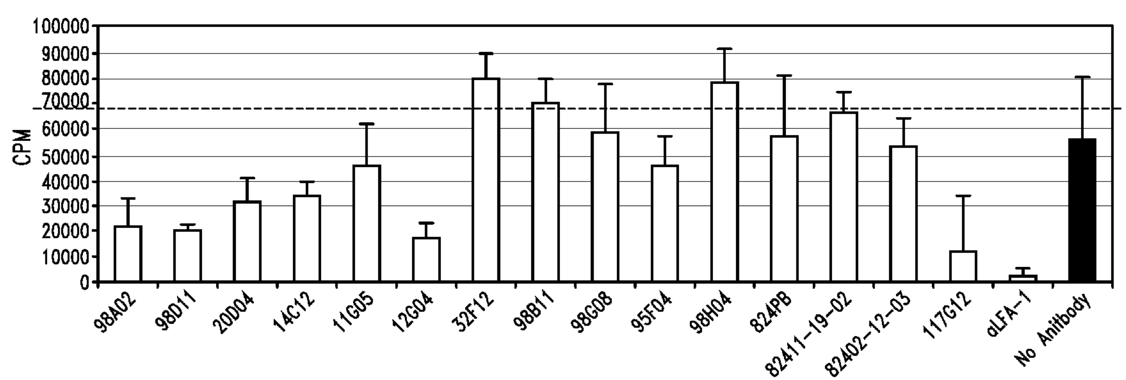
FIG. 29 shows that soluble, multimerized anti-CD83 antibodies exhibit inhibitory activity in mixed lymphocyte reaction assays. A series of anti-CD83 antibody preparations that were cross-linked using a rabbit anti-mouse antibody and then screened for inhibition of $CD4^{+}$T cellular proliferation after activation of the $CD4^{+}$T cells with CD11 cells in a mixed lymphocyte reaction assay. As shown, the 98a02, 98d11, 20d04, 14c12, 12g04, and 117g12 inhibit lymphocyte proliferation in this assay.

FIG. 29 shows that the conditions employed several monoclonal anti-CD83 antibodies can inhibit lymphocyte proliferation in a mixed lymphocyte reaction assay. For example, the 98a02, 98d11, 20d04, 14c12, 12g04, and 117g12 inhibit lymphocyte proliferation in this assay.

Figure 30:
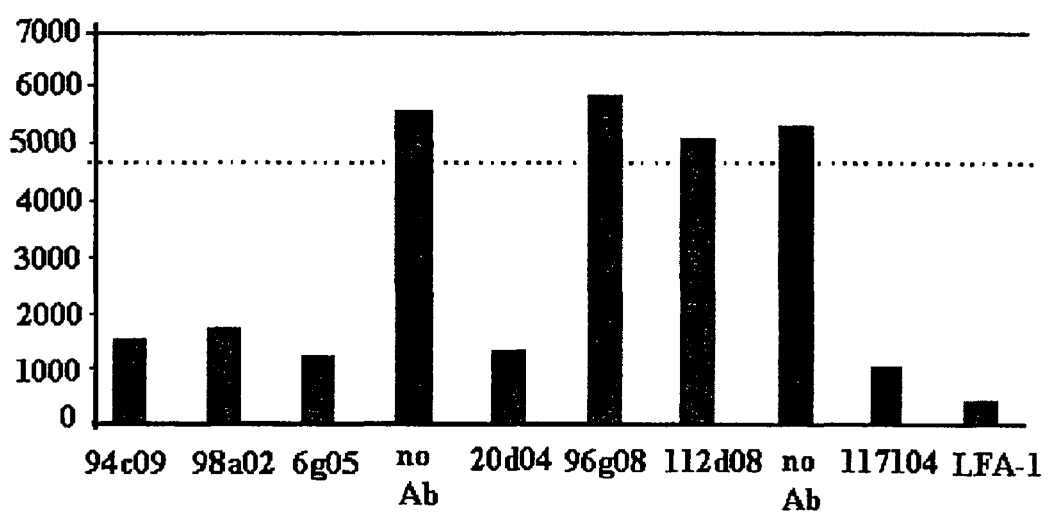
FIG. 30 shows that many anti-CD83 antibody preparations can inhibit the recall response of lymphocytes. BALBc mice were first immunized with keyhole limpet hemocyanin (KLH) prior to spleen removal and CD11c and CD4+ cell isolation. CD11c and CD4+ cells were mixed and added to microtiter wells coated with anti-CD83 antibodies. Lymphocyte proliferation was measured by tritiated thymidine incorporation. As shown, the 94c09, 98a02, 6g05, 20d04, and 117104 antibody preparations inhibited proliferation of activated lymphocytes exposed to an antigen (KLH) to which they had been immunized.

FIG. 30 shows that many anti-CD83 antibody preparations can inhibit the recall response of lymphocytes. For example, 94c09, 98a02, 6g05, 20d04, and 117104 antibody preparations inhibited proliferation of activated lymphocytes exposed to an antigen (KLH) to which they had been immunized.

These data suggest that anti-CD83 antibodies can quiet the proliferative response of CD4+T cells after stimulation by allogenic CD11 cells and/or antigen.

Example 9

Exposure to Anti-CD83 Antibodies Does Not Cause Apoptosis of Activated Lymphocytes This Example shows that exposure to anti-CD83 antibodies does not lead to apoptosis of activated lymphocytes.

Materials and Methods

Mouse (C57B16) spleen cells were isolated and activated by incubation for 24 hours with 1.0 μg/ml Concavalin A in the presence or absence of anti-CD83 antibodies and rabbit anti-mouse antibodies as a crosslinking reagent as described above. Cells were incubated for 48 hours at 37° C. Proliferative responses were measured by incorporation of tritiated thymidine. Total caspase activity and annexinV expression levels were used as a measure of apoptosis.

Homogeneous total caspase activity was measured using a kit (Roche (following the manufacturer's instructions.

To test for apoptosis using annexinV expression, cells were incubated with annexin-FITC and propidium iodide (AnnexinV-FITC kit, Calbiochem) and the percentage of positive Annexin V-FITC labeled cells was determined by Fluorescence Activated Cell sorting (FACS).

Results

Figure 31A:
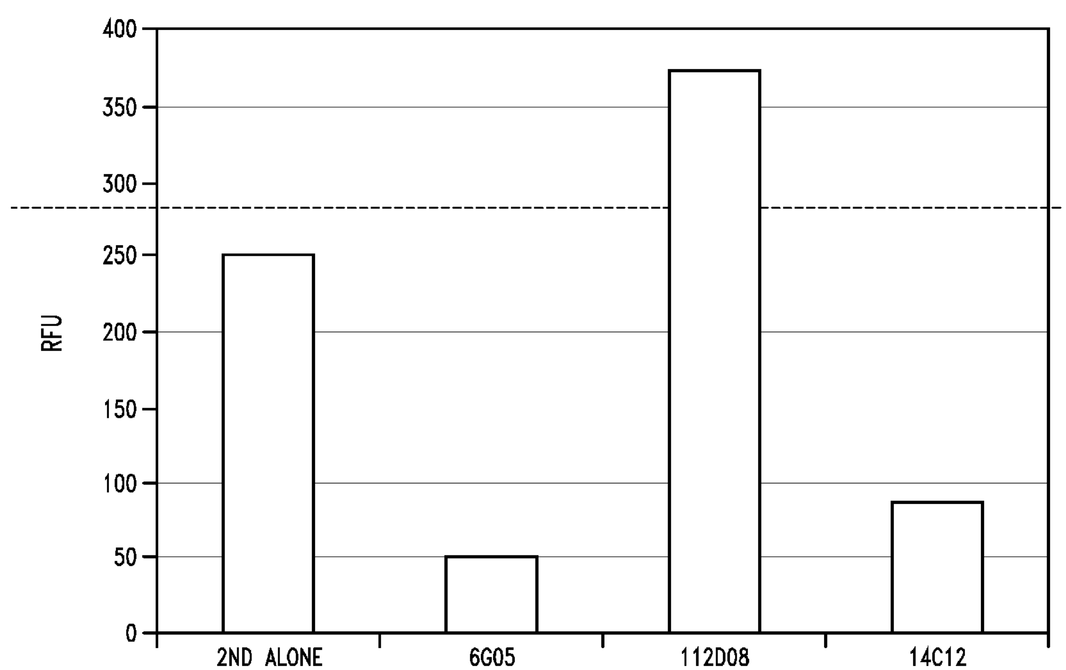
FIG. 31A-B shows that soluble but cross-linked 6g05 and 14c12 anti -CD83 antibody preparations not only inhibit activated lymphocyte cell proliferation (FIG. 31B) but also have very low caspase activity (FIG. 31A). Caspase activity was determined using a fluorogenic substrate and plotted as relative fluorescent units (RFU) on the y axis.
Figure 31B:
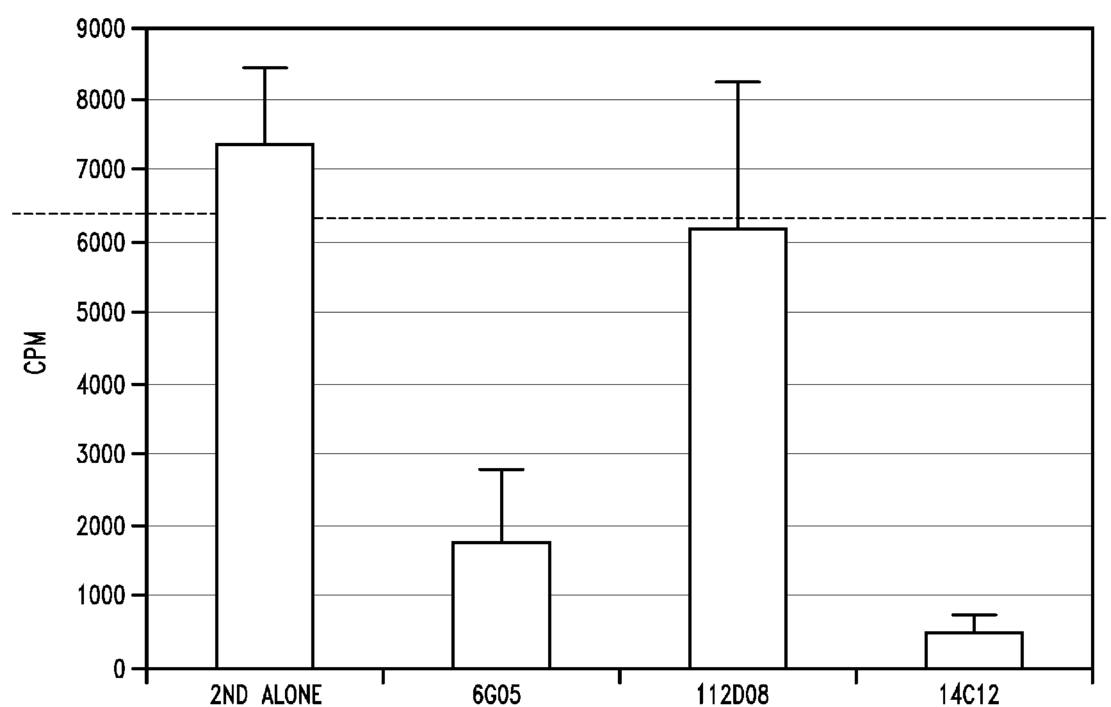
Figure 32A:
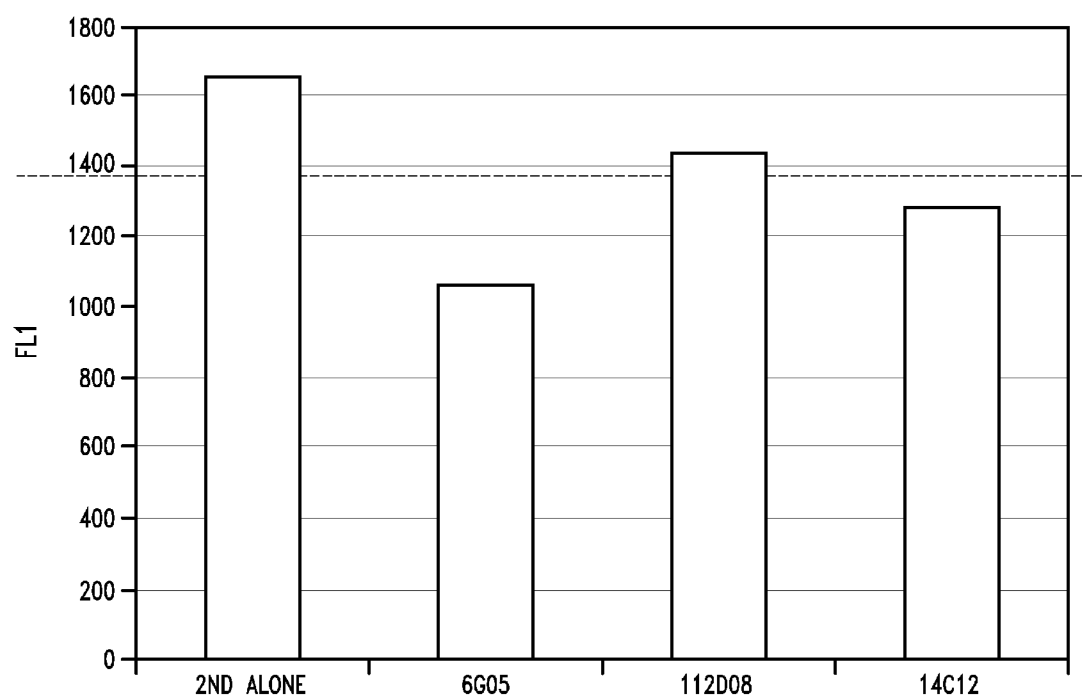
FIG. 32 shows that the percentage of activated lymphocytes that express annexinV is reduced after treatment with soluble but cross-linked 6g05 and 14c12 anti-CD83 antibody preparations.
Figure 32B:
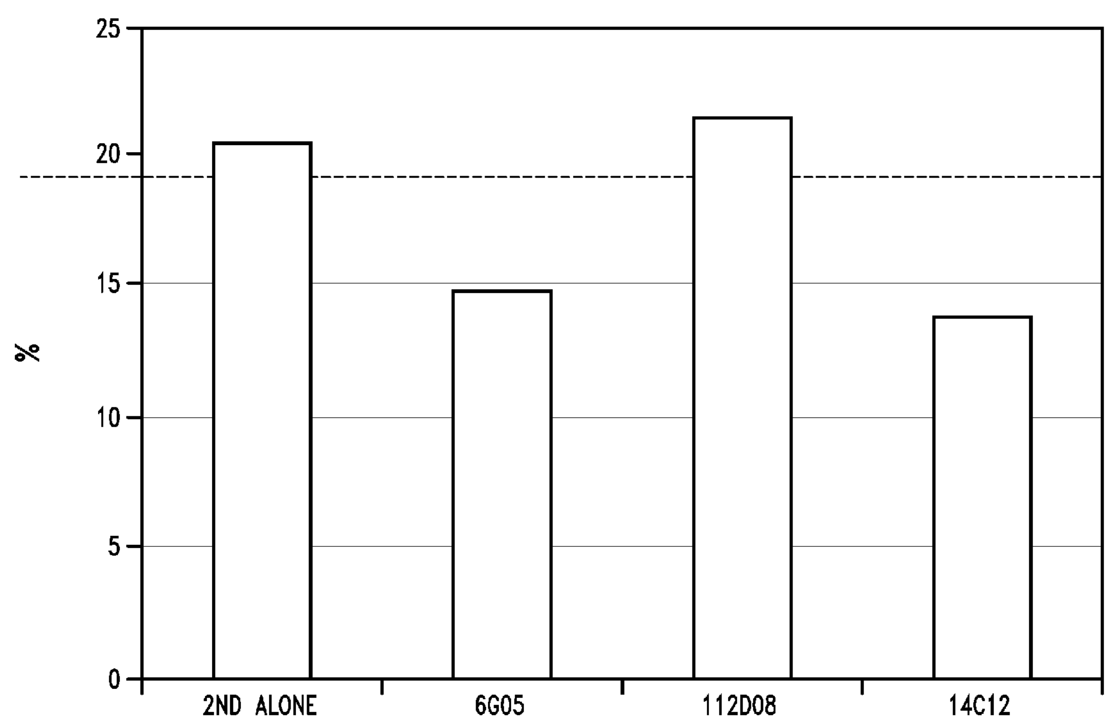

FIG. 31A-B shows that soluble but cross-linked 6g05 and 14c12 anti -CD83 antibody preparations not only inhibit activated lymphocyte cell proliferation (FIG. 31B) but also have very low caspase activity (FIG. 31A). Similarly, FIG. 32 shows that the percentage of activated lymphocytes that express annexinV is reduced after treatment with soluble but cross-linked 6g05 and 14c12 anti-CD83 antibody preparations.

These data indicate that while anti-CD83 antibodies inhibit proliferation of ConA activated splenocytes, they do not induce apoptosis of immune cells. Instead, anti-CD83 antibodies actually depress the expression of apoptosis markers.

Hence, the reduction in cell proliferation observed when activated lymphocytes are exposed to anti-CD83 antibodies is not due to increased programmed cell death.

Example 10

Exposure to Anti-CD83 Antibodies Does Not Inhibit Activation of Lymphocytes

This Example shows that exposure to anti-CD83 antibodies does not inhibit activation of lymphocytes.

Materials and Methods

Mouse (B6) spleen cells were isolated and activated using Concavalin A as described above in the presence or absence of anti-CD83 antibodies and the secondary anti-mouse crosslinking antibodies. The anti-CD83 antibody preparations employed included the 6g05, 14c12, 98b11 and 112d08 preparations. Activation of the cells was assessed using CD69 expression as a marker of cell activation.

Results

Figure 33:
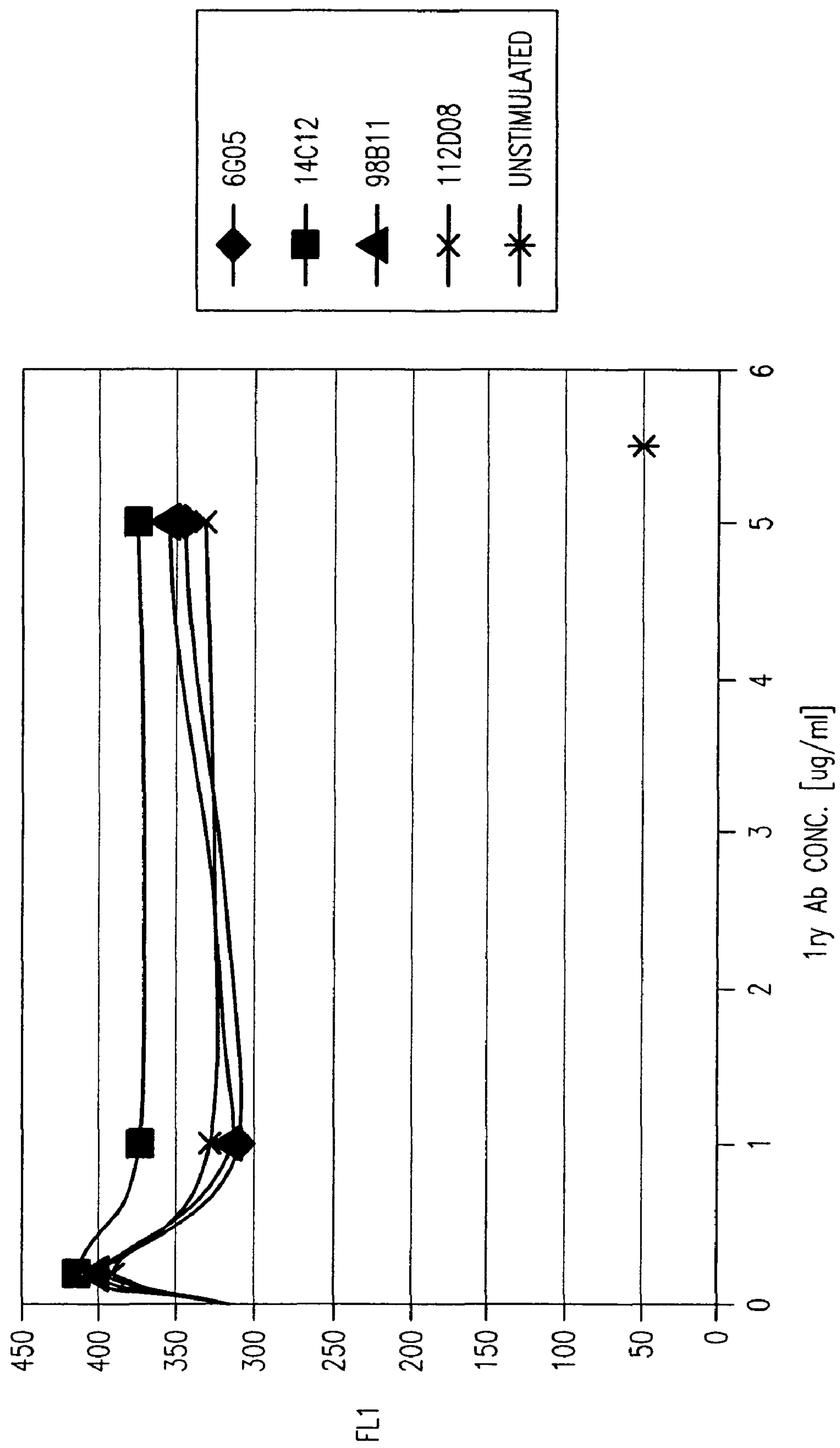
FIG. 33 shows that the activation marker CD69 is expressed on splenocytes that were activated with Concavalin A and exposed to anti-CD83 antibodies. The anti-CD83 antibodies employed were the 6g05, 14c12, 98b11 and 112d08 anti-CD83 antibody preparations that were shown to inhibit activated splenocyte proliferation.
Figure 34A:
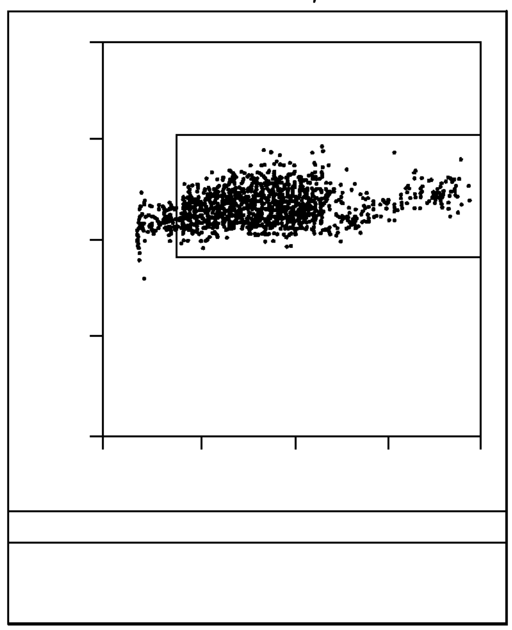
FIG. 34A-E shows that a population of activated splenocytes mixed with anti-CD83 antibody preparations have lost the blasting (dividing) cells as detected by FACS sorting. The antibody preparations employed were the rabbit anti-mouse antibody, called the $2^{nd}$ Ab (FIG. 34A), the 6g05 antibody preparation (FIG. 34B), the 98b11 antibody preparation (FIG. 34C), the 14c12 antibody preparation (FIG. 34D), and the 112d08 antibody preparation (FIG. 34E). Almost all cells exposed to the 6g05 or 98b11 antibody preparations sort as small cells with a 2N content of DNA as illustrated by the high proportion of cells towards the left (smaller) side of the population distribution compared to cells exposed to the control $2^{nd}$ Ab, 14c12 and 112d08 preparations in FIGS. 34A, C and E.
Figure 34B:
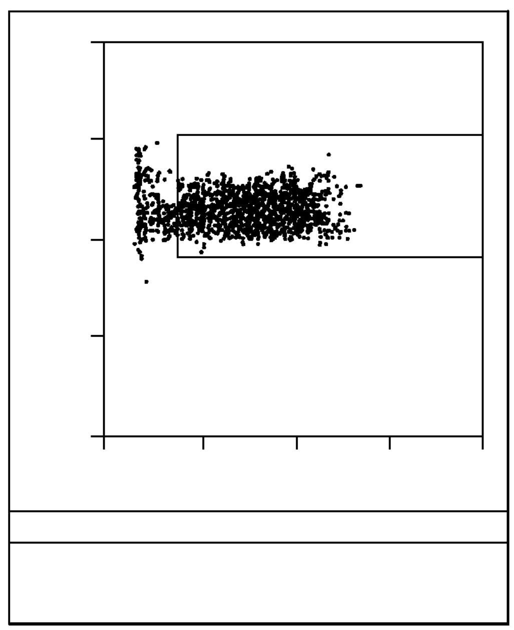
Figure 34C:
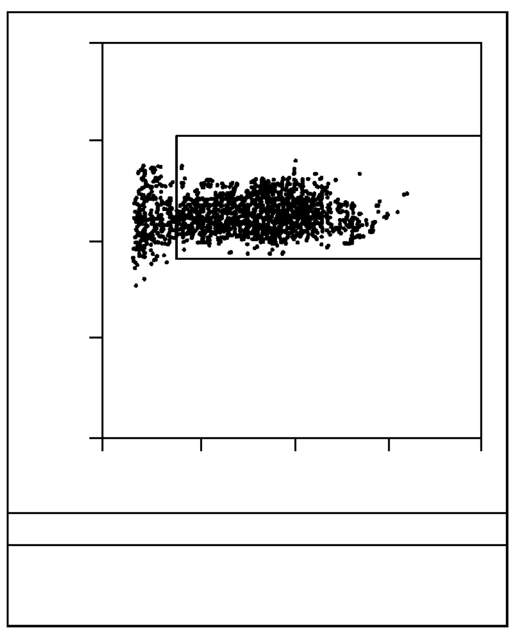
Figure 34D:
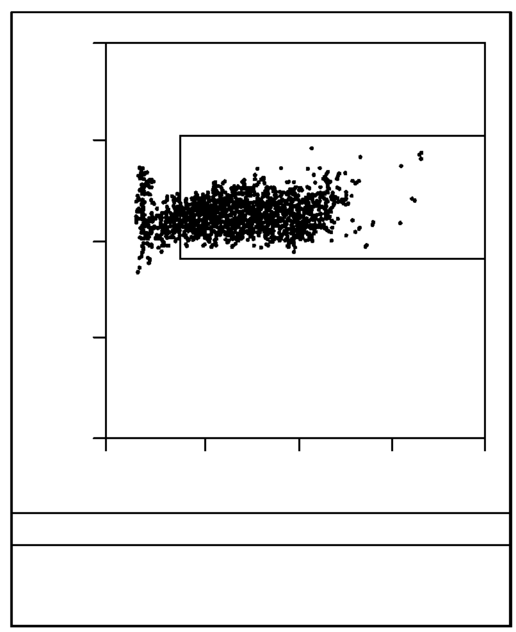
Figure 34E:
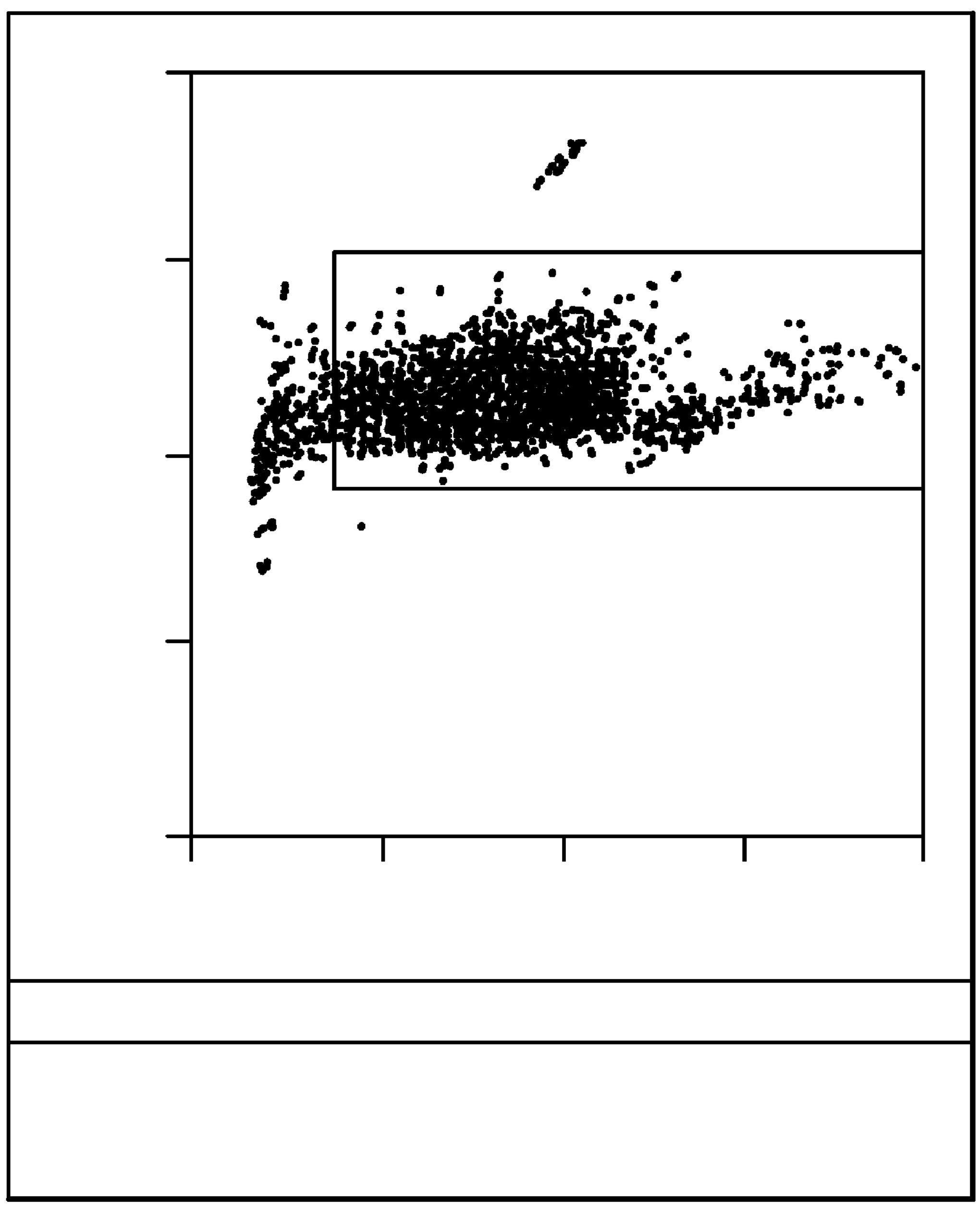

FIG. 33 illustrates that splenocytes activated with Concavalin A express the CD69 activation marker even though they were incubated with anti-CD83 antibodies. In particular, the star or asterisks in the lower right hand corner of the graph shows the level of CD69 expression observed when splenocytes are not activated with Concavalin A. However, when splenocytes were activated with Concavalin A they expressed high levels of CD69 even after incubation with any of the 6g05, 14c12, 98b11 or 112d08 anti-CD83 antibody preparations.

These results indicate that while cellular proliferation of lymphocytes exposed to anti-CD83 antibodies is arrested, the lymphocytes still undergo activation.

Example 11

Anti-CD83 Antibodies Arrest the Lymphocyte Cell Cycle in the G0/G1 Stage

This Example shows that exposure to anti-CD83 antibodies arrests activated lymphocytes in the G0/G1 stage of the cell cycle.

Materials and Methods

Mouse (B6) spleen cells were isolated and activated by incubation for 48 hours with 1.0 μg/ml Concavalin A in the presences of anti-CD83 antibodies with the crosslinking antibodies as described above. To analyze cell cycle distribution, cells were fixed and DNA was stained with propidium iodine according to the protocol described for the flowcytometer (Cold Spring Harbor, N.Y.). WinMDI software was used for background subtraction caused by debris in the DNA histogram. Each histogram was further analyzed by cycle red software to obtain the distribution of cells therein. In addition, the size and shape of the activated cells was assessed by their forward (FSC) and side (SSC) scatter during this experiment.

The anti-CD83 antibody preparations employed were the 6g05 and 14c12 preparations that had been shown to inhibit cellular proliferation and the 112d08 preparation that had little or no effect on cellular proliferation. Cells having 2N complement of DNA were assumed to be in the G1/G0 phase of the cell cycle; cells having 3N complement of DNA were assumed to be in the G2/M phase of the cell cycle; and cells having 4N complement of DNA were assumed to be in the S phase of the cell cycle. The percentage of cells having G1/G0, G2/M or S phase of the cell cycle was determined and plotted in FIG. 35A-C.

Results

FIG. 34 shows that a population of activated splenocytes mixed with anti-CD83 antibody preparations have lost the blasting (dividing) cells as detected by FACS sorting. Almost all cells sort as small cells with a 2N content of DNA as illustrated by the high proportion of cells towards the left (smaller) side of the population distribution in FIG. 34.

Figure 35A:
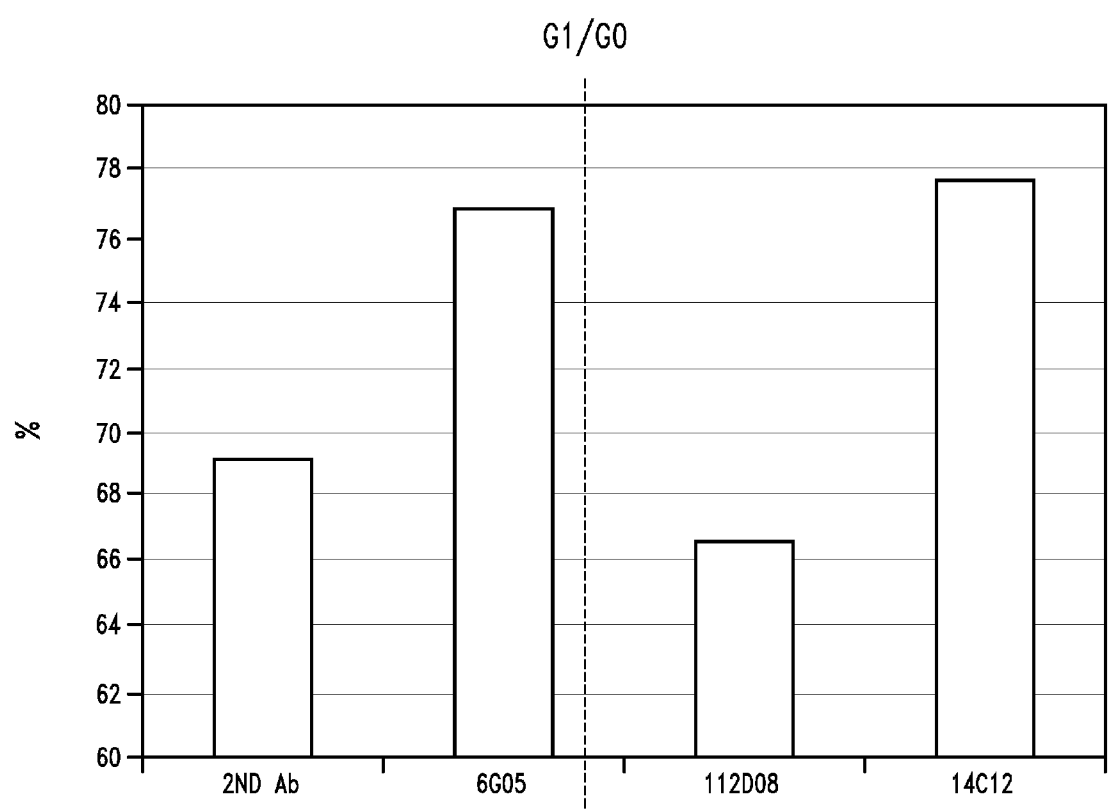
FIG. 35A shows that the proportion of cells in the G1/G0 phase of the cell cycle is increased when a population of activated splenocytes is treated with anti-CD83 antibody preparations. The antibody preparations employed were the control rabbit anti-mouse antibody, called the $2^{nd}$ Ab, the 6g05 antibody preparation, the 14c12 antibody preparation, and the negative control 112d08 antibody preparation. Both of the 6g05 and 14c12 antibody preparations arrest the activated splenocytes in the G1/G0 phase of the cell cycle.
Figure 35B:
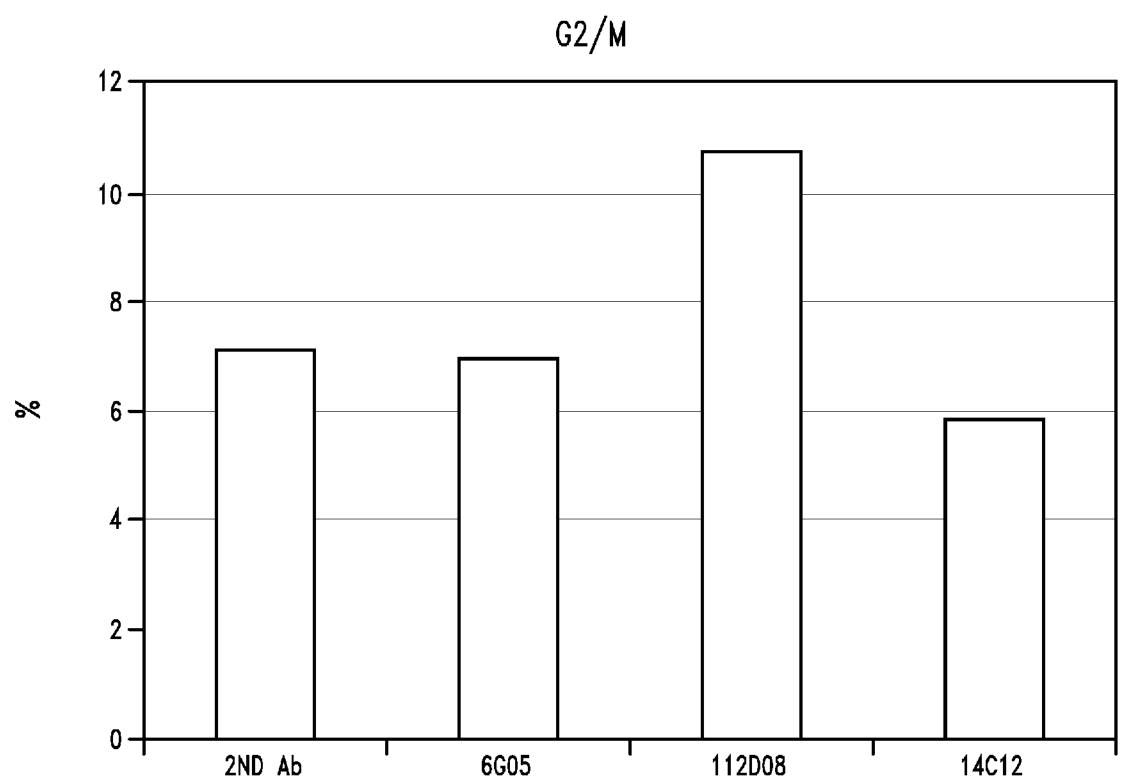
FIG. 35B shows the proportion of cells in the G2/M phase of the cell cycle after a population of activated splenocytes is treated with anti-CD83 antibody preparations. The antibody preparations employed were the control rabbit anti-mouse antibody, called the $2^{nd}$ Ab, the 6g05 antibody preparation, the 14c12 antibody preparation, and the negative control 112d08 antibody preparation.
Figure 35C:
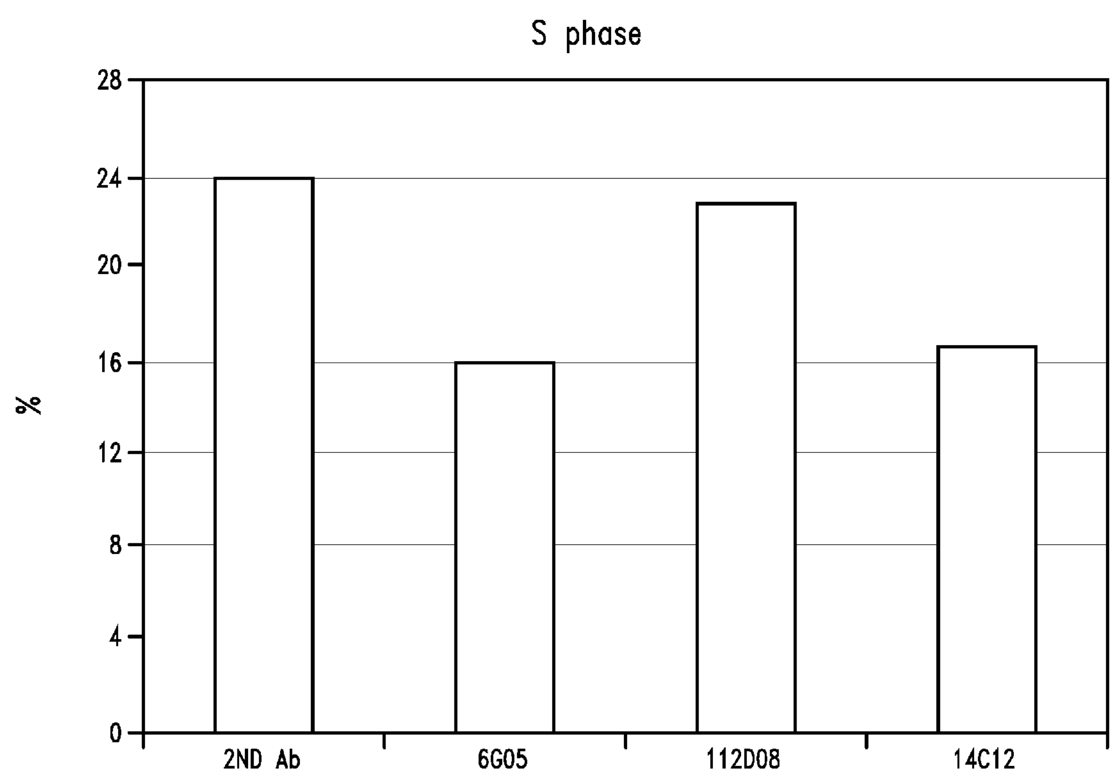
FIG. 35C shows that the proportion of cells in the S phase of the cell cycle is decreased when a population of activated splenocytes is treated with anti-CD83 antibody preparations. The antibody preparations employed were the control rabbit anti-mouse antibody, called the $2^{nd}$ Ab, the 6g05 antibody preparation, the 14c12 antibody preparation, and the negative control 112d08 antibody preparation. Activated splenocytes treated with either of the 6g05 or 14c12 antibody preparations have lesser numbers of cells in the S phase of the cell cycle.

FIG. 35A-C show that treatment of Concavalin A activated lymphocytes with either of 6g05 and 14c12 antibody preparations leads to a cellular population that was enriched in cells in the G1/G0 stage of the cell cycle. Treatment with either the rabbit anti-mouse antibody or the 112d08 antibody preparation that has little or no effect on cell proliferation did not lead to a cellular population that was enriched in cells in the G1/G0 stage of the cell cycle.

These data indicate that exposure to anti-CD83 antibodies arrests lymphocytes in the G1/G0 stage. Taken together with the data in preceding Examples, these data indicate that anti-CD83 antibodies can cause lymphocytes to enter a state of antigen specific unresponsiveness or anergy.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms “a,” “an,” and “the” include plural reference unless the context clearly dictates otherwise. Thus, for example, a reference to “a host cell” includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An isolated multimerized antibody that can bind to a CD83 polypeptide comprising amino acid sequence SEQ ID NO:97, wherein the multimerized antibody comprises amino acid sequence SEQ ID NO:70.

2. The antibody designated 96G08 comprising SEQ ID NOs:70 and 78.

3. An isolated multimerized antibody that can bind to a CD83 polypeptide comprising amino acid sequence SEQ ID NO:97, where the multimerized antibody comprises amino acid sequence SEQ ID NO:78.

4. An isolated multimerized antibody that can bind to a CD83 polypeptide comprising amino acid sequence SEQ ID NO:97, where the multimerized antibody comprises six CDRs of amino acid sequences SEQ ID NO:71, SEQ ID NO:72, SEQ ID NO:73, SEQ ID NO:77, SEQ ID NO:80, and SEQ ID NO:81.

* * * * *

SEQUENCE LISTING

```
<160> NUMBER OF SEQ ID NOS: 99

<210> SEQ ID NO 1
<211> LENGTH: 2051
<212> TYPE: DNA
<213> ORGANISM: Mus musculus

<400> SEQUENCE: 1

gcgctccagc cgcatgtcgc aaggcctcca gctcctgttt ctaggctgcg cctgcagcct     60

ggcacccgcg atggcgatgc gggaggtgac ggtggcttgc tccgagaccg ccgacttgcc    120

ttgcacagcg ccctgggacc cgcagctctc ctatgcagtg tcctgggcca aggtctccga    180

gagtggcact gagagtgtgg agctcccgga gagcaagcaa aacagctcct tcgaggcccc    240

caggagaagg gcctattccc tgacgatcca aaacactacc atctgcagct cgggcaccta    300

caggtgtgcc ctgcaggagc tcggagggca gcgcaacttg agcggcaccg tggttctgaa    360

ggtgacagga tgccccaagg aagctacaga gtcaactttc aggaagtaca gggcagaagc    420

tgtgttgctc ttctctctgg ttgttttcta cctgacactc atcattttca cctgcaaatt    480

tgcacgacta caaagcattt tcccagatat ttctaaacct ggtacggaac aagcttttct    540

tccagtcacc tccccaagca aacatttggg gccagtgacc cttcctaaga cagaaacggt    600

atgagtagga tctccactgg tttttacaaa gccaagggca catcagatca gtgtgcctga    660

atgccacccg gacaagagaa gaatgagctc catcctcaga tggcaacctt tctttgaagt    720

ccttcacctg acagtgggct ccacactact ccctgacaca gggtcttgag caccatcata    780

tgatcacgaa gcatggagta tcaccgcttc tctgtggctg tcagcttaat gtttcatgtg    840

gctatctggt caacctcgtg agtgcttttc agtcatctac aagctatggt gagatgcagg    900

tgaagcaggg tcatgggaaa tttgaacact ctgagctggc cctgtgacag actcctgagg    960

acagctgtcc tctcctacat ctgggataca tctctttgaa tttgtcctgt ttcgttgcac   1020

cagcccagat gtctcacatc tggcggaaat tgacaggcca agctgtgagc cagtgggaaa   1080

tatttagcaa ataatttccc agtgcgaagg tcctgctatt agtaaggagt attatgtgta   1140

catagaaatg agaggtcagt gaactattcc ccagcagggc cttttcatct ggaaaagaca   1200

tccacaaaag cagcaataca gagggatgcc acatttattt ttttaatctt catgtacttg   1260

tcaaagaaga atttttcatg ttttttcaaa gaagtgtgtt tctttccttt tttaaaatat   1320

gaaggtctag ttacatagca ttgctagctg acaagcagcc tgagagaaga tggagaatgt   1380

tcctcaaaat agggacagca agctagaagc actgtacagt gccctgctgg gaagggcaga   1440

caatggactg agaaaccaga agtctggcca caagattgtc tgtatgattc tggacgagtc   1500

acttgtggtt ttcactctct ggttagtaaa ccagatagtt tagtctgggt tgaatacaat   1560

ggatgtgaag ttgcttgggg aaagctgaat gtagtgaata cattggcaac tctactgggc   1620

tgttaccttg ttgatatcct agagttctgg agctgagcga atgcctgtca tatctcagct   1680
```

```
tgcccatcaa tccaaacaca ggaggctaca aaaaggacat gagcatggtc ttctgtgtga   1740

actcctcctg agaaacgtgg agactggctc agcgctttgc gcttgaagga ctaatcacaa   1800

gttcttgaag atatggacct aggggagcta ttgcgccacg acaggaggaa gttctcagat   1860

gttgcattga tgtaacattg ttgcatttct ttaatgagct gggctccttc ctcatttgct   1920

tcccaaagag attttgtccc actaatggtg tgcccatcac ccacactatg aaagtaaaag   1980

ggatgctgag cagatacagc gtgcttacct ctcagccatg actttcatgc tattaaaaga   2040

atgcatgtga a                                                        2051


<210> SEQ ID NO 2
<211> LENGTH: 196
<212> TYPE: PRT
<213> ORGANISM: Mus musculus

<400> SEQUENCE: 2

Met Ser Gln Gly Leu Gln Leu Leu Phe Leu Gly Cys Ala Cys Ser Leu
 1               5                  10                  15

Ala Pro Ala Met Ala Met Arg Glu Val Thr Val Ala Cys Ser Glu Thr
            20                  25                  30

Ala Asp Leu Pro Cys Thr Ala Pro Trp Asp Pro Gln Leu Ser Tyr Ala
        35                  40                  45

Val Ser Trp Ala Lys Val Ser Glu Ser Gly Thr Glu Ser Val Glu Leu
    50                  55                  60

Pro Glu Ser Lys Gln Asn Ser Ser Phe Glu Ala Pro Arg Arg Arg Ala
65                  70                  75                  80

Tyr Ser Leu Thr Ile Gln Asn Thr Thr Ile Cys Ser Ser Gly Thr Tyr
                85                  90                  95

Arg Cys Ala Leu Gln Glu Leu Gly Gly Gln Arg Asn Leu Ser Gly Thr
            100                 105                 110

Val Val Leu Lys Val Thr Gly Cys Pro Lys Glu Ala Thr Glu Ser Thr
        115                 120                 125

Phe Arg Lys Tyr Arg Ala Glu Ala Val Leu Leu Phe Ser Leu Val Val
    130                 135                 140

Phe Tyr Leu Thr Leu Ile Ile Phe Thr Cys Lys Phe Ala Arg Leu Gln
145                 150                 155                 160

Ser Ile Phe Pro Asp Ile Ser Lys Pro Gly Thr Glu Gln Ala Phe Leu
                165                 170                 175

Pro Val Thr Ser Pro Ser Lys His Leu Gly Pro Val Thr Leu Pro Lys
            180                 185                 190

Thr Glu Thr Val
        195


<210> SEQ ID NO 3
<211> LENGTH: 2051
<212> TYPE: DNA
<213> ORGANISM: Artificial Sequence
<220> FEATURE:
<223> OTHER INFORMATION: A synthetic mutant CD83 sequence

<400> SEQUENCE: 3

gcgctccagc cgcatgtcgc aaggcctcca gctcctgttt ctaggctgcg cctgcagcct     60

ggcacccgcg atggcgatgc gggaggtgac ggtggcttgc tccgagaccg ccgacttgcc    120

ttgcacagcg ccctgggacc cgcagctctc ctatgcagtg tcctgggcca aggtctccga    180

gagtggcact gagagtgtgg agctcccgga gagcaagcaa aacagctcct tcgaggcccc    240
```

```
caggagaagg gcctattccc tgacgatcca aaacactacc atctgcagct cgggcaccta    300
caggtgtgcc ctgcaggagc tcggagggca gcgcaacttg agcggcaccg tggttctgaa    360
ggtgacagga tgccccaagg aagctacaga gtcaactttc aggaagtaca gggcagaagc    420
tgtgttgctc ttctctctgg ttgttttcta cctgacactc atcattttca cctgcaaatt    480
tgcacgacta caaagcattt tcccagatat ttctaaacct ggtacggaac aagcttttct    540
tccagtcacc tccccaagca aacatttggg gccagtgacc cttcctaaga cagaaacggt    600
aagagtagga tctccactgg tttttacaaa gccaagggca catcagatca gtgtgcctga    660
atgccacccg gacaagagaa gaatgagctc catcctcaga tggcaacctt tctttgaagt    720
ccttcacctg acagtgggct ccacactact ccctgacaca gggtcttgag caccatcata    780
tgatcacgaa gcatggagta tcaccgcttc tctgtggctg tcagcttaat gtttcatgtg    840
gctatctggt caacctcgtg agtgcttttc agtcatctac aagctatggt gagatgcagg    900
tgaagcaggg tcatgggaaa tttgaacact ctgagctggc cctgtgacag actcctgagg    960
acagctgtcc tctcctacat ctgggataca tctctttgaa tttgtcctgt ttcgttgcac   1020
cagcccagat gtctcacatc tggcggaaat tgacaggcca agctgtgagc cagtgggaaa   1080
tatttagcaa ataatttccc agtgcgaagg tcctgctatt agtaaggagt attatgtgta   1140
catagaaatg agaggtcagt gaactattcc ccagcagggc cttttcatct ggaaaagaca   1200
tccacaaaag cagcaataca gagggatgcc acatttattt ttttaatctt catgtacttg   1260
tcaaagaaga atttttcatg ttttttcaaa gaagtgtgtt tctttccttt tttaaaatat   1320
gaaggtctag ttacatagca ttgctagctg acaagcagcc tgagagaaga tggagaatgt   1380
tcctcaaaat agggacagca agctagaagc actgtacagt gccctgctgg gaagggcaga   1440
caatggactg agaaaccaga agtctggcca caagattgtc tgtatgattc tggacgagtc   1500
acttgtggtt ttcactctct ggttagtaaa ccagatagtt tagtctgggt tgaatacaat   1560
ggatgtgaag ttgcttgggg aaagctgaat gtagtgaata cattggcaac tctactgggc   1620
tgttaccttg ttgatatcct agagttctgg agctgagcga atgcctgtca tatctcagct   1680
tgcccatcaa tccaaacaca ggaggctaca aaaaggacat gagcatggtc ttctgtgtga   1740
actcctcctg agaaacgtgg agactggctc agcgctttgc gcttgaagga ctaatcacaa   1800
gttcttgaag atatggacct aggggagcta ttgcgccacg acaggaggaa gttctcagat   1860
gttgcattga tgtaacattg ttgcatttct ttaatgagct gggctccttc ctcatttgct   1920
tcccaaagag attttgtccc actaatggtg tgcccatcac ccacactatg aaagtaaaag   1980
ggatgctgag cagatacagc gtgcttacct ctcagccatg actttcatgc tattaaaaga   2040
atgcatgtga a                                                        2051
```

```
<210> SEQ ID NO 4
<211> LENGTH: 251
<212> TYPE: PRT
<213> ORGANISM: Artificial Sequence
<220> FEATURE:
<223> OTHER INFORMATION: A synthetic mutant CD83 sequence

<400> SEQUENCE: 4

Met Ser Gln Gly Leu Gln Leu Leu Phe Leu Gly Cys Ala Cys Ser Leu
 1               5                  10                  15

Ala Pro Ala Met Ala Met Arg Glu Val Thr Val Ala Cys Ser Glu Thr
            20                  25                  30
```

-continued

```
Ala Asp Leu Pro Cys Thr Ala Pro Trp Asp Pro Gln Leu Ser Tyr Ala
        35                  40                  45

Val Ser Trp Ala Lys Val Ser Glu Ser Gly Thr Glu Ser Val Glu Leu
    50                  55                  60

Pro Glu Ser Lys Gln Asn Ser Ser Phe Glu Ala Pro Arg Arg Arg Ala
65                  70                  75                  80

Tyr Ser Leu Thr Ile Gln Asn Thr Thr Ile Cys Ser Ser Gly Thr Tyr
                85                  90                  95

Arg Cys Ala Leu Gln Glu Leu Gly Gly Gln Arg Asn Leu Ser Gly Thr
            100                 105                 110

Val Val Leu Lys Val Thr Gly Cys Pro Lys Glu Ala Thr Glu Ser Thr
        115                 120                 125

Phe Arg Lys Tyr Arg Ala Glu Ala Val Leu Leu Phe Ser Leu Val Val
    130                 135                 140

Phe Tyr Leu Thr Leu Ile Ile Phe Thr Cys Lys Phe Ala Arg Leu Gln
145                 150                 155                 160

Ser Ile Phe Pro Asp Ile Ser Lys Pro Gly Thr Glu Gln Ala Phe Leu
                165                 170                 175

Pro Val Thr Ser Pro Ser Lys His Leu Gly Pro Val Thr Leu Pro Lys
            180                 185                 190

Thr Glu Thr Val Arg Val Gly Ser Pro Leu Val Phe Thr Lys Pro Arg
        195                 200                 205

Ala His Gln Ile Ser Val Pro Glu Cys His Pro Asp Lys Arg Arg Met
    210                 215                 220

Ser Ser Ile Leu Arg Trp Gln Pro Phe Phe Glu Val Leu His Leu Thr
225                 230                 235                 240

Val Gly Ser Thr Leu Leu Pro Asp Thr Gly Ser
                245                 250
```

```
<210> SEQ ID NO 5
<211> LENGTH: 756
<212> TYPE: DNA
<213> ORGANISM: Artificial Sequence
<220> FEATURE:
<223> OTHER INFORMATION: A synthetic mutant CD83 sequence

<400> SEQUENCE: 5

atgtcgcaag gcctccagct cctgtttcta ggctgcgcct gcagcctggc acccgcgatg      60

gcgatgcggg aggtgacggt ggcttgctcc gagaccgccg acttgccttg cacagcgccc     120

tgggacccgc agctctccta tgcagtgtcc tgggccaagg tctccgagag tggcactgag     180

agtgtggagc tcccggagag caagcaaaac agctccttcg aggcccccag gagaagggcc     240

tattccctga cgatccaaaa cactaccatc tgcagctcgg gcacctacag gtgtgccctg     300

caggagctcg gagggcagcg caacttgagc ggcaccgtgg ttctgaaggt gacaggatgc     360

cccaaggaag ctacagagtc aactttcagg aagtacaggg cagaagctgt gttgctcttc     420

tctctggttg ttttctacct gacactcatc attttcacct gcaaatttgc acgactacaa     480

agcattttcc cagatatttc taaacctggt acggaacaag cttttcttcc agtcacctcc     540

ccaagcaaac atttggggcc agtgaccctt cctaagacag aaacggtaag agtaggatct     600

ccactggttt ttacaaagcc aagggcacat cagatcagtg tgcctgaatg ccacccggac     660

aagagaagaa tgagctccat cctcagatgg caacctttct ttgaagtcct tcacctgaca     720

gtgggctcca cactactccc tgacacaggg tcttga                               756
```

```
<210> SEQ ID NO 6

<400> SEQUENCE: 6

000


<210> SEQ ID NO 7
<211> LENGTH: 168
<212> TYPE: DNA
<213> ORGANISM: Artificial Sequence
<220> FEATURE:
<223> OTHER INFORMATION: A synthetic mutant CD83 sequence

<400> SEQUENCE: 7

agagtaggat ctccactggt ttttacaaag ccaagggcac atcagatcag tgtgcctgaa     60

tgccacccgg acaagagaag aatgagctcc atcctcagat ggcaaccttt ctttgaagtc    120

cttcacctga cagtgggctc cacactactc cctgacacag ggtcttga                 168


<210> SEQ ID NO 8
<211> LENGTH: 55
<212> TYPE: PRT
<213> ORGANISM: Artificial Sequence
<220> FEATURE:
<223> OTHER INFORMATION: A synthetic mutant CD83 sequence

<400> SEQUENCE: 8

Arg Val Gly Ser Pro Leu Val Phe Thr Lys Pro Arg Ala His Gln Ile
 1               5                  10                  15

Ser Val Pro Glu Cys His Pro Asp Lys Arg Arg Met Ser Ser Ile Leu
            20                  25                  30

Arg Trp Gln Pro Phe Phe Glu Val Leu His Leu Thr Val Gly Ser Thr
        35                  40                  45

Leu Leu Pro Asp Thr Gly Ser
    50                  55


<210> SEQ ID NO 9
<211> LENGTH: 205
<212> TYPE: PRT
<213> ORGANISM: Homo sapiens

<400> SEQUENCE: 9

Met Ser Arg Gly Leu Gln Leu Leu Leu Leu Ser Cys Ala Tyr Ser Leu
 1               5                  10                  15

Ala Pro Ala Thr Pro Glu Val Lys Val Ala Cys Ser Glu Asp Val Asp
            20                  25                  30

Leu Pro Cys Thr Ala Pro Trp Asp Pro Gln Val Pro Tyr Thr Val Ser
        35                  40                  45

Trp Val Lys Leu Leu Glu Gly Gly Glu Glu Arg Met Glu Thr Pro Gln
    50                  55                  60

Glu Asp His Leu Arg Gly Gln His Tyr His Gln Lys Gly Gln Asn Gly
65                  70                  75                  80

Ser Phe Asp Ala Pro Asn Glu Arg Pro Tyr Ser Leu Lys Ile Arg Asn
                85                  90                  95

Thr Thr Ser Cys Asn Ser Gly Thr Tyr Arg Cys Thr Leu Gln Asp Pro
            100                 105                 110

Asp Gly Gln Arg Asn Leu Ser Gly Lys Val Ile Leu Arg Val Thr Gly
        115                 120                 125

Cys Pro Ala Gln Arg Lys Glu Glu Thr Phe Lys Lys Tyr Arg Ala Glu
    130                 135                 140
```

-continued

```
Ile Val Leu Leu Leu Ala Leu Val Ile Phe Tyr Leu Thr Leu Ile Ile
145                 150                 155                 160

Phe Thr Cys Lys Phe Ala Arg Leu Gln Ser Ile Phe Pro Asp Phe Ser
                165                 170                 175

Lys Ala Gly Met Glu Arg Ala Phe Leu Pro Val Thr Ser Pro Asn Lys
            180                 185                 190

His Leu Gly Leu Val Thr Pro His Lys Thr Glu Leu Val
        195                 200                 205


<210> SEQ ID NO 10
<211> LENGTH: 2574
<212> TYPE: DNA
<213> ORGANISM: Homo sapiens

<400> SEQUENCE: 10

cctggcgcag ccgcagcagc gacgcgagcg aactcggccg ggcccgggcg cgcgggggcg     60

ggacgcgcac gcggcgaggg cggcgggtga gccgggggcg gggacggggg cgggacgggg    120

gcgaaggggg cggggacggg ggcgcccgcc ggcctaacgg gattaggagg gcgcgccacc    180

cgcttccgct gcccgccggg gaatcccccg ggtggcgccc agggaagttc ccgaacgggc    240

gggcataaaa gggcagccgc gccggcgccc cacagctctg cagctcgtgg cagcggcgca    300

gcgctccagc catgtcgcgc ggcctccagc ttctgctcct gagctgcgcc tacagcctgg    360

ctcccgcgac gccggaggtg aaggtggctt gctccgaaga tgtggacttg ccctgcaccg    420

ccccctggga tccgcaggtt ccctacacgg tctcctgggt caagttattg gagggtggtg    480

aagagaggat ggagacaccc caggaagacc acctcagggg acagcactat catcagaagg    540

ggcaaaatgg ttctttcgac gcccccaatg aaaggcccta ttccctgaag atccgaaaca    600

ctaccagctg caactcgggg acatacaggt gcactctgca ggacccggat gggcagagaa    660

acctaagtgg caaggtgatc ttgagagtga caggatgccc tgcacagcgt aaagaagaga    720

cttttaagaa atacagagcg gagattgtcc tgctgctggc tctggttatt ttctacttaa    780

cactcatcat tttcacttgt aagtttgcac ggctacagag tatcttccca gatttttcta    840

aagctggcat ggaacgagct tttctcccag ttacctcccc aaataagcat ttagggctag    900

tgactcctca caagacagaa ctggtatgag caggatttct gcaggttctt cttcctgaag    960

ctgaggctca ggggtgtgcc tgtctgttac actggaggag agaagaatga gcctacgctg   1020

aagatggcat cctgtgaagt ccttcacctc actgaaaaca tctggaaggg gatcccaccc   1080

cattttctgt gggcaggcct cgaaaaccat cacatgacca catagcatga ggccactgct   1140

gcttctccat ggccaccttt tcagcgatgt atgcagctat ctggtcaacc tcctggacat   1200

tttttcagtc atataaaagc tatggtgaga tgcagctgga aaagggtctt gggaaatatg   1260

aatgccccca gctggcccgt gacagactcc tgaggacagc tgtcctcttc tgcatcttgg   1320

ggacatctct ttgaattttc tgtgttttgc tgtaccagcc cagatgtttt acgtctggga   1380

gaaattgaca gatcaagctg tgagacagtg ggaaatattt agcaaataat ttcctggtgt   1440

gaaggtcctg ctattactaa ggagtaatct gtgtacaaag aaataacaag tcgatgaact   1500

attccccagc agggtctttt catctgggaa agacatccat aaagaagcaa taaagaagag   1560

tgccacattt atttttatat ctatatgtac ttgtcaaaga aggtttgtgt ttttctgctt   1620

ttgaaatctg tatctgtagt gagatagcat tgtgaactga caggcagcct ggacatagag   1680

agggagaaga agtcagagag ggtgacaaga tagagagcta tttaatggcc ggctggaaat   1740

gctgggctga cggtgcagtc tgggtgctcg cccacttgtc ccactatctg ggtgcatgat   1800
```

-continued

```
cttgagcaag ttccttctgg tgtctgcttt ctccattgta aaccacaagg ctgttgcatg   1860

ggctaatgaa gatcatatac gtgaaaatta tttgaaaaca tataaagcac tatacagatt   1920

cgaaactcca ttgagtcatt atccttgcta tgatgatggt gttttgggga tgagagggtg   1980

ctatccattt ctcatgtttt ccattgtttg aaacaaagaa ggttaccaag aagcctttcc   2040

tgtagccttc tgtaggaatt cttttgggga agtgaggaag ccaggtccac ggtctgttct   2100

tgaagcagta gcctaacaca ctccaagata tggacacacg ggagccgctg gcagaaggga   2160

cttcacgaag tgttgcatgg atgttttagc cattgttggc tttcccttat caaacttggg   2220

cccttccctt cttggtttcc aaaggcattt attgctgagt tatatgttca ctgtcccccct  2280

aatattaggg agtaaaacgg ataccaagtt gatttagtgt ttttacctct gtcttggctt   2340

tcatgttatt aaacgtatgc atgtgaagaa gggtgttttt ctgttttata ttcaactcat   2400

aagactttgg gataggaaaa atgagtaatg gttactaggc ttaatacctg ggtgattaca   2460

taatctgtac aacgaacccc catgatgtaa gtttacctat gtaacaaacc tgcacttata   2520

cccatgaact taaaatgaaa gttaaaaata aaaaacatat acaaataaaa aaaa         2574
```

```
<210> SEQ ID NO 11
<211> LENGTH: 239
<212> TYPE: PRT
<213> ORGANISM: Artificial Sequence
<220> FEATURE:
<223> OTHER INFORMATION: A synthetic 20D04 light chain sequence

<400> SEQUENCE: 11

Met Asp Met Arg Ala Pro Thr Gln Leu Leu Gly Leu Leu Leu Leu Trp
 1               5                  10                  15

Leu Pro Gly Ala Arg Cys Ala Asp Val Val Met Thr Gln Thr Pro Ala
            20                  25                  30

Ser Val Ser Ala Ala Val Gly Gly Thr Val Thr Ile Asn Cys Gln Ala
        35                  40                  45

Ser Glu Ser Ile Ser Asn Tyr Leu Ser Trp Tyr Gln Gln Lys Pro Gly
    50                  55                  60

Gln Pro Pro Lys Leu Leu Ile Tyr Arg Thr Ser Thr Leu Ala Ser Gly
65                  70                  75                  80

Val Ser Ser Arg Phe Lys Gly Ser Gly Ser Gly Thr Glu Tyr Thr Leu
                85                  90                  95

Thr Ile Ser Gly Val Gln Cys Asp Asp Val Ala Thr Tyr Tyr Cys Gln
            100                 105                 110

Cys Thr Ser Gly Gly Lys Phe Ile Ser Asp Gly Ala Ala Phe Gly Gly
        115                 120                 125

Gly Thr Glu Val Val Val Lys Gly Asp Pro Val Ala Pro Thr Val Leu
    130                 135                 140

Leu Phe Pro Pro Ser Ser Asp Glu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220
```

```
Gln Gly Thr Thr Ser Val Val Gln Ser Phe Ser Arg Lys Asn Cys
225                 230                 235


<210> SEQ ID NO 12
<211> LENGTH: 720
<212> TYPE: DNA
<213> ORGANISM: Artificial Sequence
<220> FEATURE:
<223> OTHER INFORMATION: A synthetic 20D04 anti-CD83 light chain
      sequence

<400> SEQUENCE: 12

atggacatga gggcccccac tcagctgctg gggctcctgc tgctctggct cccaggtgcc      60

agatgtgccg atgtcgtgat gacccagact ccagcctccg tgtctgcagc tgtgggaggc     120

acagtcacca tcaattgcca ggccagtgaa agcattagca actacttatc ctggtatcag     180

cagaaaccag ggcagcctcc caagctcctg atctacagga catccactct ggcatctggg     240

gtctcatcgc ggttcaaagg cagtggatct gggacagagt acactctcac catcagcggc     300

gtgcagtgtg acgatgttgc cacttactac tgtcaatgca cttctggtgg gaagttcatt     360

agtgatggtg ctgctttcgg cggagggacc gaggtggtgg tcaaaggtga tccagttgca     420

cctactgtcc tcctcttccc accatctagc gatgaggtgg caactggaac agtcaccatc     480

gtgtgtgtgg cgaataaata ctttcccgat gtcaccgtca cctgggaggt ggatggcacc     540

acccaaacaa ctggcatcga gaacagtaaa acaccgcaga attctgcaga ttgtacctac     600

aacctcagca gcactctgac actgaccagc acacagtaca acagccacaa agagtacacc     660

tgcaaggtga cccagggcac gacctcagtc gtccagagct tcagtaggaa gaactgttaa     720


<210> SEQ ID NO 13
<211> LENGTH: 454
<212> TYPE: PRT
<213> ORGANISM: Artificial Sequence
<220> FEATURE:
<223> OTHER INFORMATION: A synthetic 20D04 heavy chain sequence

<400> SEQUENCE: 13

Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Asn Asn Ala Ile Asn Trp Val Arg Gln Ala Pro Gly Lys Gly Leu Glu
    50                  55                  60

Trp Ile Gly Tyr Ile Trp Ser Gly Gly Leu Thr Tyr Tyr Ala Asn Trp
65                  70                  75                  80

Ala Glu Gly Arg Phe Thr Ile Ser Lys Thr Ser Thr Thr Val Asp Leu
                85                  90                  95

Lys Met Thr Ser Pro Thr Ile Glu Asp Thr Ala Thr Tyr Phe Cys Ala
            100                 105                 110

Arg Gly Ile Asn Asn Ser Ala Leu Trp Gly Pro Gly Thr Leu Val Thr
        115                 120                 125

Val Ser Ser Gly Gln Pro Lys Ala Pro Ser Val Phe Pro Leu Ala Pro
    130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
```

-continued

```
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
    370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Asn Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
        435                 440                 445

Ser Arg Ser Pro Gly Lys
    450


<210> SEQ ID NO 14
<211> LENGTH: 1362
<212> TYPE: DNA
<213> ORGANISM: Artificial Sequence
<220> FEATURE:
<223> OTHER INFORMATION: A synthetic 20D04 anti-CD83 heavy chain
      sequence

<400> SEQUENCE: 14

atggagacag gcctgcgctg gcttctcctg gtcgctgtgc tcaaaggtgt ccagtgtcag      60

tcggtggagg agtccggggg tcgcctggtc acgcctggga cacccctgac actcacctgc     120

accgtctctg gattctccct cagtaacaat gcaataaact gggtccgcca ggctccaggg     180

aaggggctag agtggatcgg atacatttgg agtggtgggc ttacatacta cgcgaactgg     240

gcggaaggcc gattcaccat ctccaaaacc tcgactacgg tggatctgaa gatgaccagt     300

ccgacaatcg aggacacggc cacctatttc tgtgccagag ggattaataa ctccgctttg     360
```

-continued

```
tggggcccag gcaccctggt caccgtctcc tcagggcaac ctaaggctcc atcagtcttc    420

ccactggccc cctgctgcgg ggacacaccc tctagcacgg tgaccttggg ctgcctggtc    480

aaaggctacc tcccggagcc agtgaccgtg acctggaact cgggcaccct caccaatggg    540

gtacgcacct tcccgtccgt ccggcagtcc tcaggcctct actcgctgag cagcgtggtg    600

agcgtgacct caagcagcca gcccgtcacc tgcaacgtgg cccacccagc caccaacacc    660

aaagtggaca agaccgttgc gccctcgaca tgcagcaagc ccacgtgccc accccctgaa    720

ctcctggggg gaccgtctgt cttcatcttc cccccaaaac ccaaggacac cctcatgatc    780

tcacgcaccc ccgaggtcac atgcgtggtg gtggacgtga gccaggatga ccccgaggtg    840

cagttcacat ggtacataaa caacgagcag gtgcgcaccg cccggccgcc gctacgggag    900

cagcagttca acagcacgat ccgcgtggtc agcaccctcc ccatcgcgca ccaggactgg    960

ctgaggggca aggagttcaa gtgcaaagtc cacaacaagg cactcccggc ccccatcgag   1020

aaaaccatct ccaaagccag agggcagccc ctggagccga aggtctacac catgggccct   1080

ccccgggagg agctgagcag caggtcggtc agcctgacct gcatgatcaa cggcttctac   1140

ccttccgaca tctcggtgga gtgggagaag aacgggaagg cagaggacaa ctacaagacc   1200

acgccggccg tgctggacag cgacggctcc tacttcctct acaacaagct ctcagtgccc   1260

acgagtgagt ggcagcgggg cgacgtcttc acctgctccg tgatgcacga ggccttgcac   1320

aaccactaca cgcagaagtc catctcccgc tctccgggta aa                      1362
```

```
<210> SEQ ID NO 15
<211> LENGTH: 238
<212> TYPE: PRT
<213> ORGANISM: Artificial Sequence
<220> FEATURE:
<223> OTHER INFORMATION: A synthetic 11G05 light chain sequence

<400> SEQUENCE: 15

Met Asp Thr Arg Ala Pro Thr Gln Leu Leu Gly Leu Leu Leu Leu Trp
 1               5                  10                  15

Leu Pro Gly Ala Arg Cys Ala Asp Val Val Met Thr Gln Thr Pro Ala
            20                  25                  30

Ser Val Ser Ala Ala Val Gly Gly Thr Val Thr Ile Asn Cys Gln Ser
        35                  40                  45

Ser Lys Asn Val Tyr Asn Asn Asn Trp Leu Ser Trp Phe Gln Gln Lys
    50                  55                  60

Pro Gly Gln Pro Pro Lys Leu Leu Ile Tyr Tyr Ala Ser Thr Leu Ala
65                  70                  75                  80

Ser Gly Val Pro Ser Arg Phe Arg Gly Ser Gly Ser Gly Thr Gln Phe
                85                  90                  95

Thr Leu Thr Ile Ser Asp Val Gln Cys Asp Asp Ala Ala Thr Tyr Tyr
            100                 105                 110

Cys Ala Gly Asp Tyr Ser Ser Ser Ser Asp Asn Gly Phe Gly Gly Gly
        115                 120                 125

Thr Glu Val Val Val Lys Gly Asp Pro Val Ala Pro Thr Val Leu Leu
    130                 135                 140

Phe Pro Pro Ser Ser Asp Glu Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190
```

```
Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Ser Arg Lys Asn Cys
225                 230                 235


<210> SEQ ID NO 16
<211> LENGTH: 717
<212> TYPE: DNA
<213> ORGANISM: Artificial Sequence
<220> FEATURE:
<223> OTHER INFORMATION: A synthetic 11G05 anti-CD83 light chain
      sequence

<400> SEQUENCE: 16

atggacacca gggcccccac tcagctgctg gggctcctgc tgctctggct cccaggtgcc      60

agatgtgccg acgtcgtgat gacccagact ccagcctccg tgtctgcagc tgtgggaggc     120

acagtcacca tcaattgcca gtccagtaag aatgtttata ataacaactg gttatcctgg     180

tttcagcaga aaccagggca gcctcccaag ctcctgatct attatgcatc cactctggca     240

tctggggtcc catcgcggtt cagaggcagt ggatctggga cacagttcac tctcaccatt     300

agcgacgtgc agtgtgacga tgctgccact tactactgtg caggcgatta tagtagtagt     360

agtgataatg gtttcggcgg agggaccgag gtggtggtca aaggtgatcc agttgcacct     420

actgtcctcc tcttcccacc atctagcgat gaggtggcaa ctggaacagt caccatcgtg     480

tgtgtggcga ataaatactt tcccgatgtc accgtcacct gggaggtgga tggcaccacc     540

caaacaactg gcatcgagaa cagtaaaaca ccgcagaatt ctgcagattg tacctacaac     600

ctcagcagca ctctgacact gaccagcaca cagtacaaca gccacaaaga gtacacctgc     660

aaggtgaccc agggcacgac ctcagtcgtc cagagcttca gtaggaagaa ctgttaa        717


<210> SEQ ID NO 17
<211> LENGTH: 452
<212> TYPE: PRT
<213> ORGANISM: Artificial Sequence
<220> FEATURE:
<223> OTHER INFORMATION: A synthetic 11G05 heavy chain sequence

<400> SEQUENCE: 17

Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Thr Ile Ser
        35                  40                  45

Asp Tyr Asp Leu Ser Trp Val Arg Gln Ala Pro Gly Glu Gly Leu Lys
    50                  55                  60

Tyr Ile Gly Phe Ile Ala Ile Asp Gly Asn Pro Tyr Tyr Ala Thr Trp
65                  70                  75                  80

Ala Lys Gly Arg Phe Thr Ile Ser Lys Thr Ser Thr Thr Val Asp Leu
                85                  90                  95

Lys Ile Thr Ala Pro Thr Thr Glu Asp Thr Ala Thr Tyr Phe Cys Ala
            100                 105                 110

Arg Gly Ala Gly Asp Leu Trp Gly Pro Gly Thr Leu Val Thr Val Ser
        115                 120                 125
```

-continued

```
Ser Gly Gln Pro Lys Ala Pro Ser Val Phe Pro Leu Ala Pro Cys Cys
    130                 135                 140

Gly Asp Thr Pro Ser Ser Thr Val Thr Leu Gly Cys Leu Val Lys Gly
145                 150                 155                 160

Tyr Leu Pro Glu Pro Val Thr Val Thr Trp Asn Ser Gly Thr Leu Thr
                165                 170                 175

Asn Gly Val Arg Thr Phe Pro Ser Val Arg Gln Ser Ser Gly Leu Tyr
            180                 185                 190

Ser Leu Ser Ser Val Val Ser Val Thr Ser Ser Ser Gln Pro Val Thr
        195                 200                 205

Cys Asn Val Ala His Pro Ala Thr Asn Thr Lys Val Asp Lys Thr Val
    210                 215                 220

Ala Pro Ser Thr Cys Ser Lys Pro Thr Cys Pro Pro Pro Glu Leu Leu
225                 230                 235                 240

Gly Gly Pro Ser Val Phe Ile Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Asp Asp Pro Glu Val Gln Phe Thr Trp Tyr Ile Asn Asn Glu Gln
        275                 280                 285

Val Arg Thr Ala Arg Pro Pro Leu Arg Glu Gln Gln Phe Asn Ser Thr
    290                 295                 300

Ile Arg Val Val Ser Thr Leu Pro Ile Ala His Gln Asp Trp Leu Arg
305                 310                 315                 320

Gly Lys Glu Phe Lys Cys Lys Val His Asn Lys Ala Leu Pro Ala Pro
                325                 330                 335

Ile Glu Lys Thr Ile Ser Lys Ala Arg Gly Gln Pro Leu Glu Pro Lys
            340                 345                 350

Val Tyr Thr Met Gly Pro Pro Arg Glu Glu Leu Ser Ser Arg Ser Val
        355                 360                 365

Ser Leu Thr Cys Met Ile Asn Gly Phe Tyr Pro Ser Asp Ile Ser Val
    370                 375                 380

Glu Trp Glu Lys Asn Gly Lys Ala Glu Asp Asn Tyr Lys Thr Thr Pro
385                 390                 395                 400

Ala Val Leu Asp Ser Asp Gly Ser Tyr Phe Leu Tyr Asn Lys Leu Ser
                405                 410                 415

Val Pro Thr Ser Glu Trp Gln Arg Gly Asp Val Phe Thr Cys Ser Val
            420                 425                 430

Met His Glu Ala Leu His Asn His Tyr Thr Gln Lys Ser Ile Ser Arg
        435                 440                 445

Ser Pro Gly Lys
    450


<210> SEQ ID NO 18
<211> LENGTH: 1356
<212> TYPE: DNA
<213> ORGANISM: Artificial Sequence
<220> FEATURE:
<223> OTHER INFORMATION: A synthetic 11G05 anti-CD83 heavy chain
      sequence

<400> SEQUENCE: 18

atggagacag gcctgcgctg gcttctcctg gtcgctgtgc tcaaaggtgt ccagtgtcag      60

tcggtggagg agtccggggg tcgcctggtc acgcctggga cacccctgac actcacctgc     120

acagtctctg gattcaccat cagtgactac gacttgagct gggtccgcca ggctccaggg     180
```

```
gaggggctga aatacatcgg attcattgct attgatggta acccatacta cgcgacctgg    240

gcaaaaggcc gattcaccat ctccaaaacc tcgaccacgg tggatctgaa aatcaccgct    300

ccgacaaccg aagacacggc cacgtatttc tgtgccagag ggcaggggga cctctggggc    360

ccagggaccc tcgtcaccgt ctcttcaggg caacctaagg ctccatcagt cttcccactg    420

gccccctgct gcggggacac accctctagc acggtgacct tgggctgcct ggtcaaaggc    480

tacctcccgg agccagtgac cgtgacctgg aactcgggca ccctcaccaa tggggtacgc    540

accttcccgt ccgtccggca gtcctcaggc ctctactcgc tgagcagcgt ggtgagcgtg    600

acctcaagca gccagcccgt cacctgcaac gtggcccacc cagccaccaa caccaaagtg    660

gacaagaccg ttgcgccctc gacatgcagc aagcccacgt gcccaccccc tgaactcctg    720

gggggaccgt ctgtcttcat cttcccccca aaacccaagg acaccctcat gatctcacgc    780

acccccgagg tcacatgcgt ggtggtggac gtgagccagg atgaccccga ggtgcagttc    840

acatggtaca taaacaacga gcaggtgcgc accgcccggc cgccgctacg ggagcagcag    900

ttcaacagca cgatccgcgt ggtcagcacc ctccccatcg cgcaccagga ctggctgagg    960

ggcaaggagt tcaagtgcaa agtccacaac aaggcactcc cggcccccat cgagaaaacc   1020

atctccaaag ccagagggca gcccctggag ccgaaggtct acaccatggg ccctccccgg   1080

gaggagctga gcagcaggtc ggtcagcctg acctgcatga tcaacggctt ctacccttcc   1140

gacatctcgg tggagtggga gaagaacggg aaggcagagg acaactacaa gaccacgccg   1200

gccgtgctgg acagcgacgg ctcctacttc ctctacaaca agctctcagt gcccacgagt   1260

gagtggcagc ggggcgacgt cttcacctgc tccgtgatgc acgaggcctt gcacaaccac   1320

tacacgcaga agtccatctc ccgctctccg ggtaaa                             1356
```

<210> SEQ ID NO 19
<211> LENGTH: 238
<212> TYPE: PRT
<213> ORGANISM: Artificial Sequence
<220> FEATURE:
<221> NAME/KEY: SITE
<222> LOCATION: (1)...(238)
<223> OTHER INFORMATION: Xaa = any amino acid
<220> FEATURE:
<223> OTHER INFORMATION: A synthetic 14C12 light chain sequence

<400> SEQUENCE: 19

```
Met Asp Xaa Arg Ala Pro Thr Gln Leu Leu Gly Leu Leu Leu Leu Trp
 1               5                  10                  15

Leu Pro Gly Ala Arg Cys Ala Leu Val Met Thr Gln Thr Pro Ala Ser
            20                  25                  30

Val Ser Ala Ala Val Gly Gly Thr Val Thr Ile Asn Cys Gln Ser Ser
        35                  40                  45

Gln Ser Val Tyr Asp Asn Asp Glu Leu Ser Trp Tyr Gln Gln Lys Pro
    50                  55                  60

Gly Gln Pro Pro Lys Leu Leu Ile Tyr Leu Ala Ser Lys Leu Ala Ser
65                  70                  75                  80

Gly Val Pro Ser Arg Phe Lys Gly Ser Gly Ser Gly Thr Gln Phe Ala
                85                  90                  95

Leu Thr Ile Ser Gly Val Gln Cys Asp Asp Ala Ala Thr Tyr Tyr Cys
            100                 105                 110

Gln Ala Thr His Tyr Ser Ser Asp Trp Tyr Leu Thr Phe Gly Gly Gly
        115                 120                 125
```

-continued

```
Thr Glu Val Val Val Lys Gly Asp Pro Val Ala Pro Thr Val Leu Leu
    130                 135                 140

Phe Pro Pro Ser Ser Asp Glu Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Ser Arg Lys Asn Cys
225                 230                 235


<210> SEQ ID NO 20
<211> LENGTH: 717
<212> TYPE: DNA
<213> ORGANISM: Artificial Sequence
<220> FEATURE:
<223> OTHER INFORMATION: A synthetic 14C12 anti-CD83 light chain
      sequence

<400> SEQUENCE: 20

atggacatra gggcccccac tcagctgctg gggctcctgc tgctctggct cccaggtgcc     60

agatgtgccc ttgtgatgac ccagactcca gcctccgtgt ctgcagctgt gggaggcaca    120

gtcaccatca attgccagtc cagtcagagt gtttatgata acgacgaatt atcctggtat    180

cagcagaaac cagggcagcc tcccaagctc ctgatctatc tggcatccaa gttggcatct    240

ggggtcccat cccgattcaa aggcagtgga tctgggacac agttcgctct caccatcagc    300

ggcgtgcagt gtgacgatgc tgccacttac tactgtcaag ccactcatta tagtagtgat    360

tggtatctta ctttcggcgg agggaccgag gtggtggtca aaggtgatcc agttgcacct    420

actgtcctcc tcttcccacc atctagcgat gaggtggcaa ctggaacagt caccatcgtg    480

tgtgtggcga ataaatactt tcccgatgtc accgtcacct gggaggtgga tggcaccacc    540

caaacaactg gcatcgagaa cagtaaaaca ccgcagaatt ctgcagattg tacctacaac    600

ctcagcagca ctctgacact gaccagcaca cagtacaaca gccacaaaga gtacacctgc    660

aaggtgaccc agggcacgac ctcagtcgtc cagagcttca gtaggaagaa ctgttaa       717


<210> SEQ ID NO 21
<211> LENGTH: 454
<212> TYPE: PRT
<213> ORGANISM: Artificial Sequence
<220> FEATURE:
<223> OTHER INFORMATION: A synthetic 14C12 heavy chain sequence

<400> SEQUENCE: 21

Met Glu Thr Gly Leu Arg Trp Leu Leu Leu Val Ala Val Leu Lys Gly
 1               5                  10                  15

Val His Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Arg Ser
        35                  40                  45

Ser Tyr Asp Met Ser Trp Val Arg Gln Ala Pro Gly Lys Gly Leu Glu
    50                  55                  60

Trp Val Gly Val Ile Ser Thr Ala Tyr Asn Ser His Tyr Ala Ser Trp
```

-continued

```
65                  70                  75                  80

Ala Lys Gly Arg Phe Thr Ile Ser Arg Thr Ser Thr Thr Val Asp Leu
                85                  90                  95

Lys Met Thr Ser Leu Thr Thr Glu Asp Thr Ala Thr Tyr Phe Cys Ala
            100                 105                 110

Arg Gly Gly Ser Trp Leu Asp Leu Trp Gly Gln Gly Thr Leu Val Thr
        115                 120                 125

Val Ser Ser Gly Gln Pro Lys Ala Pro Ser Val Phe Pro Leu Ala Pro
    130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
    370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Asn Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
        435                 440                 445

Ser Arg Ser Pro Gly Lys
    450
```

<210> SEQ ID NO 22
<211> LENGTH: 1362
<212> TYPE: PRT
<213> ORGANISM: Artificial Sequence
<220> FEATURE:
<223> OTHER INFORMATION: A synthetic 14C12 anti-CD83 heavy chain sequence

<400> SEQUENCE: 22

```
Ala Thr Gly Gly Ala Gly Ala Cys Ala Gly Gly Cys Cys Thr Gly Cys
 1               5                  10                  15

Gly Cys Thr Gly Gly Cys Thr Thr Cys Thr Cys Cys Thr Gly Gly Thr
            20                  25                  30

Cys Gly Cys Thr Gly Thr Gly Cys Thr Cys Ala Ala Ala Gly Gly Thr
        35                  40                  45

Gly Thr Cys Cys Ala Cys Thr Gly Thr Cys Ala Gly Thr Cys Gly Gly
    50                  55                  60

Thr Gly Gly Ala Gly Gly Ala Gly Thr Cys Cys Gly Gly Gly Gly Gly
65                  70                  75                  80

Thr Cys Gly Cys Cys Thr Gly Gly Thr Cys Ala Cys Gly Cys Cys Thr
                85                  90                  95

Gly Gly Gly Ala Cys Ala Cys Cys Cys Cys Thr Gly Ala Cys Ala Cys
            100                 105                 110

Thr Cys Ala Cys Cys Thr Gly Cys Ala Cys Ala Gly Cys Cys Thr Cys
        115                 120                 125

Thr Gly Gly Ala Thr Thr Cys Thr Cys Cys Cys Gly Cys Ala Gly Cys
    130                 135                 140

Ala Gly Cys Thr Ala Cys Gly Ala Cys Ala Thr Gly Ala Gly Cys Thr
145                 150                 155                 160

Gly Gly Gly Thr Cys Cys Gly Cys Cys Ala Gly Gly Cys Thr Cys Cys
                165                 170                 175

Ala Gly Gly Gly Ala Ala Gly Gly Gly Gly Cys Thr Gly Gly Ala Ala
            180                 185                 190

Thr Gly Gly Gly Thr Cys Gly Gly Ala Gly Thr Cys Ala Thr Thr Ala
        195                 200                 205

Gly Thr Ala Cys Thr Gly Cys Thr Thr Ala Thr Ala Ala Cys Thr Cys
    210                 215                 220

Ala Cys Ala Cys Thr Ala Cys Gly Cys Gly Ala Gly Cys Thr Gly Gly
225                 230                 235                 240

Gly Cys Ala Ala Ala Ala Gly Gly Cys Cys Gly Ala Thr Thr Cys Ala
                245                 250                 255

Cys Cys Ala Thr Cys Thr Cys Cys Ala Gly Ala Ala Cys Cys Thr Cys
            260                 265                 270

Gly Ala Cys Cys Ala Cys Gly Gly Thr Gly Gly Ala Thr Cys Thr Gly
        275                 280                 285

Ala Ala Ala Ala Thr Gly Ala Cys Cys Ala Gly Thr Cys Thr Gly Ala
    290                 295                 300

Cys Ala Ala Cys Cys Gly Ala Ala Gly Ala Cys Ala Cys Gly Gly Cys
305                 310                 315                 320

Cys Ala Cys Cys Thr Ala Thr Thr Thr Cys Thr Gly Thr Gly Cys Cys
                325                 330                 335

Ala Gly Ala Gly Gly Gly Gly Gly Thr Ala Gly Thr Thr Gly Gly Thr
            340                 345                 350

Thr Gly Gly Ala Thr Cys Thr Cys Thr Gly Gly Gly Gly Cys Cys Ala
        355                 360                 365

Gly Gly Gly Cys Ala Cys Cys Cys Thr Gly Gly Thr Cys Ala Cys Cys
    370                 375                 380

Gly Thr Cys Thr Cys Cys Thr Cys Ala Gly Gly Gly Cys Ala Ala Cys
```

-continued

```
385                 390                 395                 400

Cys Thr Ala Ala Gly Gly Cys Thr Cys Cys Ala Thr Cys Ala Gly Thr
                405                 410                 415

Cys Thr Thr Cys Cys Cys Ala Cys Thr Gly Gly Cys Cys Cys Cys Cys
            420                 425                 430

Thr Gly Cys Thr Gly Cys Gly Gly Gly Gly Ala Cys Ala Cys Ala Cys
        435                 440                 445

Cys Cys Thr Cys Thr Ala Gly Cys Ala Cys Gly Gly Thr Gly Ala Cys
    450                 455                 460

Cys Thr Thr Gly Gly Gly Cys Thr Gly Cys Cys Thr Gly Gly Thr Cys
465                 470                 475                 480

Ala Ala Ala Gly Gly Cys Thr Ala Cys Cys Thr Cys Cys Cys Gly Gly
                485                 490                 495

Ala Gly Cys Cys Ala Gly Thr Gly Ala Cys Cys Gly Thr Gly Ala Cys
            500                 505                 510

Cys Thr Gly Gly Ala Ala Cys Thr Cys Gly Gly Gly Cys Ala Cys Cys
        515                 520                 525

Cys Thr Cys Ala Cys Cys Ala Ala Thr Gly Gly Gly Gly Thr Ala Cys
    530                 535                 540

Gly Cys Ala Cys Cys Thr Thr Cys Cys Cys Gly Thr Cys Cys Gly Thr
545                 550                 555                 560

Cys Cys Gly Gly Cys Ala Gly Thr Cys Cys Thr Cys Ala Gly Gly Cys
                565                 570                 575

Cys Thr Cys Thr Ala Cys Thr Cys Gly Cys Thr Gly Ala Gly Cys Ala
            580                 585                 590

Gly Cys Gly Thr Gly Gly Thr Gly Ala Gly Cys Gly Thr Gly Ala Cys
        595                 600                 605

Cys Thr Cys Ala Ala Gly Cys Ala Gly Cys Cys Ala Gly Cys Cys Cys
    610                 615                 620

Gly Thr Cys Ala Cys Cys Thr Gly Cys Ala Ala Cys Gly Thr Gly Gly
625                 630                 635                 640

Cys Cys Cys Ala Cys Cys Cys Ala Gly Cys Cys Ala Cys Cys Ala Ala
                645                 650                 655

Cys Ala Cys Cys Ala Ala Ala Gly Thr Gly Gly Ala Cys Ala Ala Gly
            660                 665                 670

Ala Cys Cys Gly Thr Thr Gly Cys Gly Cys Cys Cys Thr Cys Gly Ala
        675                 680                 685

Cys Ala Thr Gly Cys Ala Gly Cys Ala Ala Gly Cys Cys Cys Ala Cys
    690                 695                 700

Gly Thr Gly Cys Cys Cys Ala Cys Cys Cys Cys Cys Thr Gly Ala Ala
705                 710                 715                 720

Cys Thr Cys Cys Thr Gly Gly Gly Gly Gly Gly Ala Cys Cys Gly Thr
                725                 730                 735

Cys Thr Gly Thr Cys Thr Thr Cys Ala Thr Cys Thr Thr Cys Cys Cys
            740                 745                 750

Cys Cys Cys Ala Ala Ala Ala Cys Cys Cys Ala Ala Gly Gly Ala Cys
        755                 760                 765

Ala Cys Cys Cys Thr Cys Ala Thr Gly Ala Thr Cys Thr Cys Ala Cys
    770                 775                 780

Gly Cys Ala Cys Cys Cys Cys Cys Gly Ala Gly Gly Thr Cys Ala Cys
785                 790                 795                 800

Ala Thr Gly Cys Gly Thr Gly Gly Thr Gly Gly Thr Gly Gly Ala Cys
                805                 810                 815
```

```
Gly Thr Gly Ala Gly Cys Cys Ala Gly Gly Ala Thr Gly Ala Cys Cys
            820                 825                 830

Cys Cys Gly Ala Gly Gly Thr Gly Cys Ala Gly Thr Thr Cys Ala Cys
        835                 840                 845

Ala Thr Gly Gly Thr Ala Cys Ala Thr Ala Ala Ala Cys Ala Ala Cys
    850                 855                 860

Gly Ala Gly Cys Ala Gly Gly Thr Gly Cys Gly Cys Ala Cys Cys Gly
865                 870                 875                 880

Cys Cys Cys Gly Gly Cys Cys Gly Cys Cys Gly Cys Thr Ala Cys Gly
                885                 890                 895

Gly Gly Ala Gly Cys Ala Gly Cys Ala Gly Thr Thr Cys Ala Ala Cys
            900                 905                 910

Ala Gly Cys Ala Cys Gly Ala Thr Cys Cys Gly Cys Gly Thr Gly Gly
        915                 920                 925

Thr Cys Ala Gly Cys Ala Cys Cys Cys Thr Cys Cys Cys Cys Ala Thr
    930                 935                 940

Cys Gly Cys Gly Cys Ala Cys Cys Ala Gly Gly Ala Cys Thr Gly Gly
945                 950                 955                 960

Cys Thr Gly Ala Gly Gly Gly Gly Cys Ala Ala Gly Gly Ala Gly Thr
                965                 970                 975

Thr Cys Ala Ala Gly Thr Gly Cys Ala Ala Ala Gly Thr Cys Cys Ala
            980                 985                 990

Cys Ala Ala Cys Ala Ala Gly Gly Cys Ala Cys Thr Cys Cys Cys Gly
        995                 1000                1005

Gly Cys Cys Cys Cys Cys Ala Thr Cys Gly Ala Gly Ala Ala Ala Ala
    1010                1015                1020

Cys Cys Ala Thr Cys Thr Cys Cys Ala Ala Ala Gly Cys Cys Ala Gly
1025                1030                1035                1040

Ala Gly Gly Gly Cys Ala Gly Cys Cys Cys Cys Thr Gly Gly Ala Gly
                1045                1050                1055

Cys Cys Gly Ala Ala Gly Gly Thr Cys Thr Ala Cys Ala Cys Cys Ala
            1060                1065                1070

Thr Gly Gly Gly Cys Cys Cys Thr Cys Cys Cys Cys Gly Gly Gly Ala
        1075                1080                1085

Gly Gly Ala Gly Cys Thr Gly Ala Gly Cys Ala Gly Cys Ala Gly Gly
    1090                1095                1100

Thr Cys Gly Gly Thr Cys Ala Gly Cys Cys Thr Gly Ala Cys Cys Thr
1105                1110                1115                1120

Gly Cys Ala Thr Gly Ala Thr Cys Ala Ala Cys Gly Gly Cys Thr Thr
                1125                1130                1135

Cys Thr Ala Cys Cys Cys Thr Thr Cys Cys Gly Ala Cys Ala Thr Cys
            1140                1145                1150

Thr Cys Gly Gly Thr Gly Gly Ala Gly Thr Gly Gly Gly Ala Gly Ala
        1155                1160                1165

Ala Gly Ala Ala Cys Gly Gly Gly Ala Ala Gly Gly Cys Ala Gly Ala
    1170                1175                1180

Gly Gly Ala Cys Ala Ala Cys Thr Ala Cys Ala Ala Gly Ala Cys Cys
1185                1190                1195                1200

Ala Cys Gly Cys Cys Gly Gly Cys Cys Gly Thr Gly Cys Thr Gly Gly
                1205                1210                1215

Ala Cys Ala Gly Cys Gly Ala Cys Gly Gly Cys Thr Cys Cys Thr Ala
            1220                1225                1230
```

```
Cys Thr Thr Cys Cys Thr Cys Thr Ala Cys Ala Ala Cys Ala Ala Gly
        1235                1240                1245

Cys Thr Cys Thr Cys Ala Gly Thr Gly Cys Cys Cys Ala Cys Gly Ala
    1250                1255                1260

Gly Thr Gly Ala Gly Thr Gly Gly Cys Ala Gly Cys Gly Gly Gly Gly
1265                1270                1275                1280

Cys Gly Ala Cys Gly Thr Cys Thr Thr Cys Ala Cys Cys Thr Gly Cys
                1285                1290                1295

Thr Cys Cys Gly Thr Gly Ala Thr Gly Cys Ala Cys Gly Ala Gly Gly
            1300                1305                1310

Cys Cys Thr Thr Gly Cys Ala Cys Ala Ala Cys Cys Ala Cys Thr Ala
        1315                1320                1325

Cys Ala Cys Gly Cys Ala Gly Ala Ala Gly Thr Cys Cys Ala Thr Cys
    1330                1335                1340

Thr Cys Cys Cys Gly Cys Thr Cys Thr Cys Cys Gly Gly Gly Thr Ala
1345                1350                1355                1360

Ala Ala


<210> SEQ ID NO 23
<211> LENGTH: 5
<212> TYPE: PRT
<213> ORGANISM: Oryctolagus cuniculus

<400> SEQUENCE: 23

Ser Tyr Asp Met Thr
 1               5


<210> SEQ ID NO 24
<211> LENGTH: 5
<212> TYPE: PRT
<213> ORGANISM: Oryctolagus cuniculus

<400> SEQUENCE: 24

Ser Tyr Asp Met Ser
 1               5


<210> SEQ ID NO 25
<211> LENGTH: 5
<212> TYPE: PRT
<213> ORGANISM: Oryctolagus cuniculus

<400> SEQUENCE: 25

Asp Tyr Asp Leu Ser
 1               5


<210> SEQ ID NO 26
<211> LENGTH: 5
<212> TYPE: PRT
<213> ORGANISM: Oryctolagus cuniculus

<400> SEQUENCE: 26

Ser Tyr Asp Met Ser
 1               5


<210> SEQ ID NO 27
<211> LENGTH: 8
<212> TYPE: PRT
<213> ORGANISM: Oryctolagus cuniculus

<400> SEQUENCE: 27

Tyr Ala Ser Gly Ser Thr Tyr Tyr
```

1 5

<210> SEQ ID NO 28
<211> LENGTH: 8
<212> TYPE: PRT
<213> ORGANISM: Oryctolagus cuniculus

<400> SEQUENCE: 28

Ser Ser Ser Gly Thr Thr Tyr Tyr
1 5

<210> SEQ ID NO 29
<211> LENGTH: 8
<212> TYPE: PRT
<213> ORGANISM: Oryctolagus cuniculus

<400> SEQUENCE: 29

Tyr Ala Ser Gly Ser Thr Tyr Tyr
1 5

<210> SEQ ID NO 30
<211> LENGTH: 8
<212> TYPE: PRT
<213> ORGANISM: Oryctolagus cuniculus

<400> SEQUENCE: 30

Ala Ile Asp Gly Asn Pro Tyr Tyr
1 5

<210> SEQ ID NO 31
<211> LENGTH: 8
<212> TYPE: PRT
<213> ORGANISM: Oryctolagus cuniculus

<400> SEQUENCE: 31

Ser Thr Ala Tyr Asn Ser His Tyr
1 5

<210> SEQ ID NO 32
<211> LENGTH: 11
<212> TYPE: PRT
<213> ORGANISM: Oryctolagus cuniculus

<400> SEQUENCE: 32

Glu His Ala Gly Tyr Ser Gly Asp Thr Gly His
1 5 10

<210> SEQ ID NO 33
<211> LENGTH: 8
<212> TYPE: PRT
<213> ORGANISM: Oryctolagus cuniculus

<400> SEQUENCE: 33

Glu Gly Ala Gly Val Ser Met Thr
1 5

<210> SEQ ID NO 34
<211> LENGTH: 8
<212> TYPE: PRT
<213> ORGANISM: Oryctolagus cuniculus

<400> SEQUENCE: 34

Glu Asp Ala Gly Phe Ser Asn Ala
1 5

<210> SEQ ID NO 35
<211> LENGTH: 4
<212> TYPE: PRT
<213> ORGANISM: Oryctolagus cuniculus

<400> SEQUENCE: 35

Gly Ala Gly Asp
1

<210> SEQ ID NO 36
<211> LENGTH: 6
<212> TYPE: PRT
<213> ORGANISM: Oryctolagus cuniculus

<400> SEQUENCE: 36

Gly Gly Ser Trp Leu Asp
1 5

<210> SEQ ID NO 37
<211> LENGTH: 5
<212> TYPE: PRT
<213> ORGANISM: Oryctolagus cuniculus

<400> SEQUENCE: 37

Arg Cys Ala Tyr Asp
1 5

<210> SEQ ID NO 38
<211> LENGTH: 6
<212> TYPE: PRT
<213> ORGANISM: Oryctolagus cuniculus

<400> SEQUENCE: 38

Arg Cys Ala Asp Val Val
1 5

<210> SEQ ID NO 39
<211> LENGTH: 5
<212> TYPE: PRT
<213> ORGANISM: Oryctolagus cuniculus

<400> SEQUENCE: 39

Arg Cys Ala Leu Val
1 5

<210> SEQ ID NO 40
<211> LENGTH: 6
<212> TYPE: PRT
<213> ORGANISM: Oryctolagus cuniculus

<400> SEQUENCE: 40

Gln Ser Ile Ser Thr Tyr
1 5

<210> SEQ ID NO 41
<211> LENGTH: 6
<212> TYPE: PRT
<213> ORGANISM: Oryctolagus cuniculus

<400> SEQUENCE: 41

Gln Ser Val Ser Ser Tyr
1 5

<210> SEQ ID NO 42

```
<211> LENGTH: 6
<212> TYPE: PRT
<213> ORGANISM: Oryctolagus cuniculus

<400> SEQUENCE: 42

Glu Ser Ile Ser Asn Tyr
 1               5


<210> SEQ ID NO 43
<211> LENGTH: 8
<212> TYPE: PRT
<213> ORGANISM: Oryctolagus cuniculus

<400> SEQUENCE: 43

Lys Asn Val Tyr Asn Asn Asn Trp
 1               5


<210> SEQ ID NO 44
<211> LENGTH: 12
<212> TYPE: PRT
<213> ORGANISM: Oryctolagus cuniculus

<400> SEQUENCE: 44

Gln Gln Gly Tyr Thr His Ser Asn Val Asp Asn Val
 1               5                   10


<210> SEQ ID NO 45
<211> LENGTH: 12
<212> TYPE: PRT
<213> ORGANISM: Oryctolagus cuniculus

<400> SEQUENCE: 45

Gln Gln Gly Tyr Ser Ile Ser Asp Ile Asp Asn Ala
 1               5                   10


<210> SEQ ID NO 46
<211> LENGTH: 14
<212> TYPE: PRT
<213> ORGANISM: Oryctolagus cuniculus

<400> SEQUENCE: 46

Gln Cys Thr Ser Gly Gly Lys Phe Ile Ser Asp Gly Ala Ala
 1               5                   10


<210> SEQ ID NO 47
<211> LENGTH: 11
<212> TYPE: PRT
<213> ORGANISM: Oryctolagus cuniculus

<400> SEQUENCE: 47

Ala Gly Asp Tyr Ser Ser Ser Ser Asp Asn Gly
 1               5                   10


<210> SEQ ID NO 48
<211> LENGTH: 12
<212> TYPE: PRT
<213> ORGANISM: Oryctolagus cuniculus

<400> SEQUENCE: 48

Gln Ala Thr His Tyr Ser Ser Asp Trp Leu Thr Tyr
 1               5                   10


<210> SEQ ID NO 49
<211> LENGTH: 5
<212> TYPE: RNA
```

```
<213> ORGANISM: Oryctolagus cuniculus

<400> SEQUENCE: 49

auuua                                                                    5


<210> SEQ ID NO 50
<211> LENGTH: 6
<212> TYPE: RNA
<213> ORGANISM: Oryctolagus cuniculus

<400> SEQUENCE: 50

auuuua                                                                   6


<210> SEQ ID NO 51
<211> LENGTH: 7
<212> TYPE: RNA
<213> ORGANISM: Oryctolagus cuniculus

<400> SEQUENCE: 51

auuuuua                                                                  7


<210> SEQ ID NO 52
<211> LENGTH: 157
<212> TYPE: PRT
<213> ORGANISM: Artificial Sequence
<220> FEATURE:
<223> OTHER INFORMATION: A synthetic anti-CD83 heavy chain variable
      region sequence

<400> SEQUENCE: 52

Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Asp Met Thr Trp Val Arg Gln Ala Pro Gly Lys Gly Leu Glu
    50                  55                  60

Trp Ile Gly Ile Ile Tyr Ala Ser Gly Ser Thr Tyr Tyr Ala Ser Trp
65                  70                  75                  80

Ala Lys Gly Arg Phe Thr Ile Ser Lys Thr Ser Thr Thr Val Asp Leu
                85                  90                  95

Glu Val Thr Ser Leu Thr Thr Glu Asp Thr Ala Thr Tyr Phe Cys Ser
            100                 105                 110

Arg Glu His Ala Gly Tyr Ser Gly Asp Thr Gly His Leu Trp Gly Pro
        115                 120                 125

Gly Thr Leu Val Thr Val Ser Ser Gly Gln Pro Lys Ala Pro Ser Val
    130                 135                 140

Phe Pro Leu Ala Pro Cys Cys Gly Asp Thr Pro Ser Ser
145                 150                 155


<210> SEQ ID NO 53
<211> LENGTH: 154
<212> TYPE: PRT
<213> ORGANISM: Artificial Sequence
<220> FEATURE:
<223> OTHER INFORMATION: A synthetic anti-CD83 heavy chain variable
      region sequence

<400> SEQUENCE: 53

Met Glu Thr Gly Leu Arg Trp Leu Leu Leu Val Ala Val Leu Lys Gly
```

-continued

```
 1               5                   10                  15

Val Gln Cys Gln Ser Val Glu Glu Ser Gly Gly Arg Leu Val Ser Pro
            20                  25                  30

Gly Thr Pro Leu Thr Leu Thr Cys Thr Ala Ser Gly Phe Ser Leu Ser
        35                  40                  45

Ser Tyr Asp Met Ser Trp Val Arg Gln Ala Pro Gly Lys Gly Leu Glu
    50                  55                  60

Tyr Ile Gly Ile Ile Ser Ser Ser Gly Thr Thr Tyr Tyr Ala Asn Trp
65                  70                  75                  80

Ala Lys Gly Arg Phe Thr Ile Ser Lys Thr Ser Thr Thr Val Asp Leu
                85                  90                  95

Lys Val Thr Ser Pro Thr Ile Gly Asp Thr Ala Thr Tyr Phe Cys Ala
            100                 105                 110

Arg Glu Gly Ala Gly Val Ser Met Thr Leu Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser
145                 150


<210> SEQ ID NO 54
<211> LENGTH: 154
<212> TYPE: PRT
<213> ORGANISM: Artificial Sequence
<220> FEATURE:
<223> OTHER INFORMATION: A synthetic anti-CD83 heavy chain variable
      region sequence

<400> SEQUENCE: 54

Met Glu Thr Gly Leu Arg Trp Leu Leu Leu Val Ala Val Leu Lys Gly
 1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Asp Met Ser Trp Val Arg Gln Ala Pro Gly Lys Gly Leu Glu
    50                  55                  60

Trp Ile Gly Ile Ile Tyr Ala Ser Gly Ser Thr Tyr Tyr Ala Ser Trp
65                  70                  75                  80

Ala Lys Gly Arg Val Ala Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Glu Asp Ala Gly Phe Ser Asn Ala Leu Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser
145                 150


<210> SEQ ID NO 55
<211> LENGTH: 147
<212> TYPE: PRT
<213> ORGANISM: Artificial Sequence
<220> FEATURE:
<223> OTHER INFORMATION: A synthetic anti-CD83 light chain variable
      region sequence
```

```
<400> SEQUENCE: 55

Met Asp Met Arg Ala Pro Thr Gln Leu Leu Gly Leu Leu Leu Leu Trp
 1               5                  10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Gln Ser Ile Ser Thr Tyr Leu Asp Trp Tyr Gln Gln Lys Pro Gly Gln
    50                  55                  60

Pro Pro Lys Leu Leu Ile Tyr Asp Ala Ser Asp Leu Ala Ser Gly Val
65                  70                  75                  80

Pro Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Thr His Ser Asn Val Asp Asn Val Phe Gly Gly Gly Thr Glu
        115                 120                 125

Val Val Val Lys Gly Asp Pro Val Ala Pro Thr Val Leu Leu Phe Pro
    130                 135                 140

Pro Ser Ser
145


<210> SEQ ID NO 56
<211> LENGTH: 147
<212> TYPE: PRT
<213> ORGANISM: Artificial Sequence
<220> FEATURE:
<223> OTHER INFORMATION: A synthetic anti-CD83 light chain variable
      region sequence

<400> SEQUENCE: 56

Met Asp Met Arg Ala Pro Thr Gln Leu Leu Gly Leu Leu Leu Leu Trp
 1               5                  10                  15

Leu Pro Gly Ala Arg Cys Ala Tyr Asp Met Thr Gln Thr Pro Ala Ser
            20                  25                  30

Val Glu Val Ala Val Gly Gly Thr Val Ala Ile Lys Cys Gln Ala Ser
        35                  40                  45

Gln Ser Val Ser Ser Tyr Leu Ala Trp Tyr Gln Gln Lys Pro Gly Gln
    50                  55                  60

Pro Pro Lys Pro Leu Ile Tyr Glu Ala Ser Met Leu Ala Ala Gly Val
65                  70                  75                  80

Ser Ser Arg Phe Lys Gly Ser Gly Ser Gly Thr Asp Phe Thr Leu Thr
                85                  90                  95

Ile Ser Asp Leu Glu Cys Asp Asp Ala Ala Thr Tyr Tyr Cys Gln Gln
            100                 105                 110

Gly Tyr Ser Ile Ser Asp Ile Asp Asn Ala Phe Gly Gly Gly Thr Glu
        115                 120                 125

Val Val Val Lys Gly Asp Pro Val Ala Pro Thr Val Leu Leu Phe Pro
    130                 135                 140

Pro Ser Ser
145


<210> SEQ ID NO 57
<211> LENGTH: 150
<212> TYPE: PRT
<213> ORGANISM: Artificial Sequence
<220> FEATURE:
```

```
<223> OTHER INFORMATION: A synthetic anti-CD83 light chain variable
      region sequence

<400> SEQUENCE: 57

Met Asp Met Arg Ala Pro Thr Gln Leu Leu Gly Leu Leu Leu Leu Trp
 1               5                  10                  15

Leu Pro Gly Ala Arg Cys Ala Asp Val Val Met Thr Gln Thr Pro Ala
            20                  25                  30

Ser Val Ser Ala Ala Val Gly Gly Thr Val Thr Ile Asn Cys Gln Ala
        35                  40                  45

Ser Glu Ser Ile Ser Asn Tyr Leu Ser Trp Tyr Gln Gln Lys Pro Gly
    50                  55                  60

Gln Pro Pro Lys Leu Leu Ile Tyr Arg Thr Ser Thr Leu Ala Ser Gly
65                  70                  75                  80

Val Ser Ser Arg Phe Lys Gly Ser Gly Ser Gly Thr Glu Tyr Thr Leu
                85                  90                  95

Thr Ile Ser Gly Val Gln Cys Asp Asp Val Ala Thr Tyr Tyr Cys Gln
            100                 105                 110

Cys Thr Ser Gly Gly Lys Phe Ile Ser Asp Gly Ala Ala Phe Gly Gly
        115                 120                 125

Gly Thr Glu Val Val Val Lys Gly Asp Pro Val Ala Pro Thr Val Leu
    130                 135                 140

Leu Phe Pro Pro Ser Ser
145                 150


<210> SEQ ID NO 58
<211> LENGTH: 236
<212> TYPE: PRT
<213> ORGANISM: Artificial Sequence
<220> FEATURE:
<223> OTHER INFORMATION: A synthetic M83 020B08L light chain sequence

<400> SEQUENCE: 58

Met Asp Met Arg Ala Pro Thr Gln Leu Leu Gly Leu Leu Leu Leu Trp
 1               5                  10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Gln Ser Ile Ser Thr Tyr Leu Asp Trp Tyr Gln Gln Lys Pro Gly Gln
    50                  55                  60

Pro Pro Lys Leu Leu Ile Tyr Asp Ala Ser Asp Leu Ala Ser Gly Val
65                  70                  75                  80

Pro Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Thr His Ser Asn Val Asp Asn Val Phe Gly Gly Gly Thr Glu
        115                 120                 125

Val Val Val Lys Gly Asp Pro Val Ala Pro Thr Val Leu Leu Phe Pro
    130                 135                 140

Pro Ser Ser Asp Glu Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
```

```
        180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Ser Arg Lys Asn Cys
225                 230                 235


<210> SEQ ID NO 59
<211> LENGTH: 711
<212> TYPE: DNA
<213> ORGANISM: Artificial Sequence
<220> FEATURE:
<223> OTHER INFORMATION: A synthetic M83 020B08L anti-CD83 light chain
      sequence

<400> SEQUENCE: 59

atggacatga gggcccccac tcagctgctg gggctcctgc tgctctggct cccaggtgcc      60

agatgtgcct atgatatgac ccagactcca gcctctgtgg aggtagctgt gggaggcaca     120

gtcaccatca agtgccaggc cagtcagagc attagtacct acttagactg gtatcagcag     180

aaaccagggc agcctcccaa gctcctgatc tatgatgcat ccgatctggc atctggggtc     240

ccatcgcggt tcaaaggcag tggatctggg acacagttca ctctcaccat cagcgacctg     300

gagtgtgccg atgctgccac ttactactgt caacagggtt atacacatag taatgttgat     360

aatgttttcg gcggagggac cgaggtggtg gtcaaaggtg atccagttgc acctactgtc     420

ctcctcttcc caccatctag cgatgaggtg gcaactggaa cagtcaccat cgtgtgtgtg     480

gcgaataaat actttcccga tgtcaccgtc acctgggagg tggatggcac cacccaaaca     540

actggcatcg agaacagtaa aacaccgcag aattctgcag attgtaccta caacctcagc     600

agcactctga cactgaccag cacacagtac aacagccaca aagagtacac ctgcaaggtg     660

acccagggca cgacctcagt cgtccagagc ttcagtagga agaactgtta a              711


<210> SEQ ID NO 60
<211> LENGTH: 456
<212> TYPE: PRT
<213> ORGANISM: Artificial Sequence
<220> FEATURE:
<223> OTHER INFORMATION: A synthetic M83 020B08H heavy chain sequence

<400> SEQUENCE: 60

Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Asp Met Thr Trp Val Arg Gln Ala Pro Gly Lys Gly Leu Glu
    50                  55                  60

Trp Ile Gly Ile Ile Tyr Ala Ser Gly Thr Thr Tyr Tyr Ala Asn Trp
65                  70                  75                  80

Ala Lys Gly Arg Phe Thr Ile Ser Lys Thr Ser Thr Thr Val Asp Leu
                85                  90                  95

Lys Val Thr Ser Pro Thr Ile Gly Asp Thr Ala Thr Tyr Phe Cys Ala
            100                 105                 110

Arg Glu Gly Ala Gly Val Ser Met Thr Leu Trp Gly Pro Gly Thr Leu
        115                 120                 125
```

```
Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Asn Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455
```

```
<210> SEQ ID NO 61
<211> LENGTH: 1368
<212> TYPE: DNA
<213> ORGANISM: Artificial Sequence
<220> FEATURE:
<223> OTHER INFORMATION: A synthetic M83 020B08H anti-CD83 heavy chain
      sequence

<400> SEQUENCE: 61

atggagacag gcctgcgctg gcttctcctg gtcgctgtgc tcaaaggtgt ccagtgtcag      60

tcggtggagg agtccggggg tcgcctggtc acgcctggga cacccctgac actcacctgc     120
```

-continued

```
acagtctctg gattctccct cagcagctac gacatgacct gggtccgcca ggctccaggg    180

aaggggctgg aatggatcgg aatcatttat gctagtggta ccacatacta cgcgaactgg    240

gcgaaaggcc gattcaccat ctccaaaacc tcgaccacgg tggatctgaa agtcaccagt    300

ccgacaatcg ggacacggc cacctatttc tgtgccagag agggggctgg tgttagtatg     360

accttgtggg gcccaggcac cctggtcacc gtctcctcag ggcaacctaa ggctccatca    420

gtcttcccac tggcccctg ctgcggggac acaccctcta gcacggtgac cttgggctgc     480

ctggtcaaag gctacctccc ggagccagtg accgtgacct ggaactcggg caccctcacc    540

aatggggtac gcaccttccc gtccgtccgg cagtcctcag gcctctactc gctgagcagc    600

gtggtgagcg tgacctcaag cagccagccc gtcacctgca acgtggccca cccagccacc    660

aacaccaaag tggacaagac cgttgcgccc tcgacatgca gcaagcccac gtgcccaccc    720

cctgaactcc tgggggggacc gtctgtcttc atcttccccc caaaacccaa ggacaccctc   780

atgatctcac gcacccccga ggtcacatgc gtggtggtgg acgtgagcca ggatgacccc    840

gaggtgcagt tcacatggta cataaacaac gagcaggtgc gcaccgcccg gccgccgcta    900

cgggagcagc agttcaacag cacgatccgc gtggtcagca ccctccccat cgcgcaccag    960

gactggctga ggggcaagga gttcaagtgc aaagtccaca acaaggcact cccggccccc   1020

atcgagaaaa ccatctccaa agccagaggg cagcccctgg agccgaaggt ctacaccatg   1080

ggccctcccc gggaggagct gagcagcagg tcggtcagcc tgacctgcat gatcaacggc   1140

ttctaccctt ccgacatctc ggtggagtgg gagaagaacg ggaaggcaga ggacaactac   1200

aagaccacgc cggccgtgct ggacagcgac ggctcctact tcctctacaa caagctctca   1260

gtgcccacga gtgagtggca gcggggcgac gtcttcacct gctccgtgat gcacgaggcc   1320

ttgcacaacc actacacgca gaagtccatc tcccgctctc cgggtaaa                1368
```

<210> SEQ ID NO 62
<211> LENGTH: 236
<212> TYPE: PRT
<213> ORGANISM: Artificial Sequence
<220> FEATURE:
<223> OTHER INFORMATION: A synthetic M83 006G05L light chain sequence

<400> SEQUENCE: 62

```
Met Asp Met Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Ala Ile Lys Cys Gln Ala Ser
        35                  40                  45

Gln Ser Val Ser Ser Tyr Leu Ala Trp Tyr Gln Gln Lys Pro Gly Gln
    50                  55                  60

Pro Pro Lys Pro Leu Ile Tyr Glu Ala Ser Met Leu Ala Ala Gly Val
65                  70                  75                  80

Ser Ser Arg Phe Lys Gly Ser Gly Ser Gly Thr Asp Phe Thr Leu Thr
                85                  90                  95

Ile Ser Asp Leu Glu Cys Asp Asp Ala Ala Thr Tyr Tyr Cys Gln Gln
            100                 105                 110

Gly Tyr Ser Ile Ser Asp Ile Asp Asn Ala Phe Gly Gly Gly Thr Glu
        115                 120                 125

Val Val Val Lys Gly Asp Pro Val Ala Pro Thr Val Leu Leu Phe Pro
    130                 135                 140
```

-continued

```
Pro Ser Ser Asp Glu Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Ser Arg Lys Asn Cys
225                 230                 235
```

```
<210> SEQ ID NO 63
<211> LENGTH: 711
<212> TYPE: DNA
<213> ORGANISM: Artificial Sequence
<220> FEATURE:
<223> OTHER INFORMATION: A synthetic M83 006G05L anti-CD83 light chain
      sequence

<400> SEQUENCE: 63

atggacatga gggcccccac tcaactgctg gggctcctgc tgctctggct cccaggtgcc     60

agatgtgcct atgatatgac ccagactcca gcctctgtgg aggtagctgt gggaggcaca    120

gtcgccatca agtgccaggc cagtcagagc gttagtagtt acttagcctg gtatcagcag    180

aaaccagggc agcctcccaa gcccctgatc tacgaagcat ccatgctggc ggctggggtc    240

tcatcgcggt tcaaaggcag tggatctggg acagacttca ctctcaccat cagcgacctg    300

gagtgtgacg atgctgccac ttactattgt caacagggtt attctatcag tgatattgat    360

aatgctttcg gcggagggac cgaggtggtg gtcaaaggtg atccagttgc acctactgtc    420

ctcctcttcc caccatctag cgatgaggtg gcaactggaa cagtcaccat cgtgtgtgtg    480

gcgaataaat actttcccga tgtcaccgtc acctgggagg tggatggcac cacccaaaca    540

actggcatcg agaacagtaa aacaccgcag aattctgcag attgtaccta caacctcagc    600

agcactctga cactgaccag cacacagtac aacagccaca aagagtacac ctgcaaggtg    660

acccagggca cgacctcagt cgtccagagc ttcagtagga agaactgtta a             711
```

```
<210> SEQ ID NO 64
<211> LENGTH: 459
<212> TYPE: PRT
<213> ORGANISM: Artificial Sequence
<220> FEATURE:
<223> OTHER INFORMATION: A synthetic M83 006G05L heavy chain sequence

<400> SEQUENCE: 64

Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Ser Pro
            20                  25                  30

Gly Thr Pro Leu Thr Leu Thr Cys Thr Ala Ser Gly Phe Ser Leu Ser
        35                  40                  45

Ser Tyr Asp Met Ser Trp Val Arg Gln Ala Pro Gly Lys Gly Leu Glu
    50                  55                  60

Tyr Ile Gly Ile Ile Ser Ser Ser Gly Ser Thr Tyr Tyr Ala Ser Trp
65                  70                  75                  80

Ala Lys Gly Arg Phe Thr Ile Ser Lys Thr Ser Thr Thr Val Asp Leu
```

-continued

```
                85                  90                  95

Glu Val Thr Ser Leu Thr Thr Glu Asp Thr Ala Thr Tyr Phe Cys Ser
            100                 105                 110

Arg Glu His Ala Gly Tyr Ser Gly Asp Thr Gly His Leu Trp Gly Pro
        115                 120                 125

Gly Thr Leu Val Thr Val Ser Ser Gly Gln Pro Lys Ala Pro Ser Val
    130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
        195                 200                 205

Ser Ser Ser Gln Pro Val Thr Cys Asn Val Ala His Pro Ala Thr Asn
    210                 215                 220

Thr Lys Val Asp Lys Thr Val Ala Pro Ser Thr Cys Ser Lys Pro Thr
225                 230                 235                 240

Cys Pro Pro Pro Glu Leu Leu Gly Gly Pro Ser Val Phe Ile Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Asp Asp Pro Glu Val Gln Phe Thr
        275                 280                 285

Trp Tyr Ile Asn Asn Glu Gln Val Arg Thr Ala Arg Pro Pro Leu Arg
    290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
            340                 345                 350

Gly Gln Pro Leu Glu Pro Lys Val Tyr Thr Met Gly Pro Pro Arg Glu
        355                 360                 365

Glu Leu Ser Ser Arg Ser Val Ser Leu Thr Cys Met Ile Asn Gly Phe
    370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Ala Val Leu Asp Ser Asp Gly Ser Tyr
                405                 410                 415

Phe Leu Tyr Asn Lys Leu Ser Val Pro Thr Ser Glu Trp Gln Arg Gly
            420                 425                 430

Asp Val Phe Thr Cys Ser Val Met His Glu Ala Leu His Asn His Tyr
        435                 440                 445

Thr Gln Lys Ser Ile Ser Arg Ser Pro Gly Lys
    450                 455
```

<210> SEQ ID NO 65
<211> LENGTH: 1377
<212> TYPE: DNA
<213> ORGANISM: Artificial Sequence
<220> FEATURE:
<223> OTHER INFORMATION: A synthetic M83 006G05L anti-CD83 heavy chain sequence

<400> SEQUENCE: 65

```
atggagacag gcctgcgctg gcttctcctg gtcgctgtgc tcaaaggtgt ccagtgtcag      60
tcggtggagg agtccggggg tcgcctggtc tcgcctggga cacccctgac actcacctgc     120
acagcctctg gattctccct cagtagctac gacatgagct gggtccgcca ggctccaggg     180
aaggggctgg aatacatcgg aatcattagt agtagtggta gcacatacta cgcgagctgg     240
gcgaaaggcc gattcaccat ctccaaaacc tcgaccacgg tggatctgga agtgaccagt     300
ctgacaaccg aggacacggc cacctatttc tgtagtagag aacatgctgg ttatagtggt     360
gatacgggtc acttgtgggg cccaggcacc ctggtcaccg tctcctcggg gcaacctaag     420
gctccatcag tcttcccact ggccccctgc tgcggggaca caccctctag cacggtgacc     480
ttgggctgcc tggtcaaagg ctacctcccg gagccagtga ccgtgacctg gaactcgggc     540
accctcacca atggggtacg caccttcccg tccgtccggc agtcctcagg cctctactcg     600
ctgagcagcg tggtgagcgt gacctcaagc agccagcccg tcacctgcaa cgtggcccac     660
ccagccacca acaccaaagt ggacaagacc gttgcgccct cgacatgcag caagcccacg     720
tgcccacccc ctgaactcct ggggggaccg tctgtcttca tcttcccccc aaaacccaag     780
gacaccctca tgatctcacg cacccccgag gtcacatgcg tggtggtgga cgtgagccag     840
gatgaccccg aggtgcagtt cacatggtac ataaacaacg agcaggtgcg caccgcccgg     900
ccgccgctac gggagcagca gttcaacagc acgatccgcg tggtcagcac cctccccatc     960
gcgcaccagg actggctgag gggcaaggag ttcaagtgca aagtccacaa caaggcactc    1020
ccggccccca tcgagaaaac catctccaaa gccagagggc agcccctgga gccgaaggtc    1080
tacaccatgg gccctccccg ggaggagctg agcagcaggt cggtcagcct gacctgcatg    1140
atcaacggct tctacccttc cgacatctcg gtggagtggg agaagaacgg gaaggcagag    1200
gacaactaca agaccacgcc ggccgtgctg gacagcgacg gctcctactt cctctacaac    1260
aagctctcag tgcccacgag tgagtggcag cggggcgacg tcttcacctg ctccgtgatg    1320
cacgaggcct tgcacaacca ctacacgcag aagtccatct cccgctctcc gggtaaa       1377
```

<210> SEQ ID NO 66
<211> LENGTH: 150
<212> TYPE: PRT
<213> ORGANISM: Artificial Sequence
<220> FEATURE:
<223> OTHER INFORMATION: A synthetic anti-CD83 heavy chain variable region sequence

<400> SEQUENCE: 66

```
Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Thr Ile Ser
        35                  40                  45

Asp Tyr Asp Leu Ser Trp Val Arg Gln Ala Pro Gly Glu Gly Leu Lys
    50                  55                  60

Tyr Ile Gly Phe Ile Ala Ile Asp Gly Asn Pro Tyr Tyr Ala Thr Trp
65                  70                  75                  80

Ala Lys Gly Arg Phe Thr Ile Ser Lys Thr Ser Thr Thr Val Asp Leu
                85                  90                  95

Lys Ile Thr Ala Pro Thr Thr Glu Asp Thr Ala Thr Tyr Phe Cys Ala
```

-continued

```
            100                 105                 110

Arg Gly Ala Gly Asp Leu Trp Gly Pro Gly Thr Leu Val Thr Val Ser
        115                 120                 125

Ser Gly Gln Pro Lys Ala Pro Ser Val Phe Pro Leu Ala Pro Cys Cys
    130                 135                 140

Gly Asp Thr Pro Ser Ser
145                 150


<210> SEQ ID NO 67
<211> LENGTH: 152
<212> TYPE: PRT
<213> ORGANISM: Artificial Sequence
<220> FEATURE:
<223> OTHER INFORMATION: A synthetic anti-CD83 heavy chain variable
      region sequence

<400> SEQUENCE: 67

Met Glu Thr Gly Leu Arg Trp Leu Leu Leu Val Ala Val Leu Lys Gly
 1               5                  10                  15

Val His Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Arg Ser
        35                  40                  45

Ser Tyr Asp Met Ser Trp Val Arg Gln Ala Pro Gly Lys Gly Leu Glu
    50                  55                  60

Trp Val Gly Val Ile Ser Thr Ala Tyr Asn Ser His Tyr Ala Ser Trp
65                  70                  75                  80

Ala Lys Gly Arg Phe Thr Ile Ser Arg Thr Ser Thr Thr Val Asp Leu
                85                  90                  95

Lys Met Thr Ser Leu Thr Thr Glu Asp Thr Ala Thr Tyr Phe Cys Ala
            100                 105                 110

Arg Gly Gly Ser Trp Leu Asp Leu Trp Gly Gln Gly Thr Leu Val Thr
        115                 120                 125

Val Ser Ser Gly Gln Pro Lys Ala Pro Ser Val Phe Pro Leu Ala Pro
    130                 135                 140

Cys Cys Gly Asp Thr Pro Ser Ser
145                 150


<210> SEQ ID NO 68
<211> LENGTH: 149
<212> TYPE: PRT
<213> ORGANISM: Artificial Sequence
<220> FEATURE:
<223> OTHER INFORMATION: A synthetic anti-CD83 light chain variable
      region sequence

<400> SEQUENCE: 68

Met Asp Thr Arg Ala Pro Thr Gln Leu Leu Gly Leu Leu Leu Leu Trp
 1               5                  10                  15

Leu Pro Gly Ala Arg Cys Ala Asp Val Val Met Thr Gln Thr Pro Ala
            20                  25                  30

Ser Val Ser Ala Ala Val Gly Gly Thr Val Thr Ile Asn Cys Gln Ser
        35                  40                  45

Ser Lys Asn Val Tyr Asn Asn Asn Trp Leu Ser Trp Phe Gln Gln Lys
    50                  55                  60

Pro Gly Gln Pro Pro Lys Leu Leu Ile Tyr Tyr Ala Ser Thr Leu Ala
65                  70                  75                  80

Ser Gly Val Pro Ser Arg Phe Arg Gly Ser Gly Ser Gly Thr Gln Phe
```

```
                85                  90                  95

Thr Leu Thr Ile Ser Asp Val Gln Cys Asp Asp Ala Ala Thr Tyr Tyr
            100                 105                 110

Cys Ala Gly Asp Tyr Ser Ser Ser Ser Asp Asn Gly Phe Gly Gly Gly
        115                 120                 125

Thr Glu Val Val Val Lys Gly Asp Pro Val Ala Pro Thr Val Leu Leu
    130                 135                 140

Phe Pro Pro Ser Ser
145


<210> SEQ ID NO 69
<211> LENGTH: 149
<212> TYPE: PRT
<213> ORGANISM: Artificial Sequence
<220> FEATURE:
<221> NAME/KEY: SITE
<222> LOCATION: (1)...(149)
<223> OTHER INFORMATION: Xaa = any amino acid
<220> FEATURE:
<223> OTHER INFORMATION: A synthetic anti-CD83 light chain variable
      region sequence

<400> SEQUENCE: 69

Met Asp Xaa Arg Ala Pro Thr Gln Leu Leu Gly Leu Leu Leu Leu Trp
 1               5                  10                  15

Leu Pro Gly Ala Arg Cys Ala Leu Val Met Thr Gln Thr Pro Ala Ser
            20                  25                  30

Val Ser Ala Ala Val Gly Gly Thr Val Thr Ile Asn Cys Gln Ser Ser
        35                  40                  45

Gln Ser Val Tyr Asp Asn Asp Glu Leu Ser Trp Tyr Gln Gln Lys Pro
    50                  55                  60

Gly Gln Pro Pro Lys Leu Leu Ile Tyr Leu Ala Ser Lys Leu Ala Ser
65                  70                  75                  80

Gly Val Pro Ser Arg Phe Lys Gly Ser Gly Ser Gly Thr Gln Phe Ala
                85                  90                  95

Leu Thr Ile Ser Gly Val Gln Cys Asp Asp Ala Ala Thr Tyr Tyr Cys
            100                 105                 110

Gln Ala Thr His Tyr Ser Ser Asp Trp Tyr Leu Thr Phe Gly Gly Gly
        115                 120                 125

Thr Glu Val Val Val Lys Gly Asp Pro Val Ala Pro Thr Val Leu Leu
    130                 135                 140

Phe Pro Pro Ser Ser
145


<210> SEQ ID NO 70
<211> LENGTH: 240
<212> TYPE: PRT
<213> ORGANISM: Artificial Sequence
<220> FEATURE:
<223> OTHER INFORMATION: A synthetic 96G08 light chain sequence

<400> SEQUENCE: 70

Met Asp Thr Arg Ala Pro Thr Gln Leu Leu Gly Leu Leu Leu Leu Trp
 1               5                  10                  15

Leu Pro Gly Ala Thr Phe Ala Gln Val Leu Thr Gln Thr Ala Ser Pro
            20                  25                  30

Val Ser Ala Pro Val Gly Gly Thr Val Thr Ile Asn Cys Gln Ser Ser
        35                  40                  45

Gln Ser Val Tyr Asn Asn Asp Phe Leu Ser Trp Tyr Gln Gln Lys Pro
```

```
    50                  55                  60

Gly Gln Pro Pro Lys Leu Leu Ile Tyr Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Thr Gly Thr Tyr Gly Asn Ser Ala Trp Tyr Glu Asp Ala Phe Gly Gly
        115                 120                 125

Gly Thr Glu Val Val Val Lys Arg Thr Pro Val Ala Pro Thr Val Leu
    130                 135                 140

Leu Phe Pro Pro Ser Ser Ala Glu Leu Ala Thr Gly Thr Ala Thr Ile
145                 150                 155                 160

Val Cys Val Ala Asn Lys Tyr Phe Pro Asp Gly Thr Val Thr Trp Lys
                165                 170                 175

Val Asp Gly Ile Thr Gln Ser Ser Gly Ile Asn Asn Ser Arg Thr Pro
            180                 185                 190

Gln Asn Ser Ala Asp Cys Thr Tyr Asn Leu Ser Ser Thr Leu Thr Leu
        195                 200                 205

Ser Ser Asp Glu Tyr Asn Ser His Asp Glu Tyr Thr Cys Gln Val Ala
    210                 215                 220

Gln Asp Ser Gly Ser Pro Val Val Gln Ser Phe Ser Arg Lys Ser Cys
225                 230                 235                 240


<210> SEQ ID NO 71
<211> LENGTH: 13
<212> TYPE: PRT
<213> ORGANISM: Oryctolagus cuniculus

<400> SEQUENCE: 71

Gln Ser Ser Gln Ser Val Tyr Asn Asn Asp Phe Leu Ser
 1               5                  10


<210> SEQ ID NO 72
<211> LENGTH: 7
<212> TYPE: PRT
<213> ORGANISM: Oryctolagus cuniculus

<400> SEQUENCE: 72

Tyr Ala Ser Thr Leu Ala Ser
 1               5


<210> SEQ ID NO 73
<211> LENGTH: 13
<212> TYPE: PRT
<213> ORGANISM: Oryctolagus cuniculus

<400> SEQUENCE: 73

Thr Gly Thr Tyr Gly Asn Ser Ala Trp Tyr Glu Asp Ala
 1               5                  10


<210> SEQ ID NO 74
<211> LENGTH: 723
<212> TYPE: DNA
<213> ORGANISM: Artificial Sequence
<220> FEATURE:
<223> OTHER INFORMATION: A synthetic 96G08 anti-CD83  light chain
      sequence

<400> SEQUENCE: 74
```

-continued

```
atggacacga gggcccccac tcagctgctg gggctcctgc tgctctggct cccaggtgcc      60

acatttgcgc aagtgctgac ccagactgca tcgcccgtgt ctgcacctgt gggaggcaca     120

gtcaccatca attgccagtc cagtcagagt gtttataata acgacttctt atcctggtat     180

cagcagaaac cagggcagcc tcccaaactc ctgatctatt atgcatccac tctggcatct     240

ggggtcccat cccggttcaa aggcagtgga tctgggacac agttcactct caccatcagc     300

gacctggagt gtgacgatgc tgccacttac tactgtacag gcacttatgg taatagtgct     360

tggtacgagg atgctttcgg cggagggacc gaggtggtgg tcaaacgtac gccagttgca     420

cctactgtcc tcctcttccc accatctagc gctgagctgg caactggaac agccaccatc     480

gtgtgcgtgg cgaataaata ctttcccgat ggcaccgtca cctggaaggt ggatggcatc     540

acccaaagca gcggcatcaa taacagtaga acaccgcaga attctgcaga ttgtacctac     600

aacctcagca gtactctgac actgagcagc gacgagtaca acagccacga cgagtacacc     660

tgccaggtgg cccaggactc aggctcaccg gtcgtccaga gcttcagtag gaagagctgt     720

tag                                                                   723
```

<210> SEQ ID NO 75
<211> LENGTH: 25
<212> TYPE: DNA
<213> ORGANISM: Oryctolagus cuniculus

<400> SEQUENCE: 75

```
cagtccagtc agagtgttta taata                                           25
```

<210> SEQ ID NO 76
<211> LENGTH: 20
<212> TYPE: DNA
<213> ORGANISM: Oryctolagus cuniculus

<400> SEQUENCE: 76

```
atgcatccac tctggcatct                                                  20
```

<210> SEQ ID NO 77
<211> LENGTH: 25
<212> TYPE: DNA
<213> ORGANISM: Oryctolagus cuniculus

<400> SEQUENCE: 77

```
acaggcactt atggtaatag tgctt                                            25
```

<210> SEQ ID NO 78
<211> LENGTH: 456
<212> TYPE: PRT
<213> ORGANISM: Artificial Sequence
<220> FEATURE:
<223> OTHER INFORMATION: A synthetic 96G08 heavy chain sequence

<400> SEQUENCE: 78

```
Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Asp Gly Ile Ser Trp Val Arg Gln Ala Pro Gly Lys Gly Leu Glu
    50                  55                  60

Trp Ile Gly Ile Ile Ser Ser Gly Gly Asn Thr Tyr Tyr Ala Ser Trp
```

-continued

```
65                  70                  75                  80

Ala Lys Gly Arg Phe Thr Ile Ser Arg Thr Ser Thr Thr Val Asp Leu
                85                  90                  95

Lys Met Thr Ser Leu Thr Thr Glu Asp Thr Ala Thr Tyr Phe Cys Ala
            100                 105                 110

Arg Val Val Gly Gly Thr Tyr Ser Ile Trp Gly Gln Gly Thr Leu Val
        115                 120                 125

Thr Val Ser Ser Ala Ser Thr Lys Gly Pro Ser Val Tyr Pro Leu Ala
    130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Ser Val Thr Val Pro Ser Ser Thr Trp Pro
        195                 200                 205

Ser Glu Thr Val Thr Cys Asn Val Ala His Pro Ala Ser Ser Thr Lys
    210                 215                 220

Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
                245                 250                 255

Lys Asp Val Leu Thr Ile Thr Leu Thr Pro Lys Val Thr Cys Val Val
            260                 265                 270

Val Asp Ile Ser Lys Asp Asp Pro Glu Val Gln Phe Ser Trp Phe Val
        275                 280                 285

Asp Asp Val Glu Val His Thr Ala Gln Thr Gln Pro Arg Glu Glu Gln
    290                 295                 300

Phe Asn Ser Thr Phe Arg Ser Val Ser Glu Leu Pro Ile Met His Gln
305                 310                 315                 320

Asp Trp Leu Asn Gly Lys Glu Phe Lys Cys Arg Val Asn Ser Ala Ala
                325                 330                 335

Phe Pro Ala Pro Ile Glu Lys Thr Ile Ser Lys Thr Lys Gly Arg Pro
            340                 345                 350

Lys Ala Pro Gln Val Tyr Thr Ile Pro Pro Pro Lys Glu Gln Met Ala
        355                 360                 365

Lys Asp Lys Val Ser Leu Thr Cys Met Ile Thr Asp Phe Phe Pro Glu
    370                 375                 380

Asp Ile Thr Val Glu Trp Gln Trp Asn Gly Gln Pro Ala Glu Asn Tyr
385                 390                 395                 400

Lys Asn Thr Gln Pro Ile Met Asp Thr Asp Gly Ser Tyr Phe Val Tyr
                405                 410                 415

Ser Lys Leu Asn Val Gln Lys Ser Asn Trp Glu Ala Gly Asn Thr Phe
            420                 425                 430

Thr Cys Ser Val Leu His Glu Gly Leu His Asn His His Thr Glu Lys
        435                 440                 445

Ser Leu Ser His Ser Pro Gly Lys
    450                 455

<210> SEQ ID NO 79
<211> LENGTH: 5
<212> TYPE: PRT
<213> ORGANISM: Oryctolagus cuniculus
```

<400> SEQUENCE: 79

Ser Asp Gly Ile Ser
 1               5

<210> SEQ ID NO 80
<211> LENGTH: 16
<212> TYPE: PRT
<213> ORGANISM: Oryctolagus cuniculus

<400> SEQUENCE: 80

Ile Ile Ser Ser Gly Gly Asn Thr Tyr Tyr Ala Ser Trp Ala Lys Gly
 1               5                  10                  15

<210> SEQ ID NO 81
<211> LENGTH: 8
<212> TYPE: PRT
<213> ORGANISM: Oryctolagus cuniculus

<400> SEQUENCE: 81

Val Val Gly Gly Thr Tyr Ser Ile
 1               5

<210> SEQ ID NO 82
<211> LENGTH: 1371
<212> TYPE: DNA
<213> ORGANISM: Artificial Sequence
<220> FEATURE:
<223> OTHER INFORMATION: A synthetic 96G08 anti-CD83 heavy chain sequence

<400> SEQUENCE: 82
atggagactg ggctgcgctg gcttctcctg gtcgctgtgc tcaaaggtgt ccagtgtcag 60
tcggtggagg agtccggggg tcgcctggtc acacctggga cacccctgac actcacctgc 120
acagtgtctg gaatcgacct cagtagcgat ggaataagct gggtccgcca ggctccaggg 180
aaggggctgg aatggatcgg aatcattagt agtggtggta acacatacta cgcgagctgg 240
gcaaaaggcc gattcaccat ctccagaacc tcgaccacgg tggatctgaa gatgaccagt 300
ctgacaaccg aggacacggc cacctatttc tgtgccagag ttgttggtgg tacttatagc 360
atctggggcc agggcaccct cgtcaccgtc tcgagcgctt ctacaaaggg cccatctgtc 420
tatccactgg cccctggatc tgctgcccaa actaactcca tggtgaccct gggatgcctg 480
gtcaagggct atttccctga gccagtgaca gtgacctgga actctggatc cctgtccagc 540
ggtgtgcaca ccttcccagc tgtcctgcag tctgacctct acactctgag cagctcagtg 600
actgtcccct ccagcacctg gcccagcgag accgtcacct gcaacgttgc ccacccggcc 660
agcagcacca aggtggacaa gaaaattgtg cccagggatt gtggttgtaa gccttgcata 720
tgtacagtcc cagaagtatc atctgtcttc atcttccccc caaagcccaa ggatgtgctc 780
accattactc tgactcctaa ggtcacgtgt gttgtggtag acatcagcaa ggatgatccc 840
gaggtccagt tcagctggtt tgtagatgat gtggaggtgc acacagctca gacgcaaccc 900
cgggaggagc agttcaacag cactttccgc tcagtcagtg aacttcccat catgcaccag 960
gactggctca atggcaagga gttcaaatgc agggtcaaca gtgcagcttt ccctgccccc 1020
atcgagaaaa ccatctccaa aaccaaaggc agaccgaagg ctccacaggt gtacaccatt 1080
ccacctccca aggagcagat ggccaaggat aaagtcagtc tgacctgcat gataacagac 1140
ttcttccctg aagacattac tgtggagtgg cagtggaatg ggcagccagc ggagaactac 1200

-continued

```
aagaacactc agcccatcat ggacacagat ggctcttact tcgtctacag caagctcaat   1260

gtgcagaaga gcaactggga ggcaggaaat actttcacct gctctgtgtt acatgagggc   1320

ctgcacaacc accatactga gaagagcctc tcccactctc ctggtaaatg a            1371


<210> SEQ ID NO 83
<211> LENGTH: 15
<212> TYPE: DNA
<213> ORGANISM: Oryctolagus cuniculus

<400> SEQUENCE: 83

agcgatggaa taagc                                                      15


<210> SEQ ID NO 84
<211> LENGTH: 48
<212> TYPE: DNA
<213> ORGANISM: Oryctolagus cuniculus

<400> SEQUENCE: 84

atcattagta gtggtggtaa cacatactac gcgagctggg caaaaggc                  48


<210> SEQ ID NO 85
<211> LENGTH: 24
<212> TYPE: DNA
<213> ORGANISM: Oryctolagus cuniculus

<400> SEQUENCE: 85

gttgttggtg gtacttatag catc                                            24


<210> SEQ ID NO 86
<211> LENGTH: 239
<212> TYPE: PRT
<213> ORGANISM: Artificial Sequence
<220> FEATURE:
<223> OTHER INFORMATION: A synthetic 95F04 light chain sequence

<400> SEQUENCE: 86

Met Asp Thr Arg Ala Pro Thr Gln Leu Leu Gly Leu Leu Leu Leu Trp
 1               5                  10                  15

Leu Pro Gly Ala Thr Phe Ala Gln Ala Val Val Thr Gln Thr Thr Ser
            20                  25                  30

Pro Val Ser Ala Pro Val Gly Gly Thr Val Thr Ile Asn Cys Gln Ser
        35                  40                  45

Ser Gln Ser Val Tyr Gly Asn Asn Glu Leu Ser Trp Tyr Gln Gln Lys
    50                  55                  60

Pro Gly Gln Pro Pro Lys Leu Leu Ile Tyr Gln Ala Ser Ser Leu Ala
65                  70                  75                  80

Ser Gly Val Pro Ser Arg Phe Lys Gly Ser Gly Ser Gly Thr Gln Phe
                85                  90                  95

Thr Leu Thr Ile Ser Asp Leu Glu Cys Asp Asp Ala Ala Thr Tyr Tyr
            100                 105                 110

Cys Leu Gly Glu Tyr Ser Ile Ser Ala Asp Asn His Phe Gly Gly Gly
        115                 120                 125

Thr Glu Val Val Val Lys Arg Thr Pro Val Ala Pro Thr Val Leu Leu
    130                 135                 140

Phe Pro Pro Ser Ser Ala Glu Leu Ala Thr Gly Thr Ala Thr Ile Val
145                 150                 155                 160

Cys Val Ala Asn Lys Tyr Phe Pro Asp Gly Thr Val Thr Trp Lys Val
                165                 170                 175
```

-continued

```
Asp Gly Ile Thr Gln Ser Ser Gly Ile Asn Asn Ser Arg Thr Pro Gln
            180                 185                 190

Asn Ser Ala Asp Cys Thr Tyr Asn Leu Ser Ser Thr Leu Thr Leu Ser
        195                 200                 205

Ser Asp Glu Tyr Asn Ser His Asp Glu Tyr Thr Cys Gln Val Ala Gln
    210                 215                 220

Asp Ser Gly Ser Pro Val Val Gln Ser Phe Ser Arg Lys Ser Cys
225                 230                 235


<210> SEQ ID NO 87
<211> LENGTH: 13
<212> TYPE: PRT
<213> ORGANISM: Oryctolagus cuniculus

<400> SEQUENCE: 87

Gln Ser Ser Gln Ser Val Tyr Gly Asn Asn Glu Leu Ser
 1               5                  10


<210> SEQ ID NO 88
<211> LENGTH: 7
<212> TYPE: PRT
<213> ORGANISM: Oryctolagus cuniculus

<400> SEQUENCE: 88

Gln Ala Ser Ser Leu Ala Ser
 1               5


<210> SEQ ID NO 89
<211> LENGTH: 11
<212> TYPE: PRT
<213> ORGANISM: Oryctolagus cuniculus

<400> SEQUENCE: 89

Leu Gly Glu Tyr Ser Ile Ser Ala Asp Asn His
 1               5                  10


<210> SEQ ID NO 90
<211> LENGTH: 720
<212> TYPE: DNA
<213> ORGANISM: Artificial Sequence
<220> FEATURE:
<223> OTHER INFORMATION: A synthetic 95F04 anti-CD83  light chain
      sequence

<400> SEQUENCE: 90

atggacacga gggcccccac tcagctgctg gggctcctgc tgctctggct cccaggtgcc      60

acatttgccc aagccgtggt gacccagact acatcgcccg tgtctgcacc tgtgggaggc     120

acagtcacca tcaattgcca gtccagtcag agtgtttatg gtaacaacga attatcctgg     180

tatcagcaga aaccagggca gcctcccaag ctcctgatct accaggcatc cagcctggca     240

tctggggtcc catcgcggtt caaaggcagt ggatctggga cacagttcac tctcaccatc     300

agcgacctgg agtgtgacga tgctgccact tactactgtc taggcgaata tagcattagt     360

gctgataatc atttcggcgg agggaccgag gtggtggtca aacgtacgcc agttgcacct     420

actgtcctcc tcttcccacc atctagcgct gagctggcaa ctggaacagc caccatcgtg     480

tgcgtggcga ataaatactt tcccgatggc accgtcacct ggaaggtgga tggcatcacc     540

caaagcagcg gcatcaataa cagtagaaca ccgcagaatt ctgcagattg tacctacaac     600

ctcagcagta ctctgacact gagcagcgac gagtacaaca gccacgacga gtacacctgc     660

caggtggccc aggactcagg ctcaccggtc gtccagagct tcagtaggaa gagctgttag     720
```

<210> SEQ ID NO 91
<211> LENGTH: 460
<212> TYPE: PRT
<213> ORGANISM: Artificial Sequence
<220> FEATURE:
<223> OTHER INFORMATION: A synthetic 95F04 heavy chain sequence

<400> SEQUENCE: 91

```
Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Asn Ala Met Ile Trp Val Arg Gln Ala Pro Arg Glu Gly Leu Glu
    50                  55                  60

Trp Ile Gly Ala Met Asp Ser Asn Ser Arg Thr Tyr Tyr Ala Thr Trp
65                  70                  75                  80

Ala Lys Gly Arg Phe Thr Ile Ser Arg Thr Ser Ser Ile Thr Val Asp
                85                  90                  95

Leu Lys Ile Thr Ser Pro Thr Thr Glu Asp Thr Ala Thr Tyr Phe Cys
            100                 105                 110

Ala Arg Gly Asp Gly Gly Ser Ser Asp Tyr Thr Glu Met Trp Gly Pro
        115                 120                 125

Gly Thr Leu Val Thr Val Ser Ser Ala Ser Thr Lys Gly Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365
```

```
Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460


<210> SEQ ID NO 92
<211> LENGTH: 5
<212> TYPE: PRT
<213> ORGANISM: Oryctolagus cuniculus

<400> SEQUENCE: 92

Ser Asn Ala Met Ile
 1               5


<210> SEQ ID NO 93
<211> LENGTH: 16
<212> TYPE: PRT
<213> ORGANISM: Oryctolagus cuniculus

<400> SEQUENCE: 93

Ala Met Asp Ser Asn Ser Arg Thr Tyr Tyr Ala Thr Trp Ala Lys Gly
 1               5                  10                  15


<210> SEQ ID NO 94
<211> LENGTH: 11
<212> TYPE: PRT
<213> ORGANISM: Oryctolagus cuniculus

<400> SEQUENCE: 94

Gly Asp Gly Gly Ser Ser Asp Tyr Thr Glu Met
 1               5                  10


<210> SEQ ID NO 95
<211> LENGTH: 1383
<212> TYPE: DNA
<213> ORGANISM: Artificial Sequence
<220> FEATURE:
<223> OTHER INFORMATION: A synthetic 95F04 anti-CD83  heavy chain
      sequence

<400> SEQUENCE: 95

atggagactg ggctgcgctg gcttctcctg gtcgctgtgc tcaaaggtgt ccagtgtcag      60

tcggtggagg agtccggggg tcgcctggtc acgcctggga cacccctgac actcacctgc     120

acagtctctg gaatcgacct cagtagcaat gcaatgatct gggtccgcca ggctccaagg     180

gaggggctgg aatggatcgg agccatggat agtaatagta ggacgtacta cgcgacctgg     240

gcgaaaggcc gattcaccat ctccagaacc tcgtcgatta cggtggatct gaaaatcacc     300

agtccgacaa ccgaggacac ggccacctat ttctgtgcca gaggggatgg tggcagtagt     360

gattatacag agatgtgggg cccagggacc ctcgtcaccg tctcgagcgc ttctacaaag     420

ggcccatctg tctatccact ggcccctgga tctgctgccc aaactaactc catggtgacc     480
```

-continued

```
ctgggatgcc tggtcaaggg ctatttccct gagccagtga cagtgacctg gaactctgga    540

tccctgtcca gcggtgtgca caccttccca gctgtcctgc agtctgacct ctacactctg    600

agcagctcag tgactgtccc ctccagcacc tggcccagcg agaccgtcac ctgcaacgtt    660

gcccacccgg ccagcagcac caaggtggac aagaaaattg tgcccaggga ttgtggttgt    720

aagccttgca tatgtacagt cccagaagta tcatctgtct tcatcttccc cccaaagccc    780

aaggatgtgc tcaccattac tctgactcct aaggtcacgt gtgttgtggt agacatcagc    840

aaggatgatc ccgaggtcca gttcagctgg tttgtagatg atgtggaggt gcacacagct    900

cagacgcaac cccgggagga gcagttcaac agcactttcc gctcagtcag tgaacttccc    960

atcatgcacc aggactggct caatggcaag gagttcaaat gcagggtcaa cagtgcagct   1020

ttccctgccc ccatcgagaa aaccatctcc aaaaccaaag gcagaccgaa ggctccacag   1080

gtgtacacca ttccacctcc caaggagcag atggccaagg ataaagtcag tctgacctgc   1140

atgataacag acttcttccc tgaagacatt actgtggagt ggcagtggaa tgggcagcca   1200

gcggagaact acaagaacac tcagcccatc atggacacag atggctctta cttcgtctac   1260

agcaagctca atgtgcagaa gagcaactgg gaggcaggaa atactttcac ctgctctgtg   1320

ttacatgagg gcctgcacaa ccaccatact gagaagagcc tctcccactc tcctggtaaa   1380

tga                                                                 1383
```

<210> SEQ ID NO 96
<211> LENGTH: 1383
<212> TYPE: DNA
<213> ORGANISM: Artificial Sequence
<220> FEATURE:
<223> OTHER INFORMATION: A synthetic 95F04 anti-CD83 light chain sequence

<400> SEQUENCE: 96

```
atggagactg ggctgcgctg gcttctcctg gtcgctgtgc tcaaaggtgt ccagtgtcag     60

tcggtggagg agtccggggg tcgcctggtc acgcctggga cacccctgac actcacctgc    120

acagtctctg gaatcgacct cagtagcaat gcaatgatct gggtccgcca ggctccaagg    180

gaggggctgg aatggatcgg agccatggat agtaatagta ggacgtacta cgcgacctgg    240

gcgaaaggcc gattcaccat ctccagaacc tcgtcgatta cggtggatct gaaaatcacc    300

agtccgacaa ccgaggacac ggccacctat ttctgtgcca gaggggatgg tggcagtagt    360

gattatacag agatgtgggg cccagggacc ctcgtcaccg tctcgagcgc ttctacaaag    420

ggcccatctg tctatccact ggcccctgga tctgctgccc aaactaactc catggtgacc    480

ctgggatgcc tggtcaaggg ctatttccct gagccagtga cagtgacctg gaactctgga    540

tccctgtcca gcggtgtgca caccttccca gctgtcctgc agtctgacct ctacactctg    600

agcagctcag tgactgtccc ctccagcacc tggcccagcg agaccgtcac ctgcaacgtt    660

gcccacccgg ccagcagcac caaggtggac aagaaaattg tgcccaggga ttgtggttgt    720

aagccttgca tatgtacagt cccagaagta tcatctgtct tcatcttccc cccaaagccc    780

aaggatgtgc tcaccattac tctgactcct aaggtcacgt gtgttgtggt agacatcagc    840

aaggatgatc ccgaggtcca gttcagctgg tttgtagatg atgtggaggt gcacacagct    900

cagacgcaac cccgggagga gcagttcaac agcactttcc gctcagtcag tgaacttccc    960

atcatgcacc aggactggct caatggcaag gagttcaaat gcagggtcaa cagtgcagct   1020

ttccctgccc ccatcgagaa aaccatctcc aaaaccaaag gcagaccgaa ggctccacag   1080
```

gtgtacacca ttccacctcc caaggagcag atggccaagg ataaagtcag tctgacctgc 1140
atgataacag acttcttccc tgaagacatt actgtggagt ggcagtggaa tgggcagcca 1200
gcggagaact acaagaacac tcagcccatc atggacacag atggctctta cttcgtctac 1260
agcaagctca atgtgcagaa gagcaactgg gaggcaggaa atactttcac ctgctctgtg 1320
ttacatgagg gcctgcacaa ccaccatact gagaagagcc tctcccactc tcctggtaaa 1380
tga 1383

<210> SEQ ID NO 97
<211> LENGTH: 107
<212> TYPE: PRT
<213> ORGANISM: Homo sapiens

<400> SEQUENCE: 97

```
Pro Glu Val Lys Val Ala Cys Ser Glu Asp Val Asp Leu Pro Cys Thr
 1               5                  10                  15

Ala Pro Trp Asp Pro Gln Val Pro Tyr Thr Val Ser Trp Val Lys Leu
            20                  25                  30

Leu Glu Gly Gly Glu Glu Arg Met Glu Thr Pro Gln Glu Asp His Leu
        35                  40                  45

Arg Gly Gln His Tyr His Gln Lys Gly Gln Asn Gly Ser Phe Asp Ala
    50                  55                  60

Pro Asn Glu Arg Pro Tyr Ser Leu Lys Ile Arg Asn Thr Thr Ser Cys
65                  70                  75                  80

Asn Ser Gly Thr Tyr Arg Cys Thr Leu Gln Asp Pro Asp Gly Gln Arg
                85                  90                  95

Asn Leu Ser Gly Lys Val Ile Leu Arg Val Thr
            100                 105
```

<210> SEQ ID NO 98
<211> LENGTH: 8
<212> TYPE: PRT
<213> ORGANISM: Oryctolagus cuniculus

<400> SEQUENCE: 98

```
Gln Ser Val Tyr Asp Asn Asp Glu
 1               5
```

<210> SEQ ID NO 99
<211> LENGTH: 720
<212> TYPE: DNA
<213> ORGANISM: Artificial Sequence
<220> FEATURE:
<223> OTHER INFORMATION: A synthetic 96G08 anti-CD83 light chain sequence

<400> SEQUENCE: 99
atggacacga gggcccccac tcagctgctg gggctcctgc tgctctggct cccaggtgcc 60
acatttgcgc aagtgctgac ccagactgca tcgcccgtgt ctgcacctgt gggaggcaca 120
gtcaccatca attgccagtc cagtcagagt gtttataata acgacttctt atcctggtat 180
cagcagaaac cagggcagcc tcccaaactc ctgatctatt atgcatccac tctggcatct 240
ggggtcccat cccggttcaa aggcagtgga tctgggacac agttcactct caccatcagc 300
gacctggagt gtgacgatgc gccacttact actgtacagg cacttatggt aatagtgctt 360
ggtacgagga tgctttcggc ggagggaccg aggtggtggt caaacgtacg ccagttgcac 420
ctactgtcct cctcttccca ccatctagcg ctgagctggc aactggaaca gccaccatcg 480

-continued

```
tgtgcgtggc gaataaatac tttcccgatg gcaccgtcac ctggaaggtg gatggcatca    540

cccaaagcag cggcatcaat aacagtagaa caccgcagaa ttctgcagat tgtacctaca    600

acctcagcag tactctgaca ctgagcagcg acgagtacaa cagccacgac gagtacacct    660

gccaggtggc ccaggactca ggctcaccgg tcgtccagag cttcagtagg aagagctgtt    720
```